US011850216B2

(12) United States Patent
Rashidian et al.

(10) Patent No.: US 11,850,216 B2
(45) Date of Patent: Dec. 26, 2023

(54) 18F LABELING OF PROTEINS USING SORTASES

(71) Applicants: Whitehead Institute for Biomedical Research, Cambridge, MA (US); The General Hospital Corporation, Boston, MA (US)

(72) Inventors: Mohammad Rashidian, Cambridge, MA (US); Hidde L. Ploegh, Boston, MA (US); Ralph Weissleder, Peabody, MA (US); Edmund J. Keliher, Topsfield, MA (US)

(73) Assignees: Whitehead Institute for Biomedical Research, Cambridge, MA (US); The General Hospital Corporation, Boston, MA (US)

( * ) Notice: Subject to any disclaimer, the term of this patent is extended or adjusted under 35 U.S.C. 154(b) by 64 days.

(21) Appl. No.: 16/737,620

(22) Filed: Jan. 8, 2020

(65) Prior Publication Data

US 2020/0384137 A1 Dec. 10, 2020

Related U.S. Application Data

(62) Division of application No. 15/035,924, filed as application No. PCT/US2014/065574 on Nov. 13, 2014, now Pat. No. 10,556,024.

(60) Provisional application No. 61/903,834, filed on Nov. 13, 2013.

(51) Int. Cl.
| | | |
|---|---|---|
| *A61K 51/10* | (2006.01) | |
| *A61K 51/08* | (2006.01) | |
| *G01N 33/60* | (2006.01) | |
| *C12N 9/52* | (2006.01) | |
| *C07H 5/02* | (2006.01) | |
| *C07K 16/28* | (2006.01) | |

(52) U.S. Cl.
CPC .......... *A61K 51/1096* (2013.01); *A61K 51/08* (2013.01); *C07H 5/02* (2013.01); *C07K 16/2845* (2013.01); *C12N 9/52* (2013.01); *C12Y 304/2207* (2013.01); *G01N 33/60* (2013.01); *C07K 2317/55* (2013.01); *C07K 2317/569* (2013.01); *G01N 2333/95* (2013.01); *G01N 2800/52* (2013.01); *G01N 2800/7028* (2013.01)

(58) Field of Classification Search
CPC ............... A61K 51/00; A61K 51/2123; A61K 2121/00; A61K 51/1096; A61K 51/08; A61K 51/088; C07H 5/02; C07K 16/2845; C07K 2317/55; C07K 2317/569; C12N 9/52; C12Y 304/2207; G01N 33/60; G01N 2333/95; G01N 2800/52; G01N 2800/7028

USPC ........ 424/1.49, 1.65, 1.69, 1.81, 1.85, 1.89, 424/9.1, 9.2; 530/300; 514/1, 1.1
See application file for complete search history.

(56) References Cited

U.S. PATENT DOCUMENTS

| | | | |
|---|---|---|---|
| 5,670,132 | A | 9/1997 | Griffiths et al. |
| 5,728,369 | A | 3/1998 | Griffiths et al. |
| 6,960,473 | B2 | 11/2005 | Migliaccio et al. |
| 8,206,979 | B2 | 6/2012 | Giarratana et al. |
| 8,496,912 | B2 | 7/2013 | McBride et al. |
| 8,865,875 | B2 | 10/2014 | Liu et al. |
| 8,940,501 | B2 | 1/2015 | Ploegh et al. |
| 9,267,127 | B2 * | 2/2016 | Liu .................... C12N 15/1058 |
| 9,751,945 | B2 | 9/2017 | Ploegh et al. |
| 9,878,045 | B2 | 1/2018 | Distefano et al. |
| 10,053,683 | B2 | 8/2018 | Pasqual et al. |
| 10,081,684 | B2 | 9/2018 | Ploegh et al. |
| 10,260,038 | B2 | 4/2019 | Swee et al. |
| 10,335,504 | B2 | 7/2019 | Sundaram et al. |
| 10,471,099 | B2 | 11/2019 | Lodish et al. |
| 10,556,024 | B2 * | 2/2020 | Rashidian .............. G01N 33/60 |
| 11,028,185 | B2 | 6/2021 | Ploegh et al. |
| 11,266,695 | B2 | 3/2022 | Lodish et al. |
| 11,492,590 | B2 | 11/2022 | Swee et al. |
| 2002/0122768 | A1 | 9/2002 | Liu et al. |
| 2003/0022178 | A1 | 1/2003 | Schneewind et al. |

(Continued)

FOREIGN PATENT DOCUMENTS

| | | |
|---|---|---|
| CN | 102559600 A | 7/2012 |
| JP | 2010115136 A | 5/2010 |

(Continued)

OTHER PUBLICATIONS

Extended European Search Report, dated Jun. 19, 2020, in connection with EP 19219550.1.

(Continued)

*Primary Examiner* — D. L. Jones
(74) *Attorney, Agent, or Firm* — Wolf, Greenfield & Sacks, P.C.

(57) ABSTRACT

The present invention, in some aspects, provides methods, reagents, compositions, and kits for the radiolabeling of proteins, for example, of proteins useful for positron emission tomography (PET) or single-photon emission computed tomography (SPECT) (e.g., for diagnostic and therapeutic applications), using sortase-mediated transpeptidation reactions. Some aspects of this invention provide methods for the conjugation of an agent, for example, a radioactive agent or molecule to diagnostic or therapeutic peptides or proteins. Compositions comprising sortagged, radiolabeled proteins as well as reagents for generating radiolabeled proteins are also provided. Kits comprising reagents useful for the generation of radiolabeled proteins are provided, as are precursor proteins that comprise a sortase recognition motif.

21 Claims, 23 Drawing Sheets

Specification includes a Sequence Listing.

(56) References Cited

U.S. PATENT DOCUMENTS

| | | | |
|---|---|---|---|
| 2004/0213795 | A1 | 10/2004 | Collins et al. |
| 2007/0218552 | A1 | 9/2007 | Giarratana et al. |
| 2010/0092470 | A1 | 4/2010 | Bhatt et al. |
| 2011/0070154 | A1 | 3/2011 | Hyde et al. |
| 2011/0195021 | A1 | 8/2011 | Deckert et al. |
| 2011/0195068 | A1 | 8/2011 | Langermann et al. |
| 2011/0321183 | A1 | 12/2011 | Ploegh et al. |
| 2012/0039906 | A1 | 2/2012 | Olive |
| 2012/0114649 | A1 | 5/2012 | Langermann et al. |
| 2013/0095098 | A1 | 4/2013 | Tyson |
| 2013/0108651 | A1 | 5/2013 | Carven et al. |
| 2013/0109843 | A1 | 5/2013 | Carven et al. |
| 2013/0237580 | A1 | 9/2013 | Sasikumar et al. |
| 2013/0266512 | A1 | 10/2013 | Fox et al. |
| 2014/0030697 | A1 | 1/2014 | Ploegh et al. |
| 2014/0057317 | A1 | 2/2014 | Liu et al. |
| 2014/0249296 | A1 | 9/2014 | Ploegh et al. |
| 2015/0086576 | A1 | 3/2015 | Ploegh et al. |
| 2016/0082046 | A1 | 3/2016 | Lodish et al. |
| 2016/0097773 | A1 | 4/2016 | Pasqual et al. |
| 2016/0122707 | A1 | 5/2016 | Ploegh et al. |
| 2016/0287734 | A1 | 10/2016 | Rashidian et al. |
| 2018/0280440 | A1 | 10/2018 | Lodish et al. |
| 2018/0280551 | A1 | 10/2018 | Rashidian et al. |
| 2018/0346899 | A1 | 12/2018 | Pasqual et al. |
| 2019/0112394 | A1 | 4/2019 | Ploegh et al. |
| 2019/0256818 | A1 | 8/2019 | Swee et al. |
| 2019/0359933 | A1 | 11/2019 | Swee et al. |
| 2020/0069736 | A1 | 3/2020 | Lodish et al. |
| 2020/0370016 | A1 | 11/2020 | Lipsitz et al. |

FOREIGN PATENT DOCUMENTS

| | | | |
|---|---|---|---|
| WO | WO 2000/62804 | A2 | 10/2000 |
| WO | WO 2005/051976 | A2 | 6/2005 |
| WO | WO 2005/086654 | A2 | 9/2005 |
| WO | WO 2010/078376 | A2 | 7/2010 |
| WO | WO 2010/087994 | A2 | 8/2010 |
| WO | WO 2011/101468 | A1 | 8/2011 |
| WO | WO 2011/133704 | A2 | 10/2011 |
| WO | WO 2012/142659 | A1 | 10/2012 |
| WO | WO 2013/003555 | A1 | 1/2013 |
| WO | WO 2013/155526 | A2 | 10/2013 |
| WO | WO 2014/183006 | A2 | 11/2014 |
| WO | WO 2015/073746 | A2 | 5/2015 |
| WO | WO 2020/243006 | A1 | 12/2020 |

OTHER PUBLICATIONS

Extended European Search Report, dated Nov. 30, 2012, in connection with EP 10736161.0.

Extended European Search Report, dated Nov. 9, 2016, in connection with EP 14795167.7.

Extended European Search Report, dated Jul. 26, 2019, in connection with EP 19171188.6.

Extended European Search Report, dated Jul. 26, 2019, in connection with EP 19171190.2.

Extended European Search Report, dated Oct. 13, 2016, in connection with EP 14795120.6.

Extended European Search Report, dated Apr. 29, 2019, in connection with EP 16852806.5.

Invitation to Pay Additional Fees, dated Nov. 8, 2010, in connection with PCT/US2010/000274.

International Search Report and Written Opinion, dated Dec. 22, 2010, in connection with PCT/US2010/000274.

International Preliminary Report on Patentability, dated Aug. 11, 2011, in connection with PCT/US2010/000274.

Extended European Search Report, dated Nov. 26, 2014, in connection with EP 12804570.5.

International Search Report and Written Opinion, dated Nov. 15, 2012, in connection with PCT/US2012/044584.

International Preliminary Report on Patentability, dated Jan. 16, 2014, in connection with PCT/US2012/044584.

Invitation to Pay Additional Fees, dated Sep. 5, 2014, in connection with PCT/US2014/037554.

International Search Report and Written Opinion, dated Nov. 6, 2014, in connection with PCT/US2014/037554.

International Preliminary Report on Patentability, dated Nov. 19, 2015, in connection with PCT/US2014/037554.

International Search Report and Written Opinion, dated Oct. 27, 2014, in connection with PCT/US2014/037545.

International Preliminary Report on Patentability, dated Nov. 19, 2015, in connection with PCT/US2014/037545.

Invitation to Pay Additional Fees, dated Mar. 20, 2015, in connection with PCT/US14/65574.

International Search Report and Written Opinion, dated Jun. 4, 2015, in connection with PCT/US14/65574.

Invitation to Pay Additional Fees, dated Dec. 1, 2016, in connection with PCT/US2016/055074.

International Search Report and Written Opinion, dated Feb. 6, 2017, in connection with PCT/US2016/055074.

International Preliminary Report on Patentability, dated Apr. 12, 2018, in connection with PCT/US2016/055074.

Genbank Submission; NIH/NCBI, Accession No. AAD48437; Mazmanian et al.; Aug. 11, 1999. Updated Nov. 30, 2009 and Mar. 10, 2010.

Genbank Submission; NIH/NCBI, Accession No. NP_375640. Jang et al., Aug. 26, 2013. 3 pages.

GenPept Accession No. YP 187332.1. Gill et al. Dec. 17, 2014.

[No Author Listed] Creative Biolabs. Single Domain Antibody Library. Retrieved from at www.creative-biolabs.com/single-domain-antibody-library-service.html?gclid=eaiaiqobchminozno5qo3givibczch3uhqhneaayaiaaegk-sfd_bwe on Oct. 17, 2018.

[No Author Listed], Fusion protein. Wikipedia. 7 pages. Retrieved from https://en.wikipedia.org/Fusion_protein on Feb. 8, 2019.

[No Author Listed] Polyethylene Glycol (PEG) and PEGylation of Proteins. ThermoFisher Scientific 2019. 11 pages.

Ahlgren et al., Targeting of HER2-expressing tumors with a site-specifically 99mTc-labeled recombinant affibody molecule, ZHER2:2395, with C-terminally engineered cysteine. J Nucl Med. May 2009;50(5):781-9. doi: 10.2967/jnumed.108.056929. Epub Apr. 16, 2009.

Antos et al., A straight path to circular proteins. J Biol Chem. Jun. 5, 2009;284(23):16028-36. Epub Apr. 9, 2009.

Antos et al., Lipid modification of proteins through sortase-catalyzed transpeptidation. J Am Chem Soc. Dec. 3, 2008;130(48):16338-43.

Antos et al., Site-specific N- and C-terminal labeling of a single polypeptide using sortases of different specificity. J Am Chem Soc. Aug. 12, 2009;131(31):10800-1. doi: 10.1021/ja902681k.

Barnett et al., Differential recognition of surface proteins in *Streptococcus pyogenes* by two sortase gene homologs. J Bacteriol. Apr. 2002;184(8):2181-91.

Becer et al., Click chemistry beyond metal-catalyzed cycloaddition. Angew Chem Int Ed Engl. 2009;48(27):4900-8.

Bentley et al., Engineering the substrate specificity of *Staphylococcus aureus* Sortase A. The beta6/beta7 loop from SrtB confers NPQTN recognition to SrtA. J Biol Chem. Mar. 2, 2007;282(9):6571-81. Epub Jan. 2, 2007.

Blackman et al., Tetrazine ligation: fast bioconjugation based on inverse-electron-demand Diels-Alder reactivity. J Am Chem Soc. Oct. 15, 2008;130(41):13518-9. Epub Sep. 18, 2008.

Boellaard et al., FDG PET and PET/CT: EANM procedure guidelines for tumour PET imaging: version 1.0. Eur J Nucl Med Mol Imaging. Jan. 2010;37(1):181-200. doi: 10.1007/s00259-009-1297-4.

Boonyarattanakalin et al., Synthesis of an artificial cell surface receptor that enables oligohistidine affinity tags to func-tion as metal-dependent cell-penetrating peptides. J Am Chem Soc. Mar. 18, 2006;128(14):4917.

Borjesson et al., Radiation dosimetry of 89Zr-labeled chimeric monoclonal antibody U36 as used for immuno-PET in head and

(56) References Cited

OTHER PUBLICATIONS neck cancer patients. J Nucl Med. Nov. 2009;50(11):1828-36. doi: 10.2967/jnumed.109.065862. Epub Oct. 16, 2009.
Brotzel et al., Nucleophilicities of amino acids and peptides. Org Biomol Chem. Dec. 7, 2007;5(23):3814-20. Epub Oct. 16, 2007.
Bundy et al., Site-specific incorporation of p-propargyloxyphenylalanine in a cell-free ennvironment for direct protein-protein click conjugation. Bioconjug Chem. Feb. 17, 2010;21(2):255-63.
Carrasquillo et al., (124)I-huA33 antibody PET of colorectal cancer. J Nucl Med. Aug. 2011;52(8):1173-80. doi: 10.2967/jnumed.110.086165. Epub Jul. 15, 2011.
Chan et al., Covalent attachment of proteins to solid supports and surfaces via Sortase-mediated ligation. PLoS One. Nov. 14, 2007;2(11):e1164. 5 pages.
Chang et al., Development and characterization of 89Zr-labeled panitumumab for immuno-positron emission tomographic imaging of the epidermal growth factor receptor. Mol Imaging. Jan.-Feb. 2013;12(1):17-27.
Chen et al., A general strategy for the evolution of bond-forming enzymes using yeast display. Proc Natl Acad Sci U S A. Jul. 12, 2011;108(28):11399-404. doi: 10.1073/pnas.1101046108. Epub Jun. 22, 2011.
Cheung et al., A small-scale serum-free liquid cell culture model of erythropoiesis to assess the effects of exogenous factors. J Immunol Methods. Jan. 30, 2007;319(1-2):104-17. Epub Dec. 4, 2006.
Chudakov et al., Fluorescent proteins and their applications in imaging living cells and tissues.Physiol Rev. Jul. 2010;90(3):1103-63. doi: 10.1152/physrev.00038.2009.
Clow et al., Immobilization of proteins to biacore sensor chips using *Staphylococcus aureus* sortase A. Biotechnol Lett. Sep. 2008;30(9):1603-7. Epub Apr. 15, 2008.
Cooper et al., Comparison of (64)Cu-complexing bifunctional chelators for radioimmunoconjugation: labeling efficiency, specific activity, and in vitro/in vivo stability. Bioconjug Chem. May 16, 2012;23(5):1029-39. doi: 10.1021/bc300037w. Epub Apr. 13, 2012.
Comfort et al., A comparative genome analysis identifies distinct sorting pathways in gram-positive bacteria. Infect Immun. May 2004;72(5):2710-22.
Cortez-Retamozo et al., Efficient tumor targeting by single-domain antibody fragments of camels. Int J Cancer. Mar. 20, 2002;98(3):456-62.
David et al., Facile, efficient routes to diverse protected thiols and to their deprotection and addition to create functional polymers by thiol-ene coupling. Macromolec. 2008;41(4):1151-61.
De Groeve et al., Nanobodies as tools for in vivo imaging of specific immune cell types. J Nucl Med. 2010;51(5):782-789. doi:10.2967/jnumed.109.070078.
De Marco, User-friendly expression plasmids enable the fusion of VHHs to application-specific tags. Methods Mol Biol. 2012;911:507-522. doi:10.1007/978-1-61779-968-6_32.
De Meyer et al., Nanobody-based products as research and diagnostic tools. Trends Biotechnol. May 2014;32(5):263-70. doi:10.1016/j.tibtech.2014.03.001. Epub Apr. 1, 2014.
Debets et al., Aza-dibenzocyclooctynes for fast and efficient enzyme PEGylation via copper-free (3+2) cycloaddition. Chem Commun (Camb). Jan. 7, 2010;46(1):97-9. doi: 10.1039/b917797c. Epub Nov. 6, 2009.
Delgado, et al. "Stabilities of divalent and trivalent metal ion complexes of macrocyclic triazatriacetic acids.", Inorg. Chem. 1999; 32, 3320-3326.
Denk et al., Development of a (18) F-labeled tetrazine with favorable pharmacokinetics for bioorthogonal PET imaging. Angew Chem Int Ed Engl. Sep. 1, 2014;53(36):9655-9. doi: 10.1002/anie.201404277. Epub Jul. 2, 2014.
Diamandis et al., The Biotin-(Strept) Avidin System: Principles and Applications in Biotechnology. Clin. Chem. 1991;37(5):625-36.
Dijkers et al., Biodistribution of 89Zr-trastuzumab and PET imaging of HER2-positive lesions in patients with metastatic breast cancer. Clin Pharmacol Ther. May 2010;87(5):586-92. doi: 10.1038/clpt.2010.12. Epub Mar. 31, 2010.
Divgi et al., Positron emission tomography/computed tomography identification of clear cell renal cell carcinoma: results from the REDECT trial.J Clin Oncol. Jan. 10, 2013;31(2):187-94. doi: 10.1200/JCO.2011.41.2445. Epub Dec. 3, 2012.
Dorr et al., Reprogramming the specificity of sortase enzymes. Proc Natl Acad Sci U S A. Sep. 16, 2014;111(37):13343-8. doi:10.1073/pnas.1411179111. Epub Sep. 3, 2014.
Dramsi et al., Sorting sortases: a nomenclature proposal for the various sortases of Gram-positive bacteria. Res Microbiol. Apr. 2005;156(3):289-97. Epub Jan. 28, 2005.
Engfeldt et al., Chemical synthesis of triple-labelled three-helix bundle binding proteins for specific fluorescent detection of unlabelled protein. Chembiochem. Jun. 2005;6(6):1043-50.
Evans, The rise of azide-alkyne 1,3-dipolar 'click' cycloaddition and its application to polymer science and surface modification. Australian J Chem. Jun. 18, 2007;60(6):384-95.
Evans et al., Bioorthogonal chemistry for (68) Ga radiolabelling of DOTA-containing compounds. J Labelled Comp Radiopharm. Apr. 2014;57(4):291-7. doi: 10.1002/jlcr.3153. Epub Dec. 5, 2013.
Fournier et al., Clicking polymers: a straightforward approach to novel macromolecular architectures. Chem Soc Rev. Aug. 2007;36(8):1369-80. Epub May 3, 2007.
Gebauer et al., Engineered protein scaffolds as next-generation antibody therapeutics. Curr Opin Chem Biol. Jun. 2009; 13(3):245-55. doi: 10.1016/j.cbpa.2009.04.627. Epub Jun. 6, 2009.
Goldenberg et al., Novel radiolabeled antibody conjugates. Oncogene. May 28, 2007;26(25):3734-44.
Groheux et al., Correlation of high 18F-FDG uptake to clinical, pathological and biological prognostic factors in breast cancer. Eur J Nucl Med Mol Imaging. Mar. 2011;38(3):426-35. doi: 10.1007/s00259-010-1640-9. Epub Nov. 6, 2010.
Hackenberger et al., Chemoselective ligation and modification strategies for peptides and proteins. Angew Chem Int Ed Engl. 2008;47(52):10030-74. doi: 10.1002/anie.200801313.
Hess et al., M13 bacteriophage display framework that allows sortase-mediated modification of surface-accessible phage proteins. Bioconjug Chem. Jul. 18, 2012;23(7):1478-87. doi: 10.1021/bc300130z. Epub Jul. 3, 2012.
Hirakawa et al., Design of Ca2+-independent *Staphylococcus aureus* sortase A mutants. Biotechnol Bioeng. Dec. 2012;109(12):2955-61. doi: 10.1002/bit.24585. Epub Jul. 4, 2012. PubMed PMID: 22729808.
Hochuli et al., Genetic Approach to Facilitate Purification of Recombinant Proteins with a Novel Metal Chelate Adsorbent. Nature Biotechnology. 1988, 6, 1321-1325.
Holm et al., Electrophilic affibodies forming covalent bonds to protein targets. J Biol Chem. Nov. 20, 2009;284(47):32906-13. doi:10.1074/jbc.M109.034322. Epub Sep. 15, 2009.
Idoyaga et al., Comparable T helper 1 (Th1) and CD8 T-cell immunity by targeting HIV gag p24 to CD8 dendritic cells within antibodies to Langerin, DEC205, and Clec9A. Proc Natl Acad Sci U S A. Feb. 8, 2011;108(6):2384-9. doi:10.1073/pnas.1019547108. Epub Jan. 24, 2011.
Jevsevar et al., PEGylation of therapeutic proteins. Biotechnol J. Jan. 2010;5(1):113-28.
Jokerst et al., Nanoparticle PEGylation for imaging and therapy. Nanomedicine (Lond). 2011;6(4):715-728. doi: 10.2217/nnm.11.19.
Keliher et al., High-yielding, two-step 18F labeling strategy for 18F-PARP1 inhibitors. ChemMedChem. Mar. 7, 2011;6(3):424-7. doi: 10.1002/cmdc.201000426. Epub Jan. 4, 2011.
Knowles et al., Advances in immuno-positron emission tomography: antibodies for molecular imaging in oncology. J Clin Oncol. Nov. 1, 2012;30(31):3884-92. doi: 10.1200/JCO.2012.42.4887. Epub Sep. 17, 2012.
Kolb et al., Click Chemistry: Diverse Chemical Function from a Few Good Reactions. Angew Chem Int Ed Engl. Jun. 1, 2001;40(11):2004-2021.
Kolb et al., The growing impact of click chemistry on drug discovery. Drug Discov Today. Dec. 15, 2003;8(24):1128-37.
Kruger et al., Analysis of the substrate specificity of the *Staphylococcus aureus* sortase transpeptidase SrtA. Biochemistry. Feb. 17, 2004;43(6):1541-51.

(56) References Cited

OTHER PUBLICATIONS

Kubetzko et al., PEGylation and multimerization of the anti-p185HER-2 single chain Fv fragment 4D5: effects on tumor targeting. J Biol Chem. 2006;281(46):35186-35201. doi: 10.1074/jbc.M604127200.

Langenhan et al., "Recent Carbohydrate-Based Chemoselective Ligation Applications." Current Organic Synthesis. 2005; 2, 59-81.

Levary et al., Protein-protein fusion catalyzed by sortase A. PLoS One. Apr. 6, 2011;6(4):e18342. doi: 10.1371/journal.pone.0018342. 6 pages.

Li et al., Tetrazine-trans-cyclooctene ligation for the rapid construction of 18F labeled probes. Chem Commun (Camb). Nov. 14, 2010;46(42):8043-5. doi: 10.1039/c0cc03078c. Epub Sep. 22, 2010.

Liu et al., A Brief Review of Chelators for Radiolabeling Oligomers. Materials. 2010; 3(5): 3204-3217.

Lowrie et al., Chapter 20. EPO: Treating Anemia in Chronic Renal Failure. The National Kidney Foundation. 2011;1-6.

Lu et al. Biologic properties and enucleation of red blood cells from human embryonic stem cells. Blood. Dec. 1, 2008;112(12):4475-84. doi:10.1182/blood-2008-05-157198. Epub Aug. 19, 2008.

Lundberg et al., Site-specifically conjugated anti-HER2 Affibody molecules as one-step reagents for target expression analyses on cells and xenograft samples. J Immunol Methods. Jan. 30, 2007;319(1-2):53-63. Epub Nov. 21, 2006.

Mao et al., Sortase-Mediated Protein Ligation: A New Method for Portein Engineering. J Am Chem Soc. Feb. 10, 2004;126:2670-1.

Mao, A self-cleavable sortase fusion for one-step purification of free recombinant proteins. Protein Expr Purif. Sep. 2004;37(1):253-63.

Maresso et al., Surface protein IsdC and Sortase B are required for heme-iron scavenging of Bacillus anthracis. J Bacteriol. Dec. 2006;188(23):8145-52. Epub Sep. 29, 2006.

Mariscotti et al., The Listeria monocytogenes sortase-B recognizes varied amino acids at position 2 of the sorting motif. J Biol Chem. Mar. 6, 2009;284(10):6140-6. Epub Jan. 7, 2009.

Marraffini et al., Sortase C-mediated anchoring of BasI to the cell wall envelope of Bacillus anthracis. J Bacteriol. Sep. 2007;189(17):6425-36. Epub Jun. 22, 2007.

Matsumoto et al., Site-specific tetrameric streptavidin-protein conjugation using sortase A. J Biotechnol. Mar. 10, 2011;152(1-2):37-42. doi: 10.1016/j.jbiotec.2011.01.008. Epub Jan. 22, 2011.

Matsumura et al., Emerging principles for the recognition of peptide antigens by MHC class 1 molecules, Sci. 1992;257:927-934.

Mazmanian et al., An iron-regulated sortase anchors a class of surface protein during *Staphylococcus aureus* pathogenesis. Proc Natl Acad Sci U S A. Feb. 19, 2002;99(4):2293-8. Epub Feb. 5, 2002.

Mazmanian et al., Sortase-catalysed anchoring of surface proteins to the cell wall of *Staphylococcus aureus*. Mol Microbiol. Jun. 2001;40(5):1049-57. Review.

Miharada et al., Efficient enucleation of erythroblasts differentiated in vitro from hematopoietic stem and progenitor cells. Nat Biotechnol. Oct. 2006;24(10):1255-6. Epub Sep. 17, 2006.

Moreno et al., Immunohistochemical analysis of B3 integrin (CD61):expression in pig tissues and human tumors. Histol Histopathol. 2002;17:347-352.

Nair-Gill et al., Non-invasive imaging of adaptive immunity using positron emission tomography. Immunol Rev. Feb. 2008;221:214-28. doi: 10.1111/j.1600-065X.2008.00585.x.

Namavari et al., A novel method for direct site-specific radiolabeling of peptides using [18F]FDG. Bioconjug Chem. Mar. 18, 2009;20(3):432-6. doi: 10.1021/bc800422b.

Nayak et al., PET and MRI of metastatic peritoneal and pulmonary colorectal cancer in mice with human epidermal growth factor receptor 1-targeted 89Zr-labeled panitumumab. J Nucl Med. Jan. 2012;53(1):113-20. doi: 10.2967/jnumed.111.094169.

Ning et al., Visualizing metabolically labeled glycoconjugates of living cells by copper-free and fast huisgen cycloadditions. Angew Chem Int Ed Engl. 2008;47(12):2253-5.

Olafsen et al., ImmunoPET using engineered antibody fragments: fluorine-18 labeled diabodies for same-day imaging. Tumour Biol. Jun. 2012;33(3):669-77. doi: 10.1007/s13277-012-0365-8. Epub Mar. 6, 2012.

Orlova et al., Evaluation of [(111/114m)In]CHX-A"-DTPA-ZHER2:342, an affibody ligand coniugate for targeting of HER2-expressing malignant tumors. Q J Nucl Med Mol Imaging. 2007. 314-323.

Orlova et al., Tumor imaging using a picomolar affinity HER2 binding affibody molecule. Cancer Res. Apr. 15, 2006;66(8):4339-48.

Pallen et al., An embarrassment of sortases—a richness of substrates? Trends Microbiol. Mar. 2001;9(3):97-101.

Park et al., Anchoring foreign substances on live cell surfaces using Sortase A specific binding peptide. Chem Commun (Camb). Oct. 25, 2013;49(83):9585-7. doi: 10.1039/c3cc44753g.

Parthasarathy et al., Sortase A as a novel molecular "stapler" for sequence-specific protein conjugation. Bioconjug Chem. Mar.-Apr. 2007;18(2):469-76. Epub Feb. 16, 2007.

Paterson et al., Enzyme-mediated site-specific bioconjugation of metal complexes to proteins: sortase-mediated coupling of copper-64 to a single-chain antibody. Angew Chem Int Ed Engl. Jun. 10, 2014;53(24):6115-9. doi: 10.1002/anie.201402613. Epub Apr. 28, 2014.

Pellois et al., A ligation and photorelease strategy for the temporal and spatial control of protein function in living cells. Angew Chem Int Ed Engl. Sep. 5, 2005;44(35):5713-7.

Piotukh et al., D. Directed evolution of sortase A mutants with altered substrate selectivity profiles. J Am Chem Soc. Nov. 9, 2011;133(44):17536-9. doi: 10.1021/ja205630g. Epub Oct. 13, 2011.

Pishesha et al., Engineered erythrocytes covalently linked to antigenic peptides can protect against autoimmune disease. Proc Natl Acad Sci U S A. Mar. 21, 2017;114(12):3157-3162. doi: 10.1073/pnas.1701746114. Epub Mar. 7, 2017.

Poli et al., Radretumab radioimmunotherapy in patients with brain metastasis: a 124I-L19SIP dosimetric PET study. Cancer Immunol Res. Aug. 2013;1(2):134-43. doi: 10.1158/2326-6066.CIR-13-0007. Epub May 20, 2013.

Popp et al., Making and breaking peptide bonds: protein engineering using sortase. Angew Chem Int Ed Engl. May 23, 2011;50(22):5024-32. doi:10.1002/anie.201008267. Epub Apr. 27, 2011.

Popp et al., Site-specific protein labeling via sortase-mediated transpeptidation. Curr Protoc Protein Sci. Apr. 2009;Chapter 15:Unit 15.3. doi: 10.1002/0471140864.ps1503s56.

Popp et al., Sortagging: a versatile method for protein labeling. Nat Chem Biol. Nov. 2007;3(11):707-8. Epub Sep. 23, 2007.

Popp et al., Sortase-catalyzed transformations that improve the properties of cytokines. Proc Natl Acad Sci USA. Feb. 22, 2011;108(8):3169-74. doi: 10.1073/pnas.1016863108. Epub Feb. 4, 2011.

Popp et al., Substrate filtering by the active site crossover loop in UCHL3 revealed by sortagging and gain-of-function mutations. J Biol Chem. Feb. 6, 2009;284(6):3593-602. Epub Dec. 1, 2008.

Pritz et al., Synthesis of biologically active peptide nucleic acid-peptide conjugates by sortase-mediated ligation. J Org Chem. May 11, 2007;72(10):3909-12. Epub Apr. 14, 2007.

Race et al., Crystal structure of *Streptococcus pyogenes* sortase A: implications for sortase mechanism. J Biol Chem. Mar. 13, 2009;284(11):6924-33. Epub Jan. 6, 2009.

Rashidian et al., A highly efficient catalyst for oxime ligation and hydrazone-oxime exchange suitable for bioconjugation. Bioconjug Chem. Mar. 20, 2013;24(3):333-42. doi: 10.1021/bc3004167.Epub Mar. 6, 2013.

Rashidian et al., Enzymatic labeling of proteins: techniques and approaches. Bioconjug Chem. Aug. 21, 2013;24(8):1277-94.

Rashidian et al., Noninvasive imaging of immune responses. Proc Natl Acad Sci U S A. May 12, 2015;112(19):6146-51. doi: 10.1073/pnas.1502609112. Epub Apr. 20, 2015.

Rashidian et al., The use of 18F-2-fluorodeoxyglucose (FDG) to label antibody fragments for immuno-PET of pancreatic cancer. ACS Cent Sci. Jun. 24, 2015;1(3):142-147. Epub Jun. 3, 2015.

(56) References Cited

OTHER PUBLICATIONS

Ronnmark et al., Construction and characterization of affibody-Fc chimeras produced in *Escherichia coli*. J Immunol Methods. Mar. 1, 2002;261(1-2):199-211.

Salsano et al., PET imaging using radiolabeled antibodies: future direction in tumor diagnosis and correlate applications. Research and Reports in Nuclear Medicine. 2013: 3; 9-17.

Samantaray et al., Peptide-sugar ligation catalyzed by transpeptidase sortase: a facile approach to neoglycoconjugate synthesis. J Am Chem Soc. Feb. 20, 2008;130(7):2132-3. Epub Jan. 30, 2008.

Selvaraj et al., trans-Cyclooctene—a stable, voracious dienophile for bioorthogonal labeling. Curr Opin Chem Biol. Oct. 2013;17(5):753-60. doi: 10.1016/j.cbpa.2013.07.031. Epub Aug. 23, 2013.

Sharpless et al., Just click it: Undergraduate procedures for the copper(I)-catalyzed formation of 1,2,3-triazoles from azides and terminal acetylenes. J Chem Ed. 2005;82(12):1833-6.

Shi et al. Engineered red blood cells as carriers for systemic delivery of a wide array of functional probes. Proc Natl Acad Sci U S A. Jul. 15, 2014;111(28):10131-6. doi: 10.1073/pnas.1409861111. Epub Jun. 30, 2014.

Siontorou, Nanobodies as novel agents for disease diagnosis and therapy. Int J Nanomedicine. 2013;8:4215-27. doi: 10.2147/IJN.S39428. Epub Jan. 11, 2013.

Spicer et al., Selective chemical protein modification. Nat Commun. Sep. 5, 2014;5:4740. doi: 10.1038/ncomms5740.

Strijbis et al., Protein ligation in living cells using sortase. Traffic. Jun. 2012;13(6):780-9. doi: 10.1111/j.1600-0854.2012.01345.x. Epub Mar. 23, 2012.

Swee et al., Sortase-mediated modification of αDEC205 affords optimization of antigen presentation and immunization against a set of viral epitopes. Proc Natl Acad Sci USA. Jan. 22, 2013;110(4):1428-33. doi: 10.1073/pnas.1214994110. Epub Jan. 7, 2013.

Swee et al., One-step enzymatic modification of the cell surface redirects cellular cytotoxicity and parasite tropism. ACS Chem Biol. Feb. 20, 2015;10(2):460-5. doi: 10.1021/cb500462t.

Ta et al., Enzymatic single-chain antibody tagging: a universal approach to targeted molecular imaging and cell homing in cardiovascular disease. Circ Res. Aug. 5, 2011;109(4):365-73. doi: 10.1161/CIRCRESAHA.111.249375.

Tanaka et al., PET (positron emission tomography) imaging of biomolecules using metal-DOTA complexes: a new collaborative challenge by chemists, biologists, and physicians for future diagnostics and exploration of in vivo dynamics. Org Biomol Chem. Mar. 7, 2008;6(5):815-28. doi: 10.1039/b718157b. Epub Feb. 1, 2008.

Tanaka et al., Site-specific protein modification on living cells catalyzed by Sortase. Chembiochem. Mar. 25, 2008;9(5):802-7.

Tavare et al., Engineered antibody fragments for immuno-PET imaging of endogenous CD8+ T cells in vivo. Proc Natl Acad Sci U S A. Jan. 21, 2014;111(3):1108-13. doi: 10.1073/pnas.1316922111. Epub Jan. 3, 2014.

Theile et al., Site-specific N-terminal labeling of proteins using sortase-mediated reactions. Nat Protoc. Sep. 2013;8(9):1800-7. doi: 10.1038/nprot.2013.102. Epub Aug. 29, 2013.

Tolmachev et al., Radionuclide therapy of HER2-positive microxenografts using a 177Lu-labeled HER2-specific Affibody molecule. Cancer Res. Mar. 15, 2007;67(6):2773-82.

Ton-That et al., Anchoring of surface proteins to the cell wall of *Staphylococcus aureus*. Sortase catalyzed in vitro transpeptidation reaction using LPXTG peptide and NH(2)-Gly(3) substrates. J Biol Chem. Mar. 31, 2000;275(13):9876-81.

Ton-That et al., Protein sorting to the cell wall envelope of Gram-positive bacteria. Biochim Biophys Acta. Nov. 11, 2004;1694(1-3):269-78.

Ton-That et al., Purification and characterization of sortase, the transpeptidase that cleaves surface proteins of *Staphylococcus aureus* at the LPXTG motif. Proc Natl Acad Sci U S A. Oct. 26, 1999;96(22):12424-9.

Tornoe et al., Peptidotriazoles on solid phase: [1,2,3]-triazoles by regiospecific copper(i)-catalyzed 1,3-dipolar cycloadditions of terminal alkynes to azides. J Org Chem. May 3, 2002;67(9):3057-64.

Tran et al., (99m)Tc-maEEE-Z(HER2:342), an Affibody molecule-based tracer for the detection of HER2 expression in malignant tumors. Bioconjug Chem. Nov.-Dec. 2007;18(6):1956-64. Epub Oct. 19, 2007.

Truong et al., Copper-catalyzed, directing group-assisted fluorination of arene and heteroarene C-H bonds. J Am Chem Soc. Jun. 26, 2013;135(25):9342-5. doi: 10.1021/ja4047125. Epub Jun. 12, 2013.

Tsukiji et al., Sortase-mediated ligation: A Gift from Gram-Positive Bacteria to Protein Engineering, ChemBioChem 2009;10:787-798.

Vaidyanathan et al., Synthesis of N-succinimidyl 4-[18F]fluorobenzoate, an agent for labeling proteins and peptides with 18F. Nat Protoc. 2006;1(4):1655-61.

Vosjan et al., Conjugation and radiolabeling of monoclonal antibodies with zirconium-89 for PET imaging using the bifunctional chelate p-isothiocyanatobenzyl-desferrioxamine. Nat Protoc. Apr. 2010;5(4):739-43. doi: 10.1038/nprot.2010.13. Epub Mar. 25, 2010.

Vosjan et al., Facile labelling of an anti-epidermal growth factor receptor Nanobody with 68Ga via a novel bifunctional desferal chelate for immuno-PET. Eur J Nucl Med Mol Imaging. 2011;38(4):753-763. doi:10.1007/s00259-010-1700-1.

Waldherr et al., Monitoring antiproliferative responses to kinase inhibitor therapy in mice with 3'-deoxy-3'-18F-fluorothymidine Pet. J Nucl Med. Jan. 2005;46(1):114-20.

Witte et al., Preparation of unnatural N-to-N and C-to-C protein fusions. Proc Natl Acad Sci U S A. Jul. 24, 2012;109(30):11993-8. doi: 10.1073/pnas.1205427109. Epub Jul. 9, 2012.

Witte et al., Production of unnaturally linked chimeric proteins using a combination of sortase-catalyzed transpeptidation and click chemistry. Nat Protoc. Sep. 2013;8(9):1808-19. doi: 10.1038/nprot.2013.103. Epub Apr. 4, 2014. 16 pages.

Wriggers et al., Control of Protein Functional Dynamics by Peptide Linkers, Prat. Function. Dynam. 2005;80:736-746.

Wright et al., Designing the magic bullet? The advancement of immuno-PET into clinical use. J Nucl Med. Aug. 2013;54(8):1171-4. doi: 10.2967/jnumed.113.126086.

Wu, F-18 Labeled Diabody-Luciferase Fusion Proteins for Optical-ImmunoPET. Department of Energy Final Scientific/Technical Report. Report No. DOE/SC0001220-1. University of California, Los Angeles. Jan. 18, 2013. doi: 10.2172/1060194. 11 pages.

Wu et al., The use of sortase-mediated ligation for the immobilisation of bacterial adhesins onto fluorescence-labelled microspheres: a novel approach to analyse bacterial adhesion to host cells. Biotechnol Lett. Nov. 2010;32(11):1713-8. doi: 10.1007/s10529-010-0349-y.

Wu et al., Sortase A-catalyzed transpeptidation of glycosylphosphatidylinositol derivatives for chemoenzymatic synthesis of GPI-anchored proteins. J Am Chem Soc. Feb. 10, 2010;132(5):1567-71. doi: 10.1021/ja906611x.

Xavier et al., Synthesis, preclinical validation, dosimetry, and toxicity of 68Ga-NOTA-anti-HER2 Nanobodies for iPET imaging of HER2 receptor expression in cancer. J Nucl Med. 2013;54(5):776-784. doi:10.2967/jnumed.112.111021.

Xiao et al., Protein N-terminal processing: substrate specificity of *Escherichia coli* and human methionine aminopeptidases. Biochemistry. Jul. 6, 2010;49(26):5588-99. doi: 10.1021/bi1005464.

Xiao et al., Synthesis of N-terminally linked protein dimers and trimers by a combined native chemical ligation-CuAAC click chemistry strategy. Org Lett. Sep. 17, 2009;11(18):4144-7. doi: 10.1021/ol9016468.

Yamamoto et al., Expansion of the sortase-mediated labeling method for site-specific N-terminal labeling of cell surface proteins on living cells. Chem Commun (Camb). Mar. 7, 2009;(9):1022-4. doi: 10.1039/b818792d. Epub Jan. 7, 2009.

Yang et al., Metal-catalyzed one-pot synthesis of tetrazines directly from aliphatic nitriles and hydrazine. Angew Chem Int Ed Engl. May 21, 2012;51(21):5222-5. doi: 10.1002/anie.201201117. Epub Apr. 18, 2012.

Youssef et al., The use of 18F-FDG PET in the diagnosis of cardiac sarcoidosis: a systematic review and metaanalysis including the

(56) References Cited

OTHER PUBLICATIONS

Ontario experience. J Nucl Med. Feb. 2012;53(2):241-8. doi: 10.2967/jnumed.111.090662. Epub Jan. 6, 2012.
Zaslavskaia et al., Trophic conversion of an obligate photoautotrophic organism through metabolic engineering. Science. Jun. 15, 2001;292(5524):2073-5.
Zhang et al., Positron emission tomography imaging of CD105 expression with a 64Cu-labeled monoclonal antibody: NOTA is superior to DOTA. PLoS One. 2011;6(12):e28005. doi: 10.1371/journal.pone.0028005. Epub Dec. 9, 2011.
Zhao et al., An efficient on-column expressed protein ligation strategy: application to segmental triple labeling of human apolipoprotein E3. Protein Sci. Apr. 2008;17(4):736-47. Epub Feb. 27, 2008.
Zong et al., Crystal structures of *Staphylococcus aureus* sortase A and its substrate complex. J Biol Chem. Jul. 23, 2004;279(30):31383-9. Epub Apr. 26, 2004.
Debierre-Grockiego et al., Differential effect of dexamethasone on cell death and STAT5 activation during in vitro eosinopoiesis. Br J Haematol. Dec. 2003;123(5):933-41. doi: 10.1046/j.1365-2141.2003.04700.x.
Dorn et al., In vitro proliferation and differentiation of human CD34+ cells from peripheral blood into mature red blood cells with two different cell culture systems. Transfusion. Jun. 2008;48(6):1122-32. doi: 10.1111/j.1537-2995.2008.01653.x. Epub Feb. 22, 2008.
Kijanka et al., Nanobody-based cancer therapy of solid tumors. Nanomedicine (Lond). Jan. 2015;10(1):161-74. doi: 10.2217/nnm.14.178.
Li et al., Anti-MET immunoPET for non-small cell lung cancer using novel fully human antibody fragments. Mol Cancer Ther. Nov. 2014;13(11):2607-17. doi: 10.1158/1535-7163.MCT-14-0363. Epub Aug. 20, 2014.
Reese et al. Human mesenchymal stem cells provide stromal support for efficient CD34+ transduction. J Hematother Stem Cell Res. Oct. 1999;8(5):515-23. doi: 10.1089/152581699319966.
Perez-Medina et al., A modular labeling strategy for in vivo PET and near-infrared fluorescence imaging of nanoparticle tumor targeting. J Nucl Med. Oct. 2014;55(10):1706-11. doi: 10.2967/jnumed.114.141861. Epub Jul. 24, 2014.
Trilling et al., Orientation of llama antibodies strongly increases sensitivity of biosensors. Biosens Bioelectron. Oct. 15, 2014;60:130-6. doi: 10.1016/j.bios.2014.04.017. Epub Apr. 18, 2014.
Warden-Rothman et al., Sortase-tag expressed protein ligation: combining protein purification and site-specific bioconjugation into a single step. Anal Chem. Nov. 19, 2013;85(22):11090-7. doi: 10.1021/ac402871k. Epub Oct. 28, 2013.
Wu et al., Sortase-Mediated Transpeptidation for Site-Specific Modification of Peptides, Glycopeptides, and Proteins. J Carbohydr Chem. 2012;31(1):48-66.
U.S. Appl. No. 14/558,537, filed Dec. 2, 2014, Ploegh et al.
U.S. Appl. No. 16/641,203, filed Feb. 21, 2020, Lodish et al.
U.S. Appl. No. 13/145,644, filed Sep. 8, 2011, Ploegh et al.
U.S. Appl. No. 14/588,537, filed Dec. 2, 2014, Ploegh et al.
U.S. Appl. No. 14/127,736, filed May 20, 2014, Ploegh et al.
U.S. Appl. No. 16/140,384, filed Sep. 24, 2019, Ploegh et al.
U.S. Appl. No. 13/918,278, filed Jun. 14, 2013, Ploegh et al.
U.S. Appl. No. 14/890,241, filed Nov. 10, 2015, Lodish et al.
U.S. Appl. No. 15/934,177, filed Mar. 23, 2018, Lodish et al.
U.S. Appl. No. 16/572,425, filed Sep. 16, 2019, Lodish et al.
U.S. Appl. No. 14/890,296, filed Nov. 10, 2015, Ploegh et al.
U.S. Appl. No. 16/277,721, filed Feb. 15, 2019, Swee et al.
U.S. Appl. No. 16/381,654, filed Apr. 11, 2019, Swee et al.
U.S. Appl. No. 15/035,924, filed May 11, 2016, Rashidian et al.
U.S. Appl. No. 14/875,140, filed Nov. 5, 2015, Pasqual et al.
U.S. Appl. No. 16/054,382, filed Aug. 3, 2018, Pasqual et al.
U.S. Appl. No. 15/764,087, filed Mar. 28, 2018, Rashidian et al.
EP 10736161.0, Nov. 30, 2012, Extended European Search Report.
PCT/US2010/000274, Nov. 8, 2010, Invitation to Pay Additional Fees.
PCT/US2010/000274, Dec. 22, 2010, International Search Report and Written Opinion.
PCT/US2010/000274, Aug. 11, 2011, International Preliminary Report on Patentability.
EP 12804570.5, Nov. 26, 2014, Extended European Search Report.
PCT/US2012/044584, Nov. 15, 2012, International Search Report and Written Opinion.
PCT/US2012/044584, Jan. 16, 2014, International Preliminary Report on Patentability.
EP 14795167.7, Nov. 9, 2016, Extended European Search Report.
EP 19171188.6, Jul. 26, 2019, Extended European Search Report.
EP 19171190.2, Jul. 26, 2019, Extended European Search Report.
PCT/US2014/037554, Sep. 5, 2014, Invitation to Pay Additional Fees.
PCT/US2014/037554, Nov. 6, 2014, International Search Report and Written Opinion.
PCT/US2014/037554, Nov. 19, 2015, International Preliminary Report on Patentability.
EP 14795120.6, Oct. 13, 2016, Extended European Search Report.
PCT/US2014/037545, Oct. 27, 2014, International Search Report and Written Opinion.
PCT/US2014/037545, Nov. 19, 2015, International Preliminary Report on Patentability.
PCT/US14/65574, Mar. 20, 2015, Invitation to Pay Additional Fees.
PCT/US14/65574, Jun. 4, 2015, International Search Report and Written Opinion.
EP 16852806.5, Apr. 29, 2019, Extended European Search Report.
PCT/US2016/055074, Dec. 1, 2016, Invitation to Pay Additional Fees.
PCT/US2016/055074, Feb. 6, 2017, International Search Report and Written Opinion.
PCT/US2016/055074, Apr. 12, 2018, International Preliminary Report on Patentability.
Deshayes et al., Cell-penetrating peptides: tools for intracellular delivery of therapeutics. Cell Mol Life Sci. Aug. 2005;62(16):1839-49. doi: 10.1007/s00018-005-5109-0.
Marsden et al., Model systems for membrane fusion. Chem Soc Rev. Mar. 2011;40(3):1572-85. doi: 10.1039/c0cs00115e. Epub Dec. 13, 2010.
Wang et al., Efficient delivery of genome-editing proteins using bioreducible lipid nanoparticles. Proc Natl Acad Sci U S A. Mar. 15, 2016;113(11):2868-73. doi: 10.1073/pnas.1520244113. Epub Feb. 29, 2016.
Extended European Search Report, dated Dec. 15, 2022, in connection with EP 22173120.1.
Fishburn, C.S., The pharmacology of PEGylation: balancing PD with PK to generate novel therapeutics. J Pharm Sci. Oct. 2008;97(10):4167-83. doi: 10.1002/jps.21278.
Kolate et al., PEG—a versatile conjugating ligand for drugs and drug delivery systems. J Control Release. Oct. 28, 2014;192:67-81. doi: 10.1016/j.jconrel.2014.06.046. Epub Jul. 2, 2014.
Leong et al., Adapting pharmacokinetic properties of a humanized anti-interleukin-8 antibody for therapeutic applications using site-specific pegylation. Cytokine. Nov. 7, 2001;16(3):106-19. doi: 10.1006/cyto.2001.0936.
Pepinsky et al., Production of a PEGylated Fab' of the anti-LINGO-1 Li33 antibody and assessment of its biochemical and functional properties in vitro and in a rat model of remyelination. Bioconjug Chem. Feb. 16, 2011;22(2):200-10. doi: 10.1021/bc1002746. Epub Jan. 21, 2011.

\* cited by examiner

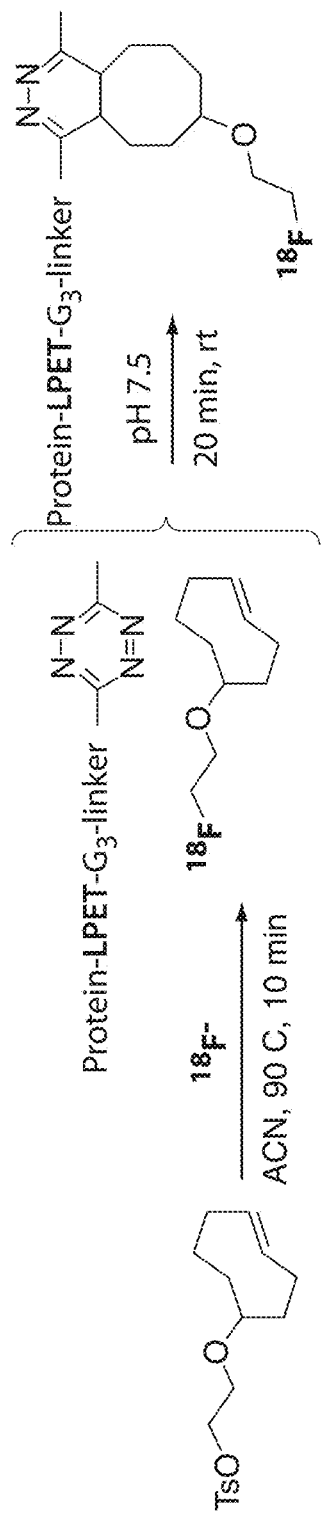
Fig. 4D
Fig. 4E (NOTA)

18F LABELING OF PROTEINS USING SORTASES

RELATED APPLICATIONS

This application is a divisional of application of U.S. patent application U.S. Ser. No. 15/035,924, filed May 11, 2016, which is national stage filing under 35 U.S.C. § 371 of international PCT application, PCT/US2014/065574, filed Nov. 13, 2014, which claims priority under 35 U.S.C. § 119(e) to U.S. Provisional Patent Application, U.S. Ser. No. 61/903,834, filed Nov. 13, 2013, each of which is incorporated herein by reference.

GOVERNMENT SUPPORT

This invention was made with government support under grant numbers AI087879, GM106409, and GM100518 awarded by the National Institutes of Health. The government has certain rights in the invention.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Jun. 1, 2023, is named W057170042US03-SUBSEQ-TNG and is 38,683 bytes in size.

BACKGROUND OF THE INVENTION

Positron emission tomography (PET) is a powerful technology for medical and biological imaging and the scope of PET applications is expanding rapidly. The development of suitable PET tracers is critical to PET technology. An increasing number of PET tracers are peptide/protein based and are useful to specifically label tissues in therapeutic and/or diagnostic applications.

Fluorine-18 ($^{18}$F) is a short-lived isotope of fluorine with suitable properties for PET-imaging. A majority of presently used radiopharmaceuticals in PET are labeled with fluorine-18. However, since the half-life of $^{18}$F isotope is only about 110 minutes, there is currently no facile and general method to efficiently and site-specifically modify proteins with $^{18}$F or other radionuclides in a short time period.

SUMMARY OF THE INVENTION

Aspects of the present disclosure relate to the recognition that efficient and facile means of labeling peptides and proteins for therapeutic and diagnostic applications are needed. In the context of PET or single-photon emission computed tomography (SPECT) diagnostic imaging utilizing peptide or protein-based tracers, quickly generating radiolabeled peptides/proteins is prerequisite to the use of such tracers given the short half-life of commonly used radioisotopes such as $^{18}$F. Surprisingly, as disclosed herein, sortagging (sortase-mediated transpeptidation) of proteins of interest using novel radiolabeled sortase substrates allows for a robust and efficient way of generating radiolabeled proteins, which are site-specifically labeled. Such methodology is useful, e.g., for quickly generating peptide/protein-based PET tracers. Other aspects of the disclosure are based on the knowledge that there exist commercially available radioactive agents used in PET or other imaging modalities, and using such agents as a radiation source for labeling peptides or proteins of interest using sortagging technology can reduce the amount of time involved in preparing radiolabeled peptide/protein tracers and/or reduce the amount of time between the preparation and administration of peptide/protein tracers. However, other sources of radiation (e.g., non-commercially available compounds/reagents) are amenable to use with the methods, compositions, reagents, systems, and kits provided herein.

Accordingly, certain aspects of the invention provide methods for labeling a protein having a sortase recognition motif, with a radiolabel. Typically, the methods comprise contacting the protein with a radiolabeled sortase substrate peptide in the presence of a sortase under conditions suitable for the sortase to transamidate the protein and the sortase substrate peptide. In some embodiments, the method comprises contacting the protein with a sortase substrate peptide in the presence of a sortase under conditions suitable for the sortase to transamidate the protein and the sortase substrate peptide, thereby producing a modified protein, wherein the sortase substrate peptide comprises a click chemistry handle (e.g., tetrazine or trans-cyclooctene); and contacting the modified protein with a radiolabeled agent, wherein the radiolabeled agent comprises a complementary click chemistry handle (e.g., tetrazine or trans-cyclooctene), which reacts with the click chemistry handle of the modified protein, thereby producing a radiolabeled protein. The protein comprises either a C-terminal or N-terminal sortase recognition motif, and the sortase substrate peptide comprises a complementary sortase recognition motif. For example, in some embodiments the protein comprises a C-terminal sortase recognition motif (e.g., LPXTG (SEQ ID NO: 1), where X is any amino acid), and the sortase substrate peptide comprises a complementary N-terminal sortase recognition motif (e.g., GGG). In some embodiments, prior to being conjugated to the protein of interest, the sortase substrate peptide is linked to a radiolabeled agent through use of nucleophile/electrophile pairings, chelation (e.g., NOTA) or click chemistry. In some embodiments, the sortase substrate peptide is linked to the agent via an oxime linkage, a hydrazone linkage, a thiosemicarbazone linkage, an amide linkage, an ester linkage, an ether linkage, a disulfide linkage, a click chemistry linkage, or other suitable linkage. In other embodiments, the sortase substrate peptide is first tethered to a protein of interest using a sortase-mediated transpeptidation reaction and subsequently modified to incorporate the label (e.g., a radiolabel, such as $^{18}$F). For example, a sortase substrate peptide comprising a click-chemistry handle may be conjugated to a protein of interest using a sortase mediated transpeptidation reaction. The protein of interest, containing the click chemistry handle, may subsequently be labeled (e.g., with a radiolabel) using any suitable click chemistry reaction known in the art. In some embodiments, the C-terminal sortase recognition motif is LPXTX or NPXTX, wherein each instance of X independently represents any amino acid residue. For example, in some embodiments, the C-terminal sortase recognition motif is LPETG (SEQ ID NO:2), LPETA (SEQ ID NO:3), NPQTN (SEQ ID NO:4), or NPKTG (SEQ ID NO:5). In some embodiments, the N-terminal recognition motif comprises an oligoglycine or an oligoalanine sequence, for example 1-10 N-terminal glycine residues (e.g., GGG) or 1-10 N-terminal alanine residues (e.g., AAA), respectively. In some embodiments, the sortase substrate peptide comprises the sequence $(G)_{n1}K$ (SEQ ID NO: 129), wherein n1 is an integer between 1 and 10, inclusive. The radiolabeled sortase substrate peptide comprises one or more radionuclide(s) suitable for diagnostic and/or therapeutic applications, such as PET. For example, in some embodiments, the radionuclide is carbon-11, carbon-14, nitrogen-13, oxygen-15, fluorine-18, rubidium-82, copper-61, copper-62, copper-64, yttrium-86, gallium-68, zirconium-89, or iodine-124. In some embodiments, the radiolabeled agent linked to the sortase substrate peptide is a radiolabeled carbohydrate, for example, a sugar such as fludeoxyglucose ($^{18}$F-FDG) or $^{14}$C—(U)-glucose. In some embodiments, the radiolabeled agent linked to the sortase substrate peptide is $^{18}$F, which in some embodiments is sourced or derived from sodium fluoride ($^{18}$F—NaF). $^{18}$F—NaF can be used as a source of $^{18}$F for labeling proteins and sortase substrate peptides using a substitution reaction where one functional group in a chemical compound is replaced by another functional group. In certain embodiments, the sortase used to transamidate the protein and sortase substrate peptide is sortase A, sortase B, sortase C or sortase D. In some embodiments, the sortase used to transamidate the protein and sortase substrate peptide is sortase A from *Staphylococcus aureus* (SrtA$_{aureus}$), sortase A from *Streptococcus pyogenes* (SrtA$_{pyogenes}$), sortase B from *S. aureus* (SrtB$_{aureus}$), sortase B from *Bacillus anthracis* (SrtBf$_{anthracis}$), sortase B from *Listeria monocytogenes* (SrtB$_{monocytogenes}$), sortase C from *Enterococcus faecalis* (SrtC$_{faecalis}$), sortase C from *Streptococcus agalactiae* (SrtC$_{agalactiae}$) sortase C from *Streptococcus pneumonia* (SrtC$_{pneumonia}$), sortase C from *Actinomyces oris* (SrtC$_{oris}$), sortase C from *Streptococcus suis* (SrtC$_{suis}$), or sortase D from *Bacillus cereus* (SrtD$_{cereus}$). In some embodiments, the methods allow for the fast and efficient conjugation of the protein to the sortase substrate peptide. For example, in some embodiments, the protein is conjugated to the sortase substrate peptide in less than 5 minutes, less than 10 minutes, less than 15 minutes, less than 20 minutes, less than 25 minutes, less than 30 minutes, less than 45 minutes, less than 60 minutes, less than 90 minutes, or less than 120 minutes. Further, in some embodiments, at least 50%, at least 60%, at least 75%, at least 90%, at least 95%, or at least 98% of the protein is labeled with the sortase substrate peptide. In some embodiments, the protein to be conjugated with a radiolabeled sortase substrate peptide is a protein suitable for diagnostic and/or therapeutic applications (e.g., PET or SPECT imaging), such as an antibody, an antibody fragment, an affibody, a single-domain antibody, a Fab fragment, or a therapeutic peptide. In some embodiments, the protein binds to a tumor cell, a tumor-associated cell, or a tumor antigen. In other embodiments, the protein binds to an immune cell, such as a T-cell, a B-cell, a plasma cell, a macrophage, a dendritic cell, a neutrophil, an eosinophil, or a mast cell. In some embodiments, the protein binds to a marker of inflammation (e.g., MHC class II molecules, CD3, CD4, CD8, CD11b). In some embodiments, the method further involves purifying the labeled (e.g., conjugated) protein, resulting, in some embodiments, in a composition of the purified protein that comprises at least 10, at least 20, at lease 30, at least 40, at least 50, at least 75, at least 100, at least 150, at least 200, at least 250, at least 300, at least 350, at least 400, at least 450, at least 500, at least 550, at least 600, at least 700, at least 800, at least 900, or at least 1000 MBq of radioactivity.

According to another aspect, compositions suitable for use in the methods, described herein, (e.g., methods for radiolabeling a protein using a sortase) are provided. In some embodiments, the compositions for use in the methods, described herein, include a radiolabeled sortase substrate peptide, a sortase, and a protein comprising a sortase recognition motif. In other embodiments, the compositions for use in the methods, described herein, include a protein that has been site-specifically conjugated to a click chemistry handle, and a radiolabel conjugated to a click chemistry handle. In yet other embodiments the compositions for use in the methods, described herein, include a sortase substrate peptide comprising a click chemistry handle, a sortase, a protein comprising a sortase recognition motif and a radiolabel conjugated to a click chemistry handle. It should be appreciated that the compositions useful for the methods, described herein, (e.g., for site-specifically radiolabeling a protein) may be provided in a kit. In some embodiments, the protein comprises a C-terminal sortase recognition motif (e.g., as described herein), and the sortase substrate peptide comprises an N-terminal recognition motif (e.g., as described herein). The sortase substrate peptide comprises a radionuclide, for example, as part of an agent linked to the peptide, which is suitable for diagnostic and/or therapeutic applications as described herein. In some embodiments, the composition further comprises a sortase as described herein. The protein in the composition is any protein suitable for the diagnostic and/or therapeutic applications described herein (e.g., an antibody, an antibody fragment, an affibody, a single-domain antibody, a Fab fragment, or a therapeutic peptide), for example, those that bind to a tumor cell, a tumor-associated cell, or a tumor antigen.

According to another aspect, compositions comprising radiolabeled proteins are provided. In some embodiments, the radiolabeled protein is generated according to the methods (e.g., methods for radiolabeling proteins using sortases) provided herein. It should be appreciated that the site-specific conjugation of a protein to a peptide or other moiety (e.g., a radiolabeled agent) may be achieved using other enzymes known in the art. For example, formylglycine generating enzyme, phosphopantetheinyltransferases, transglutaminase, farnesyltransferase, biotin ligase, lipoic acid ligase, or N-myristoyl transferase. In some embodiments, the protein is radiolabeled with a radionuclide (e.g., carbon-11, carbon-14, nitrogen-13, oxygen-15, fluorine-18, rubidium-82, copper-61, copper-62, copper-64, yttrium-86, gallium-68, zirconium-89, iodine-124, etc.) suitable for diagnostic and/or therapeutic applications described herein. In some embodiments, the protein is labeled (using a sortase substrate peptide) with a sugar, such as fludeoxyglucose ($^{18}$F-FDG) or $^{14}$C—(U)-glucose. In other embodiments, $^{18}$F sodium fluoride ($^{18}$F—NaF) is used to radiolabel an agent via a substitution reaction that comprises a click chemistry handle having a suitable leaving group. In some embodiments, the radiolabeled click chemistry handle can be used to label a protein having a complementary click chemistry handle that has been site-specifically conjugated to the protein. In some embodiments, the protein is any protein suitable for the diagnostic and/or therapeutic applications described herein (e.g., an antibody, antibody fragment, an affibody, a single-domain antibody, a Fab fragment, or a therapeutic peptide), for example, those that bind to a tumor cell, a tumor-associated cell, a tumor antigen, or a marker of inflammation. In some embodiments, the composition comprises at least 10, at least 20, at lease 30, at least 40, at least 50, at least 75, at least 100, at least 150, at least 200, at least 250, at least 300, at least 350, at least 400, at least 450, at least 500, at least 550, at least 600, at least 700, at least 800, at least 900, or at least 1000 MBq of radioactivity. In some embodiments, the composition is suitable for administration to a subject (e.g., a subject undergoing diagnostic and/or therapeutic procedure(s) described herein), and further comprises a pharmaceutically acceptable carrier. In some embodiments, the compositions suitable for administration to a subject (e.g., site-specifically radiolabeled proteins), described herein, are substantially pure. In some embodiments the compositions are at least 75%, at least 80%, at least 85%, at least 90%, at least 92%, at least 94%, at least 96%, at least 98%, at least 99%, or at least 99.5% pure. In yet other embodiments the compositions, suitable for administration to a subject, as described herein, are at least 90% pure.

According to yet another aspect, methods for modifying a sortase substrate peptide are provided. Such methods are useful for generating radiolabeled sortase substrate peptides which are suitable for use in the methods described herein (e.g., methods for labeling a protein with a radiolabeled sortase substrate peptide). Typically, the method comprises contacting a sortase substrate peptide that comprises a nucleophilic group (e.g., an aminooxy group, a hydrazide, thiosemicarbazide, or click chemistry handle, e.g., transcyclooctene) with a radiolabeled agent that comprises an electrophilic group (e.g., a carbonyl-containing functional group or click chemistry handle, e.g., tetrazine) under conditions suitable for the formation of a covalent bond between the sortase substrate peptide and agent. In some embodiments, the agent comprises a radionuclide (e.g., carbon-11, carbon-14, nitrogen-13, oxygen-15, fluorine-18, rubidium-82, copper-61, copper-62, copper-64, yttrium-86, gallium-68, zirconium-89, iodine-124, etc.) suitable for a diagnostic and/or therapeutic application described herein. In some embodiments, the agent is a sugar, such as fludeoxyglucose ($^{18}$F-FDG) or $^{14}$C—(U)-glucose. In other embodiments, the agent comprises $^{18}$F (e.g., sourced from $^{18}$F sodium fluoride ($^{18}$F—NaF). In some embodiments, the sortase substrate peptide comprises an N-terminal sortase recognition motif, e.g., an oligoglycine or an oligoalanine sequence, for example 1-10 N-terminal glycine residues (e.g., GGG) or 1-10 N-terminal alanine residues (e.g., AAA), respectively. In some embodiments, the sortase substrate peptide comprises the sequence $(G)_{n1}K$ (SEQ ID NO: 129), wherein n1 is an integer between 1 and 10, inclusive. In some embodiments, the K is modified to include a nucleophilic group (e.g., an aminooxy group). In some embodiments, the methods allow for the fast and efficient modification of a sortase substrate peptide, thus in some embodiments, the method further comprises contacting the sortase substrate peptide and/or agent with a catalyst. In some embodiments, the catalyst is m-phenylenediamine (mPDA), o-phenylenediamine, p-phenylenediamine, o-aminophenol, m-aminophenol, p-aminophenol, o-aminobenzoic acid, 5-methoxyanthranilic acid, 3,5-diaminobenzoic acid, or aniline. In some embodiments, the sortase substrate peptide is modified in less than 5 minutes, less than 10 minutes, less than 15 minutes, less than 20 minutes, less than 25 minutes, less than 30 minutes, less than 45 minutes, less than 60 minutes, less than 90 minutes, or less than 120 minutes. Further, in some embodiments, at least 50%, at least 60%, at least 75%, at least 90%, at least 95%, or at least 98% of the sortase substrate peptide is covalently linked to the agent.

According to another aspect, sortase substrate peptides linked to a radiolabeled agent are provided. In some embodiments, the sortase substrate peptide is generated according to methods provided herein. In some embodiments, the sortase substrate peptide and agent are linked by an oxime, a hydrazone, a thiosemicarbazone, or a click chemistry linkage. In some embodiments, the radiolabeled agent comprises a radionuclide (e.g., carbon-11, carbon-14, nitrogen-13, oxygen-15, fluorine-18, rubidium-82, copper-61, copper-62, copper-64, yttrium-86, gallium-68, zirconium-89, iodine-124) suitable for the diagnostic and/or therapeutic applications described herein. In some embodiments, the agent is a sugar, such as fludeoxyglucose ($^{18}$F-FDG) or $^{14}$C—(U)-glucose. In some embodiments, the sortase substrate peptide comprises an N-terminal sortase recognition motif, e.g., an oligoglycine or an oligoalanine sequence, for example, 1-10 N-terminal glycine residues (e.g., GGG) or 1-10 N-terminal alanine residues (e.g., AAA), respectively. In some embodiments, the sortase substrate peptide comprises the sequence $(G)_{n1}K$ (SEQ ID NO: 129), wherein n1 is an integer between 1 and 10, inclusive.

In yet another aspect, compositions comprising a sortase substrate peptide, a radiolabeled agent, and a catalyst are provided. Such compositions are useful for generating radiolabeled sortase substrate peptides according to the methods provided herein. In some embodiments, the sortase substrate peptide comprises an N-terminal sortase recognition motif, e.g., an oligoglycine or an oligoalanine sequence, for example, 1-10 N-terminal glycine residues (e.g., GGG) or 1-10 N-terminal alanine residues (e.g., AAA), respectively. In some embodiments, the sortase substrate peptide comprises the sequence $(G)_{n1}K$ (SEQ ID NO: 129), wherein n1 is an integer between 1 and 10, inclusive. In some embodiments, the K is modified to include a nucleophilic group (e.g., an aminooxy group). In some embodiments, the radiolabeled agent comprises a radionuclide (e.g., carbon-11, carbon-14, nitrogen-13, oxygen-15, fluorine-18, rubidium-82, copper-61, copper-62, copper-64, yttrium-86, gallium-68, zirconium-89, iodine-124, etc.) suitable for the diagnostic and/or therapeutic applications described herein. In some embodiments, the agent is a sugar, such as fludeoxyglucose ($^{18}$F-FDG) or $^{14}$C—(U)-glucose. In some embodiments, the catalyst is m-phenylenediamine (mPDA), o-phenylenediamine, p-phenylenediamine, o-aminophenol, m-aminophenol, p-aminophenol, o-aminobenzoic acid, 5-methoxyanthranilic acid, 3,5-diaminobenzoic acid, or aniline.

According to another aspect, methods of diagnosing, monitoring, and/or treating a subject using the inventive compositions are provided. Typically, the method comprises: (a) administering an inventive composition (e.g., a radiolabeled protein generated according to the methods provided herein) to the subject; and (b) detecting the radiolabel in the subject. In some embodiments, the subject has, has had, or is suspected of having cancer. In some embodiments, the subject has, has had, or is suspected of having a proliferative disease. In some embodiments, the subject has, has had, or is suspected of having an inflammatory disease or disorder. In some embodiments, detecting the radiolabel is performed using positron emission tomography (PET) or single-photon emission computed tomography (SPECT).

In another aspect, kits are provided. For example, kits useful for carrying out any of the inventive methods or for generating any of the inventive compositions are provided. In some embodiments, a kit for modifying a sortase substrate peptide comprising a sortase substrate peptide (e.g., a sortase substrate peptide comprising a nucleophilic group such as a click chemistry handle, an aminooxy group, a hydrazide, or thiosemicarbazide) a modifying agent (e.g., a radioactive agent that comprises an electrophilic group such as an click chemistry handle or a carbonyl-containing group (e.g., $^{18}$F-FDG or $^{14}$C—(U)-glucose)) and a catalyst (e.g., m-phenylenediamine (mPDA), o-phenylenediamine, p-phenylenediamine, o-aminophenol, m-aminophenol, p-aminophenol, o-aminobenzoic acid, aniline, etc.), are provided. In some embodiments, a kit (e.g., for labeling a protein) is provided that comprises a radiolabeled sortase substrate peptide, e.g., generated according to the inventive methods described herein. In some embodiments, the kit comprises a sortase, such as sortase A, sortase B, sortase C, or sortase D.

Some non-limiting examples of sortases that may be used are sortase A from *Staphylococcus aureus* (Srt$_{Aaureus}$), sortase A from *Streptococcus pyogenes* (SrtA$_{pyogenes}$), sortase B from *Staphylococcus aureus* (SrtB$_{aureus}$), sortase B from *Bacillus anthracis* (SrtB$_{anthracis}$), sortase B from *Listeria monocytogenes* (SrtB$_{monocytogenes}$), sortase C from *Enterococcus faecalis* (SrtCf$_{aecalis}$), sortase C from *Streptococcus agalactiae* (SrtC$_{agalactiae}$) sortase C from *Streptococcus pneumonia* (SrtC$_{pneumonia}$), sortase C from *Actinomyces oris* (SrtC$_{oris}$), sortase C from *Streptococcus suis* (SrtC$_{suis}$), or sortase D from *Bacillus cereus* (SrtD$_{cereus}$). In some embodiments, a kit is provided that comprises a radiolabeled protein (e.g., an antibody, an antibody fragment, an affibody, a single-domain antibody, a Fab fragment, or a therapeutic peptide) generated according to the inventive methods described herein.

The above summary is intended to provide an overview of some aspects of this invention and is not to be construed to limit the invention in any way. Additional aspects, advantages, and embodiments of this invention are described herein, and further embodiments will be apparent to those of skill in the art based on the instant disclosure. The entire contents of all references cited herein are incorporated by reference.

BRIEF DESCRIPTION OF THE DRAWINGS

(FIG. 1B) Schematic representation of the strategy to produce glucose-labeled protein using sortagging technology. From left to right, the sequences are SEQ ID NOs: 92 and 125. First the sortase substrate peptide (1) is labeled via oxime ligation with glucose using m-Phenylenediamine (mPDA) as the catalyst. Next, the product (2) is added to the sortagging reaction mixture which contains sortase and VHH4. The enzyme and non-sortagged protein is separated from the sortagged protein by incubating the solution with Ni-NTA beads. The product is analyzed by LC-MS analysis. (FIG. 1C) LC-MS analysis of the starting protein, VHH4-LPETGGHis6 (SEQ ID NO: 92). (FIG. 1D) LC-MS analysis of the glucose-labeled protein, VHH4-LPET-peptide 2 (SEQ ID NO: 69).

FIG. 2A shows SEQ ID NOs: 92 and 125 from left to right. (FIG. 2B) LC-MS analysis of the starting protein, VHH4-LPETGGHis6 (SEQ ID NO: 92). (FIG. 2C) LC-MS analysis of the labeled protein, VHH4-LPET-peptide-FDG (SEQ ID NO: 125).

(FIGS. 3A and 3B) Schematic representation of the reactions. FIG. 3B shows SEQ ID NOs: 92 and 125 from left to right. (FIG. 3C) SDS-PAGE analysis of the labeling reaction. The band correlating with $^{14}$C-radiolabeled VHH4 is indicated.

FIGS. 4A-4H show a schematic representation of the strategy for site-specific labeling of proteins with $^{18}$F using sortagging and the tetrazine (Tz)/trans-cyclooctene (TCO) reverse-electron demand Diels-Alder cycloaddition reaction. (FIG. 4A) A protein equipped at its C-terminus with the LPXTG (SEQ ID NO: 1) sortase-recognition motif, followed by a tag (e.g., 6×His (SEQ ID NO: 133)) is incubated with sortase A, which cleaves the threonine-glycine bond and via its active site cysteine residue forms a reactive acyl intermediate. Addition of a peptide comprising a series of N-terminal glycine residues (e.g., three (3) glycines) and a functional moiety of choice results in site-specific modification of the protein. FIG. 4A shows SEQ ID NOs: 1 and 105 from left to right. (FIG. 4B) A protein equipped with a sortase recognition motif is modified with a (Gly)$_3$-R, e.g., where R is a tetrazine (Tz) derivative. From left to right, FIG. 4B shows SEQ ID NOs: 92 and 125. (FIG. 4C) The formation of site-specifically modified protein is confirmed by LC-MS: shown here for VHH7-Tz, a single domain antibody specific for murine Class II MHC molecules, as an example. (FIG. 4D) Tosyl-trans-cyclooctene (TCO) and $^{18}$F—NaF are used to produce $^{18}$F-TCO and purified by HPLC. $^{18}$F-TCO is added to the Tz-modified VHH, and the reaction is allowed to proceed for ~20 min. The $^{18}$F-labeled VHH is quickly separated from free label by desalting on a PD-10 column pre-equilibrated with PBS, yielding a radio-labeled protein solution ready for injection. FIG. 4D shows SEQ ID NO: 125. (FIG. 4E) The sortase reaction was used to install a high affinity copper chelating, 1,4,7-triazacyclo-nonane-triacetic acid (NOTA), molecule at the C-terminus of a VHH protein followed by addition of $^{64}$Cu$^{2+}$ to produce $^{64}$Cu-VHH. From left to right, FIG. 4E shows SEQ ID NOs: 1, 105 and 105. (FIG. 4F) The NOTA-labeled VHH was confirmed by LC-MS. (FIG. 4G) Radio-TLC analysis of 18F-VHHs. Radio-TLC analysis of labeled VHHs was performed after size-exclusion chromatography demonstrating >98% radiochemical purity of all labeled VHHs. (FIG. 4H) Radio-TLC analysis of 64Cu-VHHs. Radio-TLC analysis of labeled VHHs was performed after size-exclusion chromatography demonstrating >98% radiochemical purity of all labeled VHHs.

(FIG. 5A) PET images of C57BL/6 (right) and Class II MHC$^{-/-}$ (left) mice 2 hours post-injection of $^{18}$F-VHH7. (FIG. 5B) PET-CT 3D-rendering of C57BL/6 mouse 2 hours post-injection of $^{18}$F-VHH7. Accumulation of $^{18}$F-VHH7 is shown in lymph nodes (bilaterally symmetrical; numbers 1, 2, 4 and 5) and thymus (3), superimposed on ribcage, along the body axis.

(FIG. 6A) PET-derived standardized uptake values (SUVs) for different tissues for a C57BL/6 mouse 2.5 hours post-injection. (FIG. 6B) Biodistribution of $^{18}$F-VHH7 in C57BL/6 and MHC-II$^{-/-}$ mice 2.5 hours post-injection. (FIG. 6C) Blood half-life measurement in the C57BL/6 mouse. Percent of injected dose per gram of blood (% ID/g) was measured at different times using decay-corrected intensities of collected bloods. (FIG. 6D) Data was fit to a two-compartment model (bi-exponential non-linear regression) to give a weighted blood half-life of 6.0 min.

(FIGS. 7A, 7B and 7C) Coronal PET-CT images, moving anterior to posterior. In (FIG. 7A) and (FIG. 7B), different sets of bilaterally symmetrically disposed lymph nodes are visible. In (FIG. 7C), tumor-associated Class II MHC positive cells are visible, attributable to influx of host-derived Class II MHC positive cells. (FIG. 7D) PET-CT as maximum intensity projections of all slices. (FIG. 7E & FIG. 7F) $^{18}$F-VHH7 detects Class II MHC$^+$ cells associated with small tumors at early stages. NOD-SCID mice were inoculated with Mel-Juso cells as in (FIG. 7A), 20 (FIG. 7E) and 6 (FIG. 7F) days prior to imaging. Transverse PET and CT images (left and right, respectively) are shown for better visualization of the Class II MHC$^+$ cells at the site of cancer cells. Images are all window-leveled to the same intensity. Tumors and associated Class II MHC$^+$ cells are highlighted with arrows. Axillary (A), brachial (B) and mediastinal (M) lymph nodes and thymus (T) are shown in (FIG. 7F). (G&H) A NOD-SCID mouse was inoculated subcutaneously on the back of the neck with 5×10$^6$ human Mel-Juso melanoma cells and imaged 30 days post injection with $^{18}$F-VHHDC13. Tumor-associated CD11b positive cells are visible, attributable to influx of host-derived CD11b positive cells. (FIG. 7I & FIG. 7J) FACS analysis of tumor-infiltrating immune cells. The next day following the imaging, tumors were excised and digested with collagenase D, and tumor-infiltrating cells were obtained after Percoll gradient. Cell suspensions were then stained for FACS analysis. (FIG. 7I) Histograms show the FACS staining with the VHH7 of mouse CD45$^+$ tumor-infiltrating cells. Histograms on the left are gated on CD11c$^+$CD11b$^+$ cells (dendritic cells) and histograms on the right are gated on CD11c$^-$CD11b$^+$ cells (macrophages and other myeloid cells) for the indicated time points. (FIG. 7J) Tumor-infiltrating cells were harvested 30 days after tumor inoculation as in (FIG. 7I) and stained with VHHDC13. Histograms show the levels of CD11b as measured by VHHDC13 on the indicated cell populations. Spleen from the same mouse is shown for comparison. For left panel (spleen): gray, red and black represent CD11b$^-$, CD11b$^+$CD11c$^+$ and CD11b$^+$CD11c$^-$, respectively. For the right panel (tumor): the left is CD45–CD11b– and the peak on the right is CD45$^+$CD11b$^+$. Experiments are representative of two mice for each time point and FACS staining.

(FIGS. 8A, 8B and 8C) PET images of C57BL/6 mouse 4 h, 8 h, and 24 h post-injection of $^{18}$F-VHH7, respectively, demonstrating specificity for Class II MHC organs. FIG. 8E) PET image of C57BL/6 mouse 4 h post-injection of $^{18}$F-VHHDC13, demonstrating specificity for myeloid cells. (FIGS. 8D and 8F) Complete Freund's adjuvant (CFA) was injected to the left paw of C57BL/6 mice and $^{64}$Cu-VHH7 (for FIG. 8D) or $^{64}$Cu-VHHDC13 (for FIG. 8F) was used to image inflammation 24 h after CFA injection. Images were obtained 4 h post injection of $^{64}$Cu-VHHs; inflammation around the injection site is clearly visible, attributable to influx of host-derived Class II$^+$ or myeloid cells for (FIG. 8D) and (FIG. 8F), respectively (arrows). Images are all window-leveled to the same intensity for better comparison.

(FIGS. 9A and 9B) Complete Freund's adjuvant (CFA) was injected to the left paw of C57BL/6 mice and 18F-VHHDC13 (for FIG. 9A) or 18F-VHH7 (for FIG. 9B) was used to image their targets 24 h after CFA injection. PET-CT Images were obtained 1.5 h post injection of 18F-VHHs; Images are all window-leveled to the same intensity for comparison.

(FIG. 10A) $^{18}$FDG is added to a solution of tetrazine-aminooxy and a catalyst, p-phenylenediamine, to produce $^{18}$F-FDG oxime-tetrazine. (FIG. 10B) Excess tetrazine-aminooxy can be captured by adding the highly water soluble sugar, glucosamine 6-sulfate. The $^{18}$F-FDG oxime-tetrazine can then be purified from the rest of the reaction mixture due to the change in hydrophilicity. (FIG. 10C) First, (1) A single domain antibody fragment (VHH) equipped at its C-terminus with the LPXTG (SEQ ID NO: 1) sortase recognition motif is linked to a (glycine)$_3$-TCO using a sortase to generate a VHH having the TCO click chemistry handle. Second, (2) the $^{18}$F-FDG oxime-tetrazine generated in (FIG. 10B) is added to the VHH that has been sortagged to TCO to create an $^{18}$F-labeled VHH. From top to bottom and left to right, FIG. 10C shows SEQ ID NOs: 1, 105, and 105.

(FIG. 12A) A VHH having a sortase recognition sequence (LPXTG (SEQ ID NO: 1)) is contacted with a sortase substrate peptide having three glycines (G)$_3$ conjugated to a tetrazine derivative in the presence of sortase to produce a VHH having a site-specific tetrazine click-chemistry handle. From left to right, FIG. 12A shows SEQ ID NOs: 1 and 105. (FIG. 12B) Tosyl-trans-cyclooctene (TCO) and $^{18}$F—NaF are used to produce $^{18}$F-TCO and purified by HPLC. (FIG. 12C) The VHH having a site-specific tetrazine click-chemistry handle is reacted to the $^{18}$F-TCO to generate a VHH that is site-specifically labeled with 18F. FIG. 12C shows SEQ ID NO: 105. (FIG. 12D) The formation of site-specifically 18Fmodified VHH is confirmed by LC-MS. (FIG. 12E) The sortase reaction was used to install a high affinity copper chelating, 1,4,7-triazacyclononane-triacetic acid (NOTA), molecule at the C-terminus of a VHH protein followed by addition of $^{64}$Cu$^{2+}$ to produce VHH-$^{64}$Cu. The $^{64}$Cu in this figure may be replaced with $^{68}$Ga. From left to right, FIG. 12E shows SEQ ID NOs: 1, 105, and 105.

DEFINITIONS

Figure 1A:
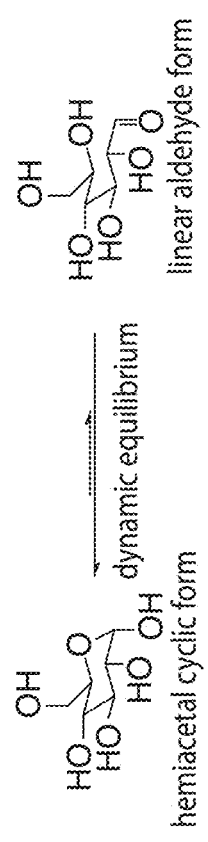
FIGS. 1A-1D show the dynamic equilibrium between cyclic hemiacetal and linear aldehyde forms of glucose (FIG. 1A) the modification of a sortase substrate peptide (FIG. 1B), and identification of sortagged protein (VHH4) using the modified substrate (FIGS. 1C-1D).

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, IN 1972). The invention additionally encompasses compounds as individual isomers substantially free of other isomers, and alternatively, as mixtures of various isomers.

In a formula, --- is absent, a coordination bond between a ligand and a metal, or a single bond.

When a range of values is listed, it is intended to encompass each value and subrange within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_4$ 5, and $C_{5-6}$ alkyl.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms ($C_{1-20}$ aliphatic). In certain embodiments, the aliphatic group has 1-10 carbon atoms ($C_{1-10}$ aliphatic). In certain embodiments, the aliphatic group has 1-6 carbon atoms ($C_{1-6}$ aliphatic). In certain embodiments, the aliphatic group has 1-5 carbon atoms ($C_{1-5}$ aliphatic). In certain embodiments, the aliphatic group has 1-4 carbon atoms ($C_{1-4}$ aliphatic). In certain embodiments, the aliphatic group has 1-3 carbon atoms ($C_{1-3}$ aliphatic). In certain embodiments, the aliphatic group has 1-2 carbon atoms ($C_{1-2}$ aliphatic). Aliphatic group substituents include, but are not limited to, any of the substituents described herein, that result in the formation of a stable moiety.

The term "heteroaliphatic", as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms ($C_{1-20}$alkyl). In another embodiment, the alkyl group employed contains 1-15 carbon atoms ($C_{1-15}$alkyl). In another embodiment, the alkyl group employed contains 1-10 carbon atoms ($C_{1-10}$alkyl). In another embodiment, the alkyl group employed contains 1-8 carbon atoms ($C_{1-8}$alkyl). In another embodiment, the alkyl group employed contains 1-6 carbon atoms ($C_{1-6}$alkyl). In another embodiment, the alkyl group employed contains 1-5 carbon atoms ($C_{1-5}$alkyl). In another embodiment, the alkyl group employed contains 1-4 carbon atoms ($C_{1-4}$alkyl). In another embodiment, the alkyl group employed contains 1-3 carbon atoms ($C_{1-3}$alkyl). In another embodiment, the alkyl group employed contains 1-2 carbon atoms ($C_{1-2}$alkyl). Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents. Alkyl group substituents include, but are not limited to, any of the substituents described herein, that result in the formation of a stable moiety. The term "alkylene," as used herein, refers to a biradical derived from an alkyl group, as defined herein, by removal of two hydrogen atoms. Alkylene groups may be cyclic or acyclic, branched or unbranched, substituted or unsubstituted. Alkylene group substituents include, but are not limited to, any of the substituents described herein, that result in the formation of a stable moiety.

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms ($C_{2-20}$alkenyl). In some embodiments, the alkenyl group employed in the invention contains 2-15 carbon atoms ($C_{2-15}$alkenyl). In another embodiment, the alkenyl group employed contains 2-10 carbon atoms ($C_{2-10}$alkenyl). In still other embodiments, the alkenyl group contains 2-8 carbon atoms ($C_{2-8}$alkenyl). In yet other embodiments, the alkenyl group contains 2-6 carbons ($C_{2-6}$alkenyl). In yet other embodiments, the alkenyl group contains 2-5 carbons ($C_{2-5}$alkenyl). In yet other embodiments, the alkenyl group contains 2-4 carbons ($C_{2-4}$alkenyl). In yet other embodiments, the alkenyl group contains 2-3 carbons ($C_{2-3}$alkenyl). In yet other embodiments, the alkenyl group contains 2 carbons ($C_2$alkenyl). Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety. The term "alkenylene," as used herein, refers to a biradical derived from an alkenyl group, as defined herein, by removal of two hydrogen atoms. Alkenylene groups may be cyclic or acyclic, branched or unbranched, substituted or unsubstituted. Alkenylene group substituents include, but are not limited to, any of the substituents described herein, that result in the formation of a stable moiety.

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms ($C_{2-20}$alkynyl). In some embodiments, the alkynyl group employed in the invention contains 2-15 carbon atoms ($C_{2-15}$alkynyl). In another embodiment, the alkynyl group employed contains 2-10 carbon atoms ($C_{2-10}$alkynyl). In still other embodiments, the alkynyl group contains 2-8 carbon atoms ($C_{2-8}$alkynyl). In still other embodiments, the alkynyl group contains 2-6 carbon atoms ($C_{2-6}$alkynyl). In still other embodiments, the alkynyl group contains 2-5 carbon atoms ($C_{2-5}$alkynyl). In still other embodiments, the alkynyl group contains 2-4 carbon atoms ($C_{2-4}$alkynyl). In still other embodiments, the alkynyl group contains 2-3 carbon atoms ($C_{2-3}$alkynyl). In still other embodiments, the alkynyl group contains 2 carbon atoms ($C_2$alkynyl). Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety. The term "alkynylene," as used herein, refers to a biradical derived from an alkynylene group, as defined herein, by removal of two hydrogen atoms. Alkynylene groups may be cyclic or acyclic, branched or unbranched, substituted or unsubstituted. Alkynylene group substituents include, but are not limited to, any of the substituents described herein, that result in the formation of a stable moiety.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" is a monocyclic, saturated carbocyclyl group having from 3 to 14 ring carbon atoms ("C$_{3-14}$ cycloalkyl"). In some embodiments, a cycloalkyl group has 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-14}$ cycloalkyl. In certain embodiments, the cycloalkyl group is a substituted C$_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

The term "unsaturated" or "partially unsaturated" refers to a moiety that includes at least one double or triple bond.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

The term "halo" or "halogen" refers to fluorine (fluoro, —F), chlorine (chloro, —Cl), bromine (bromo, —Br), or iodine (iodo, —I).

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH($R^{bb}$), —NHC(=O)$R^{aa}$, —NHCO$_2R^{aa}$, —NHC(=O)N($R^{bb}$)$_2$, —NHC(=N$R^{bb}$)N($R^{bb}$)$_2$, —NHSO$_2R^{aa}$, —NHP(=O)(O$R^{cc}$)$_2$, and —NHP(=O)(N$R^{bb}$)$_2$, wherein $R^{aa}$, $R^{bb}$ and $R^{cc}$ are as defined herein, and wherein $R^{bb}$ of the group —NH($R^{bb}$) is not hydrogen.

The term "disubstituted amino" refers to an amino group wherein the nitrogen atom directly attached to the parent molecule is substituted with two groups other than hydrogen, and includes groups selected from —N($R^{bb}$)$_2$, —N$R^{bb}$C(=O)$R^{aa}$, —N$R^{bb}$CO$_2R^{aa}$, —N$R^{bb}$C(=O)N($R^{bb}$)$_2$, —N$R^{bb}$C(=N$R^{bb}$)N($R^{bb}$)$_2$, —N$R^{bb}$SO$_2R^{aa}$, —N$R^{bb}$P(=O)(O$R^{cc}$)$_2$, and —N$R^{bb}$P(=O)(N$R^{bb}$)$_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N($R^{bb}$)$_3$ and —N($R^{bb}$)$_3^+X^-$, wherein $R^{bb}$ and $X^-$ are as defined herein.

In certain embodiments, the substituent present on the nitrogen atom is an nitrogen protecting group (also referred to herein as an "amino protecting group"). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2R^{aa}$, —SO$_2R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(═O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(═O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(═O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{cc}$, —P(=O)(R$^{aa}$)$_2$, —P(=O)(OR$_{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is a sulfur protecting group (also referred to as a "thiol protecting group"). Sulfur protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$_{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

The terms "aminooxy," or "aminooxy group," are used interchangeably herein and refer to functional groups having the general formula:

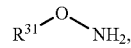

wherein R$^{31}$ is optionally substituted aliphatic, optionally substituted heteroaliphatic, optionally substituted aryl, optionally substituted heteroaryl, or optionally substituted heterocyclyl. In some embodiments, R$^{31}$ is an amino acid, wherein the point of attachment for the oxygen is on the side chain of the amino acid. In certain embodiments, the amino acid is within a polypeptide.

The term "tautomers" or "tautomeric" refers to two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The terms "carbonyl," or "carbonyl group," are used interchangeably herein and refer to functional groups composed of a carbon atom double-bonded to any oxygen atom. Carbonyls have the general formula:

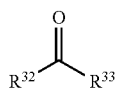

wherein each of $R^{32}$ and $R^{33}$ independently represents hydroxyl, optionally substituted amino, optionally substituted aliphatic, optionally substituted heteroaliphatic, optionally substituted aryl, optionally substituted heteroaryl, or optionally substituted heterocyclyl. Examples of carbonyls include, but are not limited to, aldehydes, ketones, carboxylic acids, esters, amides, enones, acyl halides, acid anhydrides, and imides. In some embodiments, a carbonyl-containing compound refers to a compound having an aldehyde group, or a compound capable of forming an aldehyde group through isomerization. For example, in some embodiments, certain sugars (e.g., reducing sugars) such as glucose, form aldehydes through isomerization. A sugar is classified as a reducing sugar if it has an open-chain form with an aldehyde group or a free hemiacetal group. Monosaccharides which contain an aldehyde group are known as aldoses, and those with a ketone group are known as ketoses. The aldehyde can be oxidized via a redox reaction in which another compound is reduced. Thus, a reducing sugar is one that is capable of reducing certain chemicals. Sugars with ketone groups in their open chain form are capable of isomerizing via a series of tautomeric shifts to produce an aldehyde group in solution. Therefore, ketone-bearing sugars like fructose are considered reducing sugars but it is the isomer containing an aldehyde group which is reducing since ketones cannot be oxidized without decomposition of the sugar. This type of isomerization is catalyzed by the base present in solutions which test for the presence of aldehydes.

The term "hydrazide," as used herein, refers to functional groups having the general formula:

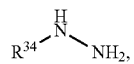

wherein $R^{34}$ is optionally substituted aliphatic, optionally substituted heteroaliphatic, optionally substituted aryl, optionally substituted heteroaryl, or optionally substituted heterocyclyl. In some embodiments, $R^{34}$ is an amino acid, wherein the point of attachment for the oxygen is on the side chain of the amino acid. In certain embodiments, the amino acid is within a polypeptide.

The term "hydrazone," as used herein, refers to compound having the general formula:

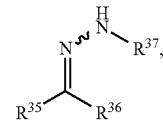

wherein each of $R^{35}$, $R^{36}$, and $R^{37}$ is independently optionally substituted aliphatic, optionally substituted heteroaliphatic, optionally substituted aryl, optionally substituted heteroaryl, or optionally substituted heterocyclyl. The term "hydrazone linkage," as used herein, refers to the formula:

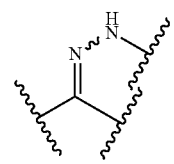

Hydrazones can be prepared from, for example, joining of a compound comprising a hydrazide group and a compound comprising a carbonyl.

The term "acyl," as used herein, is a subset of a substituted alkyl group, and refers to a group having the general formula —C(=O)$R^4$, —C(=O)O$R^4$, —C(=O)—O—C(=O)RA, —C(=O)S$R^4$, or —C(=O)N($R^4$)$_2$, wherein each instance of $R^4$ is independently hydrogen, optionally substituted aliphatic, optionally substituted heteroaliphatic, optionally substituted aryl, optionally substituted heteroaryl, or optionally substituted heterocyclyl. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety.

The term "azide" or "azido," as used herein, refers to a group of the formula (—N$_3$).

The term "agent," as used herein, refers to any molecule, entity, or moiety that can be conjugated to a sortase recognition motif, a sortase substrate peptide, or any other enzymatic recognition motif or enzymatic substrate peptide known in the art. For example, an agent may be a protein, an amino acid, a peptide, a polynucleotide, a carbohydrate, a detectable label, a tag, a metal atom, a contrast agent, a non-polypeptide polymer, a synthetic polymer, a recognition element, a lipid, or chemical compound, such as a small molecule. In some embodiments, the agent is radioactive or comprises a radiolabel. In some embodiments, the agent is enriched for a particular isotope of an element. In some embodiments, the agent comprises a radionuclide (e.g., a radioactive atom) or isotope selected from the group consisting of carbon-11, carbon-14, nitrogen-13, oxygen-15, fluorine-18, rubidium-82, copper-61, copper-62, copper-64, yttrium-86, gallium-68, zirconium-89, and iodine-124. The agent may connected to a radionuclide by a carbon bond, for example, an $^{18}$F may be linked to the agent by a C-$^{18}$F bond. In some embodiments, the agent is a carbonyl- (e.g., an aldehyde- or ketone-) containing group that comprises a radionuclide. In some embodiments, the agent is fludeoxyglucose ($^{18}$F-FDG). In other embodiments, the agent is an alkene (e.g., a TCO) that comprises a radionuclide, such as $^{18}$F. Radiolabeling of tosyl-trans-cyclooctene (TCO) with $^{18}$F can be achieved with [$^{18}$F]—F/K222/K$_2$CO$_3$ in DMSO for approximately 10 minutes at 90° C. to produce 18F-TCO (Keliher, E. J. et al. "Two-Step 18F Labeling Strategy for 18F-PARP1 Inhibitors.", *ChemMedChem* 6, 424-427, 2011) and purified by HPLC. In some embodiments, the agent is $^{14}$C—(U)-glucose. In some embodiments, the agent cannot be genetically encoded. In some such embodiments, the agent is a lipid, an amino acid, a nucleotide, a carbohydrate, or a small molecule. For example, in some embodiments, the agent is a radioactive carbohydrate, which in addition to FDG and $^{14}$C—(U)-glucose, includes, but is not limited to, 2-deoxy-2-fluoro-D-mannose [$^{18}$F]; 6-deoxy-6-fluoro-D-fructose [$^{18}$F]; citric acid [1,5-$^{14}$C]; deoxy-D-glucose, 2-[1-$^{14}$C], galactose 1-phosphate D-[$^{14}$C(U)]; galactose, D-[1-$^{14}$C]; glucosamine hydrochloride D-[6-$^3$H(N)]; glucosamine, N-acetyl-D-[1-$^{14}$C]; glucose 1-phosphate, α-D-[$^{14}$C(U)]; glucose, 3-O-[methyl-D-1-$^3$H]; glucose, D-[6-$^{14}$C]; glucose, L-[1-$^{14}$C]; glycerol, [$^{14}$C(U)]; inositol, Myo-[2-$^3$H(N)]; inulin-carboxyl, [carboxyl-$^{14}$C]; inulin-methoxy, [methoxy-$^3$H]; lactose, [D-glucose-1-$^{14}$C]; mannitol, D-[1-$^{14}$C]; mannose, D-[2-$^3$H(N)]; methyl α-D-glucopyranoside, [glucose-$^{14}$C(U)]; methyl-D-glucose, 3-0-[methyl-$^{14}$C]; myo-inositol, [3H]; starch, [$^{14}$C(U)]; uridine diphospho-D-glucose, [6-$^3$H]; and xylose, D-[U-$^{14}$C]. The particular isotope used to label any of the foregoing radioactive carbohydrates can be substituted with any other isotope described herein. In some embodiments, the radioactive agent is a small molecule or compound, which include, but is not limited to, acetic acid, -[1-$^{14}$C]; benzylamine HCL, [7-$^{14}$C]; biotin, [8,9-$^3$H(N)]-(VitaminH); choline chloride, [methyl-$^{14}$C]; D-(+) Biotin, [3H(G)]; ethyl maleimide, N-[ethyl-1-$^{14}$C]; ketoglutaric acid, α-[1-$^{14}$C]; lactic acid, L-[$^{14}$C(U)]; malic acid, L-[1,4(2,3)-$^{14}$C]; mephenytoin, S[4-$^{14}$C]; methyl-tetrahydrofolic acid, 5-[$^{14}$C]-barium salt, NAD, [carbonyl-$^{14}$C]; nociceptin, [leucyl-3,4, 5-$^3$H]; NSP [$^3$H]—, (N-succininidyl[2,3-$^3$H]propionate); polyethylene glycol, [1,2-$^3$H]; pyruvic acid, [1-$^{14}$C]; sodium bicarbonate [$^{14}$C]; tetraethylammonium bromide, [1-$^{14}$C]; urea, [14C]; adenosine 3",5"-cyclic phosphoric acid, 2"-O-succinyl, [$^{125}$I]-iodotyrosine methyl ester; and deoxyuridine [$^{125}$I]-iodo-2". The particular isotope used to label any of the foregoing radioactive small molecules or compounds can be substituted with any other isotope described herein. In some embodiments, the radioactive agent is a lipid, which includes, but is not limited to, 3-indolylacetic acid, [5-$^3$H(N)]; 5-hydroxy tryptamine, [3H]; acetyl coenzyme A [acetyl-1-$^{14}$C]; arachidonic acid [1-$^{14}$C]; carnitine hydrochloride, L-[N-methyl-$^{14}$C]; cholesteryl hexadecyl ether, [cholesteryl-1,2-$^3$H(N)]; choline chloride, [methyl-$^3$H]; farnesyl pyrophosphate, triammonium salt, [1-$^3$H(N)]; geranylgeranyl pyrophosphate, [1-$^{3H}$(N)]glycerol [2-$^3$H]; glycerol 3-phosphate, ammonium salt, L-[$^{14}$C(U)]; glycerol tri oleate, [1-$^{14}$C]; glycerol tri oleate, [9,10(N)-$^3$H]; hydroxy-3-methylglutaryl coenzyme A, DL-3-[glutaryl-3-$^{14}$C]; hydroxycholesterol, 25-[26,27-$^3$H]; iloprost, [3H]; inositol-1,4,5-triphosphate, D-[inositol-1-$^3$H(N)]; isopentenyl pyrophosphate, [4-$^{14}$C]; leukotriene [14,15,19,20-$^3$H(N)]; linoleic acid, [1-$^{14}$C]; lysopalmitoyl phosphatidylcholine, L-1-[palmitoyl-1-$^{14}$C]; lysophosphatidic acid, 1-Oleoyl-[oleoyl-9,10-$^3$H]; mevanolactone, RS-[2-$^{14}$C]; myristic acid (tetradecanoic acid), [9,10-$^3$H(N)]; oleic acid [1-$^{14}$C]; oleoyl coenzyme A [oleoyl-1-$^{14}$C]; palmitic acid [1-$^{14}$C]; palmitoyl carnitine chloride, L-[palmitoyl-1-$^{14}$C]; palmitoyl coenzyme A, [palmitoyl-1-$^{14}$C]; phenylethylamine hydrochloride, beta-ethyl 1,$^{14}$C; phosphatidic acid, L-α-dipalmitoyl-[glycerol-$^{14}$C(U)]; phosphatidylcholine [dipalmitoyl-1-$^{14}$C]; phosphatidylinositol [MYO-inositol-2-$^3$H(N)]; hexadecyl PAF, 1-O-hexadecyl-[acetyl-$^3$H(N)]-[acetyl-$^3$H]; retinoic acid, [11,12-$^3$H(N)]; retinol, [11,12-$^3$H(N)]; sphingomyelin [choline-methyl-$^{14}$C]; stearic acid, [1-$^{14}$C]; taurine, [2,2,$^3$H]; taurocholic acid, [carbonyl-$^{14}$C]; triolein [9 10-$^3$H(N)]; and verapamil hydrochloride, [N-Methyl-$^3$H]. The particular isotope used to label any of the foregoing radioactive lipids can be substituted with any other isotope described herein. In some embodiments, the agent is a radioactive nucleotide, which includes, but is not limited to, adenine, [2,8-$^3$H]; adenosine 5'-diphosphate [8-$^{14}$C]; adenosine 5'-triphosphate, [2,5',8-$^3$H]; caffeine, [1-methyl-$^{14}$C]; cytidine 5'-triphosphate, [5-$^3$H]; deoxy guanosine 5'-triphosphate, [8-$^3$H(N)]—, (dGTP, [8-$^3$H(N)]; deoxycytidine 5-triphosphate 5,5-$^3$H; deoxythymidine 5'-triphosphate [methyl-$^3$H]; deoxyuridine 5'-triphosphate, [5-$^3$H(N)]-(dUTP [5-$^3$H(N)]); guanosine 5'-triphosphate, [8-3H], (GTP, [3H]); hypoxanthine monohydrochloride, $^3$H; nitrobenzyl-thioinosine, [benzyl-$^3$H]; thymidine [2-$^{14}$C]; thymidine, [6-3H]; uracil, 5,6,$^3$H; uridine diphosphate glucose, [glucose-$^{14}$C(U)]; and uridine, [U-14C]. The particular isotope used to label any of the foregoing radioactive nucleotides can be substituted with any other isotope described herein. Additional agents suitable for use in embodiments of the present invention will be apparent to the skilled artisan. The invention is not limited in this respect.

The term "amino acid," as used herein, includes any naturally occurring and non-naturally occurring amino acid. There are many known non-natural amino acids any of which may be included in the polypeptides or proteins described herein. See, for example, S. Hunt, *The Non-Protein Amino Acids: In Chemistry and Biochemistry of the Amino Acids*, edited by G. C. Barrett, Chapman and Hall, 1985. Some non-limiting examples of non-natural amino acids are 4-hydroxyproline, desmosine, gamma-aminobutyric acid, beta-cyanoalanine, norvaline, 4-(E)-butenyl-4 (R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and para-substituted phenylalanines (e.g., substituted with —C(=O)C$_6$H$_5$; —CF$_3$; —CN; -halo; —NO$_2$; —CH$_3$), disubstituted phenylalanines, substituted tyrosines (e.g., further substituted with —C(=O)C$_6$H$_5$; —CF$_3$; —CN; -halo; —NO$_2$; —CH$_3$), and statine. In the context of amino acid sequences, "X" or "Xaa" represents any amino acid residue, e.g., any naturally occurring and/or any non-naturally occurring amino acid residue.

The term "antibody", as used herein, refers to a protein belonging to the immunoglobulin superfamily. The terms antibody and immunoglobulin are used interchangeably. With some exceptions, mammalian antibodies are typically made of basic structural units each with two large heavy chains and two small light chains. There are several different types of antibody heavy chains, and several different kinds of antibodies, which are grouped into different isotypes based on which heavy chain they possess. Five different antibody isotypes are known in mammals, IgG, IgA, IgE, IgD, and IgM, which perform different roles, and help direct the appropriate immune response for each different type of foreign object they encounter. In some embodiments, an antibody is an IgG antibody, e.g., an antibody of the IgG1, 2, 3, or 4 human subclass. Antibodies from mammalian species (e.g., human, mouse, rat, goat, pig, horse, cattle, camel) are within the scope of the term, as are antibodies from non-mammalian species (e.g., from birds, reptiles, amphibia) are also within the scope of the term, e.g., IgY antibodies.

Only part of an antibody is involved in the binding of the antigen, and antigen-binding antibody fragments, their preparation and use, are well known to those of skill in the art. As is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). Suitable antibodies and antibody fragments for use in the context of some embodiments of the present invention include, for example, human antibodies, humanized antibodies, domain antibodies, F(ab'), F(ab')$_2$, Fab, Fv, Fc, and Fd fragments, antibodies in which the Fc and/or FR and/or CDR1 and/or CDR2 and/or light chain CDR3 regions have been replaced by homologous human or non-human sequences; antibodies in which the FR and/or CDR1 and/or CDR2 and/or light chain CDR3 regions have been replaced by homologous human or non-human sequences; antibodies in which the FR and/or CDR1 and/or CDR2 and/or light chain CDR3 regions have been replaced by homologous human or non-human sequences; and antibodies in which the FR and/or CDR1 and/or CDR2 regions have been replaced by homologous human or non-human sequences. In some embodiments, so-called single chain antibodies (e.g., ScFv), (single) domain antibodies, and other intracellular antibodies may be used in the context of the present invention. Domain antibodies, camelid and camelized antibodies and fragments thereof, for example, VHH domains, or nanobodies, such as those described in patents and published patent applications of Ablynx NV and Domantis are also encompassed in the term antibody. Further, chimeric antibodies, e.g., antibodies comprising two antigen-binding domains that bind to different antigens, are also suitable for use in the context of some embodiments of the present invention. In some embodiments, the term antibody may also refer to "antibody mimetics," which are organic compounds the can specifically bind antigens, but are not structurally related to antibodies. For example, antibody mimetics known as "affibodies," or "affibody molecules," are small proteins engineered to bind e.g., target proteins or peptides with affinities comparable to monoclonal antibodies. In some embodiments, an affibody includes a protein scaffold based on the Z domain (the immunoglobulin G binding domain) of protein A, and in contrast to antibodies, affibody molecules are composed of alpha helices and lack disulfide bridges. Methods for engineering and producing affibodies are known, and include those described in Nord et al., "A combinatorial library of an α-helical bacterial receptor domain." *Prot. Eng.* 1995; 8 (6): 601-608; Nord et al., "Binding proteins selected from combinatorial libraries of an α-helical bacterial receptor domain." *Nature Biotechnol.* 1997; 15 (8): 772-777; Ståhl et al., "The use of gene fusions to protein A and protein G in immunology and biotechnology." *Pathol. Biol.* (Paris) 1997; 45 (1): 66-76; Rönnmark et al., "Construction and characterization of affibody-Fc chimeras produced in *Escherichia coli.*" *J. Immunol. Methods.* 2002; 261 (1-2): 199-211; Rönnmark et al., "Affibody-beta-galactosidase immunoconjugates produced as soluble fusion proteins in the *Escherichia coli* cytosol." *J. Immunol. Methods.* 2003; 281 (1-2): 149-160; Nord et al., "Recombinant human factor VIII-specific affinity ligands selected from phage-displayed combinatorial libraries of protein A." *Eur. J. Biochem.* 2001; 268 (15): 1-10; Engfeldt et al., "Chemical synthesis of triple-labeled three-helix bundle binding proteins for specific fluorescent detection of unlabeled protein." *Chem. BioChem.* 2005; 6 (6): 1043-1050; Ahlgren et al., "Targeting of HER2-expressing tumors with a site-specifically 99mTc-labeled recombinant affibody molecule, ZHER2:2395, with C-terminally engineered cysteine." *J. Nucl. Med.* 2009; 50 (5): 781-789; Orlova et al., "Evaluation of [(111/114m)In]CHX-A"-DTPA-ZHER2:342, an affibody ligand conjugate for targeting of HER2-expressing malignant tumors." *Q. J. Nucl. Med. Mol. Imaging.* 2007; 51 (4): 314-23; Tran et al., "(99m)Tc-maEEE-Z(HER2:342), an Affibody molecule-based tracer for the detection of HER2 expression in malignant tumors". *Bioconjug. Chem.* 2007; 18 (6): 1956-64; Orlova et al., "Tumor imaging using a picomolar affinity HER2 binding affibody molecule." *Cancer Res.* 2006; 66 (8): 4339-48; Holm et al., "Electrophilic Affibodies Forming Covalent Bonds to Protein Targets." *The Journal of Biological Chemistry* 2009; 284 (47): 32906-13; Renberg et al., "Affibody molecules in protein capture microarrays: evaluation of multidomain ligands and different detection formats." *J. Proteome Res.* 2007; 6 (1): 171-179; Lundberg et al., "Site-specifically conjugated anti-HER2 Affibody molecules as one-step reagents for target expression analyses on cells and xenograft samples." *J. Immunol. Methods* 2007; 319 (1-2): 53-63; Tolmachev et al., "Radionuclide therapy of HER2-positive microxenografts using a 177Lu-labeled HER2-specific Affibody molecule." *Cancer Res.* 2007; 67 (6): 2773-82; and Gebauer & Skerra, "Engineered protein scaffolds as next-generation antibody therapeutics." *Current Opinion in Chemical Biology* 2009; 13 (3): 245-55; Siontorou C., "Nanobodies as novel agents for disease diagnosis and therapy." *Int. J. Nanomedicine* 2013; 8: 4215-4227; the entire contents of each are hereby incorporated by reference in their entirety.

The term "antigen-binding antibody fragment," as used herein, refers to a fragment of an antibody that comprises the paratope, or a fragment of the antibody that binds to the antigen the antibody binds to, with similar specificity and affinity as the intact antibody. Antibodies, e.g., fully human monoclonal antibodies, may be identified using phage display (or other display methods such as yeast display, ribosome display, bacterial display). Display libraries, e.g., phage display libraries, are available (and/or can be generated by one of ordinary skill in the art) that can be screened to identify an antibody that binds to an antigen of interest, e.g., using panning. See, e.g., Sidhu, S. (ed.) *Phage Display in Biotechnology and Drug Discovery* (Drug Discovery Series; CRC Press; 1$^{st}$ ed., 2005; Aitken, R. (ed.) *Antibody Phage Display: Methods and Protocols* (Methods in Molecular Biology) Humana Press; 2nd ed., 2009.

The term "binding agent," as used herein, refers to any molecule that binds another molecule with high affinity. In some embodiments, a binding agent binds its binding partner with high specificity. Examples for binding agents include, without limitation, antibodies, antibody fragments, nucleic acid molecules, receptors, ligands, aptamers, and adnectins.

The term "click chemistry" refers to a chemical philosophy introduced by K. Barry Sharpless of The Scripps Research Institute, describing chemistry tailored to generate covalent bonds quickly and reliably by joining small units comprising reactive groups together (see H. C. Kolb, M. G. Finn and K. B. Sharpless (2001). Click Chemistry: Diverse Chemical Function from a Few Good Reactions. *Angewandte Chemie International Edition* 40 (11): 2004-2021. Click chemistry does not refer to a specific reaction, but to a concept including, but not limited to, reactions that mimic reactions found in nature. In some embodiments, click chemistry reactions are modular, wide in scope, give high chemical yields, generate inoffensive byproducts, are stereospecific, exhibit a large thermodynamic driving force to favor a reaction with a single reaction product, and/or can be carried out under physiological conditions. In some embodiments, a click chemistry reaction exhibits high atom economy, can be carried out under simple reaction conditions, use readily available starting materials and reagents, uses no toxic solvents or uses a solvent that is benign or easily removed (preferably water), and/or provides simple product isolation by non-chromatographic methods (crystallisation or distillation). In some embodiments, the click chemistry reaction is a [2+3] dipolar cycloaddition. In certain embodiments, the click chemistry reaction is a Diels-Alder cycloaddition.

The term "click chemistry handle," as used herein, refers to a reactant, or a reactive group, that can partake in a click chemistry reaction. Exemplary click chemistry handles are demonstrated in U.S. Patent Publication 20130266512, which is incorporated by reference herein. For example, a strained alkyne, e.g., a cyclooctyne, is a click chemistry handle, since it can partake in a strain-promoted cycloaddition (see, e.g., Table 1). In general, click chemistry reactions require at least two molecules comprising click chemistry handles that can react with each other. Such click chemistry handle pairs that are reactive with each other are sometimes referred to herein as partner click chemistry handles. For example, an azide is a partner click chemistry handle to a cyclooctyne or any other alkyne. Exemplary click chemistry handles suitable for use according to some aspects of this invention are described herein, for example, in Tables 1 and 2. In some embodiments, the click chemistry partners are a conjugated diene and an optionally substituted alkene, In other embodiments, the click chemistry partners are an optionally substituted tetrazine and an optionally substituted trans-cyclooctene (TCO). In some embodiments, the click chemistry partners are optionally substituted tetrazine (Tz) and optionally substituted trans-cyclooctene (TCO). Tz and TCO react with each other in a reverse-electron demand Diels-Alder cycloaddition reaction (See e.g., Example 2, FIG. 4; Blackman et al., "The Tetrazine Ligation: Fast Bioconjugation based on Inverse-electron-demand Diels-Alder Reactivity." *J. Am. Chem. Soc.* 2008; 130, 13518-13519). In other embodiments, the click chemistry partners are an optionally substituted alkyne and an optionally substituted azide. For example, a difluorinated cyclooctyne, a dibenzocyclooctyne, a biarylazacyclooctynone, or a cyclopropyl-fused bicyclononyne can be paired with an azide as a click chemistry pair. In other embodiments, the click chemistry partners are reactive dienes and suitable tetrazine dienophiles. For example, TCO, norbornene, or biscyclononene can be paired with a suitable tetrazine dienophile as a click chemistry pair. In yet other embodiments, tetrazoles can act as latent sources of nitrile imines, which can pair with unactivated alkenes in the presence of ultraviolet light to create a click chemistry pair, termed a "photo-click" chemistry pair. The click chemistry pair may also be a cysteine and a maleimide. For example the cysteine from a peptide (e.g., GGGC (SEQ ID NO: 124)) may be reacted with a maleimide that is associated with a chelating agent (e.g., NOTA). Other suitable click chemistry handles are known to those of skill in the art (See, e.g., Table 1; Spicer et al., "Selective chemical protein modification." *Nature Communications.* 2014; 5:4740). For two molecules to be conjugated via click chemistry, the click chemistry handles of the molecules have to be reactive with each other, for example, in that the reactive moiety of one of the click chemistry handles can react with the reactive moiety of the second click chemistry handle to form a covalent bond. Such reactive pairs of click chemistry handles are well known to those of skill in the art and include, but are not limited to, those described in Table 1.

TABLE 1

Exemplary click chemistry handles and reactions.

| | Exemplary rate constant ($M^{-1}s^{-1}$) |
|---|---|
| $R^{41}$—≡≡≡ + $R^{42}$—$N_3$ ⟶ [triazole with $R^{41}$, $R^{42}$]<br><br>1,3-dipolar cycloaddition | $1 \times 10^{-3a}$ |
| [cyclooctyne]—$R^{41}$ + $R^{42}$—$N_3$ ⟶ [cyclooctyne-fused triazole with $R^{41}$, $R^{42}$]<br><br>strain-promoted cycloaddition | |

TABLE 1-continued

Exemplary click chemistry handles and reactions.

Exemplary rate constant ($M^{-1}s^{-1}$)

Diels-Alder reaction

Thiol-ene reaction

Strain-promoted cycloaddition — $8 \times 10^{-2a}$

Strain-promoted cycloaddition — $2.3^a$

Strain-promoted cycloaddition — $1^a$

TABLE 1-continued

Exemplary click chemistry handles and reactions.

| Reaction | Exemplary rate constant (M⁻¹s⁻¹) |
|---|---|
| Strain-promoted cycloaddition | $0.1^a$ |
| Inverse-electron demand Diels-Alder (IEDDA) | $9^a$ |
| Inverse-electron demand Diels-Alder (IEDDA) | $17{,}500^a$ $35{,}000^b$ |
| Inverse-electron demand Diels-Alder (IEDDA) | $>50{,}000^a$ $880^b$ |
| 1,3-dipolar cycloaddition ("photo-click") | $0.9^a$ |

TABLE 1-continued

Exemplary click chemistry handles and reactions.

| | Exemplary rate constant ($M^{-1}s^{-1}$) |
|---|---|
| 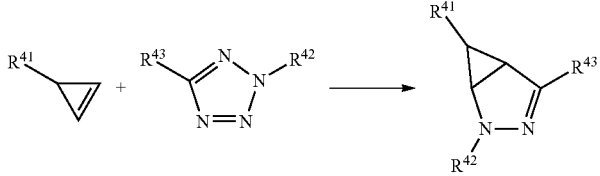<br>1,3-dipolar cycloaddition ("photo-click") | 58[a] |

Each of $R^{41}$, $R^{42}$, and $R^{43}$ is indpendently hydrogen, optionally substituted aliphatic, optionally substituted heteroaliphatic, optionally substituted aryl, optionally substituted heteroaryl, or optionally substituted heterocyclyl. In certain embodiments, at least one of $R^{41}$, $R^{42}$, and $R^{43}$ independently comprises a sortase recognition motif. In certain embodiments, one of $R^{41}$, $R^{42}$, and $R^{43}$ independently comprises a sortase recognition motif. In certain embodiments, two of $R^{41}$, $R^{42}$, and $R^{43}$ independently comprise a sortase recognition motif. In certain embodiments, each of $R^{41}$, $R^{42}$, and $R^{43}$ independently comprises a sortase recognition motif. In some embodiments, at least one of $R^{41}$, $R^{42}$, and $R^{43}$ is independently $R_R$—LPXT—$[X]_y$—, wherein each occurrence of X independently represents any amino acid residue; each occurrence of y is an integer between 0 and 10, inclusive; and each occurrence of $R_R$ independently represents a protein or an agent (e.g., a protein, peptide, a detectable label, a binding agent, a small molecule), and, optionally, a linker. Each instance of $R_3$ is independently H, substituted or unsubstituted alkyl (e.g., —$CH_3$), or substituted or unsubstituted aryl.
[a]Exemplary rate constant for small-molecule models.
[b]Exemplary on-protein rate constant.

In some embodiments, click chemistry handles used can react to form covalent bonds in the absence of a metal catalyst. Such click chemistry handles are well known to those of skill in the art and include the click chemistry handles described in Becer, Hoogenboom, and Schubert (Table 2), "Click Chemistry beyond Metal-Catalyzed Cycloaddition," *Angewandte Chemie International Edition* (2009) 48: 4900-4908:

TABLE 2

Exemplary click chemistry reactions.

| | Reagent A | Reagent B | Mechanism | Notes on reaction[a] |
|---|---|---|---|---|
| 0 | azide | alkyne | Cu-catalyzed [3 + 2] azide-alkyne cycloaddition (CuAAC) | 2 h at 60° C. in $H_2O$ |
| 1 | azide | cyclooctyne | strain-promoted [3 + 2] azide-alkyne cycloaddition (SPAAC) | 1 h at RT |
| 2 | azide | activated alkyne | [3 + 2] Huisgen cycloaddition | 4 h at 50° C. |
| 3 | azide | electron-deficient alkyne | [3 + 2] cycloadditttion | 12 h at RT in $H_2O$ |
| 4 | azide | aryne | [3 + 2] cycloaddition | 4 h at RT in THF with crown ether or 24 h at RT in $CH_3CN$ |
| 5 | tetrazine | alkene | Diels-Alder retro-[4 + 2] cycloaddition | 40 min at 25° C. (100% yield) $N_2$ is the only by-product |
| 6 | tetrazole | alkene | 1,3-dipolar cycloaddition (photoclick) | few min UV irradiation and then overnight at 4° C. |
| 7 | dithioster | diene | hetero-Diels-Alder cycloaddition | 10 min at RT |
| 8 | anthracene | maleimide | [4 + 2] Diels-Alder reaction | 2 days at reflux in toluene |
| 9 | thiol | alkene | radical addition (thio click) | 30 min UV (quantitative conv.) or 24 h UV irradiation (>96%) |
| 10 | thiol | enone | Michael addition | 24 h at RT in $CH_3CN$ |
| 11 | thiol | maleimide | Michael addition | 1 h at 40° C. in THF or 16 h at RT in dioxane |
| 12 | thiol | para-fluoro | nucleophilic substitution | overnight at RT in DMF or 60 min at 40° C. in DMF |
| 13 | amine | para-fluoro | nucleophilic substitution | 20 min MW at 95° C. in NMP as solvent |

[a]RT = room temperature, DMF = N,N-dimethylformamide, NMP = N-methylpyrolidone, THF = tetrahydrofuran, $CH_3CN$ = acetonitrile.

Methods and compositions for using click chemistry in combination with sortagging technologies are known, and include those described by Ploegh et al., international PCT application, PCT/US2012/044584, filed Jun. 28, 2012, published as WO 2013/003555 on Jan. 3, 2013; and Ploegh et al., U.S. patent application U.S. Ser. No. 13/918,278, filed Jun. 14, 2013; the entire contents of each of which are incorporated herein by reference.

The term "conjugated" or "conjugation" refers to an association of two molecules, for example, two proteins or a protein and an agent, e.g., a small molecule, with one another in a way that they are linked by a direct or indirect covalent or non-covalent interaction. In certain embodiments, the association is covalent, and the entities are said to be "conjugated" to one another. In some embodiments, a protein is post-translationally conjugated to another molecule, for example, a second protein, a small molecule, a detectable label, a click chemistry handle, or a binding agent, by forming a covalent bond between the protein and the other molecule after the protein has been formed, and, in some embodiments, after the protein has been isolated. In some embodiments, two molecules are conjugated via a linker connecting both molecules. For example, in some embodiments where two proteins are conjugated to each other to form a protein fusion, the two proteins may be conjugated via a polypeptide linker, e.g., an amino acid sequence connecting the C-terminus of one protein to the N-terminus of the other protein. In some embodiments, two proteins are conjugated at their respective C-termini, generating a C—C conjugated chimeric protein. In some embodiments, two proteins are conjugated at their respective N-termini, generating an N—N conjugated chimeric protein. In some embodiments, conjugation of a protein to a peptide is achieved by transpeptidation using a sortase. See, e.g., Ploegh et al., International PCT Patent Application, PCT/US2010/000274, filed Feb. 1, 2010, published as WO/2010/087994 on Aug. 5, 2010, and Ploegh et al., International Patent Application, PCT/US2011/033303, filed Apr. 20, 2011, published as WO/2011/133704 on Oct. 27, 2011, the entire contents of each of which are incorporated herein by reference, for exemplary sortases, proteins, recognition motifs, reagents, and methods for sortase-mediated transpeptidation. In other embodiments, conjugation of a protein to a peptide or other moiety may be achieved using other enzymes known in the art, for example, formylglycine generating enzyme, sialyltransferase, phosphopantetheinyl-transferase, transglutaminase, farnesyltransferase, biotin ligase, lipoic acid ligase, or N-myristoyl transferase. Exemplary techniques and approaches for enzymatic labeling of proteins can be found in Rashidian, M., et al. "Enzymatic Labeling of Proteins: Techniques and Approaches", Bioconjugate Chem., 2013; 24, 1277-1294; which is incorporated by reference.

The term "detectable label" refers to a moiety that has at least one element or isotope incorporated into the moiety which enables detection of the molecule, e.g., a protein or peptide, or other entity, to which the label is attached. Labels can be directly attached (i.e., via a bond) or can be attached by a linker. It will be appreciated that the label may be attached to or incorporated into a molecule, for example, a protein, polypeptide, a carbohydrate, or other entity, at any position. In some embodiments, a detectable label contains isotopic moieties, which may be radioactive or heavy isotopes, including, but not limited to, $^{2}$H, $^{3}$H, $^{11}$C, $^{13}$C, $^{14}$C, $^{61}$Cu, $^{62}$Cu, $^{13}$N, $^{15}$N, $^{15}$O, $^{18}$F, $^{31}$P, $^{32}$P, $^{35}$S, $^{67}$Ga, $^{68}$Ga, $^{76}$Br, $^{99}$mTc (Tc-99m), $^{111}$In, $^{123}$I, $^{124}$I, $^{125}$I, $^{131}$I, $^{153}$Gd, $^{89}$Zr, $^{86}$Y, $^{169}$Yb, $^{82}$Rb, and $^{186}$Re. In certain embodiments, a label comprises a radioactive isotope, preferably an isotope which emits detectable particles, such as a particles, R particles or rays, such as γ rays.

The term "linker," as used herein, refers to a chemical group or molecule covalently linked to a molecule, for example, a protein, and a chemical group or moiety, for example, a click chemistry handle. In some embodiments, the linker is positioned between, or flanked by, two groups, molecules, or moieties and connected to each one via a covalent bond, thus connecting the two. In some embodiments, the linker is an amino acid or a plurality of amino acids. In some embodiments, the linker comprises 1, 2, 3, 4, 5, 6, 7, 8, 9, 10, 11, 12, 13, 14, 15, 16, 17, 18, 19, 20, or more than 20 amino acids. In some embodiments, the linker comprises a poly-glycine sequence. In some embodiments, the linker comprises a non-protein structure. In some embodiments, the linker is an organic molecule, group, polymer, or chemical moiety (e.g., polyethylene, polyethylene glycol).

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms "nucleic acid," "DNA," "RNA," and/or similar terms include nucleic acid analogs, i.e. analogs having other than a phosphodiester backbone. Nucleic acids can be purified from natural sources, produced using recombinant expression systems, chemically synthesized, and, optionally, purified. Where appropriate, e.g., in the case of chemically synthesized molecules, nucleic acids can comprise nucleoside analogs such as analogs having chemically modified bases or sugars, and backbone modifications. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The term "oxime," as used herein, refers to compound having the general formula:

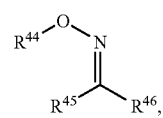

wherein each of $R^{44}$, $R^{45}$, and $R^{46}$ is independently hydrogen, optionally substituted aliphatic, optionally substituted heteroaliphatic, optionally substituted aryl, optionally substituted heteroaryl, or optionally substituted heterocyclyl. The term "oxime linkage," as used herein, refers to a linker comprising the O—N=C moiety. In certain embodiments, the oxime linkage can be formed by joining of a compound comprising an aminooxy group and a compound comprising a carbonyl.

The terms "protein," "peptide" and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as an aminooxy group, a hydrazide group, a thiosemicarbazide group, a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof.

The term "small molecule" is used herein to refer to molecules, whether naturally-occurring or artificially created (e.g., via chemical synthesis) that have a relatively low molecular weight. Typically, a small molecule is an organic compound (i.e., it contains carbon). A small molecule may contain multiple carbon-carbon bonds, stereocenters, and other functional groups (e.g., amines, hydroxyl, carbonyls, heterocyclic rings, etc.). In some embodiments, small molecules are monomeric and have a molecular weight of less than about 1500 g/mol. In certain embodiments, the molecular weight of the small molecule is less than about 1000 g/mol or less than about 500 g/mol. In certain embodiments, the small molecule is a drug, for example, a drug that has already been deemed safe and effective for use in humans or animals by the appropriate governmental agency or regulatory body.

The term "sortase," as used herein, refers to an enzyme able to carry out a transpeptidation reaction conjugating the C-terminus of a protein or peptide to the N-terminus of a protein or peptide via transamidation. Sortases are also referred to as transamidases, and typically exhibit both a protease and a transpeptidation activity. Various sortases from prokaryotic organisms have been identified. For example, some sortases from Gram-positive bacteria cleave and translocate proteins to proteoglycan moieties in intact cell walls. Among the sortases that have been isolated from Staphylococcus aureus, are sortase A (Srt A) and sortase B (Srt B). Thus, in certain embodiments, a transamidase used in accordance with the present invention is sortase A, e.g., from S. aureus, also referred to herein as SrtA$_{aureus}$. In certain embodiments, a transamidase is a sortase B, e.g., from S. aureus, also referred to herein as SrtB$_{aureus}$.

Sortases have been classified into four classes, designated A, B, C, and D, designated sortase A, sortase B, sortase C, and sortase D, respectively, based on sequence alignment and phylogenetic analysis of 61 sortases from Gram-positive bacterial genomes (Dramsi S, Trieu-Cuot P, Bierne H, Sorting sortases: a nomenclature proposal for the various sortases of Gram-positive bacteria. Res Microbiol. 156(3): 289-97, 2005; the entire contents of which are incorporated herein by reference). These classes correspond to the following subfamilies, into which sortases have also been classified by Comfort and Clubb (Comfort D, Clubb R T. "A comparative genome analysis identifies distinct sorting pathways in gram-positive bacteria" Infect Immun., 72(5):2710-22, 2004; the entire contents of which are incorporated herein by reference): Class A (Subfamily 1), Class B (Subfamily 2), Class C (Subfamily 3), Class D (Subfamilies 4 and 5). The aforementioned references disclose numerous sortases and recognition motifs. See also Pallen, M. J.; Lam, A. C.; Antonio, M.; Dunbar, K. TRENDS in Microbiology, 2001, 9(3), 97-101; the entire contents of which are incorporated herein by reference. Those skilled in the art will readily be able to assign a sortase to the correct class based on its sequence and/or other characteristics such as those described in Drami, et al., supra. The term "sortase A" is used herein to refer to a class A sortase, usually named SrtA in any particular bacterial species, e.g., SrtA from S. aureus. Likewise "sortase B" is used herein to refer to a class B sortase, usually named SrtB in any particular bacterial species, e.g., SrtB from S. aureus. The invention encompasses embodiments relating to a sortase A from any bacterial species or strain. The invention encompasses embodiments relating to a sortase B from any bacterial species or strain. The invention encompasses embodiments relating to a class C sortase from any bacterial species or strain. The invention encompasses embodiments relating to a class D sortase from any bacterial species or strain.

Amino acid sequences of Srt A and Srt B and the nucleotide sequences that encode them are known to those of skill in the art and are disclosed in a number of references cited herein, the entire contents of all of which are incorporated herein by reference. The amino acid sequence of a sortase-transamidase from Staphylococcus aureus also has substantial homology with sequences of enzymes from other Gram-positive bacteria, and such transamidases can be utilized in the ligation processes described herein. For example, for SrtA there is about a 31% sequence identity (and about 44% sequence similarity) with best alignment over the entire sequenced region of the S. pyogenes open reading frame. There is about a 28% sequence identity with best alignment over the entire sequenced region of the A. naeslundii open reading frame. It will be appreciated that different bacterial strains may exhibit differences in sequence of a particular polypeptide, and the sequences herein are exemplary.

In certain embodiments a transamidase bearing 18% or more sequence identity, 20% or more sequence identity, 30% or more sequence identity, 40% or more sequence identity, or 50% or more sequence identity with an S. pyogenes, A. naeslundii, S. mutans, E. faecalis or B. subtilis open reading frame encoding a sortase can be screened, and enzymes having transamidase activity comparable to Srt A or Srt B from S. aureus can be utilized (e.g., comparable activity sometimes is 10% of Srt A or Srt B activity or more).

Thus in some embodiments of the invention the sortase is a sortase A (SrtA). SrtA recognizes the motif LPXTX (wherein each occurrence of X represents independently any amino acid residue), with common recognition motifs being, e.g., LPKTG (SEQ ID NO:6), LPATG (SEQ ID NO:7), LPNTG (SEQ ID NO:8). In some embodiments LPETG (SEQ ID NO:2) is used as the sortase recognition motif. However, motifs falling outside this consensus may also be recognized. For example, in some embodiments the motif comprises an 'A' rather than a 'T' at position 4, e.g., LPXAG (SEQ ID NO:9), e.g., LPNAG (SEQ ID NO:10). In some embodiments the motif comprises an 'A' rather than a 'G' at position 5, e.g., LPXTA (SEQ ID NO:11), e.g., LPNTA (SEQ ID NO:12), e.g., LPETA (SEQ ID NO:3). In some embodiments the motif comprises a 'G' rather than 'P' at position 2, e.g., LGXTG (SEQ ID NO:13), e.g., LGATG (SEQ ID NO:14). In some embodiments the motif comprises an 'I' rather than 'L' at position 1, e.g., IPXTG (SEQ ID NO:15), e.g., IPNTG (SEQ ID NO:16) or IPETG (SEQ ID NO: 17). Additional suitable sortase recognition motifs will be apparent to those of skill in the art, and the invention is not limited in this respect. It will be appreciated that the terms "recognition motif" and "recognition sequence", with respect to sequences recognized by a transamidase or sortase, are used interchangeably.

In some embodiments of the invention the sortase is a sortase B (SrtB), e.g., a sortase B of *S. aureus, B. anthracis*, or *L. monocytogenes*. Motifs recognized by sortases of the B class (SrtB) often fall within the consensus sequences NPXTX, e.g., NP[Q/K]-[T/s]-[N/G/s], such as NPQTN (SEQ ID NO:4) or NPKTG (SEQ ID NO:5). For example, sortase B of *S. aureus* or *B. anthracis* cleaves the NPQTN (SEQ ID NO:4) or NPKTG (SEQ ID NO:5) motif of IsdC in the respective bacteria (see, e.g., Marraffini, L. and Schneewind, O., Journal of Bacteriology, 189(17), p. 6425-6436, 2007). Other recognition motifs found in putative substrates of class B sortases are NSKTA (SEQ ID NO:18), NPQTG (SEQ ID NO:19), NAKTN (SEQ ID NO:20), and NPQSS (SEQ ID NO:21). For example, SrtB from *L. monocytogenes* recognizes certain motifs lacking P at position 2 and/or lacking Q or K at position 3, such as NAKTN (SEQ ID NO:22) and NPQSS (SEQ ID NO:23) (Mariscotti J F, Garcia-Del Portillo F, Pucciarelli M G. The *Listeria monocytogenes* sortase-B recognizes varied amino acids at position two of the sorting motif. J Biol Chem. 2009 Jan. 7.)

In some embodiments, the sortase is a sortase C (Srt C). Sortase C may utilize LPXTX as a recognition motif, with each occurrence of X independently representing any amino acid residue.

In some embodiments, the sortase is a sortase D (Srt D). Sortases in this class are predicted to recognize motifs with a consensus sequence NA-[E/A/S/H]-TG (SEQ ID NO: 128) (Comfort D, supra). Sortase D has been found, e.g., in *Streptomyces* spp., *Corynebacterium* spp., *Tropheryma whipplei, Thermobifida fusca*, and *Bifidobacterium longhum*. LPXTA (SEQ ID NO:24) or LAXTG (SEQ ID NO:25) may serve as a recognition sequence for sortase D, e.g., of subfamilies 4 and 5, respectively subfamily-4 and subfamily-5 enzymes process the motifs LPXTA (SEQ ID NO:26) and LAXTG (SEQ ID NO:27), respectively). For example, *B. anthracis* Sortase C has been shown to specifically cleave the LPNTA (SEQ ID NO:28) motif in *B. anthracis* BasI and BasH (see Marrafini, supra).

See Barnett and Scott for description of a sortase that recognizes QVPTGV (SEQ ID NO:29) motif (Barnett, T C and Scott, J R, *Differential Recognition of Surface Proteins in Streptococcus pyogenes by Two Sortase Gene Homologs*. Journal of Bacteriology, Vol. 184, No. 8, p. 2181-2191, 2002; the entire contents of which are incorporated herein by reference). Additional sortases, including, but not limited to, sortases and sortase variants recognizing additional sortase recognition motifs are also suitable for use in some embodiments of this invention. For example, sortases described in Chen I. et al., "A general strategy for the evolution of bond-forming enzymes using yeast display." *Proc Natl Acad Sci USA*. 2011 Jul. 12; 108(28):11399; Dorr, B. M., et al., "Reprogramming the specificity of sortase enzymes." *Proc.*  *Natl. Acad. Sci. U.S.A*. 2014, 111, 13343-13348; the entire contents of each of which are incorporated herein by reference.

In some embodiments, a variant of a naturally occurring sortase may be used. Such variants may be produced through processes such as directed evolution, site-specific modification, etc. Considerable structural information regarding sortase enzymes, e.g., sortase A enzymes, is available, including NMR or crystal structures of SrtA alone or bound to a sortase recognition sequence (see, e.g., Zong Y, et al. J. Biol Chem. 2004, 279, 31383-31389). Three dimensional structure information is also available for other sortases, e.g., *S. pyogenes* SrtA (Race, P R, et al., J Biol Chem. 2009, 284(11):6924-33). The active site and substrate binding pocket of *S. aureus* SrtA have been identified. One of ordinary skill in the art can generate functional variants by, for example, avoiding deletions or substitutions that would disrupt or substantially alter the active site or substrate binding pocket of a sortase. In some embodiments a functional variant of *S. aureus* SrtA comprises His at position 120, Cys at position 184, and Arg at position 197, wherein Cys at position 184 is located within a TLXTC (SEQ ID NO: 95) motif. Functional variants of other SrtA proteins may have His, Cys, Arg, and TLXTC (SEQ ID NO: 95) motifs at positions that correspond to the positions of these residues in *S. aureus* SrtA. In some embodiments, a sortase variant comprises a sequence at least 80%, 85%, 90%, 91%, 92%, 93%, 94%, 95%, 96%, 97%, 98%, or 99% identical to a wild type sortase A sequence or catalytic domain thereof, e.g., at least 80%, 85%, 90%, 91%, 92%, 93%, 94%, 95%, 96%, 97%, 98%, or 99% identical to amino acids 60-206 of SEQ ID NO: 87 or SEQ ID NO: 88, or at least 80%, 85%, 90%, 91%, 92%, 93%, 94%, 95%, 96%, 97%, 98%, or 99% identical to amino acids 26-206 of SEQ ID NO: 87 or SEQ ID NO: 88. In some embodiments, a sortase variant comprises 1, 2, 3, 4, 5, 6, 7, 8, 9, 10, 11, 12, 13, 14, or 15 amino acid substitutions relative to amino acids 60-206 of SEQ ID NO: 87 or relative to amino acids 26-206 of SEQ ID NO: 87 or SEQ ID NO: 88.

In some embodiments, a transamidase having higher transamidase activity than a naturally occurring sortase may be used. In some embodiments the activity of the transamidase is at least about 10, 15, 20, 40, 60, 80, 100, 120, 140, 160, 180, or 200 times as high as that of *S. aureus* sortase A. In some embodiments the activity is between about 10 and 50 times as high as that of *S. aureus* sortase A, e.g., between about 10 and 20 times as high, between about 20 and 30 times as high, between about 30 and 50 times as high. In some embodiments the activity is between about 50 and about 150 times as high as that of *S. aureus* sortase A, e.g., between about 50 and 75 times as high, between about 75 and 100 times as high, between about 100-125 times as high, or between about 125 and 150 times as high. For example, variants of *S. aureus* sortase A with up to a 140-fold increase in LPETG-coupling (SEQ ID NO: 2) activity compared with the starting wild-type enzyme have been identified (Chen, I., et al., *PNAS* 108(28): 11399-11404, 2011). In some embodiments such a sortase variant is used in a composition or method of the invention. In some embodiments a sortase variant comprises any one or more of the following substitutions relative to a wild type *S. aureus* SrtA: P94S or P94R, D160N, D165A, K190E, and K196T mutations.

One of ordinary skill in the art will appreciate that the foregoing descriptions of substitutions utilize standard notation of the form $X_1NX_2$, in which $X_1$ and $X_2$, represent amino acids and N represents an amino acid position, $X_1$ represents an amino acid present in a first sequence (e.g., a wild type *S. aureus* SrtA sequence), and X₂ represents an amino acid that is substituted for X₁ at position N, resulting in a second sequence that has X₂ at position N instead of X₁. It should be understood that the present disclosure is not intended to be limited in any way by the identity of the original amino acid residue X₁ that is present at a particular position N in a wild type SrtA sequence used to generate a SrtA variant and is replaced by X₂ in the variant. Any substitution which results in the specified amino acid residue at a position specified herein is contemplated by the disclosure. Thus a substitution may be defined by the position and the identity of X₂, whereas X₁ may vary depending, e.g., on the particular bacterial species or strain from which a particular SrtA originates. Thus in some embodiments, a sortase A variant comprises any one or more of the following: an S residue at position 94 (S94) or an R residue at position 94 (R94), an N residue at position 160 (N₁₆₀), an A residue at position 165 (A165), an E residue at position 190 (E190), a T residue at position 196 (T196) (numbered according to the numbering of a wild type SrtA, e.g., SEQ ID NO: 87). For example, in some embodiments a sortase A variant comprises two, three, four, or five of the aforementioned mutations relative to a wild type *S. aureus* SrtA (e.g., SEQ ID NO: 87). In some embodiments a sortase A variant comprises an S residue at position 94 (S94) or an R residue at position 94 (R94), and also an N residue at position 160 (N160), an A residue at position 165 (A165), and a T residue at position 196 (T196). For example, in some embodiments a sortase A variant comprises P94S or P94R, and also D160N, D165A, and K196T. In some embodiments a sortase A variant comprises an S residue at position 94 (S94) or an R residue at position 94 (R94) and also an N residue at position 160 (N160), A residue at position 165 (A165), a E residue at position 190, and a T residue at position 196. For example, in some embodiments a sortase A variant comprises P94S or P94R, and also D160N, D165A, K190E, and K196T. In some embodiments a sortase A variant comprises an R residue at position 94 (R94), an N residue at position 160 (N160), a A residue at position 165 (A165), E residue at position 190, and a T residue at position 196. In some embodiments a sortase comprises P94R, D160N, D165A, K190E, and K196T.

It is to be further understood that the disclosure contemplates variants of any wild-type sortase A. Those skilled in the art will appreciate that wild-type sequences of sortase A may vary, e.g., SrtA from various species may have gaps, insertions, and/or may vary in length relative to the amino acid sequence of exemplary wild-type *S. aureus* SrtA. Those skilled in the art will appreciate that the positions described herein in regard to substitutions or other alterations pertain to the sequence of exemplary wild type *S. aureus* SrtA, unless otherwise indicated, and that such positions may be adjusted when making corresponding substitutions in different bacterial SrtA sequences in order to account for such gaps, insertions, and/or length differences. For example, as noted above, certain sortase variants comprise a substitution at amino acid position 94 (e.g., the amino acid is changed to an S residue). However, the amino acid at position 94 in *S. aureus* SrtA may correspond to an amino acid at a different position (e.g., position Z) in SrtA from a second bacterial species when the sequences are aligned. When generating a variant of the SrtA of the second bacterial species comprising a substitution at "position 94" (based on the wild type *S. aureus* SrtA sequence numbering), it is the amino acid at position Z of the SrtA from the second bacterial species that should be changed (e.g., to S) rather than the amino acid at position 94. Those skilled in the art will understand how to align any original wild-type sortase A sequence to be used for generating a SrtA variant with an exemplary wild-type *S. aureus* sortase A sequence for purposes of determining the positions in the original wild-type sortase A sequence that correspond to the exemplary wild-type *S. aureus* sortase A sequence when taking into account gaps and/or insertions in the alignment of the two sequences.

In some embodiments, amino acids at position 94, 160, 165, 190, and/or 196 are altered in a variant as compared with the amino acids present at those positions in a wild type *S. aureus* SrtA, and the other amino acids of the variant are identical to those present at the corresponding positions in a wild type SrtA, e.g., a wild type *S. aureus* SrtA. In some embodiments, one or more of the other amino acids of a variant, e.g., 1, 2, 3, 4, 5, 6, 7, 8, 9, or 10 of the other amino acids differ from those present at corresponding position(s) in a wild type SrtA, e.g., a wild type *S. aureus* SrtA. In some embodiments a variant may have any of the properties or degrees of sequence identity specified in the definition of "variants" above.

An exemplary wild type *S. aureus* SrtA sequence (Gene ID: 1125243, NCBI RefSeq Acc. No. NP_375640.1) is shown below, with the afore-mentioned positions underlined:

(SEQ ID NO: 87)
MKKWTNRLMTIAGVVLILVAAYLFAKPHIDNYLHDKDKDEKIEQYDKNVK

EQASKDNKQQAKPQIPKDKSKVAGYIEIPDADIKEPVYPGPATPEQLNRG

VSFAEENESLDDQNISIAGHTFIDRPNYQFTNLKAAKKGSMVYFKVGNET

RKYKMTSIRD̲VKPTD̲VEVLDEQKGKDKQLTLITCDDYNE̲KTGVWE̲KRKIF

VATEVK.

One of ordinary skill in the art will appreciate that different subspecies, strains, and isolates may differ in sequence at positions that do not significantly affect activity. For example, another exemplary wild type *S. aureus* SrtA sequence (Gene ID: 3238307, NCBI RefSeq Acc. No. YP_187332.1; GenBank Acc. No. AAD48437) has a K residue at position 57 and a G residue at position 167, as shown below in SEQ ID NO: 88:

(SEQ ID NO: 88)
MKKWTNRLMTIAGVVLILVAAYLFAKPHIDNYLHDKDKDEKIEQYDKNVK

EQASKDKKQQAKPQIPKDKSKVAGYIEIPDADIKEPVYPGPATPEQLNRG

VSFAEENESLDDQNISIAGHTFIDRPNYQFTNLKAAKKGSMVYFKVGNET

RKYKMTSIRD̲VKPTD̲VGVLDEQKGKDKQLTLITCDDYNE̲KTGVWE̲KRKIF

VATEVK

Either or both of these amino acids (i.e., K57 and/or G167) may be present in or introduced into any SrtA sequence, e.g., any *S. aureus* SrtA sequence, whether naturally occurring or generated by man. Furthermore, as described herein, any sortase sequence may further comprise a tag (e.g., 6×His (SEQ ID NO: 133)), a spacer, or both. For example, the N- or C-terminus may be extended to encompass a tag, optionally separated from the rest of the sequence by a spacer, In some embodiments a sortase variant comprising the following sequence may be used, in which amino acid substitutions relative to a wild type *S. aureus* SrtA of SEQ ID NO: 87 or SEQ ID NO: 88 are shown in underlined bold letters:

(SEQ ID NO: 89)
MQAKPQIPKDKSKVAGYIEIPDADIKEPVYPGPATR<u>E</u>QLNRGVSFAEENE

SLDDQNISIAGHTFIDRPNYQFTNLKAAKKGSMVYFKVGNETRKYKMTSI

R<u>N</u>VKPT<u>A</u>VEVLDEQKGKDKQLTLITCDDYNE<u>E</u>TGVWE<u>T</u>RKIFVATEVK.

As will be appreciated, amino acids 2-148 of the above sequence correspond to amino acids 60-206 of the full length *S. aureus* SrtA sequence (the catalytic domain). For example, the "R" residue at position 36 of SEQ ID NO: 89 corresponds to the "P" residue at position 94 in SEQ ID NO: 87 or 88. It is also contemplated in some embodiments to use sortase variants that have other substitutions at one or more of positions 94, 160, 165, 190, and 196 (numbered according to the numbering of SEQ ID NO: 87 or 88), e.g., wherein such substitutions utilize an amino acid that would be a conservative substitution at the relevant position as compared with the sequence of SEQ ID NO: 89.

The use of sortases found in any gram-positive organism, such as those mentioned herein and/or in the references (including databases) cited herein is contemplated in the context of some embodiments of this invention. Also contemplated is the use of sortases found in gram negative bacteria, e.g., *Colwellia psychrerythraea, Microbulbifer degradans, Bradyrhizobium japonicum, Shewanella oneidensis*, and *Shewanella putrefaciens*. Such sortases recognize sequence motifs outside the LPXTX consensus, for example, LP[Q/K]T[A/S]T (SEQ ID NO: 96). In keeping with the variation tolerated at position 3 in sortases from gram-positive organisms, a sequence motif LPXT[A/S], e.g., LPXTA (SEQ ID NO:30) or LPSTS (SEQ ID NO:31) may be used.

Those of skill in the art will appreciate that any sortase recognition motif known in the art can be used in some embodiments of this invention, and that the invention is not limited in this respect. For example, in some embodiments the sortase recognition motif is selected from: LPKTG (SEQ ID NO:32), LPITG (SEQ ID NO:33), LPDTA (SEQ ID NO:34), SPKTG (SEQ ID NO:35), LAETG (SEQ ID NO:36), LAATG (SEQ ID NO:37), LAHTG (SEQ ID NO:38), LASTG (SEQ ID NO:39), LAETG (SEQ ID NO:40), LPLTG (SEQ ID NO:41), LSRTG (SEQ ID NO:42), LPETG (SEQ ID NO:2), VPDTG (SEQ ID NO:43), IPQTG (SEQ ID NO:44), YPRRG (SEQ ID NO:45), LPMTG (SEQ ID NO:46), LPLTG (SEQ ID NO:47), LAFTG (SEQ ID NO:48), LPQTS (SEQ ID NO:49), it being understood that in various embodiments of the invention the fifth residue may be replaced with any other amino acid residue. For example, the sequence used may be LPXT, LAXT, LPXA, LGXT, IPXT, NPXT, NPQS (SEQ ID NO:50), LPST (SEQ ID NO:51), NSKT (SEQ ID NO:52), NPQT (SEQ ID NO:53), NAKT (SEQ ID NO:54), LPIT (SEQ ID NO:55), LAET (SEQ ID NO:56), or NPQS (SEQ ID NO:57). The invention encompasses embodiments in which 'X' in any sortase recognition motif disclosed herein or known in the art is amino acid, for example, any naturally occurring or any non-naturally occurring amino acid. In some embodiments, X is selected from the 20 standard amino acids found most commonly in proteins found in living organisms. In some embodiments, e.g., where the recognition motif is LPXTG (SEQ ID NO:1) or LPXT, X is D, E, A, N, Q, K, or R. In some embodiments, X in a particular recognition motif is selected from those amino acids that occur naturally at position 3 in a naturally occurring sortase substrate. For example, in some embodiments X is selected from K, E, N, Q, A in an LPXTG (SEQ ID NO:1) or LPXT motif where the sortase is a sortase A. In some embodiments X is selected from K, S, E, L, A, N in an LPXTG (SEQ ID NO:1) or LPXT motif and a class C sortase is used.

In some embodiments, a sortase recognition sequence further comprises one or more additional amino acids, e.g., at the N- or C-terminus. For example, one or more amino acids (e.g., up to five amino acids) having the identity of amino acids found immediately N-terminal to, or C-terminal to, a five amino acid recognition sequence in a naturally occurring sortase substrate may be incorporated. Such additional amino acids may provide context that improves the recognition of the recognition motif.

The term "sortase substrate," as used herein, refers to any molecule that is recognized by a sortase, for example, any molecule that can partake in a sortase-mediated transpeptidation reaction. In some embodiments, "sortase substrate" and "sortase substrate peptide" are used interchangeably. A typical sortase-mediated transpeptidation reaction involves a substrate comprising a C-terminal sortase recognition motif, e.g., an LPXTX motif, and a second substrate comprising an N-terminal sortase recognition motif, e.g., an N-terminal polyglycine or polyalanine. In some embodiments, a sortase recognition motif, though described as being "C-terminal" or N-terminal," is not required to be at the immediate C- or N-terminus. For example, in some embodiments, other amino acids, for example a tag (e.g., a 6xHis-tag (SEQ ID NO: 133)), are found at the immediate C-terminus of a protein comprising a C-terminal sortase recognition motif, and the C-terminal sortase recognition motif is adjacent (e.g., within 5, 10, 15 or 20 amino acids) thereto. A sortase substrate may be a peptide or a protein, for example, a peptide comprising a sortase recognition motif such as an LPXTX motif or a polyglycine or polyalanine, wherein the peptide is conjugated to an agent, e.g., a radiolabeled compound or small molecule. Accordingly, both proteins and non-protein molecules can be sortase substrates as long as they comprise a sortase recognition motif. Some examples of sortase substrates are described in more detail elsewhere herein and additional suitable sortase substrates will be apparent to the skilled artisan. The invention is not limited in this respect.

The term "sortagging," as used herein, refers to the process of adding a tag or agent, e.g., a moiety or molecule, for example, a radiolabeled compound or small molecule, onto a target molecule, for example, a target protein for use in PET applications via a sortase-mediated transpeptidation reaction. Examples of additional suitable tags include, but are not limited to, amino acids, nucleic acids, polynucleotides, sugars, carbohydrates, polymers, lipids, fatty acids, and small molecules. Other suitable tags will be apparent to those of skill in the art and the invention is not limited in this aspect. In some embodiments, a tag comprises a sequence useful for purifying, expressing, solubilizing, and/or detecting a polypeptide. In some embodiments, a tag can serve multiple functions. In some embodiments, a tag comprises an HA, TAP, Myc, 6xHis (SEQ ID NO: 133), Flag, streptavidin, biotin, or GST tag, to name a few examples. In some embodiments, a tag is cleavable, so that it can be removed, e.g., by a protease. In some embodiments, this is achieved by including a protease cleavage site in the tag, e.g., adjacent or linked to a functional portion of the tag. Exemplary proteases include, e.g., thrombin, TEV protease, Factor Xa, PreScission protease, etc. In some embodiments, a "self-cleaving" tag is used. See, e.g., Wood et al., International PCT Application PCT/US2005/05763, filed on Feb. 24, 2005, and published as WO/2005/086654 on Sep. 22, 2005.

The term "subject" includes, but is not limited to, vertebrates, more specifically a mammal (e.g., a human, horse, pig, rabbit, dog, sheep, goat, non-human primate, cow, cat, guinea pig or rodent), a fish, a bird or a reptile or an amphibian. In some embodiments, the subject is a human subject. As used herein, "patient" refers to a subject afflicted with a disease or disorder. The term "patient" includes human and veterinary subjects.

The term "target protein," as used herein in the context of sortase-mediated modification of proteins, refers to a protein that is modified by the conjugation of an agent, for example a radioactive agent that renders the protein suitable for diagnostic and/or therapeutic applications such as PET. The term "target protein" may refer to a wild type or naturally occurring form of the respective protein, or to an engineered form, for example, to a recombinant protein variant comprising a sortase recognition motif not contained in a wild-type form of the protein. The term "modifying a target protein," as used herein in the context of sortase-mediated protein modification, refers to a process of altering a target protein comprising a sortase recognition motif via a sortase-mediated transpeptidation reaction. Typically, the modification leads to the target protein being conjugated to an agent, for example, a peptide, protein, detectable label, or small molecule. In certain embodiments, the modification provides radiolabeled proteins.

The terms "thiosemicarbazide" or "thiosemicarbazide group," are used interchangeably herein, and refer to functional groups having the general formula:

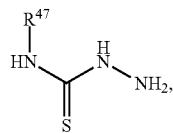

wherein $R^{47}$ is optionally substituted aliphatic, optionally substituted heteroaliphatic, optionally substituted aryl, optionally substituted heteroaryl, or optionally substituted heterocyclyl. In some embodiments, $R^{47}$ is an optionally substituted amino acid. In certain embodiments, the amino acid is within a peptide chain.

The term "thiosemicarbazone," as used herein, refers to compound having the general formula:

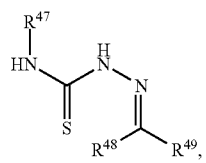

wherein each of $R^{47}$, $R^{48}$, and $R^{49}$ is independently optionally substituted aliphatic, optionally substituted heteroaliphatic, optionally substituted aryl, optionally substituted heteroaryl, or optionally substituted heterocyclyl In some embodiments, at least one of $R^{47}$, $R^{48}$, and $R^{49}$ is an optionally substituted amino acid. The term "thiosemicarbazone linkage," as used herein, refers to the formula:

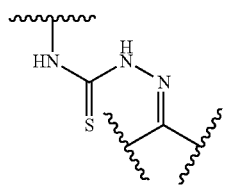

DETAILED DESCRIPTION OF CERTAIN EMBODIMENTS

Site-specific enzymatic labeling of proteins has emerged as a general method for derivatizing proteins with various types of modifications. For example, the transpeptidation reaction catalyzed by sortases can be used for various types of modifications. For conventional sortase modifications, target proteins are engineered to include a sortase recognition motif (e.g., LPXTG; SEQ ID NO:1) near their C-termini. When incubated with peptides containing one or more N-terminal glycine residues and a sortase, these sortase substrates undergo a transacylation reaction resulting in the exchange of residues C-terminal to the threonine residue in the case of the LPXTG (SEQ ID NO: 1) recognition sequence with the oligoglycine peptide, resulting in the protein C-terminus being ligated to the N-terminus of the peptide.

This invention is based, at least in part, on the recognition that sortases can be exploited to conjugate a variety of moieties to diagnostic and/or therapeutic proteins. Such sortase-mediated conjugation (e.g., "sortagging") approaches can be used to confer new functions to diagnostic/therapeutic proteins. For example, the conjugation of a radioactive agent (e.g., a radiolabel) to a desired protein that binds to specific tissues or cells (e.g., an antibody) allows for the use of such in positron emission tomography (PET), single-photon emission computed tomography (SPECT), or combined imaging methods such as PET/CT (PET with concurrent computed tomography imaging) or PET/MRI (PET with concurrent magnetic resonance imaging). For another example, sortase-mediated conjugation of radionuclides to therapeutic proteins or antibodies may further provide tumoricidal effects, e.g., in the treatment of cancer.

Some aspects of this disclosure provide methods, reagents, compositions, systems, and kits that can be used to modify proteins, for example, by conjugating such proteins to an agent or molecule comprising a radionuclide. Also provided are reagents and techniques which allow for the conjugation of any agent or molecule comprising a carbonyl group (e.g., an aldehyde or ketone) or a click chemistry handle to a sortase peptide substrate. Such modified substrates, in turn, can be conjugated to a protein of interest using the sortase-mediated transpeptidation techniques described herein. Notably, many commercially available reagents can be employed using the methodology provided herein, which further provides for efficiently and reproducibly radiolabeling proteins of interest.

$^{18}$F-fludeoxyglucose (FDG) is an analog of glucose wherein the radioactive isotope fluorine-18 ($^{18}$F) is substituted for the typical hydroxyl group at the 2' position of glucose. The uptake of $^{18}$F-FDG by tissues is a marker for the tissue uptake of glucose, which in turn is closely correlated with certain types of tissue metabolism. After $^{18}$F-FDG is injected into a patient, a PET scanner can form two dimensional or three dimensional images of the distribution of $^{18}$F-FDG within the body. The images can be assessed by a nuclear medicine physician or radiologist to provide diagnoses of various medical conditions. Because of the wide use and availability of FDG, methods and reagents provided herein were developed, in part, to utilize FDG as a ready source of $^{18}$F for radiolabeling proteins of interest, e.g., proteins suitable for PET diagnostic/therapeutic applications.

However, any (radioactive) molecule or agent can be utilized in the present invention. For example, as described in Example 2, another readily available source of $^{18}$F, $^{18}$F sodium fluoride ($^{18}$F—NaF) can be used, in a substitution reaction, with sortagging technology and click chemistry reactions such as a tetrazine (Tz)/trans-cyclooctene (TCO) reverse-electron demand Diels-Alder cycloaddition reaction to modify proteins (e.g., antibodies). As another example, described in Example 3, a tetrazine-aminooxy molecule can be reacted with $^{18}$F-FDG to generate an 18F-labeled click chemistry handle. This radiolabeled click chemistry handle may be used to label a pre-prepared sortagged protein (e.g., VHH-TCO) to form a final $^{18}$F-labeled protein.

In some embodiments, the molecule or agent comprises a carbonyl group or a click chemistry handle. Molecules and agents that include a carbonyl group also include those that can form a carbonyl group through isomerization. For example, reducing sugars, such as glucose and FDG, can isomerize to form a linear molecule having an aldehyde group, and are thus amenable for use in the methods provided herein.

Certain aspects of the present invention make use of electrophile-nucleophile pairs to generate sortase substrate peptides comprising desired modifications, such as the incorporation of a radiolabel. These sortase substrate peptides, can then be used to modify proteins of interest using the sortase-mediated transpeptidation methods described herein. For example, carbonyl groups (e.g., aldehydes and ketones) react with aminooxy groups, hydrazides, and thiosemicarbazides to form oximes, hydrazones, and thiosemicarbazones, respectively. Thus, modifying agents (e.g., radioactive agents such as FDG, $^{14}$C—(U)-glucose, etc.) that include a carbonyl can be chemically joined to sortase substrate peptides that comprise an aminooxy functional group, hydrazide, or thiosemicarbazide. Without wishing to be bound by any particular theory, it is believed that the alpha effect renders the nucleophilic nitrogen atoms of aminooxy groups, hydrazides, and thiosemicarbazides less basic but more nucleophilic than an amino group. Because of this enhanced nucleophilicity, these reactions are thermodynamically favorable in water. When ligation reactions are performed at mildly acidic pH (e.g., 4.0-5.5) enhanced selectivity is observed since the attenuated basicity of aminooxy groups, hydrazides, and thiosemicarbazides leaves these nucleophiles unprotonated while potentially competing amino groups are protonated (and therefore are not nucleophilic). Oxime, hydrazone, and thiosemicarbazone linkages are stable from pH 5 to pH 7, and have been used extensively in chemoselective ligation applications including e.g., the formation of peptide conjugates, in vivo protein labeling, and the generation of enzyme inhibitors (See, e.g., Rashidian et al., "A highly efficient catalyst for oxime ligation and hydrazone-oxime exchange suitable for bioconjugation." *Bioconjug. Chem.* 2013 Mar. 20; 24(3):333-42; Langenhan et al., "Recent Carbohydrate-Based Chemoselective Ligation Applications." *Current Organic Synthesis.* 2005; 2, 59-81; the entire contents of each are incorporated herein by reference).

In another embodiment, a sortase substrate peptide is first tethered to a protein of interest using a sortase-mediated transpeptidation reaction and subsequently modified to incorporate a label (e.g., a radiolabel, such as $^{18}$F). For example, a sortase substrate peptide comprising a click-chemistry handle may be tethered to a protein of interest using a sortase-mediated transpeptidation reaction. The protein of interest, containing the complementary click chemistry handle, is then labeled (e.g., with a radiolabel) using any suitable click chemistry reaction known in the art.

Another means of modifying proteins and peptide substrates for use in the methods described herein makes use of the tetrazine (Tz)/trans-cyclooctene (TCO) reverse-electron demand Diels-Alder cycloaddition reaction (See, e.g., Example 2, FIG. 4). The TCO-tetrazine reaction is the fastest known bioorthogonal reaction to date, with an estimated second order rate constant of 2000±400 $M^{-1}s^{-1}$ (Blackman et al., "The Tetrazine Ligation: Fast Bioconjugation based on Inverse-electron-demand Diels-Alder Reactivity." *J. Am. Chem. Soc.* 2008; 130, 13518-13519). Additionally, use of catalysts, as described herein, allow for the quick formation of these linkages, for example, in about 5 minutes, in about 10 minutes, in about 25 minutes, or in about 30 minutes. Once modified, these sortase substrate peptides may be used in a sortagging reaction which conjugates the substrate peptide to a desired protein (e.g., comprising a complementary sortase recognition motif), for example, in about 10 minutes, in about 25 minutes, in about 30 minutes or in about 45 minutes. Alternatively sortase substrate peptides may be modified following the sortagging reaction. These reaction times are amenable to the use of $^{18}$F-labeled, or other radioactive agents, and therefore represent a novel, fast, and facile method to generate radiolabeled proteins for use in diagnostic and/or therapeutic applications such as PET.

Radiolabeled Proteins

Another aspect of the present invention provides radiolabeled proteins. The radiolabeled proteins can be prepared from modified proteins of Formula (I).

In certain embodiments, provided herein is a modified protein of Formula (I):

(I)

wherein
  $L^1$ is a linker comprising at least four amino acids formed by enzymatic conjugation between two enzyme recognition sequences; and
  $R^1$ comprises a reactive group capable of undergoing a click chemistry reaction.

As generally defined herein, $L^1$ is a linker formed by enzymatic conjugation between two enzyme recognition sequences. In certain embodiments, $L^1$ comprises at least four amino acids. In certain embodiments, $L^1$ comprises at least five amino acids. In certain embodiments, $L^1$ comprises at least six amino acids. In certain embodiments, $L^1$ comprises at least seven amino acids. In certain embodiments, $L^1$ is a linker formed by sortase-mediated transpeptidation of two sortase recognition sequences. In certain embodiments, $L^1$ is -LPXTGGGK- (SEQ ID NO: 104), -LPXTGGG- (SEQ ID NO: 105), -NPXTGGGK- (SEQ ID NO: 106), -NPXTGGG- (SEQ ID NO: 107), -LPXTAAA- (SEQ ID NO: 108), -NPXTAAA- (SEQ ID NO: 109), -LPXTGGGG- (SEQ ID NO: 110), or -LPGAG- (SEQ ID NO: 111), wherein each instance of X is independently an amino acid. In certain embodiments, X is E. In certain embodiments, X is Q. In certain embodiments, X is K.

In certain embodiments, the modified protein is formed by enzymatic conjugation of

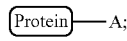

and a compound of Formula (a): B—R$^1$ (a), wherein each of A and B is independently an enzyme recognition sequence. In certain embodiments, the modified protein is formed by sortase-mediated transpeptidation of

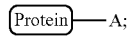

and the compound of Formula (a): B—R$^1$ (a), wherein A comprises a C-terminal sortase recognition sequence, and B comprises a N-terminal sortase recognition sequence; or A comprises a N-terminal sortase recognition sequence, and B comprises a C-terminal sortase recognition sequence.

In certain embodiments, A comprises LPXTX or NPXTX, and B comprises an oligoglycine or an oligoalanine sequence; wherein each instance of X is independently an amino acid. In certain embodiments, B comprises LPXTX or NPXTX, and A comprises an oligoglycine or an oligoalanine sequence; wherein each instance of X is independently an amino acid. In certain embodiments, A is LPETG (SEQ ID NO:2), LPETA (SEQ ID NO:3), NPQTN (SEQ ID NO:4), or NPKTG (SEQ ID NO:5), and B is GGG or AAA. In certain embodiments, A comprises an oligoglycine or an oligoalanine sequence, and B comprises LPXTX or NPXTX, wherein each instance of X is independently an amino acid. In certain embodiments, B is LPETG (SEQ ID NO:2), LPETA (SEQ ID NO:3), NPQTN (SEQ ID NO:4), or NPKTG (SEQ ID NO:5), and A is GGG or AAA.

As used herein, the enzyme recognition sequence is an amino acid sequence recognized by a transamidase enzyme. In certain embodiments, the transamidase recognition sequence is a sortase recognition sequence or a sortase recognition motif. In certain embodiments, the sortase is sortase A (SrtA). In certain embodiments, the sortase is sortase B (SrtB).

As generally defined herein, R$^1$ is a reactive group capable of undergoing a click chemistry reaction.

Click chemistry is a chemical approach introduced by Sharpless in 2001 and describes chemistry tailored to generate substances quickly and reliably by joining small units together. See, e.g., Kolb, Finn and Sharpless *Angewandte Chemie International Edition* (2001) 40: 2004-2021; Evans, *Australian Journal of Chemistry* (2007) 60: 384-395). Exemplary coupling reactions (some of which may be classified as "Click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgon cycloaddition; thiolyne addition; imine formation; Michael additions (e.g., maleimide addition); Diels-Alder reaction and inverse electron demand Diels-Alder reaction; and [4+1] cycloadditions (e.g. between isonitriles (isocyanides) and tetrazines). In certain embodiments, the click chemistry reaction is a Diels-Alder reaction. It is to be understood that the click chemistry reaction may be followed by additional one or more chemical transformations. In certain embodiments, the click chemistry reaction is a Diels-Alder reaction followed by an retro-Diels-Alder reaction.

In certain embodiments, R$^1$ is a reactive group capable of undergoing a [3+2]cycloaddition. In certain embodiments, R$^1$ comprises a dipolarophile. In certain embodiments, R$^1$ comprises an alkynyl group. In certain embodiments, R$^1$ comprises a 1,3-dipole. In certain embodiments, R$^1$ comprises an azido. In certain embodiments, R$^1$ is a reactive group capable of undergoing a Diels-Alder cycloaddition. In certain embodiments, R$^1$ comprises a conjugated diene. In certain embodiments, R$^1$ comprises a tetrazine or a quadricyclane. In certain embodiments, R$^1$ comprises a tetrazine. In certain embodiments, R$^1$ comprises an unsubstituted tetrazine. In certain embodiments, R$^1$ comprises a substituted tetrazine.

In certain embodiments, R$^1$ is of Formula (i):

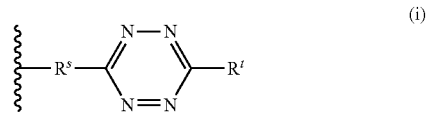

wherein
R$^t$ is hydrogen, optionally substituted aliphatic, optionally substituted heteroaliphatic, optionally substituted aryl, optionally substituted heteroaryl, or optionally substituted heterocyclyl; and
R$^s$ is a bond, optionally substituted aliphatic, optionally substituted heteroaliphatic, optionally substituted arylene, optionally substituted heteroarylene, or optionally substituted heterocyclylene.

As generally defined herein, R$^t$ is hydrogen, optionally substituted aliphatic, optionally substituted heteroaliphatic, optionally substituted aryl, optionally substituted heteroaryl, or optionally substituted heterocyclyl. In certain embodiments, R$^t$ is hydrogen. In certain embodiments, R$^t$ is optionally substituted aliphatic. In certain embodiments, R$^t$ is optionally substituted C$_{1-6}$ alkyl. In certain embodiments, R$^t$ is unsubstituted C$_{1-6}$ alkyl. In certain embodiments, R$^t$ is methyl or ethyl. In certain embodiments, R$^t$ is substituted C$_{1-6}$ alkyl. In certain embodiments, R$^t$ is optionally substituted aryl. In certain embodiments, R$^t$ is optionally substituted phenyl. In certain embodiments, R$^t$ is optionally substituted heteroaryl. In certain embodiments, R$^t$ is optionally substituted pyridine.

As generally defined herein, R$^s$ is a bond, optionally substituted aliphatic, optionally substituted heteroaliphatic, optionally substituted arylene, optionally substituted heteroarylene, or optionally substituted heterocyclylene. In certain embodiments, R$^s$ is a bond. In certain embodiments, R$^s$ is optionally substituted aliphatic. In certain embodiments, R$^s$ is optionally substituted C$_{1-6}$ alkyl. In certain embodiments, R$^s$ is unsubstituted C$_{1-6}$ alkyl. In certain embodiments, R$^s$ is methyl or ethyl. In certain embodiments, R$^s$ is substituted C$_{1-6}$ alkyl. In certain embodiments, R$^s$ is optionally substituted heteroaliphatic. In certain embodiments, R$^s$ is optionally substituted arylene. In certain embodiments, R$^s$ is optionally substituted phenyl. In certain embodiments, R$^s$ is optionally substituted heteroarylene. In certain embodiments, R$^s$ is optionally substituted pyridine.

In certain embodiments, R$^1$ comprises a dienophile. In certain embodiments, R$^1$ comprises an optionally substituted alkene. In certain embodiments, R¹ comprises a cyclooctene. In certain embodiments, R¹ comprises a substituted cyclooctene of the formula:

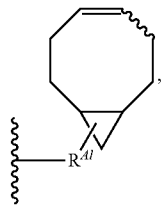

wherein $R^{A1}$ is a bond, optionally substituted aliphatic, optionally substituted heteroaliphatic, optionally substituted arylene, optionally substituted heteroarylene, or optionally substituted heterocyclylene. R¹ comprises a substituted cyclooctene of the formula:

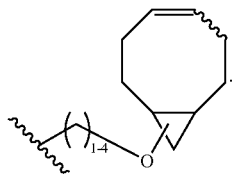

In certain embodiments, R¹ comprises a trans-cyclooctene. In certain embodiments, R¹ comprises a substituted trans-cyclooctene of the formula

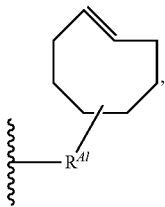

wherein $R^{A1}$ is as defined herein. In certain embodiments, R¹ comprises a substituted trans-cyclooctene of the formula

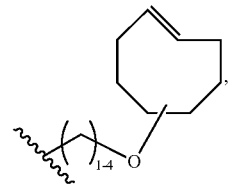

wherein $R^{A1}$ is as defined herein. In certain embodiments, R¹ comprises an unsubstituted trans-cyclooctene.

Another aspect of the invention provides a radioactive protein of Formula (II)

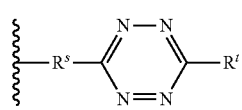

(II)

wherein
L¹ is a linker comprising at least four amino acids formed by enzymatic conjugation between two enzyme recognition sequences; and
L² is optionally substituted aliphatic, optionally substituted heteroaliphatic, optionally substituted arylene, optionally substituted heteroarylene, or optionally substituted heterocyclylene.

In certain embodiments, the linker L² is formed by a click chemistry reaction. In certain embodiments, the linker L² is formed by a [3+2] cycloaddition. In certain embodiments, the linker L² is formed by a Diels-Alder cycloaddition. In certain embodiments, the linker L² is formed by a Diels-Alder cycloaddition followed by one or more chemical transformations. In certain embodiments, the linker L² is formed by a Diels-Alder cycloaddition followed by retro-Diels-Alder reaction.

As generally defined herein, L² is optionally substituted aliphatic, optionally substituted heteroaliphatic, optionally substituted arylene, optionally substituted heteroarylene, or optionally substituted heterocyclylene. In certain embodiments, L² is optionally substituted aliphatic. In certain embodiments, L² is optionally substituted heteroaliphatic. In certain embodiments, L² is optionally substituted arylene. In certain embodiments, L² is optionally substituted cycloalkylene. In certain embodiments, L² is optionally substituted heteroarylene.

In certain embodiments, the radioactive protein of Formula (II) is formed by a click chemistry reaction of the modified protein of Formula (I) and a compound of Formula (b): ¹⁸F—R² (b), wherein R² is a reactive group capable of undergoing the click chemistry reaction.

As generally defined herein, R² is a reactive group capable of undergoing a click chemistry reaction. In certain embodiments, R² is a reactive unsaturated group capable of undergoing a [3+2] cycloaddition. In certain embodiments, R² comprises a dipolarophile. In certain embodiments, R² comprises an alkynyl group. In certain embodiments, R² comprises a 1,3-dipole. In certain embodiments, R² comprises an azido. In certain embodiments, R² is a reactive group capable of undergoing a Diels-Alder cycloaddition. In certain embodiments, R² comprises a conjugated diene. In certain embodiments, R² comprises a tetrazine or a quadricyclane. In certain embodiments, R² comprises a tetrazine. In certain embodiments, R² comprises an unsubstituted tetrazine. In certain embodiments, R² comprises a substituted tetrazine.

In certain embodiments, R² is of Formula (i):

$$\begin{array}{c}\text{(i)}\\ \xi\text{—}R^s\text{—}\underset{N=N}{\overset{N-N}{\diagdown}}\text{—}R^t\end{array}$$

wherein
$R^t$ is hydrogen, optionally substituted aliphatic, optionally substituted heteroaliphatic, optionally substituted aryl, optionally substituted heteroaryl, or optionally substituted heterocyclyl; and
$R^s$ is a bond, optionally substituted aliphatic, optionally substituted heteroaliphatic, optionally substituted arylene, optionally substituted heteroarylene, or optionally substituted heterocyclylene.

In certain embodiments, R² comprises a dienophile. In certain embodiments, R² comprises an optionally substituted alkene. In certain embodiments, R² comprises a cyclooctene.

In certain embodiments, $R^2$ comprises a trans-cyclooctene. In certain embodiments, $R^2$ comprises a substituted trans-cyclooctene. In certain embodiments, $R^2$ comprises an unsubstituted trans-cyclooctene.

In certain embodiments, a compound of Formula (b): $^{18}F$—$R^2$ (b), is of Formula (b-1):

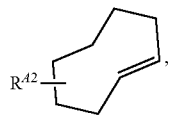

(b-1)

wherein $R^{A2}$ is optionally substituted aliphatic, optionally substituted heteroaliphatic, optionally substituted aryl, optionally substituted heteroaryl, or optionally substituted heterocyclyl; and $R^{A2}$ comprises $^{18}F$. In certain embodiments, $R^{A2}$ is optionally substituted aliphatic. In certain embodiments, $R^{A2}$ is optionally substituted heteroaliphatic. In certain embodiments, $R^{A2}$ is —O—$C_{1-6}$alkylene, wherein the $C_{1-6}$alkylene comprises $^{18}F$.

In certain embodiments, a compound of Formula (b) is of Formula (b-1-a):

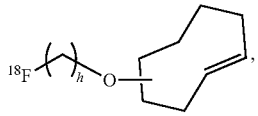

(b-1-a)

wherein h is an integer of 1 to 5, inclusive.

Compounds of Formula (b-1-a) can be prepared from a compound of Formula (b-1-a-i):

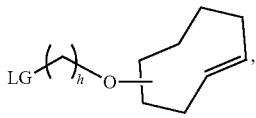

(b-1-a-i)

with a proper nucleophile comprising $^{18}F$, wherein h is as defined herein, LG is a leaving group. In certain embodiments, the compounds of Formula (b-1) can be prepared according to Scheme S6 or Scheme S6-a.

The term "leaving group" is given its ordinary meaning in the art of synthetic organic chemistry and refers to an atom or a group capable of being displaced by a nucleophile. Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties. In certain embodiments, LG is —OTs.

In certain embodiments, a compound of Formula (b) is of Formula (b-1-b):

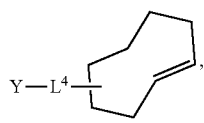

(b-1-b)

wherein $L^4$ and Y are as defined herein.

In certain embodiments, a compound of Formula (b) is of Formula (b-1-c):

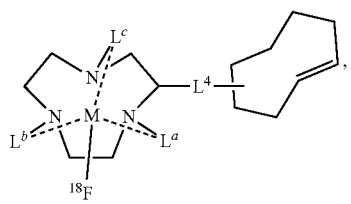

(b-1-c)

wherein $L^4$, M, $L^a$, $L^b$, and $L^c$ are as defined herein, and --- indicates a coordination bond or absent, as valency permits. In certain embodiments, ---- is a single coordination bond. In certain embodiments, --- is absent.

In certain embodiments, a compound of Formula (b) is of the formula:

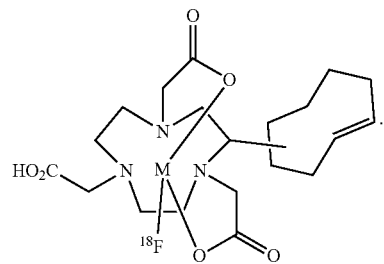

In certain embodiments, a compound of Formula (b): $^{18}F$—$R^2$ (b), is of Formula (b-2):

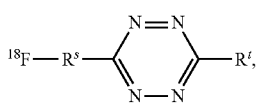

(b-2)

wherein $R^s$ and $R^t$ are as defined herein.

In certain embodiments, a compound of Formula (b) is of Formula (b-2-a):

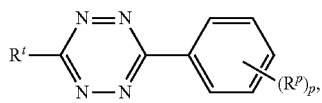

(b-2-a)

wherein $R^t$, $R^p$, and p are as defined herein.

In certain embodiments, a compound of Formula (b) is of Formula (b-2-a1):

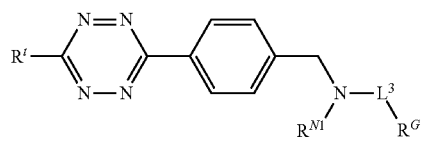

(b-2-a1)

wherein $R^t$, $R^{N1}$, $L^3$, $R^{q1}$, and q1 are as defined herein; and $R^G$ is an optionally substituted carbohydrate group; provided that $R^G$ comprises $^{18}F$.

A "carbohydrate group" or a "carbohydrate" refers to a monosaccharide or a polysaccharide (e.g., a disaccharide or oligosaccharide). Exemplary monosaccharides include, but are not limited to, natural sugars, such as allose, altrose, glucose, mannose, gulose, idose, galactose, talose, ribose, arabinose, xylose, and lyxose. Disaccharides are two joined monosaccharides. Exemplary disaccharides include, but are not limited to, sucrose, maltose, cellobiose, and lactose. Typically, an oligosaccharide includes between three and ten monosaccharide units (e.g., raffinose, stachyose). The carbohydrate group may be a natural sugar or a modified sugar. Exemplary modified sugars include, but are not limited to, sugars where the hydroxyl group is replaced with an amino group and/or alkyl group (e.g., such as desosamine), 2'-deoxyribose wherein a hydroxyl group is removed, 2'-fluororibose wherein a hydroxyl group is replace with a fluorine, or N-acetylglucosamine, or a nitrogen-containing form of glucose (e.g., 2'-fluororibose, deoxyribose, and hexose), and the like. Various carbohydrates are further described below and herein. Carbohydrates may exist in many different forms, for example, conformers, cyclic forms, acyclic forms, stereoisomers, tautomers, anomers, and isomers. In certain embodiments, $R^G$ is an optionally substituted glucose.

In certain embodiments, a compound of Formula (b) is of Formula (b-2-a2):

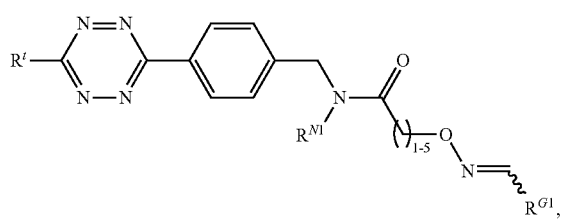

(b-2-a2)

wherein $R^t$, $R^{N1}$ are as defined herein; and $R^{G1}$ is an optionally substituted carbohydrate group or a fragment thereof; provided that $R^{G1}$ comprises $^{18}F$.

The oxime compounds of Formula (b-2-a2)

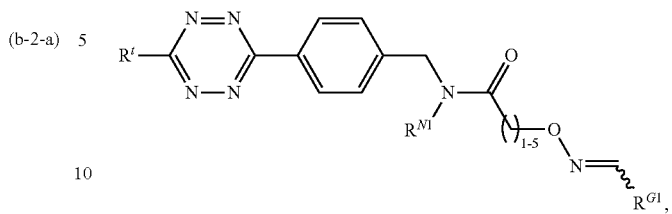

(b-2-a2)

can be prepared from optionally substituted tetrazine-aminooxy and a radiolabeled optionally substituted aldehyde of the formula $R^{as}$—CHO, wherein $R^{as}$ is optionally substituted aliphatic, optionally substituted heteroaliphatic, optionally substituted aryl, optionally substituted heteroaryl, or optionally substituted heterocyclyl (Scheme S1). In certain embodiments, $R^{as}$ is an optionally substituted carbohydrate group or a fragment thereof. In certain embodiments, $R^{as}$ is an optionally substituted glucose or a fragment thereof. In certain embodiments, the reaction is carried out in the presence of a catalyst. In certain embodiments, the catalyst is m-phenylenediamine, p-phenylenediamine, or p-anisidine. In certain embodiments, the catalyst is m-phenylenediamine. In certain embodiments, the molar ratio of the optionally substituted tetrazine-aminooxy to the catalyst is from about 10:1 to 1:10. In certain embodiments, the molar ratio of the optionally substituted tetrazine-aminooxy to the catalyst is from about 1:1 to 1:8. In certain embodiments, the molar ratio of the optionally substituted tetrazine-aminooxy to the catalyst is from about 1:1 to 1:6. In certain embodiments, the molar ratio of the optionally substituted tetrazine-aminooxy to the catalyst is from about 1:2 to 1:4. In certain embodiments, the molar ratio of the optionally substituted tetrazine-aminooxy to the catalyst is about 1:4.

Scheme S1.

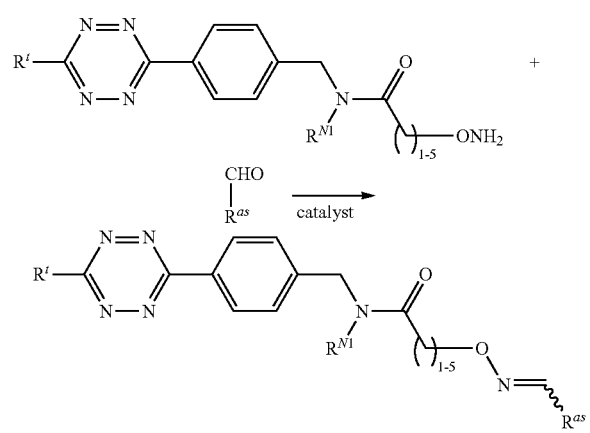

In certain embodiments, $R^{as}$ is an optionally substituted carbohydrate group or a fragment thereof, provided $R^{as}$ comprises $^{18}F$. In certain embodiments, $R^{as}$ is an optionally substituted glucose or a fragment thereof. In certain embodiments, $R^{as}$ is $^{18}F$-FDG of a fragment thereof.

As provided in Scheme S1, the resulting oxime product can be easily purified from the reaction mixture to the change in hydrophilicity.

In certain embodiments of Scheme S1, the excess of tetrazine-aminooxy can be captured by reacting with another water soluble carbohydrate. In certain embodiments, the water soluble carbohydrate is glucosamine 6-sulfate.

In certain embodiments, a compound of Formula (b) is of Formula (b-2-a2):

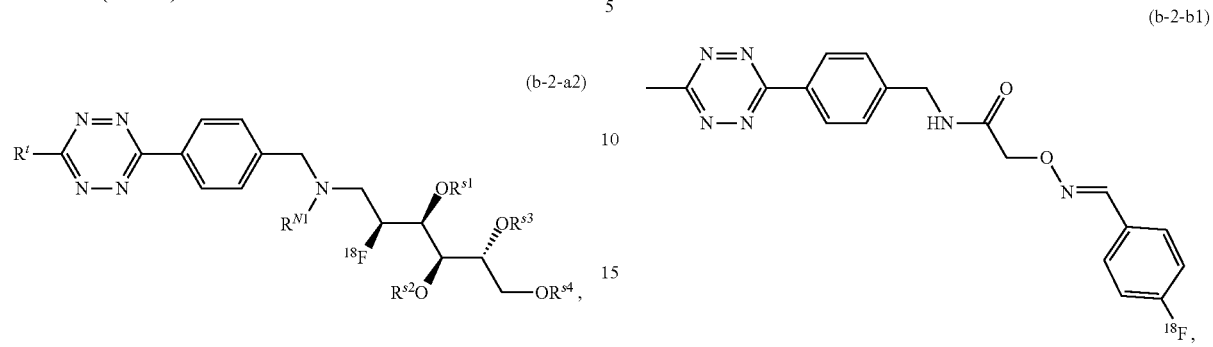

(b-2-a2)

wherein $R^t$, $R^{N1}$, $L^3$, $R^{s1}$, $R^{s2}$, $R^{s3}$, and $R^{s4}$ are as defined herein.

In certain embodiments, a compound of Formula (b) is of Formula (b-2-a3):

(b-2-a3)

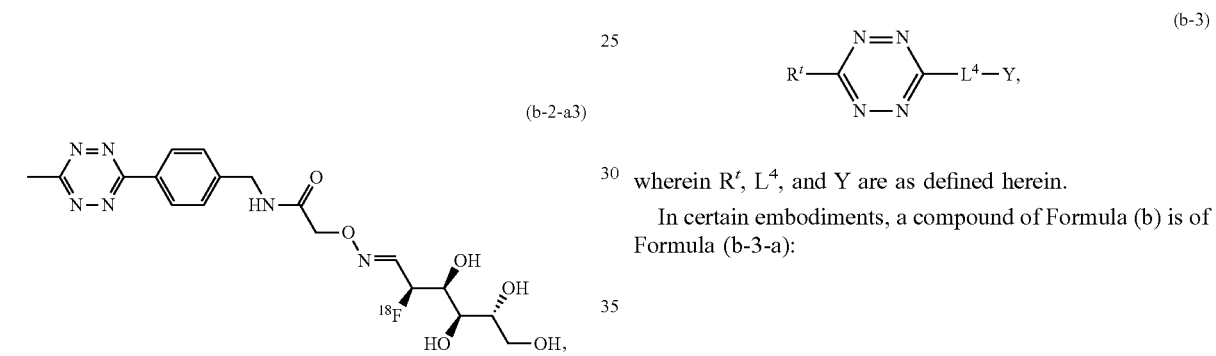

wherein $R^t$, $R^{N1}$, $L^3$, $R^{s1}$, $R^{s2}$, $R^{s3}$, and $R^{s4}$ are as defined herein.

In certain embodiments, a compound of Formula (b) is of Formula (b-2-b):

(b-2-b)

wherein $R^t$, $R^{N1}$, $L^3$, $R^{q1}$, and q1 are as defined herein.

In certain embodiments, a compound of Formula (b) is of Formula (b-2-b1):

(b-2-b1)

In certain embodiments, a compound of Formula (b) is of Formula (b-3):

(b-3)

wherein $R^t$, $L^4$, and Y are as defined herein.

In certain embodiments, a compound of Formula (b) is of Formula (b-3-a):

(b-3-a)

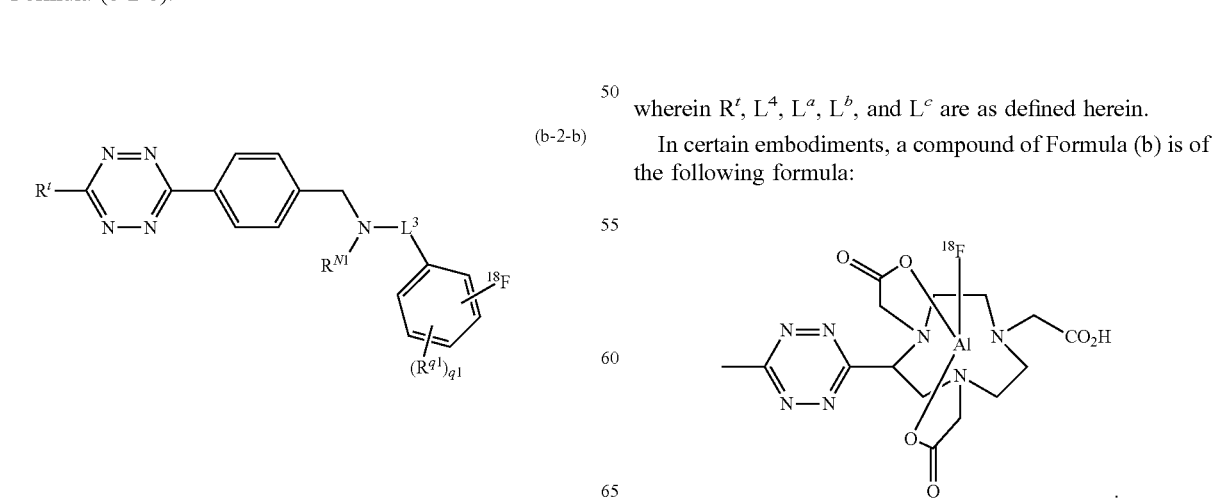

wherein $R^t$, $L^4$, $L^a$, $L^b$, and $L^c$ are as defined herein.

In certain embodiments, a compound of Formula (b) is of the following formula:

In certain embodiments, the linker $L^2$ is of Formula (ii):

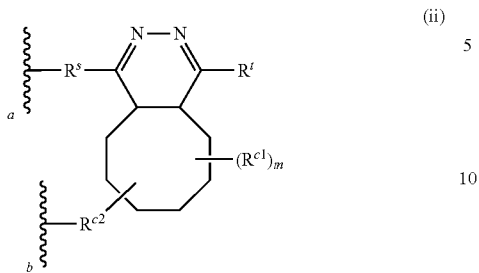

(ii)

wherein
- $R^t$ is hydrogen, optionally substituted aliphatic, optionally substituted heteroaliphatic, optionally substituted aryl, optionally substituted heteroaryl, or optionally substituted heterocyclyl;
- $R^s$ is a bond, optionally substituted aliphatic, optionally substituted heteroaliphatic, optionally substituted arylene, optionally substituted heteroarylene, or optionally substituted heterocyclylene;
- each instance of $R^{c1}$ is hydrogen, optionally substituted aliphatic, optionally substituted heteroaliphatic, optionally substituted aryl, optionally substituted heteroaryl, or optionally substituted heterocyclyl; or optionally two $R^{c1}$ taken with the intervening atoms to form an optionally substituted carbocyclyl or optionally substituted heterocyclyl ring;
- $R^{c2}$ is a bond, optionally substituted aliphatic, optionally substituted heteroaliphatic, optionally substituted arylene, optionally substituted heteroarylene, or optionally substituted heterocyclylene;
- m is 0, 1, 2, 3, 4, 5, 6, 7, or 8, as valency permits;
- a indicates point of attachment to $L^1$; and
- b indicates point of attachment to $^{18}F$.

In certain embodiments, m is 0. In certain embodiments, m is 1. In certain embodiments, m is 2. In certain embodiments, m is 3. In certain embodiments, m is 4.

As generally defined herein, each instance of $R^{c1}$ is independently hydrogen, optionally substituted aliphatic, optionally substituted heteroaliphatic, optionally substituted aryl, optionally substituted heteroaryl, or optionally substituted heterocyclyl. In certain embodiments, $R^{c1}$ is hydrogen. In certain embodiments, $R^{c1}$ is optionally substituted aliphatic. In certain embodiments, $R^{c1}$ is optionally substituted alkyl. In certain embodiments, $R^{c1}$ is optionally substituted heteroaliphatic. In certain embodiments, two $R^{c1}$ taken with the intervening atoms to form an optionally substituted carbocyclyl. In certain embodiments, two $R^{c1}$ taken with the intervening atoms to form an optionally substituted cyclopropyl.

As generally defined herein, $R^{c2}$ is a bond, optionally substituted aliphatic, optionally substituted heteroaliphatic, optionally substituted arylene, optionally substituted heteroarylene, or optionally substituted heterocyclylene. In certain embodiments, $R^{c2}$ is a bond. In certain embodiments, $R^{c2}$ is optionally substituted aliphatic. In certain embodiments, $R^{c2}$ is optionally substituted alkyl. In certain embodiments, $R^{c2}$ is optionally substituted heteroaliphatic. In certain embodiments, $R^{c2}$ is optionally substituted alkoxy. In certain embodiments, $R^{c2}$ is an optionally substituted amino group.

In certain embodiments, the linker $L^2$ is of Formula (ii-a):

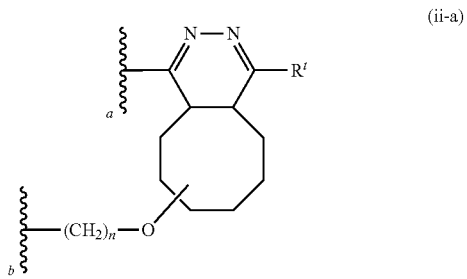

(ii-a)

wherein n is an integer between 1 and 8, inclusive.

In certain embodiments, n is 1. In certain embodiments, n is 2. In certain embodiments, n is 3. In certain embodiments, n is 4. In certain embodiments, n is 5. In certain embodiments, n is 6. In certain embodiments, n is 7. In certain embodiments, n is 8.

In certain embodiments, the linker $L^2$ is of Formula (ii-b):

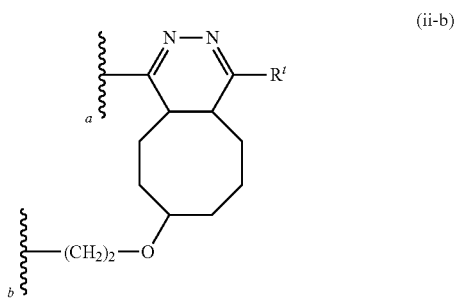

(ii-b)

wherein n is an integer between 1 and 8, inclusive.

In certain embodiments, the linker $L^2$ is of Formula (iii):

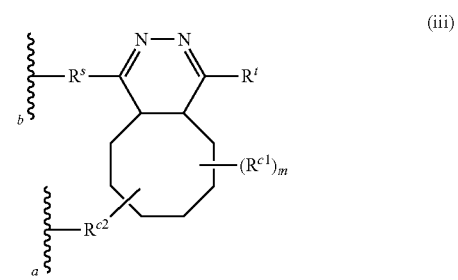

(iii)

wherein
- $R^t$ is hydrogen, optionally substituted aliphatic, optionally substituted heteroaliphatic, optionally substituted aryl, optionally substituted heteroaryl, or optionally substituted heterocyclyl;
- $R^s$ is a bond, optionally substituted aliphatic, optionally substituted heteroaliphatic, optionally substituted arylene, optionally substituted heteroarylene, or optionally substituted heterocyclylene;
- each instance of $R^{c1}$ is hydrogen, optionally substituted aliphatic, optionally substituted heteroaliphatic, optionally substituted aryl, optionally substituted heteroaryl, or optionally substituted heterocyclyl;
- $R^{c2}$ is a bond, optionally substituted aliphatic, optionally substituted heteroaliphatic, optionally substituted arylene, optionally substituted heteroarylene, or optionally substituted heterocyclylene;

m is 0, 1, 2, 3, 4, 5, 6, 7, or 8, as valency permits;

a indicates point of attachment to $L^1$; and b indicates point of attachment to $^{18}F$.

In certain embodiments, the linker $L^2$ is of Formula (iii-a):

In certain embodiments, wherein $-L^2-F^{18}$ is of Formula (iii-b):

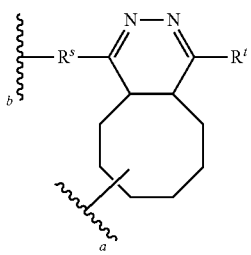

(iii-b)

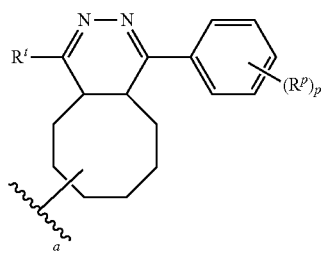

wherein each instance of $R^p$ is independently hydrogen, optionally substituted aliphatic, optionally substituted heteroaliphatic, optionally substituted aryl, optionally substituted heteroaryl, optionally substituted heterocyclyl, hydroxyl, or optionally substituted amino; provided at least one $R^p$ is not hydrogen and comprises $F^{18}$; and p is 1, 2, 3, 4, or 5.

In certain embodiments, p is 1. In certain embodiments, p is 2. In certain embodiments, p is 3. In certain embodiments, p is 4. In certain embodiments, p is 3. In certain embodiments, p is 5.

As generally defined herein, $R^p$ is hydrogen, optionally substituted aliphatic, optionally substituted heteroaliphatic, optionally substituted aryl, optionally substituted heteroaryl, optionally substituted heterocyclyl, hydroxyl, or optionally substituted amino; wherein at least one $R^p$ is not hydrogen and comprises $F^{18}$. In certain embodiments, $R^p$ is hydrogen. In certain embodiments, $R^p$ is optionally substituted aliphatic. In certain embodiments, RP is optionally substituted $C_{1-6}$ alkyl. In certain embodiments, $R^p$ is unsubstituted $C_{1-6}$ alkyl. In certain embodiments, $R^p$ is methyl or ethyl. In certain embodiments, $R^p$ is substituted $C_{1-6}$ alkyl. In certain embodiments, $R^p$ is optionally substituted aryl. In certain embodiments, $R^p$ is optionally substituted phenyl. In certain embodiments, $R^p$ is optionally substituted heteroaryl. In certain embodiments, $R^p$ is optionally substituted pyridine. In certain embodiments, least one RP is not hydrogen and comprises $F^{18}$.

In certain embodiments, wherein $-L^2-F^{18}$ is of Formula (iii-b1):

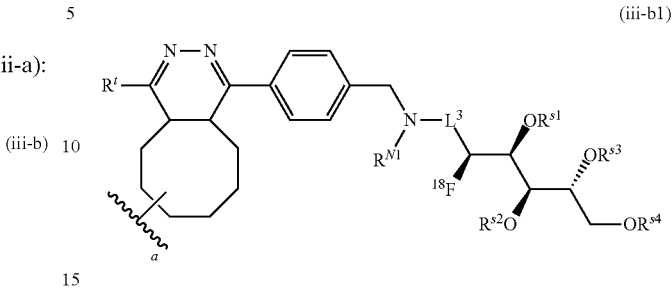

(iii-b1)

wherein $L^3$ is a bond, optionally substituted aliphatic, optionally substituted heteroaliphatic, optionally substituted arylene, optionally substituted heteroarylene, or optionally substituted heterocyclylene;

$R^{N1}$ is independently hydrogen, optionally substituted aliphatic, optionally substituted heteroaliphatic, optionally substituted aryl, or optionally substituted heteroaryl, or a nitrogen protecting group; and each of $R^{s1}$, $R^{s2}$, $R^{s3}$, and $R^{s4}$ is independently hydrogen, optionally substituted aliphatic, optionally substituted heteroaliphatic, optionally substituted aryl, or optionally substituted heteroaryl, or an oxygen protecting group.

As generally defined herein, $L^3$ is a bond, optionally substituted aliphatic, optionally substituted heteroaliphatic, optionally substituted arylene, optionally substituted heteroarylene, or optionally substituted heterocyclylene. In certain embodiments, $L^3$ is a bond. In certain embodiments, $L^3$ is optionally substituted aliphatic. In certain embodiments, $L^3$ is optionally substituted heteroaliphatic. In certain embodiments, $L^3$ comprises an oxime moiety. In certain embodiments, $L^3$ is of the formula

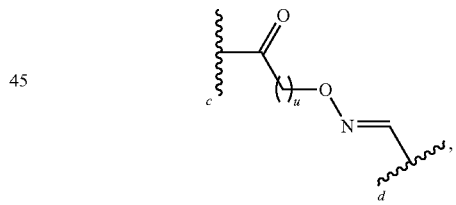

wherein c indicates the point of attachment to $-N-R^{N1}-$;
d indicates the point of attachment to $-CH^{18}F-$; and u is 1, 2, 3, 4, or 5. In certain embodiments, $L^3$ is C=O.

In certain embodiments, $R^{N1}$ is independently hydrogen. In certain embodiments, $R^{N1}$ is optionally substituted aliphatic. In certain embodiments, $R^{N1}$ is optionally substituted alkyl. In certain embodiments, $R^{N1}$ is an amino protectin group.

In certain embodiments, $R^{s1}$ is independently hydrogen. In certain embodiments, $R^{s1}$ is optionally substituted aliphatic. In certain embodiments, $R^{s1}$ is optionally substituted alkyl. In certain embodiments, $R^{s1}$ is an oxygen protectin group. In certain embodiments, $R^{s1}$ is acyl (e.g. acetyl).

In certain embodiments, $R^{s2}$ is independently hydrogen. In certain embodiments, $R^{s2}$ is optionally substituted aliphatic. In certain embodiments, $R^{s2}$ is optionally substituted alkyl. In certain embodiments, $R^{s2}$ is an oxygen protectin group. In certain embodiments, $R^{s2}$ is acyl (e.g. acetyl).

In certain embodiments, $R^{s3}$ is independently hydrogen. In certain embodiments, $R^{s3}$ is optionally substituted aliphatic. In certain embodiments, $R^{s3}$ is optionally substituted alkyl. In certain embodiments, $R^{s3}$ is an oxygen protectin group. In certain embodiments, $R^{s3}$ is acyl (e.g. acetyl).

In certain embodiments, $R^{s4}$ is independently hydrogen. In certain embodiments, $R^{s4}$ is optionally substituted aliphatic. In certain embodiments, $R^{s4}$ is optionally substituted alkyl. In certain embodiments, $R^{s4}$ is an oxygen protectin group. In certain embodiments, $R^{s4}$ is acyl (e.g. acetyl).

In certain embodiments, $R^{s1}$, $R^{s2}$, $R^{s3}$, and $R^{s4}$ are all hydrogen.

In certain embodiments, $R^{N1}$, $R^{s1}$, $R^{s2}$, $R^{s3}$, and $R^{s4}$ are all hydrogen.

In certain embodiments, $R^{N1}$, $R^{s1}$, $R^{s2}$, $R^{s3}$, and $R^{s4}$ are all hydrogen; and $R^t$ is optionally substituted aliphatic. In certain embodiments, $R^{N1}$, $R^{s1}$, $R^{s2}$, $R^{s3}$, and $R^{s4}$ are all hydrogen; and $R^t$ is optionally substituted $C_{1-6}$ alkyl. In certain embodiments, $R^{N1}$, $R^{s1}$, $R^{s2}$, $R^{s3}$, and $R^{s4}$ are all hydrogen; and $R^t$ is methyl or ethyl.

In certain embodiments, wherein $-L^2-F^{18}$ is of the formula

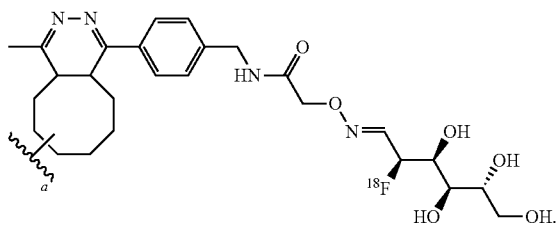

In certain embodiments, wherein $-L^2-F^{18}$ is of Formula (iii-b2):

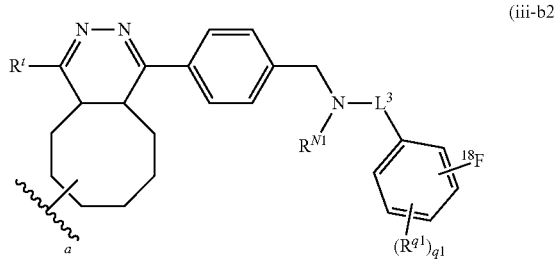

wherein
L³ is a bond, optionally substituted aliphatic, optionally substituted heteroaliphatic, optionally substituted arylene, optionally substituted heteroarylene, or optionally substituted heterocyclylene;
$R^{N1}$ is independently hydrogen, optionally substituted aliphatic, optionally substituted heteroaliphatic, optionally substituted aryl, or optionally substituted heteroaryl, or a nitrogen protecting group;
each instance of $R^{q1}$ is independently hydrogen, optionally substituted aliphatic, optionally substituted heteroaliphatic, optionally substituted aryl, optionally substituted heteroaryl, optionally substituted heterocyclyl, hydroxyl, or optionally substituted amino; and
q1 is 0, 1, 2, 3, or 4.

In certain embodiments, $R^t$ is optionally substituted aliphatic and $R^q$ is hydrogen. In certain embodiments, $R^t$ is optionally substituted $C_{1-6}$ alkyl; L³ is

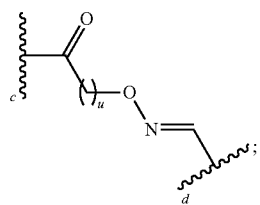

u is 1; and $R^{q1}$ is hydrogen.

In certain embodiments, $-L^2-F^{18}$ is of the formula:

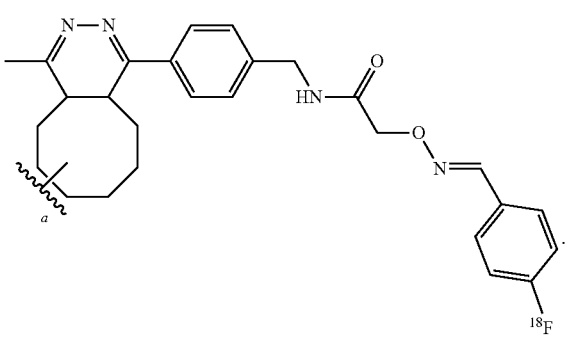

In certain embodiments, $-L^2-F^{18}$ is of Formula (iii-b3):

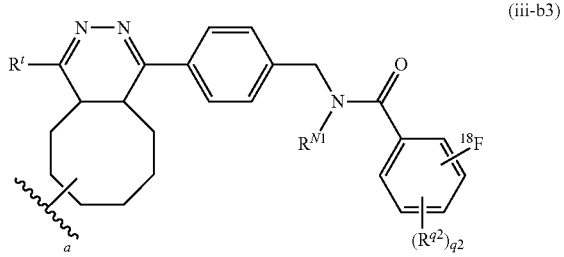

(iii-b3)

wherein
$R^{N1}$ is independently hydrogen, optionally substituted aliphatic, optionally substituted heteroaliphatic, optionally substituted aryl, or optionally substituted heteroaryl, or a nitrogen protecting group; and
each instance of $R^{q2}$ is independently hydrogen, optionally substituted aliphatic, optionally substituted heteroaliphatic, optionally substituted aryl, optionally substituted carbocyclyl, optionally substituted heteroaryl, optionally substituted heterocyclyl, hydroxyl, or optionally substituted amino; and
q2 is 0, 1, 2, 3, or 4.

In certain embodiments, q2 is 0. In certain embodiments, q2 is 1. In certain embodiments, q1 is 2. In certain embodiments, q2 is 3. In certain embodiments, q2 is 4.

In certain embodiments, $R^{q2}$ is hydrogen. In certain embodiments, $R^{q2}$ is optionally substituted aliphatic. In certain embodiments, $R^{q2}$ is optionally substituted $C_{1-6}$ alkyl.

In certain embodiments, $R^t$ is optionally substituted aliphatic and $R^{q2}$ is hydrogen.

In certain embodiments, -L²-F¹⁸ is of the formula:

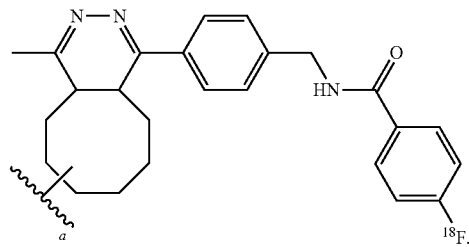

In certain embodiments, wherein -L²-F¹⁸ is of Formula (iii-b4):

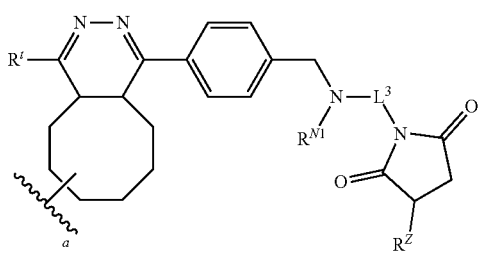

wherein
- L³ is a bond, optionally substituted aliphatic, optionally substituted heteroaliphatic, optionally substituted arylene, optionally substituted heteroarylene, or optionally substituted heterocyclylene;
- $R^{N1}$ is independently hydrogen, optionally substituted aliphatic, optionally substituted heteroaliphatic, optionally substituted aryl, or optionally substituted heteroaryl, or a nitrogen protecting group; and
- $R^Z$ is independently hydrogen, optionally substituted aliphatic, optionally substituted heteroaliphatic, optionally substituted aryl, or optionally substituted heteroaryl, wherein RZ comprise ¹⁸F.

In certain embodiments, wherein -L²-F¹⁸ is of Formula (iii-b4-a):

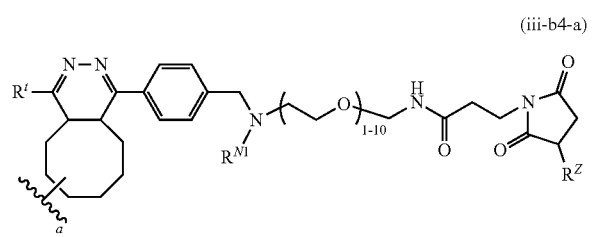

In certain embodiments, $R^Z$ is an optionally substituted thiol.

In certain embodiments, -L²-F¹⁸ is of Formula (iii-c):

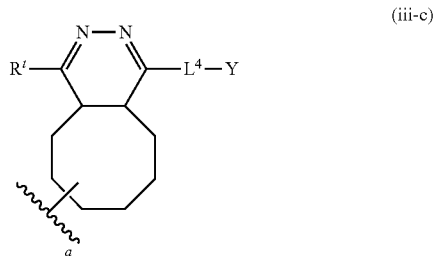

wherein
- Y is a ligand capable of chelating to a pharmaceutically acceptable metal complex comprising F¹⁸; and
- L⁴ is a bond, optionally substituted aliphatic, optionally substituted heteroaliphatic, optionally substituted arylene, optionally substituted cycloalkylene, optionally substituted heteroarylene, or optionally substituted heterocyclylene.

As generally defined herein, Y is a ligand capable of chelating to a pharmaceutically acceptable metal complex comprising F¹⁸. As used herein, a ligand refers to an ion or molecule (functional group) that binds to a central metal atom to form a coordination complex. The bonding between metal and ligand generally involves formal donation of one or more of the ligand's electron pairs. The nature of metal-ligand bonding can range from covalent to ionic. Exemplary monodentate ligands include, but are not limited to, CO, organonitriles (e.g., $CH_3CN$, $CH_3CH_2CN$), monosubstituted amines, disubstituted amines, trisubstituted amines, heterocyclyls (e.g., pyridine, piperidine), dialkylcyanamides, triphenylphosphine oxide, THF, DMF, or NMF. Exemplary bidentate ligands include, but are not limited to, 1,5-cyclooctadiene, norbornadiene, 1,2-ethylenediamine, tetramethylethylenediamine, 1,2-dimethoxyethane, diglyme, or 2,5-dithiahexane. Exemplary tridentate ligands include, but are not limited to, conjugated cyclic triene (e.g., cycloheptatriene), conjugated acyclic triene, arenes (e.g., benzene, toluene, xylene, mesitylene, naphthalene), tetraazamacrocyles (e.g., tetraazacyclododecane), polyamines (e.g., diethylenetriamine), and trithiocylononane. In certain embodiments, the ligand is a polydentate ligand. In certain embodiments, the ligand comprises 1,4,7-triazacyclononane-triacetic acid (NOTA), 1,4,7,10-tetraazacyclododecane-tetraacetic acid (DOTA), or triazacyclononane-phosphinate (TRAP).

The phrase "pharmaceutically acceptable" means that the metal complex is suitable for administration to a subject. In certain embodiments, the metal complex is a halide metal complex. In certain embodiments, the metal is a pharmaceutically acceptable metal. In certain embodiments, the metal is IIA or IIIA group metal. In certain embodiments, the metal is an early transition metal. In certain embodiments, the metal is Al.

In certain embodiments, L⁴ is a bond. In certain embodiments, L⁴ is an optionally substituted aliphatic. In certain embodiments, L⁴ is an optionally substituted heteroaliphatic.

In certain embodiments, -L²-F¹⁸ is of Formula (iii-c1):

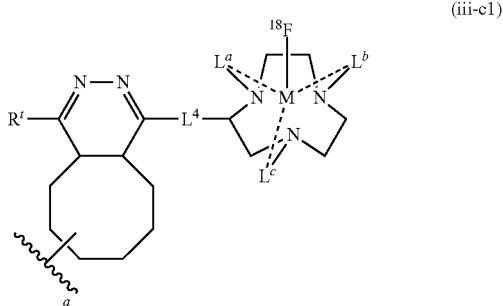

(iii-c1)

wherein
M is a pharmaceutically acceptable metal;
each of $L^a$, $L^b$, and $L^c$ is independently optionally substituted aliphatic, optionally substituted heteroaliphatic, optionally substituted arylene, optionally substituted cycloalkylene, optionally substituted heteroarylene, or optionally substituted heterocyclylene; and
"---" indicates a coordination bond or absend, as valency permits.

In certain embodiments, $L^a$ is optionally substituted aliphatic. In certain embodiments, $L^a$ is optionally substituted heteroaliphatic. In certain embodiments, $L^a$ is optionally substituted heteroalkylene. In certain embodiments, $L^a$ is —(CH₂)₁₋₃—C(=O)O—, wherein the chelation point to M is O. In certain embodiments, $L^a$ is —CH₂—C(=O)O—. In certain embodiments, $L^a$ is —(CH₂)₁₋₃—C(=O)OH, wherein the chelation point to M is O. In certain embodiments, $L^a$ is —CH₂—C(=O)OH.

In certain embodiments, $L^b$ is optionally substituted aliphatic. In certain embodiments, $L^b$ is optionally substituted heteroaliphatic. In certain embodiments, $L^b$ is optionally substituted heteroalkylene. In certain embodiments, $L^b$ is —(CH₂)₁₋₃—C(=O)O— wherein the chelation point to M is O. In certain embodiments, $L^b$ is —CH₂—C(=O)O—. In certain embodiments, $L^b$ is —(CH₂)₁₋₃—C(=O)OH, wherein the chelation point to M is O. In certain embodiments, $L^b$ is —CH₂—C(=O)OH.

In certain embodiments, $L^c$ is optionally substituted aliphatic. In certain embodiments, $L^c$ is optionally substituted heteroaliphatic. In certain embodiments, $L^c$ is optionally substituted heteroalkylene. In certain embodiments, $L^c$ is —(CH₂)₁₋₃—C(=O)O— wherein the point of attachment to M is O. In certain embodiments, $L^c$ is —CH₂—C(=O)O—. In certain embodiments, $L^c$ is —(CH₂)₁₋₃—C(=O)OH, wherein chelation point to M is O. In certain embodiments, $L^c$ is —CH₂—C(=O)OH.

As generally defined herein, "---" indicates the chelation formed between M and the ligand, as valency permits. In certain embodiments, M forms one chelating bond with the ligand. In certain embodiments, M forms two chelating bonds with the ligand. In certain embodiments, M forms three chelating bonds with the ligand.

In certain embodiments, -L²-F¹⁸ is of Formula (iii-c2):

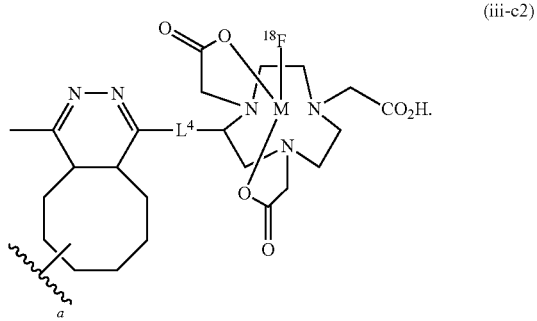

(iii-c2)

In certain embodiments, the radioactive protein is one of the following formulae (wherein the sequence LPXTGGG corresponds to SEQ ID NO: 105):

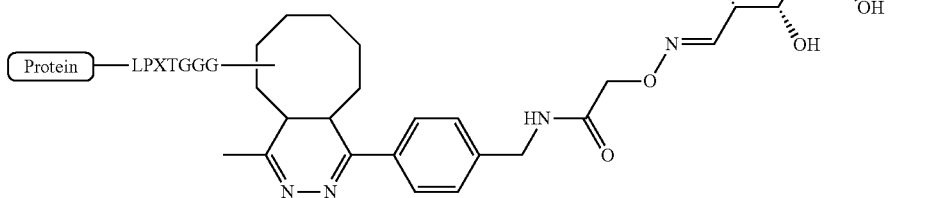

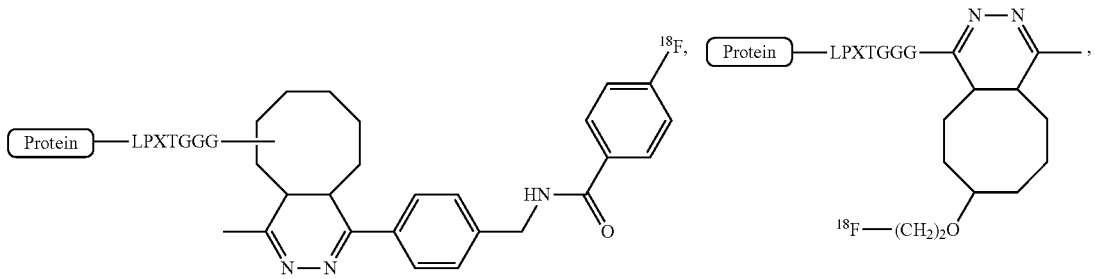

-continued

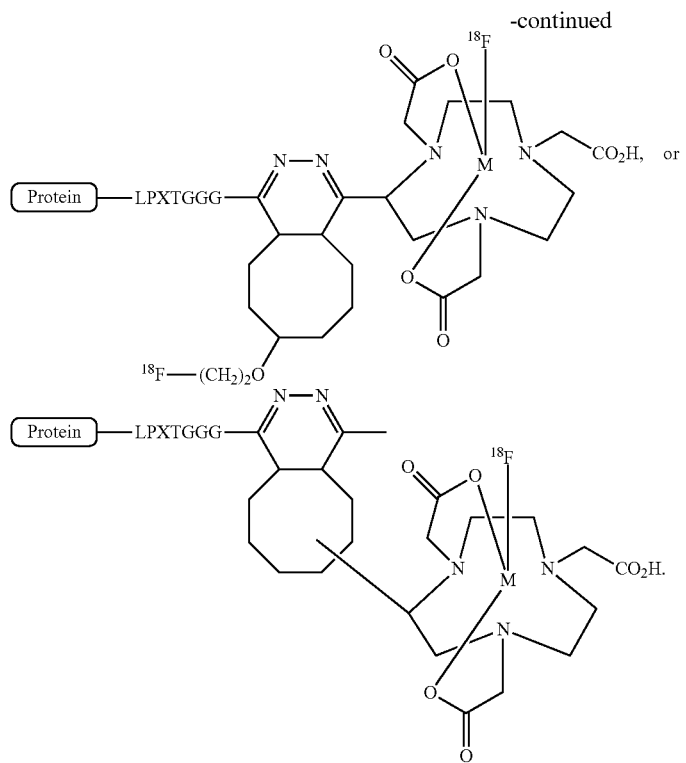

In certain embodiments, the linker $L^2$ is of one of the following formulae:

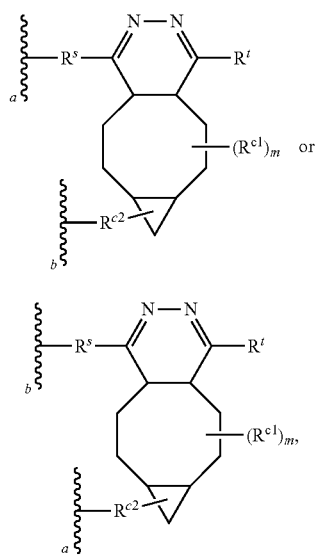

wherein $R^s$, $R^t$, $R^{c1}$, $R^{c2}$, and m are as defined herein.

In certain embodiments, provided herein is a radioactive protein of Formula (III)

wherein
$L^t$ is as defined herein; and
$R^3$ comprises a ligand capable of chelating to a pharmaceutically acceptable radioactive metal complex.

In certain embodiments, $L^1$-$R^3$ is of the following formula:

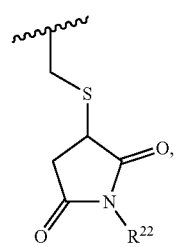

wherein $R^{z2}$ is optionally substituted aliphatic, optionally substituted heteroaliphatic, optionally substituted aryl, or optionally substituted heteroaryl, or a nitrogen protecting group; wherein $R^{z2}$ comprises a ligand capable of chelating to a pharmaceutically acceptable radioactive metal complex.

In certain embodiments, $R^3$ comprises mono-dentecate ligand. In certain embodiments, $R^3$ comprises a polydentecate ligand. In certain embodiments, $R^3$ comprises 1,4,7-triazacyclononane-triacetic acid (NOTA), 1,4,7,10-tetraazacyclododecane-tetraacetic acid (DOTA), or triazacyclononane-phosphinate (TRAP).

In certain embodiments, the metal is $^{64}Cu^{2+}$. In certain embodiments, the metal is $^{68}Ga^{3+}$.

In certain embodiments, the radioactive protein is one of the following formulae (wherein the sequence LPXTGGG corresponds to SEQ ID NO: 105):

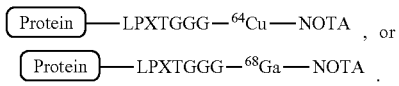

In certain embodiments, provided herein is a radioactive protein of Formula (IV)

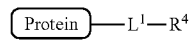

wherein
- $L^1$ is a linker comprising at least four amino acids formed by enzymatic conjugation between two enzyme recognition sequences;
- $R^4$ comprises a radioactive optionally substituted carbohydrate; and
- $R^4$ is linked to the C-terminus of the adjacent amino acid in $L^1$.

As generally defined herein, $R^4$ comprises a radioactive optionally substituted carbohydrate. In certain embodiments, $R^4$ comprises a radioactive optionally substituted glucose. In certain embodiments, $R^4$ comprises a radioactive glucose comprising $^{18}F$. In certain embodiments, $R^4$ comprises an optionally substituted glucose comprising $^{18}F$. In certain embodiments, $R^4$ is linked to the C-terminus of the adjacent amino acid in $L^1$. In certain embodiments, $R^4$ is linked to the side chain of the adjacent amino acid in $L^1$.

In certain embodiments, $R^4$ is of Formula (iv):

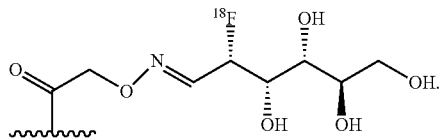 [SMILES: *C(=O)CO/N=C/[C@H]([18F])[C@@H](O)[C@H](O)[C@H](O)CO]

wherein
- v is 1, 2, 3, 4, or 5; and
- each of $R^{s5}$, $R^{s6}$, $R^{s7}$, and $R^{s8}$ is independently hydrogen, optionally substituted aliphatic, optionally substituted heteroaliphatic, optionally substituted aryl, or optionally substituted heteroaryl, or an oxygen protecting group.

In certain embodiments, $R^{s5}$ is independently hydrogen. In certain embodiments, $R^{s5}$ is optionally substituted aliphatic. In certain embodiments, $R^{s5}$ is optionally substituted alkyl. In certain embodiments, $R^{s5}$ is an oxygen protectin group. In certain embodiments, $R^{s5}$ is acyl (e.g. acetyl).

In certain embodiments, $R^{s6}$ is independently hydrogen. In certain embodiments, $R^{s6}$ is optionally substituted aliphatic. In certain embodiments, $R^{s6}$ is optionally substituted alkyl. In certain embodiments, $R^{s6}$ is an oxygen protectin group. In certain embodiments, $R^{s6}$ is acyl (e.g. acetyl).

In certain embodiments, $R^{s7}$ is independently hydrogen. In certain embodiments, $R^{s7}$ is optionally substituted aliphatic. In certain embodiments, $R^{s7}$ is optionally substituted alkyl. In certain embodiments, $R^{s7}$ is an oxygen protectin group. In certain embodiments, $R^{s7}$ is acyl (e.g. acetyl).

In certain embodiments, $R^{s8}$ is independently hydrogen. In certain embodiments, $R^{s8}$ is optionally substituted aliphatic. In certain embodiments, $R^{s8}$ is optionally substituted alkyl. In certain embodiments, $R^{s8}$ is an oxygen protectin group. In certain embodiments, $R^{s8}$ is acyl (e.g. acetyl).

In certain embodiments, $R^4$ is of the formula:

In certain embodiments, the radioactive protein is of the following formula (wherein the sequence LPXTGG corresponds to SEQ ID NO: 135):

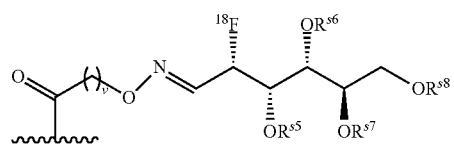

wherein $R^{s5}$, $R^{s6}$, $R^{s7}$, and $R^{s8}$ are as defined herein; and $L^G$ is optionally substituted aliphatic or optionally substituted heteroaliphatic.

In certain embodiments, $L^G$ is optionally substituted aliphatic. In certain embodiments, $L^G$ is optionally substituted $C_{1-10}$ alkyl. In certain embodiments, $L^G$ is optionally substituted heteroaliphatic. In certain embodiments, $L^G$ is of the formula:

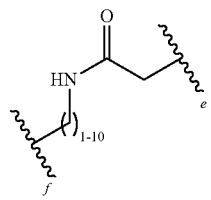

wherein e indicates the point of attachment to oxygen and f indicates the point of attachment to the alpha carbon of the amino acid.

In certain embodiments, the radioactive protein is of the following formula (wherein the sequence LPXTGG corresponds to SEQ ID NO: 135):

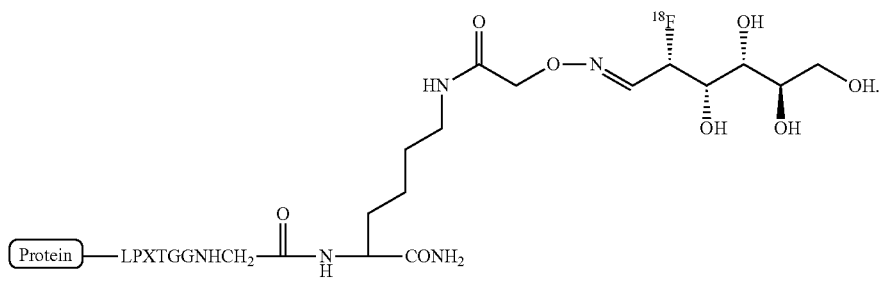

In certain embodiments, (Protein) is an antibody, a nuclear factor, a neuropeptide, a receptor protein, an enzyme, a structural protein, or a fragment thereof. In certain embodiments, (Protein) is an antibody or a fragment thereof. In certain embodiments, (Protein) is VHH or a fragment thereof.

Synthesis of Intermediates and Radiolabeled Proteins

The oxime compounds of Formula (b-2-a2)

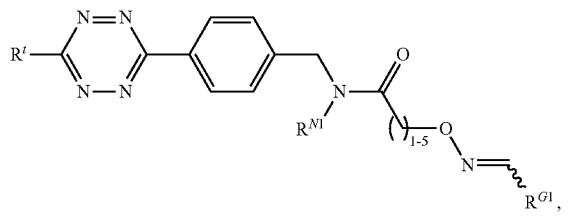

(b-2-a2)

can be prepared from optionally substituted tetrazine-aminooxy and a radiolabeled optionally substituted aldehyde or optionally substituted ketone of the formula $R^{as}$—CO—$R^{bs}$, wherein $R^{G1}$ is as defined herein; each of $R^{as}$ and $R^{bs}$ is independently hydrogen, optionally substituted aliphatic, optionally substituted heteroaliphatic, optionally substituted aryl, optionally substituted heteroaryl, or optionally substituted heterocyclyl; provided $R^{as}$ and $R^{bs}$ are not both hydrogen (Scheme S1).

Scheme S1.

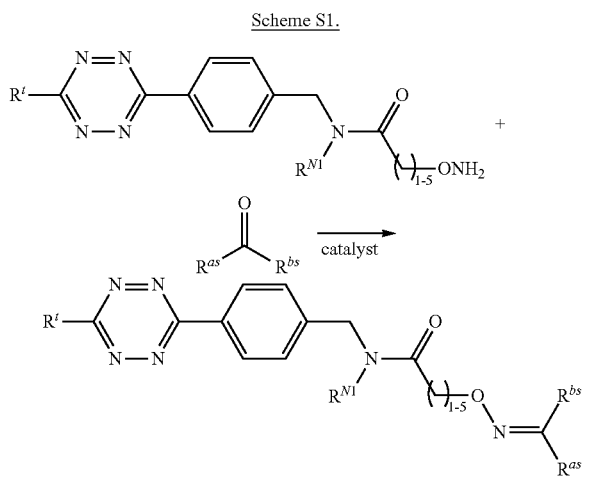

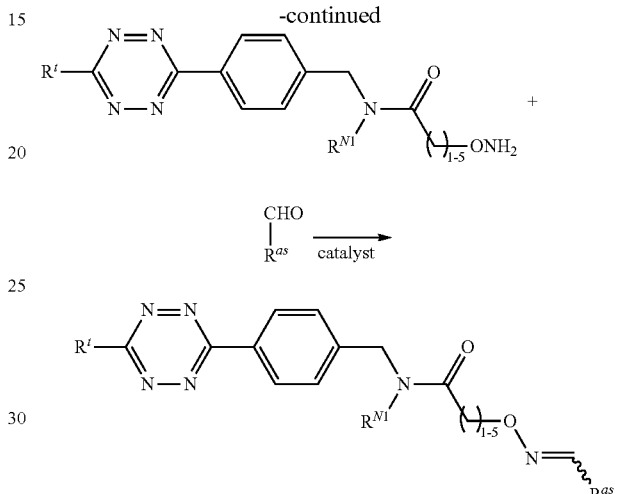

In certain embodiments, $R^{as}$ is an optionally substituted carbohydrate group or a fragment thereof. In certain embodiments, $R^{as}$ is an optionally substituted glucose or a fragment thereof. In certain embodiments, the reaction is carried out in the presence of a catalyst. In certain embodiments, the catalyst is m-phenylenediamine, p-phenylenediamine, or p-anisidine. In certain embodiments, the catalyst is m-phenylenediamine. In certain embodiments, the molar ratio of the optionally substituted tetrazine-aminooxy to the catalyst is from about 10:1 to 1:10. In certain embodiments, the molar ratio of the optionally substituted tetrazine-aminooxy to the catalyst is from about 1:1 to 1:8. In certain embodiments, the molar ratio of the optionally substituted tetrazine-aminooxy to the catalyst is from about 1:1 to 1:6. In certain embodiments, the molar ratio of the optionally substituted tetrazine-aminooxy to the catalyst is from about 1:2 to 1:4. In certain embodiments, the molar ratio of the optionally substituted tetrazine-aminooxy to the catalyst is about 1:4.

In certain embodiments, $R^{as}$ is an optionally substituted carbohydrate group or a fragment thereof, provided $R^{as}$ comprises $^{18}$F. In certain embodiments, $R^{as}$ is an optionally substituted glucose or a fragment thereof. In certain embodiments, $R^{as}$ is $^{18}$F-FDG of a fragment thereof.

As provided in Scheme S1, the resulting oxime product can be easily purified from the reaction mixture to the change in hydrophilicity.

In certain embodiments of Scheme S1, the excess of tetrazine-aminooxy can be captured by reacting with another water soluble carbohydrate. In certain embodiments, the water soluble carbohydrate is glucosamine 6-sulfate.

The compound of Formula (b-2-b)

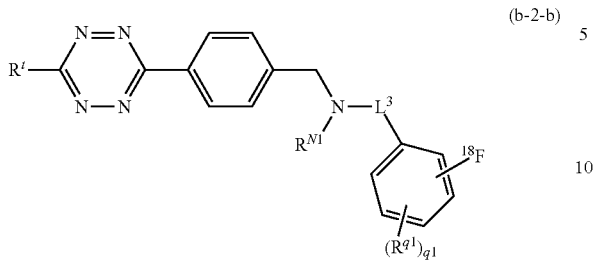

can be prepared from reacting an optionally substituted tetrazine comprising a nucleophic group with an electrophile comprising $^{18}$F such as $^{18}$F-SFB. Exemplary synthesis of Formula (b-2-b) is provided in Scheme S2.

Scheme S2

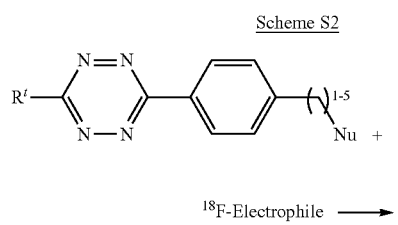

$^{18}$F-Electrophile ⟶

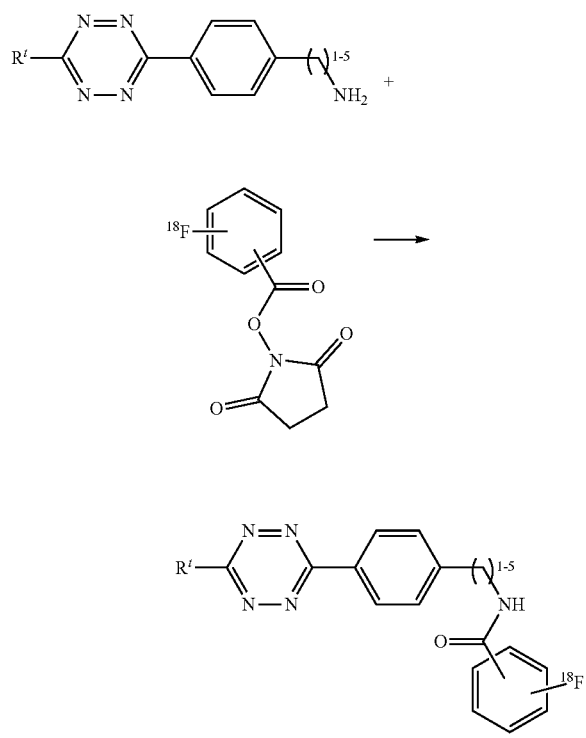

In certain embodiments, the Nu is an amino group. In certain embodiments, the electrophile is an optionally substituted N-succinimidyl comprising $^{18}$F. In certain embodiments, the optionally substituted N-succinimidyl is $^{18}$F-SFB of the formula

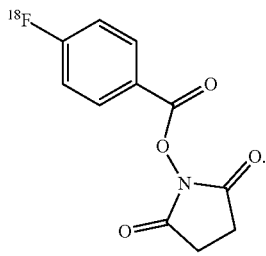 [SMILES: O=C(ON1C(=O)CCC1=O)c1ccc([18F])cc1]

Figure 11:
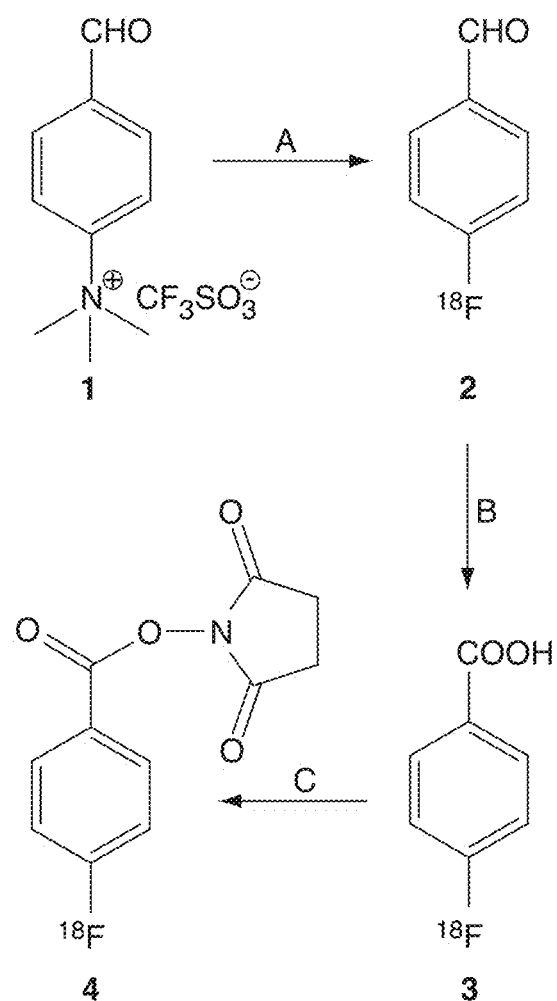
FIG. 11 shows a scheme for the synthesis of N-succinimidyl 4-[18F]fluorobenzoate (SFB). The reaction conditions are as follows: (A) Kryptofix 222, [18F]fluoride, DMSO, 120-140° C.; B) KMnO4, NaOH, 120° C.; C) DSC, pyridine, CH3CN, 150° C. (Vaidyanathan et al., *Nature Protocols*, 2006, (1), 1655-1661).
Figures 12A, 12B, 12C:
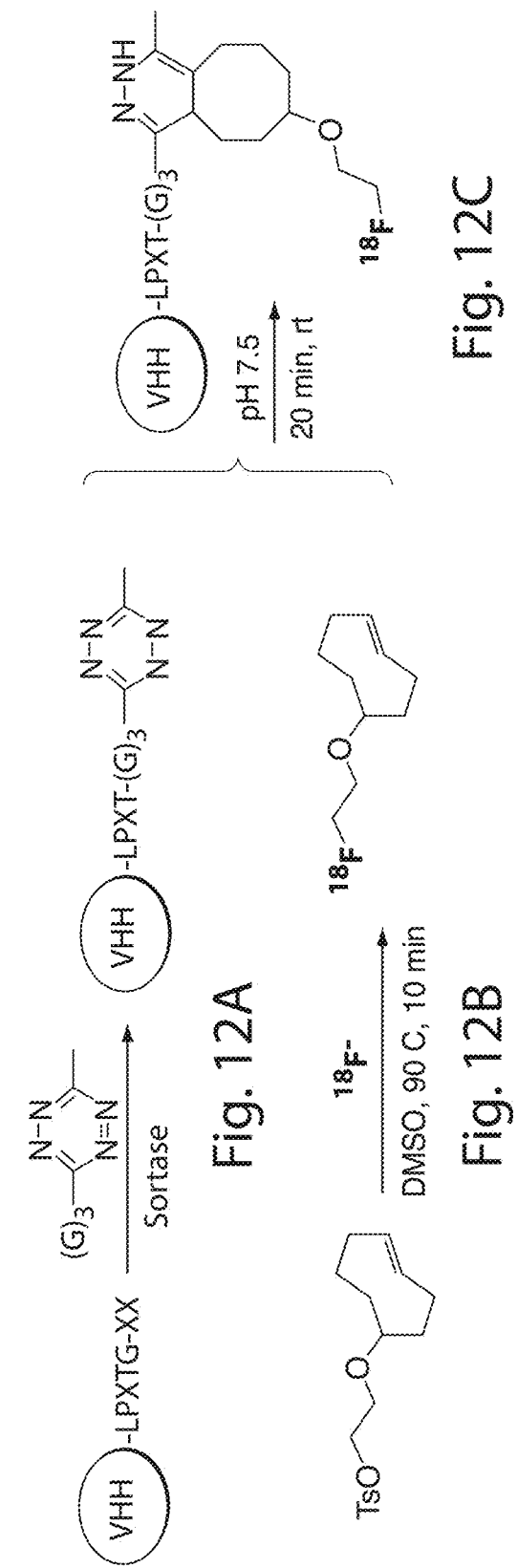
FIGS. 12A-12E show a schematic of site-specific 18F or 64Cu-labeling of single domain antibodies (VHHs) using sortase.
Figure 12D:
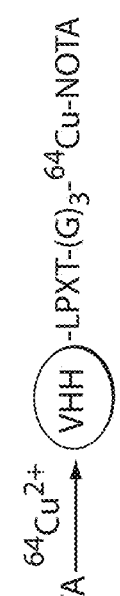
Figure 12D:
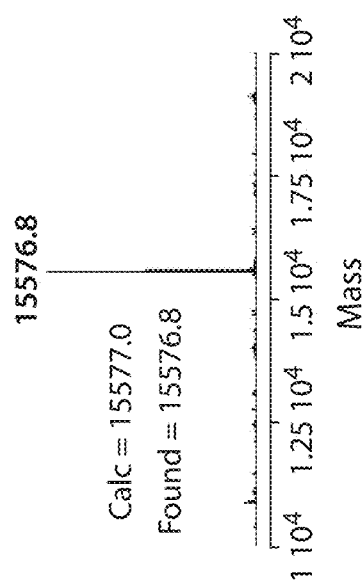
Figure 12E:
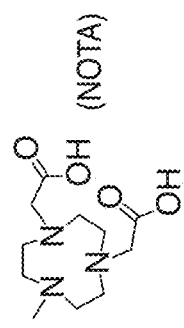
Figure 13:
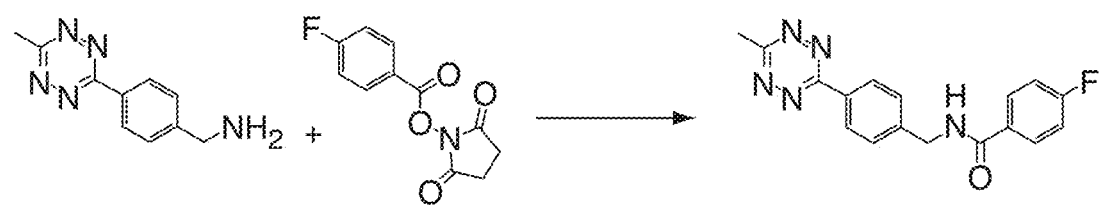
FIG. 13 shows tetrazine-amine (left) reacted with 18F-SFB to produce tetrazine-18F. The product may be reacted with a site specific TCO-labeled protein to form the final 18F-labeled protein.
Figure 14:
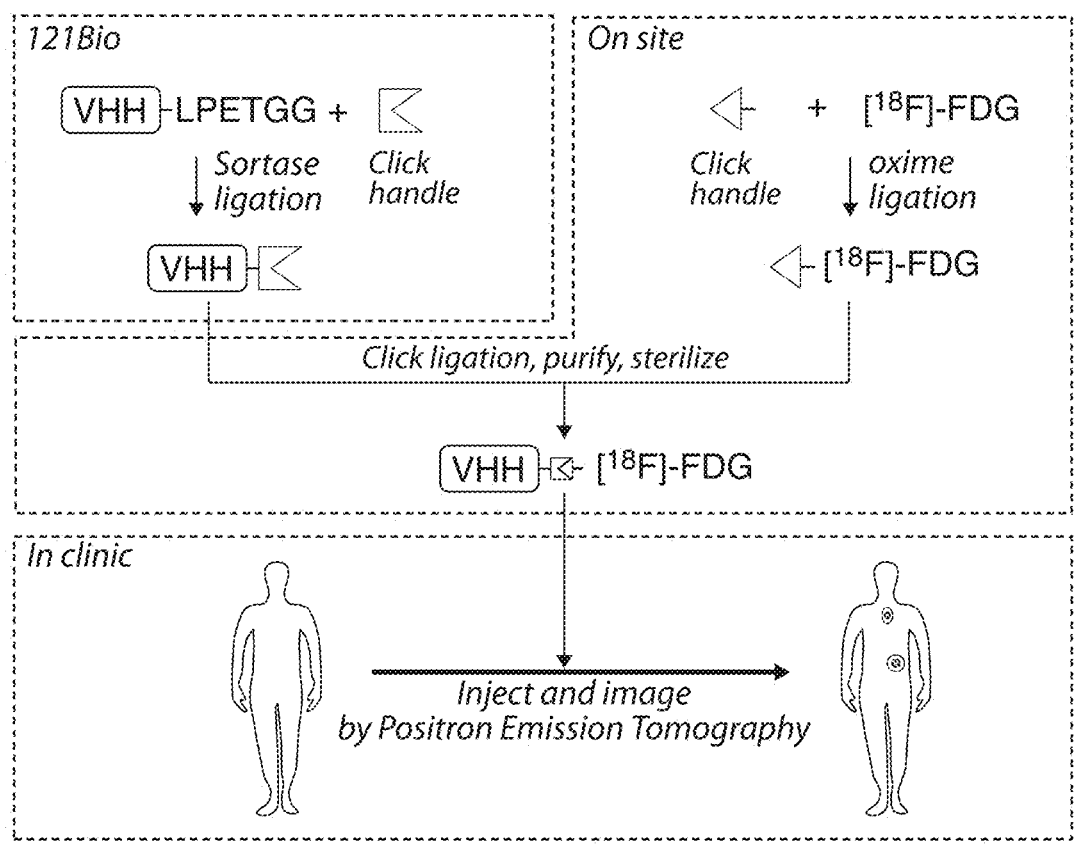
FIG. 14 shows exemplary application of the radioactive protein and compositions thereof. SEQ ID NO: 127 is shown.

Exemplary synthesis of $^{18}$F-SFB can be found in FIG. 11.

The radioactive protein of Formula (II) can be prepared from a modified protein of Formula (I) with a compound of Formula (b): $^{18}$F—R$^2$ (b), wherein R$^2$ is a reactive group capable of undergoing the click chemistry reaction (Scheme S3):

Scheme S3.

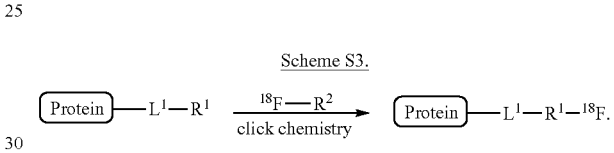

In certain embodiments, R$^1$ is the first click chemistry handle and R$^2$ is the second click chemistry handle. In certain embodiments, R$^2$ is the first click chemistry handle and R$^1$ is the second click chemistry handle.

Click chemistry should be modular, wide in scope, give high chemical yields, generate inoffensive byproducts, be stereospecific, be physiologically stable, exhibit a large thermodynamic driving force (e.g., >84 kJ/mol to favor a reaction with a single reaction product), and/or have high atom economy. Several reactions have been identified which fit this concept:

(1) The Huisgen 1,3-dipolar cycloaddition (e.g., the Cu(I)-catalyzed stepwise variant, often referred to simply as the "click reaction"; see, e.g., Tornoe et al., *Journal of Organic Chemistry* (2002) 67: 3057-3064). Copper and ruthenium are the commonly used catalysts in the reaction. The use of copper as a catalyst results in the formation of 1,4-regioisomer whereas ruthenium results in formation of the 1,5-regioisomer;

(2) Other cycloaddition reactions, such as the Diels-Alder cycloaddition;

(3) Nucleophilic addition to small strained rings like epoxides and aziridines;

(4) Nucleophilic addition to activated carbonyl groups; and (4) Addition reactions to carbon-carbon double or triple bonds.

In certain embodiments, the click chemistry is a Diels-Alder cycloaddition. Exemplary Diels-Alder cycloadditions can be found in U.S. Patent Publication No. 20130266512, which is incorporated by reference herein;

The radioactive protein of Formula (III) can be prepared from a compound comprising an aminooxy moiety with an optionally substituted aldehyde (Scheme S4, wherein from top to bottom and left to right, the sequences are SEQ ID NOs: 1, 105, and 105):

Scheme S4.

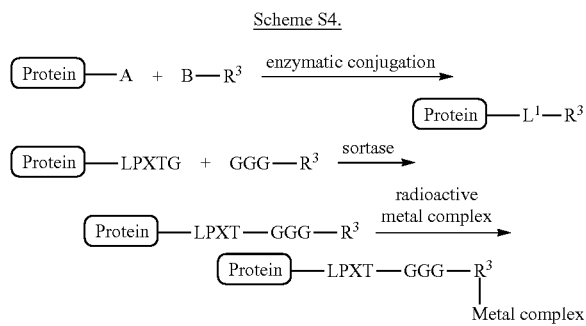

The radioactive protein of Formula (IV) can be prepared from a compound comprising an aminooxy moiety with an optionally substituted aldehyde or an optionally substituted ketone (Scheme S5), wherein $L^G$ is as defined herein.

Scheme S5.

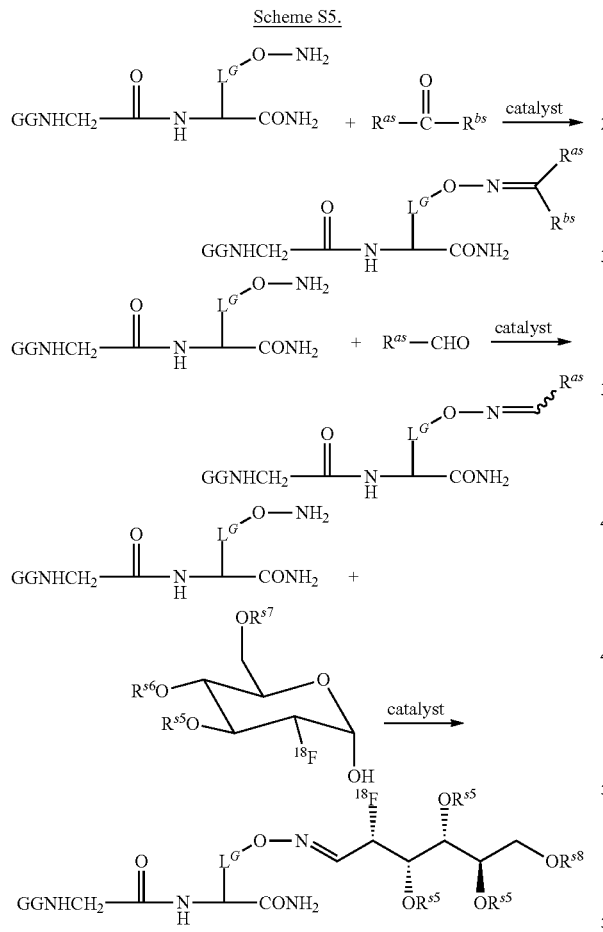

In certain embodiments, the aldehyde is an optionally substituted carbohydrate comprising an aldehyde group or is capable of forming one through isomerism. In certain embodiments, the optionally substituted aldehyde is an optionally substituted monosaccharide. In certain embodiments, the optionally substituted aldehyde is optionally substituted glucose, optionally substituted glyceraldehyde, or optionally substituted galactose. In certain embodiments, the optionally substituted aldehyde is optionally substituted glucose.

In certain embodiments, the catalyst is m-phenylenediamine (mPDA), o-phenylenediamine, p-phenylenediamine, o-aminophenol, m-aminophenol, p-aminophenol, o-aminobenzoic acid, 5-methoxyanthranilic acid, 3,5-diaminobenzoic acid or aniline. In certain embodiments, the catalyst is m-phenylenediamine (mPDA).

In certain embodiments, the radioactive optionally substituted cyclooctene is synthesized by a nucleophilic reaction with an $^{18}F$ anion with a substituted cyclooctene comprising a leaving group LG (Scheme S6), wherein LG is as defined herein and $L^{61}$ is optionally substituted aliphatic, optionally substituted heteroaliphatic, optionally substituted arylene, optionally substituted heteroarylene, or optionally substituted heterocyclylene.

Scheme S6

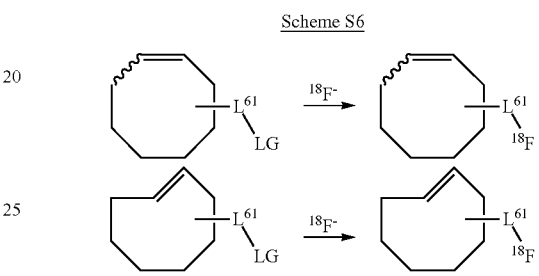

In certain embodiments, $L^{61}$ is optionally substituted heteroaliphatic. In certain embodiments, $L^{61}$ is straight chain heteroaliphatic. In certain embodiments, $L^{61}$ is —O—$C_{1-8}$alkylene. In certain embodiments, $L^{61}$ is —O—$(CH_2)_{1-8}$—.

In certain embodiments, the radioactive optionally substituted cyclooctene is synthesized as shown in Scheme S6-a, wherein $L^{61}$ is as defined herein.

Scheme S6-a

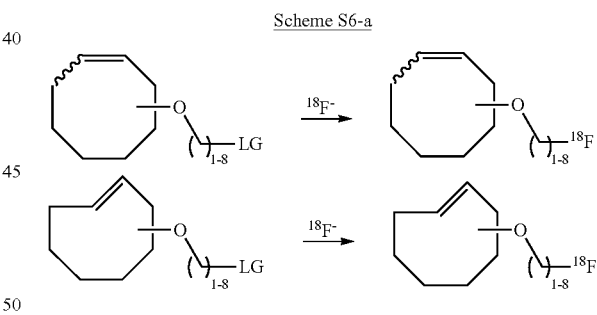

In certain embodiments, the $^{18}F^-$ anion is from an inorganic salt comprising $^{18}F^-$ anion. In certain embodiments, the $^{18}F^-$ anion is from a metal salt comprising $^{18}F^-$ anion. In certain embodiments, the $^{18}F^-$ anion is from IA, IIA, or IIIA metal fluoride. In certain embodiments, the $^{18}F^-$ anion is from transition metal complex comprising $^{18}F^-$.

In certain embodiments, the enzymatic conjugation is a modification using a formylglycine generating enzyme (FGE). In certain embodiments, the protein is an antibody. In certain embodiments, the enzyme is FGE. In certain embodiments, the FGE recognition sequence is CXPXR. In certain embodiments, the FGE recognition sequence is LCTPSRGSLFTGR (SEQ ID NO: 113). In certain embodiments, the radioactive protein is prepared according to Scheme E1.

Scheme E1

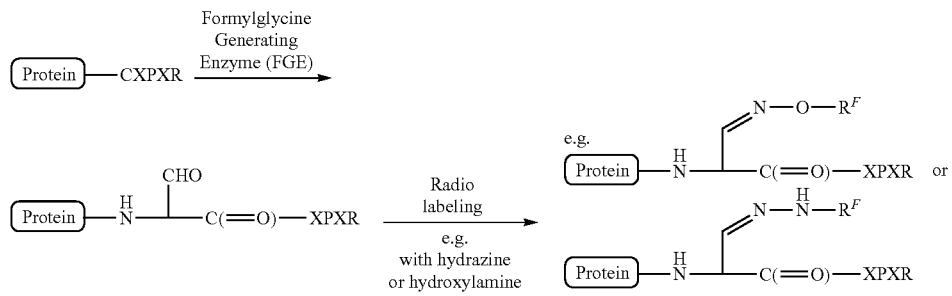

$R^F$ is a reactive group capable of undergoing a click chemistry reaction, comprising a radioactive optionally substituted carbohydrate, or comprising a ligand capable of chelating to a pharmaceutically acceptable radioactive metal complex.
X = an independently amino acid.

It is to be understood that the —CHO group generated from the FGE modification can undergo any suitable reaction to incorporate a radioactive label, for example, a click chemistry handle, a radioactive carbohydrate, or a ligand capable of chelating to a pharmaceutically acceptable radioactive metal complex. Exemplary transformations such as reacting with hydrazine or hydroxylamine are shown in the Scheme E1.

In certain embodiments, the enzymatic conjugation is a modification using sialyltransferases. In certain embodiments, the protein is a cell surface polypeptide. In certain embodiments, the protein is a glycan. An exemplary sialylation is shown in Scheme E2, wherein $R^4$ is as defined herein.

Scheme E2

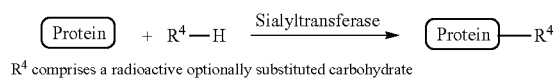

$R^4$ comprises a radioactive optionally substituted carbohydrate

In certain embodiments, $R^4$ comprises radioactive optionally substituted glucose. In certain embodiments, $R^4$ comprises $^{18}F$-FDG. In certain embodiments, $R^4$ comprises radioactive optionally substituted aldolase. In certain embodiments, $R^4$ comprises radioactive optionally substituted mannose.

In certain embodiments, the enzymatic conjugation is a modification using phosphopantetheinyltransferases (PPTases). In certain embodiments, the protein is peptide carrier protein (PCP). In certain embodiments, the protein is acyl carrier protein (ACP). In certain embodiments, the PPT recognition sequence comprises a serine residue. In certain embodiments, the PPTase recognition sequence is DSLEFIASKLA (SEQ ID NO: 114), VLDSLEFIASKLA (SEQ ID NO: 115), or GSQDVLDSLEFIASKLA (SEQ ID NO: 116). In certain embodiments, the phosphopantetheinyltransferase is Sfp. An exemplary modification using PPTase is shown in Scheme E3, wherein $R^F$ is as defined herein.

Scheme E3

-continued

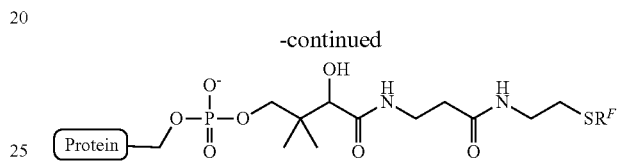

In certain embodiments, the enzymatic conjugation is a modification using polypeptidyltransferases (OGTases). In certain embodiments, the protein is nuclear pore protein. In certain embodiments, the OGTase is UDP-Glc-NAc. In certain embodiments, the OGTase recognition sequence comprises a serine residue or threonine residue. Exemplary modifications using polypeptidyltransferases are shown in Scheme E4, wherein $R^F$ is as defined herein.

Scheme E4

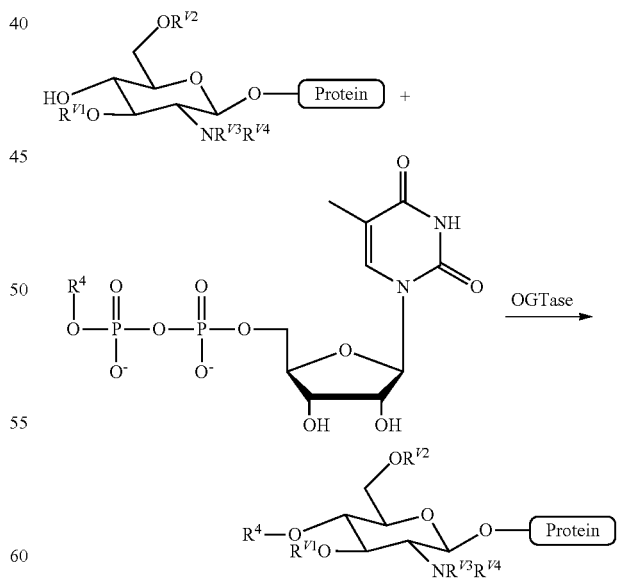

-continued

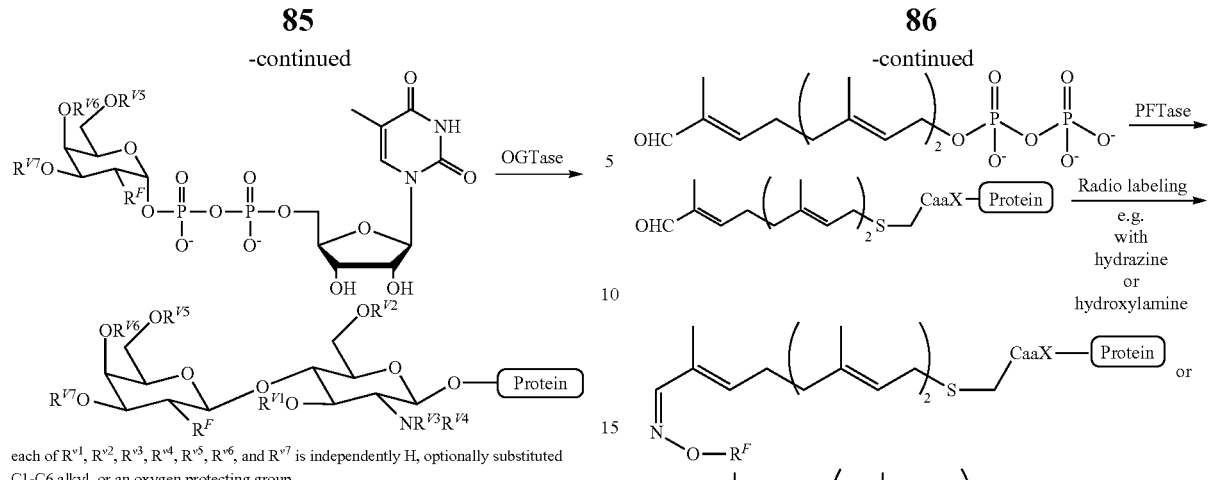

each of $R^{v1}$, $R^{v2}$, $R^{v3}$, $R^{v4}$, $R^{v5}$, $R^{v6}$, and $R^{v7}$ is independently H, optionally substituted C1-C6 alkyl, or an oxygen protecting group In certain embodiments, the enzymatic conjugation is a modification using transglutaminase (TGases). In certain embodiments, the protein is an antibody. In certain embodiments, the TGase recognition sequence comprises a glutamine (Q) residue. In certain embodiments, the TGase recognition sequence comprises XXQXX. In certain embodiments, the protein recognition sequence is GGGSLLQG (SEQ ID NO: 117), PNPQLPF (SEQ ID NO: 118), PKPQQFM (SEQ ID NO: 119), or GQQQLG (SEQ ID NO: 120). In certain embodiments, the protein recognition sequence comprises a lysine (K) residue. In certain embodiments, the protein recognition sequence is MRHKGS (SEQ ID NO: 121). An exemplary modification using TGases is shown in Scheme E5, wherein $R^F$ is as defined herein.

Scheme E5

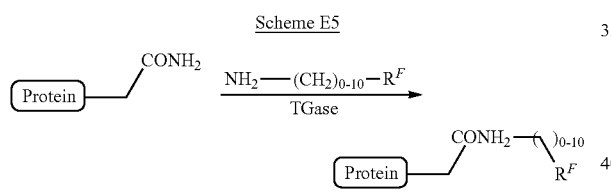

In certain embodiments, the enzymatic conjugation is a modification using protein farnesyltransferase (PFTase). In certain embodiments, the protein is an antibody. In certain embodiments, the PFTase recognition sequence comprises CaaX, wherein each instance of a is independently an aliphatic amino acid and X is as defined herein. Exemplary modifications using PFTases are shown in Scheme E6, wherein $R^F$ is as defined herein.

Scheme E6

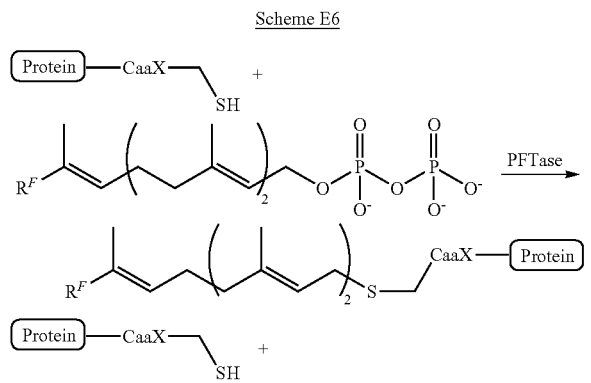

-continued

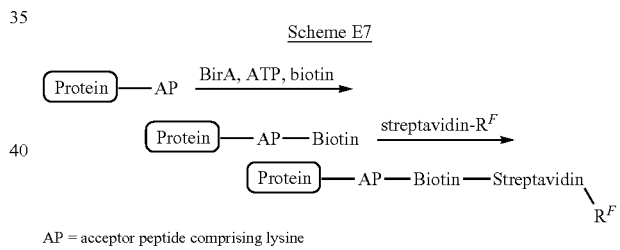

In certain embodiments, the enzymatic conjugation is a modification using biotin ligases. In certain embodiments, the protein is an antibody. In certain embodiments, the biotin ligase recognition sequence comprises lysine (K). In certain embodiments, the biotin ligase recognition sequence comprises GLNDIFEAQKIEWHE (SEQ ID NO: 122). In certain embodiments, the enzyme is E. coli biotin ligase, BirA. An exemplary modification using biotin ligases is shown in Scheme E7, wherein $R^F$ is as defined herein.

Scheme E7

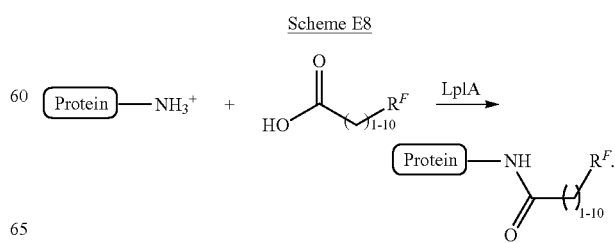

AP = acceptor peptide comprising lysine

In certain embodiments, the enzymatic conjugation is a modification using lipoic acid ligases (LplAs). In certain embodiments, the protein is an antibody. In certain embodiments, the protein is a growth factor receptor. In certain embodiments, the LplA recognition sequence comprises GFEIDKVWYDLDA (SEQ ID NO: 123). In certain embodiments, the enzyme is E. coli Lpl. An exemplary modification using LplAs is shown in Scheme E8, wherein $R^F$ is as defined herein.

Scheme E8

In certain embodiments, the enzymatic conjugation is a modification using N-myristoyltransferase (NMT). In certain embodiments, the protein is an antibody. In certain embodiments, the protein is a tyrosine kinase. In certain embodiments, the protein is a HIV-1 matrix protein. In certain embodiments, the protein is a HIV Gag. In certain embodiments, the protein is an ADP-ribosylating factor. In certain embodiments, the NMT recognition sequence comprises GXXXS/T, wherein X is any amino acid. An exemplary modification using NMT is shown in Scheme E9, wherein $R^F$ is as defined herein.

Scheme E9

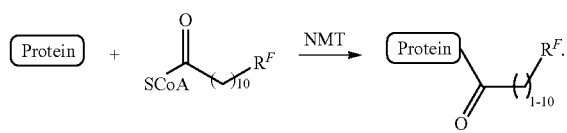

In certain embodiments, $R^F$ is a reactive group capable of undergoing a click chemistry reaction. In certain embodiments, $R^F$ is $R^1$ as defined herein. In certain embodiments, $R^F$ is optionally substituted tetrazine. In certain embodiments, $R^F$ is optionally substituted tetrazine comprising $^{18}F$. In certain embodiments, $R^F$ is optionally substituted tetrazine comprising $^{18}F$-FDG or a fragment thereof. In certain embodiments, $R^F$ is optionally substituted tetrazine comprising $^{18}F$-SFB or a fragment thereof. In certain embodiments, $R^F$ is optionally substituted cyclooctene. In certain embodiments, $R^F$ is optionally substituted trans-cyclooctene. In certain embodiments, $R^F$ is optionally substituted trans-cyclooctene comprising $^{18}F$. In certain embodiments, $R^F$ is comprises a ligand capable of chelating to a pharmaceutically acceptable radioactive metal complex. In certain embodiments, $R^F$ is $R^3$ as defined herein. In certain embodiments, $R^F$ comprises a ligand capable of chelating to a pharmaceutically acceptable metal complex comprising $F^{18}$. In certain embodiments, $R^F$ is Y as defined herein. In certain embodiments, $R^F$ comprises a radioactive optionally substituted carbohydrate. In certain embodiments, $R^F$ is $R^4$ as defined herein. In certain embodiments, $R^F$ comprises $^{18}F$-FDG or a fragment thereof.

Methods and Reagents for Sortase-Mediated Radiolabeling of Proteins

The present invention provides methods, compositions, reagents, and kits for the modification or labeling of proteins and peptides using sortase-mediated transpeptidation of sortase substrate peptides that have been modified to include a desired modification, e.g., a radiolabel, or are isotopically enriched. Typically, a method of labeling a protein as provided herein comprises conjugating the target protein with an agent or a click chemistry handle via a sortase-mediated transpeptidation reaction. In order for a sortase-mediated transpeptidation to be possible, both the target protein and the agent must be recognized by the sortase and must be capable of acting as a substrate of the sortase in the transpeptidation reaction. Accordingly, the methods for labeling of proteins provided herein involve target proteins and agents that comprise or are conjugated to a sortase recognition motif. Some proteins and some agents (e.g., peptides comprising a radiolabel and/or a reactive moiety) may comprise a suitable sortase recognition motif. However, in some embodiments, the target protein and/or the agent is engineered to comprise a suitable sortase recognition motif, for example, via protein engineering (e.g., using recombinant technologies) or via chemical synthesis (e.g., linking a non-protein agent to a sortase recognition motif). Methods for modifying, engineering, or synthesizing proteins (e.g., to include a sortase recognition motif and/or reactive moiety) are known, and include those described by Green and Sambrook, *Molecular Cloning: A Laboratory Manual* (4th ed., Cold Spring Harbor Laboratory Press, Cold Spring Harbor, N.Y. (2012)), and Nilsson et al., "Chemical Synthesis of Proteins." *Annu. Rev. Biophys. Biomol. Struct.* 2005; 34: 91-118; the entire contents of each are hereby incorporated by reference.

It should be appreciated that enzymes other than sortase may be used for the enzymatic modification of proteins as described herein. Exemplary enzymatic modifications include, but are not limited to, modifications by formylglycine generating enzyme (FGE), modifications by sialyltransferase, modifications by phosphopantetheinyltransferase (PPTases), O-GlcNAc modifications by polypeptidyltransferase (OGTases), modifications by transglutaminase (TGases), modifications by protein farnesyltransferase (PFTases), modifications by biotin ligases, and modifications by lipoic acid ligase (Rashidian et al., *Bioconjugate Chem.* 2013, 24, 1277-1294). In certain embodiments, a transglutaminase may be used to site-specifically incorporate an agent into a protein by catalyzing an acyl transfer reaction between the carboxamide group of a glutamine residue and a variety of unbranched primary amines, commonly the F-amino group of lysine. As another example, a protein farnesyltransferase may be used to transfer a farnesyl group to the cysteine of a CaaX tetrapeptide sequence at the carboxyl terminus of a protein, where C is cysteine, a is an aliphatic amino acid, and X is any amino acid. In certain embodiments, a formylglycine generating enzyme (FGE) is used to modify any of the proteins described herein. FGE recognizes a pentapeptide consensus sequence, CxPxR (where x is any amino acid), and site-specifically oxidizes the cysteine in this sequence to an aldehyde-bearing formylglyine. The FGE recognition sequence, or aldehyde tag, can be inserted into heterologous recombinant proteins produced in either prokaryotic or eukaryotic expression systems. By introducing this motif into proteins and subsequently reacting it with FGE, an aldehyde group can be site-specifically added to the protein, which can then be used for covalent modification using complementary aminooxy- or hydrazide-functionalized reagents. Other enzymes that may be used for the labeling of proteins include, but are not limited to, phosphopantetheinyltransferase, biotin ligase, lipoic acid ligase and N-myristoyl transferase. Exemplary enzymes and their corresponding recognition motifs are shown in table 3.

TABLE 3

Kinetic parameters of different enzymes used for protein labeling

| enzyme | encoded tag peptide | $k_{cat}$ min$^{-1}$ | $K_M$ μM | $k_{cat}/K_M$ min$^{-1}$/μM | site of the peptide |
|---|---|---|---|---|---|
| Formylglycine generating enzyme | CXPXR or 13-mer LCTPSRGSLFTGR | — | — | — | C or N terminus |
| Phosphopantetheinyl transferase | ACP, PCP or ybbR tags (11 mer: DSLEFIASKLA; 13 mer: VLDSLEFIASKLA; 17 mer: GSQDVLDSLEFIASKLA) | (for 500 μM ybbR 13 mer and biotin-CoA) 14.7        60.8        0.242 | | | C or N terminus or flexible loops |
| Sortase | LPXTG | 16.2 | 5,500 | 0.003 | Any section |
| Transglutaminase | XXQXX | 45 | 7 | 6 | Any section |
| Farnesyltransferase | CaaX | (for yPFTase and 2.4 μM CVIA) for FPP: 31.2        1.71        18.2 for FPP-aldehyde: 7.8        1.87        4.17 | | | C terminus |
| Biotin ligase | GLNDIFEAQKIEWHE | (for *Escherichia coli* biotin ligase and biotin) 9.6        4.2        2.3 | | | C or N terminus |
| Lipoic acid ligase | GFEIDKVWYDLDA | 2.88 | — | — | C or N terminus or flexible loops |

Typically, a method for protein labeling as provided herein comprises contacting a target protein comprising a sortase recognition motif (e.g., a diagnostic protein comprising a C-terminal recognition motif), with an agent comprising a complementary sortase recognition motif (e.g., a sortase substrate peptide comprising an N-terminal recognition motif (e.g., GGG)), in the presence of a sortase under conditions suitable for the sortase to conjugate the target protein to the agent via a sortase-mediated transpeptidation reaction.

For example, some embodiments provide methods for labeling a target protein with a radioactive agent (e.g., a sortase substrate peptide comprising a radioactive agent) by sortagging the agent to a diagnostic or therapeutic protein comprising a sortase recognition motif. The methods include contacting the target protein with a sortase substrate peptide conjugated to an agent (e.g., a radioactive agent) in the presence of a sortase under conditions suitable for the sortase to ligate (e.g., transamidate) the sortase substrate to the target protein. In some embodiments, the target protein comprises a C-terminal sortase recognition motif, and the sortase substrate peptide conjugated to the agent comprises an N-terminal sortase recognition motif. In other embodiments, the target protein comprises an N-terminal sortase recognition motif, and the sortase substrate peptide conjugated to the agent comprises a C-terminal sortase recognition motif. The C- and N-terminal recognition motif are recognized as substrates by the sortase being employed and ligated in a transpeptidation reaction.

In some embodiments, the methods involve contacting a target protein with a sortase substrate peptide conjugated to an agent (e.g., an agent comprising a reactive moiety such as a click chemistry handle) in the presence of a sortase under conditions suitable for the sortase to transamidate the sortase substrate peptide to the target protein. Following the transpeptidation reaction, the target protein is then reacted with a complementary click chemistry handle which results in attaching a label (e.g., a radiolabel) to the target protein. For example, as described in Example 2, in some embodiments a target protein (e.g., an antibody) is sortagged with a sortase substrate peptide comprising a reactive moiety (e.g., a tetrazine derivative click chemistry handle), and the sortagged protein is then reacted with a partner reactive moiety (e.g., a trans-cyclooctene-containing molecule labeled with $^{18}$F) to yield a radiolabeled protein. See, e.g., Example 2, FIG. 4.

Sortase-mediated transpeptidation reactions (also sometimes referred to as transacylation reactions) are catalyzed by the transamidase activity of sortase, which forms a peptide linkage (an amide linkage), between an acyl donor compound and a nucleophilic acyl acceptor containing an NH$_2$—CH$_2$-moiety. In some embodiments, the sortase employed to carry out a sortase-mediated transpeptidation reaction is sortase A (SrtA). In some embodiments, the sortase employed to carry out a sortase-mediated transpeptidation reaction is sortase B (SrtB). However, it should be noted that any sortase, or transamidase, including engineered sortases, catalyzing a transacylation reaction can be used in the present invention, as the invention is not limited to the use of any particular sortase.

In certain embodiments, a sortase-mediated transpeptidation reaction for C-terminal modification or labeling of a protein, for example, of a diagnostic or therapeutic protein, is provided that comprises the step of contacting a protein comprising a C-terminal sortase recognition sequence of the structure:

PRT-Sortase recognition motif-C(=O)—X$^{51}$R$^{51}$ wherein:
  PRT is a target protein;
  the sortase recognition motif is a C-terminal sortase recognition motif, e.g., an LP(Xaa)TG (SEQ ID NO:1) motif, wherein Xaa represents any amino acid residue;
  X$^{51}$ is —O—, —NR$^{x51}$—, or —S—; wherein R$^{x51}$ is hydrogen, substituted or unsubstituted aliphatic, or substituted or unsubstituted heteroaliphatic;
  R$^{51}$ is H, acyl, substituted or unsubstituted aliphatic, substituted or unsubstituted heteroaliphatic, substituted or unsubstituted aryl, or substituted or unsubstituted heteroaryl;

with a nucleophilic moiety conjugated to an agent, according to the formula:

Sortase recognition motif-Agent wherein
the sortase recognition motif is an N-terminal sortase recognition motif, for example, a polyglycine ($G_{n1}$) (SEQ ID NO: 131) or polyalanine ($A_{n1}$) (SEQ ID NO: 132) motif (wherein n1 is an integer between 0-100 inclusive) or a $(G)_{n1}K$ (SEQ ID NO: 129) motif, wherein n1 is an integer between 1 and 10, inclusive;
the agent is any molecule or compound comprising one or more radionuclides, for example, an amino acid, a peptide, a protein, a nucleotide, a polynucleotide, a carbohydrate (e.g., $^{18}$F-FDG, $^{14}$C—(U)-glucose, etc.), a click chemistry handle, a tag, a metal atom, a non-polypeptide polymer, a synthetic polymer, a small molecule, a lipid, a compound, or a label;
in the presence of a sortase, under conditions suitable to form a modified protein of formula:

PRT-Sortase recognition sequence-Agent.

In certain embodiments, a sortase-mediated transpeptidation reaction for N-terminal modification or labeling of a protein, for example, of a diagnostic or therapeutic protein, is provided that comprises a step of contacting a protein comprising an N-terminal sortase recognition sequence of the structure:

Sortase recognition motif-PRT wherein:
PRT is a target protein;
the sortase recognition motif is an N-terminal sortase recognition motif, for example, a polyglycine ($G_{n2}$) (SEQ ID NO: 131) or polyalanine ($A_{n2}$) (SEQ ID NO: 132) motif (wherein n2 is an integer between 0-100 inclusive);
with an agent conjugated to a C-terminal sortase recognition motif, of the formula:

Agent-Sortase recognition motif-C(=O)—$X^{61}R^{61}$ wherein
the agent is any molecule or compound comprising one or more radionuclides, for example, an amino acid, a peptide, a protein, a nucleotide, a polynucleotide, a carbohydrate (e.g., $^{18}$F-FDG, $^{14}$C—(U)-glucose, etc.), a click chemistry handle, a tag, a metal atom, a non-polypeptide polymer, a synthetic polymer, a small molecule, a lipid, a compound, or a label;
the sortase recognition motif is a C-terminal sortase recognition motif, e.g., an LP(Xaa)TG motif (SEQ ID NO:1), wherein Xaa represents any amino acid residue;
$X^{61}$ is —O—, —$NR^{x61}$—, or —S—; wherein $R^{x61}$ is hydrogen, substituted or unsubstituted aliphatic, or substituted or unsubstituted heteroaliphatic; and
$R^{61}$ is H, acyl, substituted or unsubstituted aliphatic, substituted or unsubstituted heteroaliphatic, substituted or unsubstituted aryl, or substituted or unsubstituted heteroaryl;
in the presence of a sortase, under conditions suitable to form a protein of formula:

Agent-Sortase recognition sequence-PRT.

Any C-terminal sortase recognition motif may be used in the present invention. The invention is not limited in this respect. The C-terminal sortase recognition motif need only be compatible with the sortase being used. In some embodiments, the C-terminal sortase recognition motif is LPXT, wherein X is a standard or non-standard amino acid. In some embodiments, X is selected from D, E, A, N, Q, K, or R. In some embodiments, the recognition sequence is selected from LPXT, LPXT, SPXT, LAXT, LSXT, NPXT, VPXT, IPXT, and YPXR. In some embodiments, X is selected to match a naturally occurring transamidase recognition sequence. In some embodiments, the transamidase recognition sequence is selected from LPKT (SEQ ID NO:58), LPIT (SEQ ID NO:59), LPDT (SEQ ID NO:60), SPKT (SEQ ID NO:61), LAET (SEQ ID NO:62), LAAT (SEQ ID NO:63), LAET (SEQ ID NO:64), LAST (SEQ ID NO:65), LAET (SEQ ID NO:66), LPLT (SEQ ID NO:67), LSRT (SEQ ID NO:68), LPET (SEQ ID NO:69), VPDT (SEQ ID NO:70), IPQT (SEQ ID NO:71), YPRR (SEQ ID NO:72), LPMT (SEQ ID NO: 73), LPLT (SEQ ID NO:74), LAFT (SEQ ID NO:75), LPQT (SEQ ID NO:76), NSKT (SEQ ID NO:77), NPQT (SEQ ID NO:78), NAKT (SEQ ID NO:79), and NPQS (SEQ ID NO:80). In some embodiments, e.g., in certain embodiments in which sortase A is used, the transamidase recognition motif comprises the amino acid sequence $X_1PX_2X_3G$, where $X_1$ is leucine, isoleucine, valine, or methionine; $X_2$ is any amino acid; $X_3$ is threonine, serine, or alanine; P is proline and G is glycine. In some embodiments, the C-terminal glycine is omitted. In specific embodiments, as noted above, $X_1$ is leucine and $X_3$ is threonine. In certain embodiments, $X_2$ is aspartate, glutamate, alanine, glutamine, lysine, or methionine. In certain embodiments, e.g., where sortase B is utilized, the recognition sequence often comprises the amino acid sequence $NPX_1TX_2$, where $X_1$ is glutamine or lysine; $X_2$ is asparagine or glycine; N is asparagine; P is proline, and T is threonine. The invention encompasses the recognition that selection of X may be based at least in part in order to confer desired properties on the compound containing the recognition motif. In some embodiments, X is selected to modify a property of the compound that contains the recognition motif, such as to increase or decrease solubility in a particular solvent. In some embodiments, X is selected to be compatible with reaction conditions to be used in synthesizing a compound comprising the recognition motif, e.g., to be unreactive towards reactants used in the synthesis. One of ordinary skill will appreciate that, in certain embodiments involving naturally-occurring C-terminal sortase recognition motifs or engineered motifs comprising five amino acids, the C-terminal amino acid of the C-terminal sortase recognition motif may be omitted. For example, an acyl group, may replace the C-terminal amino acid of the sortase recognition motif. In some embodiments, the acyl group is an ester. In some embodiments, the acyl group is

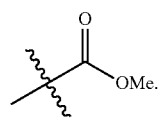 [SMILES: *C(=O)OC]

In some embodiments, the agent to be conjugated to the target protein is a protein. In some embodiments, the agent is a peptide. In some embodiments, the agent is a radionuclide. In some embodiments, the agent is a peptide comprising a radionuclide, e.g., a radiolabeled sortase substrate peptide. In some embodiments, the agent is isotopically enriched (e.g., the agent has been enriched in one particular isotope of an element and depleted in other isotopic forms of the element). In some embodiments, the agent comprises a reactive moiety, such as a click chemistry handle (e.g., tetrazine, tetrazine-aminooxy, tetrazine dienophiles, azide, tetrazoles, nitrile imines, trans-cyclooctene (TCO), difluorinated cyclooctyne, dibenzocyclooctyne, biarylazacyclooctynone, cyclopropyl-fused bicyclononyne, norbornene, biscyclononene, and unactivated alkenes).

In certain embodiments, n2 (designating the number of amino acids in the N-terminal sortase recognition motif) is an integer from 0 to 50, inclusive. In certain embodiments, n2 is an integer from 0 to 20, inclusive. In certain embodiments, n2 is 0. In certain embodiments, n2 is 1. In certain embodiments, n2 is n1, wherein n1 is an integer of 1 to 10, inclusive. In certain embodiments, n1 is 2. In certain embodiments, n1 is 3. In certain embodiments, n1 is 4. In certain embodiments, n1 is 5. In certain embodiments, n1 is 6.

Any sortase that can carry out a transpeptidation reaction under conditions suitable for conjugating e.g., a radiolabeled sortase substrate peptide to a target protein, can be used this invention. Examples of suitable sortases include, but are not limited to, sortase A and sortase B, for example, from *Staphylococcus aureus*, or *Streptococcus pyogenes*. Additional sortases suitable for use in this invention will be apparent to those of skill in the art, including, but not limited to any of the 61 sortases described in Dramsi S, Trieu-Cuot P, Bierne H, Sorting sortases: a nomenclature proposal for the various sortases of Gram-positive bacteria. *Res Microbiol.* 156(3):289-97, 2005, the entire contents of which are incorporated herein by reference. Sortases belonging to any class of sortases, e.g., class A, class B, class C, and class D sortases, and sortases belonging to any sub-family of sortases (subfamily 1, subfamily 2, subfamily 3, subfamily 4 and sub-family 5) can be used in this invention.

Any amino acid sequence recognized by a sortase can be used in the present invention. It will be understood by those of skill in the art, however, that in order for a certain sortase to carry out a transpeptidation reaction, the sortase recognition motif of the target protein to be modified and the sortase recognition motif the agent is conjugated to need to be recognized by that sortase. Numerous suitable sortase recognition motifs are provided herein, and additional suitable sortase recognition motifs will be apparent to the skilled artisan. Aside from naturally occurring sortase recognition motifs, some embodiments of this invention contemplate the use of non-naturally occurring sortase recognition motifs and sortases recognizing such motifs, for example, sortase motifs and sortases described in Piotukh et al., Directed evolution of sortase A mutants with altered substrate selectivity profiles. *J Am Chem Soc.* 2011 Nov. 9; 133(44):17536-9; and Chen I, Dorr B M, and Liu D R. A general strategy for the evolution of bond-forming enzymes using yeast display. *Proc Natl Acad Sci USA.* 2011 Jul. 12; 108(28): 11399-404; the entire contents of each of which are incorporated herein by reference. In some embodiments, a recognition sequence, e.g., a sortase recognition sequence as provided herein further comprises one or more additional amino acids, e.g., at the N- and/or C-terminus. For example, one or more amino acids (e.g., up to 5 amino acids) having the identity of amino acids found immediately N-terminal to, or C-terminal to, a five amino acid recognition sequence in a naturally occurring sortase substrate may be incorporated. Such additional amino acids may provide context that improves the recognition of the recognition motif.

In some embodiments, suitable sortase recognition motifs may be naturally present in a target protein, for example, an N-terminal or C-terminal recognition motif sequence, in which case no further engineering of the target protein may be required. The skilled artisan will understand that the choice of a suitable sortase for the (radio)labeling of a given target protein may depend on the sequence of the target protein, e.g., on whether or not the target protein comprises a sequence at its C-terminus or its N-terminus that can be recognized as a substrate by any known sortase. In some embodiments, use of a sortase that recognizes a naturally occurring C-terminal or N-terminal recognition motif is preferred since further engineering of the target protein can be avoided.

Sortases, sortase-mediated transacylation reactions, and their use in transpeptidation (sometimes also referred to as transacylation) for protein engineering are well known to those of skill in the art (see, e.g., Ploegh et al., International PCT Patent Application, PCT/US2010/000274, filed Feb. 1, 2010, published as WO 2010/087994 on Aug. 5, 2010; Ploegh et al., International PCT Patent Application PCT/US2011/033303, filed Apr. 20, 2011, published as WO 2011/133704 on Oct. 27, 2011; and Ploegh et al., PCT/US2012/044584, filed Jun. 28, 2012, published as WO 2013/003555 on Jan. 3, 2013; the entire contents of each are incorporated herein by reference).

In some embodiments, methods for radiolabeling a protein having a sortase recognition motif are provided. The methods comprise contacting the protein with a sortase substrate peptide in the presence of a sortase under conditions suitable for the sortase to transamidate the protein and the sortase substrate peptide, wherein the sortase substrate peptide comprises a radiolabeled agent. In some embodiments, the sortase substrate peptide comprises a reactive moiety, such as a click chemistry handle, which can be reacted with an agent comprising a complementary click chemistry handle and optionally radiolabel (e.g., $^{18}$F). In some embodiments, the radiolabeled agent is linked to the sortase substrate peptide by an oxime, a hydrazone, or a thiosemicarbazone, or through the use of click chemistry, as described herein. Typically, the protein comprises a C-terminal sortase recognition motif (as provided herein) and the sortase substrate peptide comprises an N-terminal sortase recognition motif (as provided herein). However, as described above, in some embodiments the protein to be radiolabeled comprises an N-terminal sortase recognition motif and the sortase substrate peptide comprises a C-terminal sortase recognition motif.

Typically, the sortase substrate peptide comprises a radionuclide, or is linked (e.g., as described herein) to an agent (e.g., a small molecule) that comprises a radionuclide. The radionuclide is any radionuclide suitable for use in diagnostic and/or therapeutic applications, for example PET. Such radionuclides (isotopes) include, but are not limited to, those radionuclides with positron emission (e.g., beta plus decay), such as carbon-11, carbon-14, nitrogen-13, oxygen-15, fluorine-18, rubidium-82, copper-61, copper-62, copper-64, yttrium-86, gallium-68, zirconium-89, or iodine-124. In some embodiments, because of its favorable half-life (~110 minutes), agents comprising fluorine-18 ($^{18}$F) are conjugated to a sortase substrate peptide, for use in labeling a target protein. For example, fludeoxyglucose (FDG, or $^{18}$F-FDG) is a radioactive analog of glucose that is the most prevalent radiopharmaceutical used in PET. Because of its wide-spread use and availability, it is especially suited to the methods and uses described herein. Similarly, sodium fluoride having $^{18}$F ($^{18}$F—NaF) is widely available and can be used as a source of $^{18}$F for labeling proteins and sortase substrate peptides with $^{18}$F (e.g., using substitution reactions known in the art). Thus, in some embodiments, proteins are labeled using sortagging technology that makes use of sortase substrate peptides linked to FDG or comprising $^{18}$F, as described herein. In some embodiments, the sortase substrate peptides are linked to $^{14}C$—(U)-glucose. However, those of skill in the art will understand that any agent comprising a suitable radionuclide (e.g., for use in diagnostic and/or therapeutic applications) can be linked to a sortase substrate peptide and used to label a target protein, as described herein, and the invention is not limited in this respect.

Because of the half-lives of certain isotopes (e.g., $^{18}F$), the methods, compositions, reagents, and kits of the instant invention provide fast and efficient means to generate radiolabeled proteins. For example, in some embodiments, a target protein is labeled (e.g., sortagged with a radioactive sortase substrate peptide) in less than 5 minutes, less than 10 minutes, less than 15 minutes, less than 20 minutes, less than 25 minutes, less than 30 minutes, less than 45 minutes, less than 60 minutes, less than 90 minutes, or less than 120 minutes. Additionally, in some embodiments, the methods, compositions, reagents, and kits provided herein allow for an efficient labeling reaction, wherein at least 50%, at least 75%, at least 90%, at least 95%, or at least 98% of the protein is labeled with the agent. Methods for determining the efficiency (e.g., the amount of labeled protein compared to un-labeled protein) of the labeling reaction are known, and include liquid chromatography-mass spectrometry (LC-MS). See, e.g., Lee et al., "LC/MS applications in drug development." *Mass Spectrometry Reviews.* 1999; 18 (3-4): 187-279 and Wysocki et al., "Mass spectrometry of peptides and proteins." *Methods.* 2005; 35 (3): 211-22; the entire contents of each are hereby incorporated by reference.

In some embodiments, the methods described herein generate an amount of purified, radiolabeled protein having a suitable amount of radioactivity for use in therapeutic and/or diagnostic applications, such as PET. For example, in some embodiments, the methods produce an amount of radiolabeled protein comprising at least 10, at least 20, at least 30, at least 40, at least 50, at least 75, at least 100, at least 150, at least 200, at least 250, at least 300, at least 350, at least 400, at least 450, at least 500, at least 550, at least 600, at least 700, at least 800, at least 900, or at least 1000 MBq of radioactivity.

In some embodiments, the protein to be labeled is a protein that is useful in diagnostic and/or therapeutic applications, e.g., as described herein. In some embodiments, the protein is an antibody, an affibody, a single-domain antibody, a Fab fragment, or a therapeutic peptide. In some embodiments, the protein comprises a VHH domain (e.g., VHH4, VHH7).

In some embodiments, the protein binds to a tumor cell, a tumor-associated cell (e.g., neovasculature cell), or a tumor antigen. In other embodiments, the protein binds to any immune cell. Some examples of immune cells include T-cells, B-cells, plasma cells, macrophages, dendritic cells, neutrophils, eosinophils, or mast cells. In some embodiments, the protein binds to a marker of inflammation. For example, in some embodiments, the protein is an antibody useful in diagnostic applications involving PET. Use of antibodies for PET based applications is referred to as immunoPET (See, e.g., Knowles et al., "Advances in immuno-positron emission tomography: antibodies for molecular imaging in oncology." *J Clin Oncol.* 2012; 30:3884-3892; the entire contents of which are hereby incorporated by reference). Such antibodies include monoclonal antibodies known to target or bind cancerous cells or tissues in a subject's body. For example, a non-limiting list of antibodies approved by the U.S. Food and Drug Administration (FDA) and the European Medicines Agency is provided in Table 4 of Salsano and Treglia, "PET imaging using radiolabeled antibodies: future direction in tumor diagnosis and correlate applications." *Research and Reports in Nuclear Medicine.* 2013: 3; 9-17, the entire contents of which are hereby incorporated by reference. The table is reproduced below.

TABLE 4

List of monoclonal antibodies approved by the US Food and Drug Administration and the European Medicines Agency in cancer therapy.

| Antibody | Brand name | Type | Target: antibody type | Application | Company | Approval year EU | USA |
|---|---|---|---|---|---|---|---|
| Rituximab | Rituxan, MabThera | Chimeric IgG1 | CD20 | Non-Hodgkin lymphoma | Genentech | 1998 | 1997 |
| Trastuzumab | Herceptin | Humanized IgG1 | HER2 | Beast cancer | Genentech/Roche | 2000 | 1998 |
| Gemtuzumab ozogamicin | Mylotarg* | Humanized IgG4, immunotoxin | CD33 | Acute myeloid leukemia | Wyeth/Pfizer | NA | 2000 |
| Alemtuzumab | MabCampath, Campath-IH | Humanized IgG1 | CD52 | Chronic myeloid leukemia | Genzyme | 2001 | 2001 |
| Ibritumomab tiuxecan | Zevalin | Murine IgG1 | CD20 | Non-Hodgkin lymphoma | Biogen Idec | 2004 | 2002 |
| Tositumomab | Bexxar | Murine IgG2a | CD20 | Non-Hodgkin lymphoma | Corixa/GSK | NA | 2003 |
| Cecuximab | Erbitux | Chimeric IgG1 | EGFR | Colorectal cancer, head and neck cancer | Imclone/Lilly | 2004 | 2004 |
| Bevacizumab | Avastin | Humanized IgG1 | VEGF | Colorectal cancer, non-small cell lung cancer | Genentech/Roche | 2005 | 2004 |
| Panitumumab | Vectibix | Human IgG2 | EGFR | Colorectal cancer | Amgen | 2007 | 2006 |
| Ofatumumab | Arzerra | Human IgG1 | CD20 | Chronic lymphocytic leukemia | Genmab | 2010 | 2009 |
| Denosumab | Prolia | Human IgG2 | RANK ligand | Bone metastases, giant cell tumor of bone | Amgen | 2010 | 2010 |
| Ipilimumab | Yervoy | Human IgG1 | CTLA-4 | Melanoma | BMS | 2011 | 2011 |
| Brentuximab vedotin | Adcetris | Chimeric IgG1, drug-conjugate | CD30 | Anaplastic large cell lymphoma, Hodgkin lymphoma | Seattle Genetics | 2012 | 2011 |

TABLE 4-continued

List of monoclonal antibodies approved by the US Food and Drug Administration and the European Medicines Agency in cancer therapy.

| Antibody | Brand name | Type | Target: antibody type | Application | Company | Approval year EU | Approval year USA |
|---|---|---|---|---|---|---|---|
| Pertuzumab | Perjeta | Humanized IgG1 | HER2 | Breast cancer | Genentech/Roche | 2013 | 2012 |
| Ado-trastuzumab emtansine | Kadcyla | Humanized IgG1, drug-conjugate | HER2 | Breast cancer | Genentech/Roche | in review | 2013 |

Note:
*withdrawn in 2010.
Abbreviations: CTLA 4, cytotoxic T-lymphocyte antigen 4; EGFR, epidermal growth factor receptor; HER, human epidermal receptor; NA, not approved; VEGF, vascular endothelial growth factor.

Any of the antibodies disclosed in Table 4 of Salsano and Treglia can be labeled according to the methods provided herein. Other antibodies amenable to labeling as described herein include, but are not limited to, those described in Wright and Lapi, "Designing the magic bullet? The advancement of immuno-PET into clinical use." J. Nucl. Med. 2013 August; 54(8):1171-4; the entire contents of which are hereby incorporated by reference. These antibodies (see below) were successfully labeled with isotopes and were used in PET based diagnostic and/or therapeutic applications. However, the antibodies were labeled via chemical means that are not always amenable to quickly generating labeled antibodies with isotopes having a short half-life. Thus, such antibodies can be quickly and efficiently labeled with any desired isotope according to the methods, compositions, reagents, and kits provided herein. Antibodies disclosed by Wright and Lapi, include:

Humanized A33 (huA33), which recognizes A33 antigen, which is known to be expressed in greater than 95% of human colon adenocarcinomas. In a study utilizing radiolabeled huA33 (Carrasquillo et al., "$^{124}$I-huA33 antibody PET of colorectal cancer." J. Nucl. Med. 2011; 52:1173-1180; the entire contents of which are hereby incorporated by reference), 25 patients with primary or metastatic colorectal cancer (CRC) were administered 44.4-396 MBq (median, 343 MBq) of $^{124}$I-huA33 with a total of 10 mg of huA33. No adverse side effects were observed during the treatment that could be attributed to the huA33. The antibody could be administered via intravenous administration or hepatic arterial infusion (HAI), with HAI giving no detectable advantage over intravenous injection. Eleven patients had 12 primary tumors, 10 of which were detected via immuno-PET. Ten patients had liver metastases, all of which were detected by $^{124}$I-huA33. Four of 7 patients with nodal metastases displayed uptake of the $^{124}$I-huA33, and 2 of 5 patients had lung lesions that were visualized by immuno-PET.

Radretumab (L19SIP), which targets an epitope contained in the extra-domain B of fibronectin, was labeled with $^{124}$I and used to establish provisional doses of $^{131}$I-labeled radretumab in 6 patients with brain metastasis (Poli et al., "Radretumab radioimmunotherapy in patients with brain metastasis: a $^{124}$I-L19SIP dosimetric PET study. Cancer Immunol Res. 2013:OF1-OF10; the entire contents of which are hereby incorporated by reference).

Girentuximab (cG250), a chimeric antibody that binds carbonic anhydrase IX (CAIX), expressed in >95% of clear cell renal carcinoma (ccRCC), was labeled with $^{124}$I and used to detect such cancers (Divgi et al., "Positron emission tomography/computed tomography identification of clear cell renal cell carcinoma: results from the REDECT Trial." J. Clin. Oncol. 2013; 31:187-194; the entire contents of which are hereby incorporated by reference).

Panitumumab, a fully humanized antibody that binds epidermal growth factor receptor (EGFR), was successfully labeled with $^{89}$Zr and used to image colorectal tumor xenografts (Nayak et al., "PET and MR imaging of metastatic peritoneal and pulmonary colorectal cancer in mice with human epidermal growth factor receptor 1-targeted $^{89}$Zr-Labeled panitumumab." J. Nucl. Med. 2012; 53:113-120; Chang et al., "Development and characterization of $^{89}$Zr-labeled panitumumab for immuno-positron emission tomographic imaging of the epidermal growth factor receptor." Mol. Imaging. 2013; 12:17-27; the entire contents of each are hereby incorporated by reference).

U36, a chimeric antibody that recognizes the v6 region of CD44, was labeled with $^{89}$Zr to image head and neck squamous cell carcinoma (Börjesson et al. "Radiation dosimetry of $^{89}$Zr-labeled chimeric monoclonal antibody U36 as used for immuno-PET in head and neck cancer patients." J. Nucl. Med. 2009; 50:1828-1836; the entire contents of which are hereby incorporated by reference).

Trastuzumab, cetuximab, and bevacizumab (see Table 4 above), were also successfully labeled with $^{89}$Zr and used in PET applications (Dijkers et al., "Biodistribution of $^{89}$Zr-trastuzumab and PET imaging of HER2-positive lesions in patients with metastatic breast cancer." Clin. Pharmacol. Ther. 2010; 87:586-592; www.cancer.gov/clinicaltrials/search/results?protocolsearchid511815785. Accessed Jul. 15, 2013; the entire contents of each are hereby incorporated by reference).

In some embodiments, the protein (e.g., antibody) to be radiolabeled binds to a tumor antigen. In general, a tumor antigen can be any antigenic substance produced by tumor cells (e.g., tumorigenic cells, or in some embodiments tumor stromal cells, e.g., tumor-associated cells such as cancer-associated fibroblasts). In many embodiments, a tumor antigen is a molecule (or portion thereof) that is differentially expressed by tumor cells as compared with non-tumor cells. In other embodiments, a tumor antigen is expressed on the surface of the cell. Tumor antigens may include, e.g., proteins that are normally produced in very small quantities and are expressed in larger quantities by tumor cells, proteins that are normally produced only in certain stages of development, proteins whose structure (e.g., sequence or post-translational modification(s)) is modified due to a mutation in tumor cells, or normal proteins that are (under normal conditions) sequestered from the immune system. Tumor antigens may be useful in, e.g., identifying or detecting tumor cells (e.g., for purposes of diagnosis and/or for purposes of monitoring subjects who have received treatment for a tumor, e.g., to test for recurrence) and/or for purposes of targeting various agents (e.g., therapeutic agents) to tumor cells. For example, in some embodiments, a radiolabeled antibody is provided comprising an antibody or antibody fragment that binds a tumor antigen, thereby allowing detection of the tumor in vivo, e.g., using PET. In some embodiments, a tumor antigen is an expression product of a mutated gene, e.g., an oncogene or mutated tumor suppressor gene, an overexpressed or aberrantly expressed cellular protein, an antigen encoded by an oncogenic virus (e.g., HBV; HCV; herpesvirus family members such as EBV, KSV; papilloma virus, etc.), or an oncofetal antigen. Oncofetal antigens are normally produced in the early stages of embryonic development and largely or completely disappear by the time the immune system is fully developed. Examples are alphafetoprotein (AFP, found, e.g., in germ cell tumors and hepatocellular carcinoma) and carcinoembryonic antigen (CEA, found, e.g., in bowel cancers and occasionally in lung and breast cancers). Tyrosinase is an example of a protein normally produced in very low quantities but whose production is greatly increased in certain tumor cells (e.g., melanoma cells). Other exemplary tumor antigens include, e.g., CA-125 (found, e.g., in ovarian cancer); MUC-1 (found, e.g., in breast cancer); epithelial tumor antigen (found, e.g., in breast cancer); melanoma-associated antigen (MAGE; found, e.g., in malignant melanoma); and prostatic acid phosphatase (PAP, found in prostate cancer). In some embodiments, a tumor antigen is at least in part exposed at the cell surface of tumor cells. In some embodiments, a tumor antigen comprises an abnormally modified polypeptide or lipid, e.g., an aberrantly modified cell surface glycolipid or glycoprotein. It will be appreciated that a tumor antigen may be expressed by a subset of tumors of a particular type and/or by a subset of cells in a tumor.

Other exemplary therapeutic/diagnostic antibodies that are useful in the production of radiolabeled antibodies or proteins according to the methods provided herein include, but are not limited to, the following antibodies (the target of the antibody is listed in parentheses together with exemplary non-limiting therapeutic indications):

Abciximab (glycoprotein IIb/IIIa; cardiovascular disease), Adalimumab (TNF-α, various auto-immune disorders, e.g., rheumatoid arthritis), Alemtuzumab (CD52; chronic lymphocytic leukemia), Basiliximab (IL-2Rα receptor (CD25); transplant rejection), Bevacizumab (vascular endothelial growth factor A; various cancers, e.g., colorectal cancer, non-small cell lung cancer, glioblastoma, kidney cancer; wet age-related macular degeneration), Catumaxomab (CD3 and EpCAM, malignant ascites), Cetuximab (EGF receptor, various cancers, e.g., colorectal cancer, head and neck cancer), Certolizumab (e.g., Certolizumab pegol) (TNF alpha; Crohn's disease, rheumatoid arthritis), Daclizumab (IL-2Rα receptor (CD25); transplant rejection), Eculizumab (complement protein $C_5$; paroxysmal nocturnal hemoglobinuria), Efalizumab (CD11a; psoriasis), Gemtuzumab (CD33; acute myelogenous leukemia (e.g., conjugated to calicheamicin)), Ibritumomab tiuxetan (CD20; Non-Hodgkin lymphoma (e.g., labeled with yttrium-90 or indium-111)), Infliximab (TNF alpha; various auto-immune disorders, e.g., rheumatoid arthritis) Muromonab-CD3 (T Cell CD3 receptor; transplant rejection), Natalizumab (alpha-4 (a4) integrin; multiple sclerosis, Crohn's disease), Omalizumab (IgE; allergy-related asthma), Palivizumab (epitope of RSV F protein; Respiratory Syncytial Virus infection), Panitumumab (EGF receptor; cancer, e.g., colorectal cancer), Ranibizumab (vascular endothelial growth factor A; wet age-related macular degeneration) Rituximab (CD20; non-Hodgkin lymphoma), Tositumomab (CD20; non-Hodgkin lymphoma), Trastuzumab (ErbB2; breast cancer), and any antigen-binding fragments thereof.

In some embodiments, the protein (e.g., antibody) to be radiolabeled binds a marker of inflammation. In some embodiments the protein to be radiolabeled is a VHH7 or a VHHDC13, which binds murine MHC class II molecules and CD11b, respectively. The protein (e.g., VHH7 or VHHDC13) may contain additional sequences, including, but not limited to an enzyme recognition sequence (e.g., a sortase recognition sequence), an epitope tag (e.g., a His tag) or a PELB leader sequence. A PELB leader sequence is a sequence of amino acids that, when conjugated to a protein, directs the protein to the bacterial periplasm, where it is removed by a signal peptidase. Protein secretion may increase the stability of cloned gene products. In some embodiments the proteins, described herein may contain a PELB comprising the amino acid sequence MKYLLPTAAAGLLLLAAQPAMA (SEQ ID No: 82). The VHH7 or VHHDC13 protein, may comprise a sortase recognition motif, a His epitope tag and a PELB leader sequence. In some embodiments, the VHHDC13 is encoded by a nucleic acid comprising the nucleic acid sequence set forth in (SEQ ID NO: 83), which encodes the amino acid sequence set forth in (SEQ ID NO: 84). In other embodiments, the VHH7 is encoded by a nucleic acid comprising the nucleic acid sequence set forth in (SEQ ID NO: 85), which encodes the amino acid sequence set forth in (SEQ ID NO: 86). In other embodiments, the VHH4 is encoded by a nucleic acid comprising the nucleic acid sequence set forth in (SEQ ID NO: 90), which encodes the amino acid sequence set forth in (SEQ ID NO: 91).

```
                                          (SEQ ID NO: 83)
ATGAAATACCTATTGCCTACGGCAGCCGCTGGATTGTTATTACTCGCGGC

CCAGCCGGCCATGGCCCAGGTGCAGCTGCAGGAGTCAGGGGGAGGATTGG

TGCAAACTGGGGCTCTCTGAGACTCTCCTGTGCAGCCTCTGGAGTTGAC

TTCAATTGGTATAGTATGGGGTGGTTCCGCCAGGCTCCAGGGAAGGAGCG

TGAATACGTTGCAAGTATAGACCAAGGTGGTGAATTAGATTATGCCATCT

CCGTGAAGGGACGATTTACTATCTCCAGAGACAACGCCAAGAACATGGTG

TATCTCCAAATGAACAGCCTGAAACCTGAGGACACGGCCGTTTATTACTG

TGCAGCAGATTTCAGCGGGCGCGGCGCGAGTAATCCAGATAAGTATAAAT

ACTGGGGCCAGGGGACCCAGGTCACCGTCTCCTCAGGAGGACTGCCGGAA

ACCGGCGGCCACCACCATCACCATCACTAATAG.
```

```
                                          (SEQ ID NO: 84)
MKYLLPTAAAGLLLLAAQPAMAQVQLQESGGGLVQTGGSLRLSCAASGVD

FNWYSMGWFRQAPGKEREYVASIDQGGELDYAISVKGRFTISRDNAKNMV

YLQMNSLKPEDTAVYYCAADFSGRGASNPDKYKYWGQGTQVTVSSGGLPE

TGGHHHHHH.
```

```
                                          (SEQ ID NO: 85)
ATGAAATACCTATTGCCTACGGCAGCCGCTGGATTGTTATTACTCGCGGC

CCAGCCGGCCATGGCCCAGGTGCAGCTGCAGGAGTCAGGGGGAGGATTGG

TGCAGGCTGGGGACTCTCTGAGACTCTCCTGCGCAGCCTCTGGACGCACC

TTCAGTCGCGGTGTAATGGGCTGGTTCCGCCGGGCTCCAGGGAAGGAGCG

TGAGTTTGTAGCAATCTTTAGCGGGAGTAGCTGGAGTGGTCGTAGTACAT
```

-continued

ACTATTCAGACTCCGTAAAGGGCCGATTCACCATCTCCAGAGACAACGCC

AAGAACACGGTGTATCTGCAAATGAACGGCCTGAAACCTGAGGACACGGC

CGTTTATTACTGTGCAGCGGGATATCCGGAGGCGTATAGCGCCTATGGTC

GGGAGAGTACATATGACTACTGGGGCCAGGGGACCCAGGTCACCGTCTCC

TCAGGAGGACTGCCGGAAACCGGCGGCCACCACCATCACCATCACTAATA

G.

(SEQ ID NO: 86)
MKYLLPTAAAGLLLLAAQPAMAQVQLQESGGGLVQAGDSLRLSCAASGRT

FSRGVMGWFRRAPGKEREFVAIFSGSSWSGRSTYYSDSVKGRFTISRDNA

KNTVYLQMNGLKPEDTAVYYCAAGYPEAYSAYGRESTYDYWGQGTQVTVS

SGGLPETGGHHHHHH.

(SEQ ID NO: 90)
ATGAAATACCTATTGCCTACGGCAGCCGCTGGATTGTTATTACTCGCGGC

CCAGCCGGCCATGGCCCAGGTGCAGCTGCAGGAGTCAGGGGGAGGATTGG

TGCAGGCTGGGGGTCTCTGAGACTCTCCTGTGCAGCCTCTGGAAGCACC

CTCAGTAGCTATGGCATGGGCTGGTACCGCCAGGCTCCAGGGAAGCAACG

TGAAGTGGTCGCAACTATTAGTGCTACTGGTAGCATAAGCTATGCAGACT

CCGTGAAGGGCCGATTCACCATCTCCAGAGACAGTGCCAAGAACACGATG

TATCTGCAACTGAACAGCCTGACACCTGAGGACACGGCCGTCTATTACTG

TAACACAATTTATAGGTCTACTCTCTACTGGGGCCAGGGGACCCAGGTCA

CCGTCTCCTCAGGAGGACTGCCGGAAACCGGCGGCCACCACCATCACCAT

CAC.

(SEQ ID NO: 91)
MKYLLPTAAAGLLLLAAQPAMAQVQLQESGGGLVQAGGSLRLSCAASGST

LSSYGMGWYRQAPGKQREVVATISATGSISYADSVKGRFTISRDSAKNTM

YLQLNSLTPEDTAVYYCNTIYRSTLYWGQGTQVTVSSGGLPETGGHHHHH

H.

As one example, described in Example 2, radiolabeled VHH7 allowed for the successful in vivo imaging of immune cells, which localize to lymph tissues, as well as sites of inflammation surrounding tumors. In some embodiments, the radiolabeled proteins (e.g., radiolabeled antibodies or antibody fragments), described herein, may be used to image an immune response. The in vivo imaging of the inflammatory response, e.g., by labeling sites of inflammation using the methods and compositions provided herein, allows for non-invasive diagnosis, monitoring, and treatment of inflammatory disorders, as described herein. Other exemplary inflammatory markers to which radiolabeled proteins of the instant disclosure may bind include, but are not limited to, cytokines, tumor necrosis factor (TNF)-α, IL-6, IL-1 beta, IL-8, IL-10, IL-12, IL-16, IL-18, monocyte chemoattractant protein-1 (MCP-1), GRO-α (Growth Related Oncogene-α), matrix metalloproteinase-8 (MMP-8), CSFs (colony-stimulating factors), epithelial cell-derived neutrophil-activating peptide-78 (ENA-78), regulated on activation normal T cell expressed and secreted (RANTES) CCL5, CXCL6 (granulocyte chemotactic protein-2), CXCL9 MIG, CXCL10; IP-10, CXCL11, CXCL13 (BCA-1), Exodus-1 (CCL20), MIF (macrophage migration inhibitory factor): MIP-1alpha (CCL3), MIP-1beta (CCL4), CD11b, CD11c, CD13, CD15, CD66, CD14, CD64, CD66b, CD18, CD16, CD62L, CD67, HLA-DR, sHLA-G, Dihydroepiandrotendione (DHEA)-S, Cortisol CRF (corticotrophin-releasing factor), CRF-binding protein, alpha-defensin, beta-defensin, neutrophil defensins (HNP 1-3), bactericidal/permeability-increasing protein (BPI), calprotectin (MRP8/14), surfactant protein-A, surfactant protein-D, serum amyloid P component, serum amyloid A, complement factors, mannan-binding lectin, fibrinogen, prothrombin, factor VIII, von Willebrand factor, plasminogen, mannan-bindinglectin, c-reactive protein, Pentraxin 3, scavenger receptors, C-type lectins, Toll-like receptor (TLR)-4, TLR-2, TLR-3, TLR-6, intracellular pattern recognition receptors (Nod1, Nod2, RIG-1, MDA-5), RAGE (receptor for advanced glycation endproduct), alpha 2-macroglobulin, ferritin, hepcidin, ceruloplasmin, haptoglobin, orosomucoid, alpha 1-antitrypsin, alpha 1-antichymotrypsin, lipopolysaccharide-binding protein (LBP), albumin, transferrin (including lactoferrin), transthyretin, retinol-binding protein, antithrombin, transcortin, adrenocorticotropin, Urocortin, estriol, MMP-1, MMP-2, TIMP-2, MMP-3, MMP-7, MMP-9, arachidonate lipoxygenase metabolites, prostaglandins, prostacyclins, thromboxanes, leukotrienes, Catalase, Caspase-1 (NALP3 inflammasome), leptin, adiponectin, resistin, visfatin, Retinol binding protein 4 (RBP4), endotoxin, Epidermal growth factor (EGF), insulin-like growth factor binding protein-1 (IGFBP-1), neutrophil elastase, leukocyte elastase (ELA2, neutrophil), SLPI (secretory leukocyte protease inhibitor), S100 calcium binding protein B, Heat shock protein, Endothel in-1, -2, Angiopoietin-2, Calcium-binding protein, Soluble Triggering receptor expressed on myeloid cells 1 (sTREMi), Protein-Z (vitamin K-dependent plasma glycoprotein), and Tissue factor and Platelet activating factor (PAF).

In other embodiments, the radiolabeled proteins (e.g., radiolabeled antibodies or antibody fragments), described herein, may be used to image immune cells independent of an immune response. This may be done using antibodies that detect specific immune cell markers that are not indicative of an active immune response. As one example, naïve T cells may be imaged using any of the radiolabelled antibodies or antibody fragments, described herein, that bind to the naïve T cell markers CD3, CD4, CD45RA, CD45RB, CD197, or CD62L. Further information on various immune cell types may be found in, e.g., Zhu, J., et al., Differentiation of effector CD4 T cell populations. Annu. Rev. Immunol., 28 (2010), pp. 445-489; S. Crotty, Follicular helper CD4 T cells (TFH), Annu. Rev. Immunol., 29 (2011), pp. 621-663. Of course it would be understood that certain of these markers (e.g., CD3, CD4) would also be expressed on T cells involved in an immune response and could be used as targets for imaging an immune response.

The inventive radiolabeled proteins (e.g., antibodies or antibody fragments) may be used to non-invasively image tumor and/or T cell markers. In some embodiments, the radiolabeled antibodies or antibody fragments detect markers including, but not limited to PD-L1, PD-1, PD-2, CTLA-4, CD3, CD4, CD8, or CD28.

In certain embodiments, the inventive radiolabeled proteins (e.g., antibodies or antibody fragments) bind to proteins involved in immune checkpoint pathways. "Immune checkpoint pathways" or "immune checkpoints" are naturally existing inhibitory pathways of the immune system that play important roles in maintaining self-tolerance and modulating the duration and level of effector output (e.g., in the case of T cells, the levels of cytokine production, proliferation or target killing potential) of physiological immune responses in order to minimize damage to the tissues of the individual mounting the immune response. Such pathways may, for example, downmodulate T cell activity or enhance regulatory T cell immunosuppressive activity. Examples of immune checkpoint pathways include, but are not limited to the PD-1 pathway and the CTLA-4 pathway and the TIM3 pathway. Tumors frequently co-opt certain immune-checkpoint pathways as a major mechanism of immune resistance, e.g., against T cells that are specific for tumor antigens. Furthermore, chronic antigen exposure, such as occurs in cancer, can lead to high levels of expression of immune checkpoint proteins (e.g., PD1, PD-L1, PD-L2) by immune cells, which can induce a state of T cell exhaustion or anergy. Certain immune checkpoint proteins such as CTLA4 and PD1 are highly expressed on T regulatory ($T_{Reg}$) cells and may enhance their proliferation. Many tumours are highly infiltrated with $T_{Reg}$ cells that likely suppress effector immune responses, Thus, blockade of the PD1 pathway and/or the CTLA4 pathway may enhance antitumour immune responses by diminishing the number and/or suppressive activity of intratumoral $T_{Reg}$ cells. Certain aspects of the invention utilize the radiolabeled proteins (e.g., radiolabeled antibodies or antibody fragments) for diagnosing or monitoring a disease or condition (e.g., cancer) or the response of a disease or condition (e.g., cancer) to therapy. For example, the radiolabeled antibodies or antibody fragments may be used to detect whether a tumor expresses an immune checkpoint marker (e.g., an immune checkpoint protein) and/or to detect whether a tumor contains immune cells that express an immune checkpoint marker (e.g., an immune checkpoint protein). In other embodiments, the inventive radiolabeled proteins (e.g., radiolabeled antibodies or antibody fragments) bind to an immune checkpoint modulator. In some embodiments the immune checkpoint modulator is an immune checkpoint inhibitor. "Immune checkpoint inhibitor" refers to any agent that inhibits (suppresses, reduces activity of) an immune checkpoint pathway. In some embodiments the immune checkpoint modulator is an immune checkpoint activator. "Immune checkpoint activator" refers to any agent that activates (stimulates, increases activity of) an immune checkpoint pathway.

Immune checkpoint inhibitors, e.g., monoclonal antibodies that bind to immune checkpoint proteins such as CTLA4, PD1, PD-L1 have shown notable efficacy in treating a variety of different cancers, including cancers that are advanced, have failed to respond to conventional chemotherapeutic agents, and/or have a poor prognosis, such as metastatic melanoma (see, e.g., Pardoll, D M, The blockade of immune checkpoints in cancer immunotherapy, Nat Rev Cancer. 2012; 12(4):252-64). However, not all subjects with tumors of a particular type may experience benefit from treatment with a given immune checkpoint inhibitor. One or ordinary skill would appreciate that a benefit could be, e.g., stable disease rather than progressive disease, eventual reduced number and/or volume of tumor lesions, increased mean survival, etc. Detection of immune checkpoint markers using any of the methods, described herein, may be used to determine whether or not to administer a therapeutic and/or to select a therapeutic (e.g., from among multiple different therapeutic options). For example, a radiolabeled antibody or antibody fragment that binds PD-L1 can be used to detect whether a tumor within a patient expresses PD-L1. Patients having a PD-L1 positive tumor may then be administered a therapeutic that targets the PD1 pathway, e.g., a therapeutic (such as an antibody) that targets PD1 or PD-L1. A radiolabeled protein (e.g., radiolabeled antibody or antibody fragment) that binds PD1 can be used to detect whether a tumor within a patient is positive for PD1 (e.g., due to the presence of immune cells that express high levels of PD1). Patients having a PD1 positive tumor may then be administered a therapeutic agent that targets the PD1 pathway, In some embodiments a radiolabeled protein (e.g., radiolabeled antibody or antibody fragment) that binds TIM3 can be used to detect whether a tumor within a patient is positive for TIM3 (e.g., due to the presence of immune cells that express high levels of TIM3). Patients having a TIM3 positive tumor may then be administered a therapeutic that targets the TIM3 pathway, e.g., a therapeutic (such as an antibody) that targets TIM3. In some embodiments a radiolabeled protein (e.g., radiolabeled antibody or antibody fragment) that binds CTLA4 can be used to detect whether a tumor within a patient is positive for CTLA4 (e.g., due to the presence of immune cells that express high levels of CTLA4). Patients having a CTLA4 positive tumor may then be administered a therapeutic that targets the CTLA4 pathway, e.g., a therapeutic (such as an antibody) that targets CTLA4. In some embodiments a subject with a tumor may be imaged with two, three, or more radiolabeled proteins (e.g., antibodies, antibody fragments) that bind to different immune checkpoint proteins (e.g., proteins involved in different immune checkpoint pathways). One or more immune checkpoint pathways that are positive in the tumor are identified. The patient is then treated with one or more agent(s) that target those immune checkpoint pathways for which a tumor (or one or more tumor(s)) in the subject is positive. In some embodiments, if the tumor is negative for a particular immune checkpoint pathway or immune checkpoint protein, an alternative treatment may be administered instead of an immune checkpoint inhibitor that would target that immune checkpoint pathway or immune checkpoint protein. Other aspects of the invention utilize the radiolabeled antibodies or antibody fragments for monitoring the response to a therapeutic or monitoring expression of a protein, such as an immune checkpoint inhibitor protein. For example, a radiolabeled antibody or antibody fragment, described herein, may be used to detect whether an immune response has been generated or enhanced or suppressed at a site of interest, such as at the site of a tumor or a site of infection, or whether the tumor expresses an immune checkpoint protein (e.g., PD-L1). In some embodiments a radiolabeled protein that binds to an immune cell, e.g., a T cell, may be administered to a subject before, concurrently, and/or after administration of a treatment intended to enhance or inhibit an immune response. Images may be compared from before and after treatment to assess the effect of the treatment on the immune response. In some embodiments, the inventive radiolabeled proteins may be used to monitor the response to a therapeutic at least every 1 day, at least every 5 days, at least every 10 days, at least every 15 days, at least every 30 days, at least every 45 days, at least every 60 days, at least every 120 days, at least every 180 days, at least every 240 days or at least every year. In some embodiments a subject may be monitored for, e.g., up to 3, 6, 9 months, up to 1, 2, 5, years, or more. In some embodiments, a therapeutic agent that targets an immune checkpoint inhibitor pathway is a monoclonal antibody. In some embodiments, the monoclonal antibody is a chimeric, humanized, or human monoclonal antibody. In some embodiments, the antibody is an IgG antibody, e.g., an IgG1 or IgG4 antibody. In some embodiments, a therapeutic agent that targets the CTLA4 pathway is a monoclonal antibody that binds to CTLA4, such as ipilimumab (Yervoy) or tremelimumab. In some embodiments, a therapeutic agent that targets the PD1 pathway is a monoclonal antibody that binds to PD1, such as nivolumab (a fully human IgG4 monoclonal antibody), pidilizumab (also known as CT-011, a humanized IgG1 monoclonal antibody), or pembrolizumab (Keytruda, formerly lambrolizumab; also known as MK-3475), a humanized IgG4 monoclonal antibody), or MEDI0680 (AMP-514, a humanized IgG4mAb against PD-1). In some embodiments, a therapeutic agent that targets the PD1 pathway is a monoclonal antibody that binds to PD-L1 such as BMS-936559 (a fully human IgG4 monoclonal antibody), MPDL3280A (human monoclonal, Genentech), MSB0010718C (Merck Serono), or MEDI4736. In some embodiments, a therapeutic agent that targets the PD1 pathway is a monoclonal antibody that binds to PD-L2. In some embodiments, a therapeutic agent that targets the PD1 pathway is a recombinant fusion protein comprising extracellular domain of PD-L2 such as AMP-224. A variety of PD1 pathway inhibitors, e.g., antibodies that bind to PD-1, PD-L1, or PD-L2 are described in U.S. Pat. Pub. No. 20040213795, 20110195068, 20120039906, 20120114649, 20130095098, 20130108651, 20130109843, 20130237580, and 20130291136, all of which are incorporated by reference herein.

In some embodiments, the subject suffers from a solid tumor. In some embodiments, the subject suffers from melanoma, renal cell carcinoma, non-small-cell lung cancer, ovarian cancer, brain cancer (e.g., glioblastoma), lymphoma (e.g., Non-Hodgkin lymphoma), hepatocellular, esophageal, breast (e.g., triple negative breast cancer), multiple myeloma, or pancreatic cancer. In some embodiments, the subject has a metastatic cancer, stage III cancer, or stage IV cancer.

It would be understood that the immune checkpoint inhibitor could be administered as a single agent or in combination with one or more other anti-tumor agents.

One aspect of the invention relates to radiolabelled proteins (e.g., antibodies or antibody fragments) that are capable of reaching their targets and are cleared quickly from the circulation. Whole antibodies and their fragments have different characteristics that determine their targeting properties, such as how quickly they reach the target antigen and clear from the blood, which organ clears the antibody from the blood, penetration into the tumor and amount of the injected radiolabeled antibody or antibody fragment binding to the target. Once antibodies target their respective antigens, they generally bind with high avidity, which in turn determines their tumor residence time, whereas the unbound antibody is processed by various organs in the body and eventually degraded and excreted. Whole IgG, which is the principal antibody form used, clears very slowly from the blood, requiring several days before a sufficient amount leaves the circulation to allow the specific concentration taken into the tumor to be distinguished from blood and adjacent tissue radioactivity. Its slow clearance is in part owing to its large size (approximately 150,000 Da) that impedes its extravasation, resulting in a slow tumor accretion. As the molecular size of an antibody is reduced from a divalent $F(ab')_2$ fragment (approximately 100,000 Da) to the monovalent binding Fab fragment (approximately 50,000 Da), there is a progressively faster clearance from the blood. Molecular engineering has enabled the formation of even smaller antibody structures, such as scFv (approximately 25,000 Da), which are cleared even more rapidly from the blood. See Goldenberg D. M. et al., "Novel radiolabeled antibody conjugates." Oncogene. 2007, 26, 3734-3744; the entire contents of which are hereby incorporated by reference. Accordingly, in some embodiments the radiolabeled proteins (e.g., antibodies or antibody fragments), described herein, have a molecular weight of less than 60 kDa, less than 55 kDa, less than 50 kDa, less than 45 kDa, less than 40 kDa, less than 35 kDa, less than 30 kDa, less than 25 kDa less than 20 kDa, less than 15 kDa, less than 10 kDa, or less than 5 kDa. In other embodiments the radiolabelled proteins (e.g., antibodies or antibody fragments), described herein, have a molecular weight ranging from 5 kDa-15 kDa, from 5 kDa-20 kDa, from 5 kDa-25 kDa, from 5 kDa-30 kDa, from 5 kDa-35 kDa, from 5 kDa-40 kDa, from 5 kDa-45 kDa, from 5 kDa-55 kDa, from 5 kDa-60 kDa, from 15 kDa-20 kDa, from 15 kDa-25 kDa, from 15 kDa-30 kDa, from 15 kDa-35 kDa, from 15 kDa-40 kDa, from 15 kDa-45 kDa, from 15 kDa-50 kDa, from 15 kDa-55 kDa, from 15 kDa-60 kDa, from 25 kDa-35 kDa, from 25 kDa-45 kDa, from 25 kDa-55 kDa, from 25 kDa-60 kDa, from 35 kDa-45 kDa, from 35 kDa-55 kDa, from 35 kDa-60 kDa, from 45 kDa-55 kDa, from 45 kDa-60 kDa, or from 50 kDa-60 kDa. In yet other embodiments the radiolabelled proteins (e.g., antibodies or antibody fragments), described herein, are expediently cleared from the circulation following injection into a patient. In some embodiments, at least 95% of the radiolabelled proteins (e.g., antibodies or antibody fragments) are cleared from the blood within 20 minutes, within 30 minutes, within 40 minutes, within 60 minutes, within 80 minutes, within 30 minutes, within 40 minutes, within 60 minutes, within 90 minutes, within 2 hours, within 3 hours, within 4 hours, within 6 hours, within 8 hours, within 10 hours or within 12 hours. In other embodiments, at least 95% of the radiolabelled proteins (e.g., antibodies or antibody fragments) are cleared from the body within 20 minutes, within 30 minutes, within 40 minutes, within 60 minutes, within 80 minutes, within 30 minutes, within 40 minutes, within 60 minutes, within 90 minutes, within 2 hours, within 3 hours, within 4 hours, within 6 hours, within 8 hours, within 10 hours or within 12 hours.

In some embodiments, the agent conjugated to a target protein is a protein, a detectable label, a radiolabeled compound or small molecule, or any other agent described herein. It should be appreciated that the inventive radiolabeled proteins, described herein, may be used for non-invasive diagnosis of disease, monitoring of disease progression, monitoring of response to treatment, or for the treatment of a disease.

In some embodiments, the methods provided herein further comprise purifying the labeled protein. Methods for purifying proteins are well known in the art, and include those described by Green and Sambrook, *Molecular Cloning: A Laboratory Manual* (4th ed., Cold Spring Harbor Laboratory Press, Cold Spring Harbor, N.Y. (2012)), the entire contents of which are incorporated herein by reference. In some embodiments, a target protein may further include a purification tag, detectable label, or both. For example, the fusion protein may comprise a poly-histidine tag (e.g., a 6×His-tag (SEQ ID NO: 133)) for purification purposes (e.g., nickel or cobalt affinity based purification; see Hochuli et al., *Nature Biotechnology.* 1988, 6, 1321-1325). In some embodiments, the poly-histidine tag comprises 4, 5, 6, 7, 8, 9, or 10 histidines.

According to another embodiment of the invention, methods for modifying a sortase substrate peptide are provided. Such methods are useful for generating sortase substrate peptides having a desired label, such as a radiolabel (e.g., by linking a radioactive agent to the sortase substrate peptide). Such modified sortase substrate peptides can then be used to generate radiolabeled proteins using sortagging technology, as described herein. In some embodiments, the method comprises contacting a sortase substrate peptide that comprises a nucleophilic group with a radiolabeled agent that comprises an electrophilic group under conditions suitable for the formation of a covalent bond (linkage) between the sortase substrate peptide and agent. In some embodiments, the nucleophilic/electrophilic pairings are any of those suitable for use in click chemistry, as described herein. In some embodiments, the nucleophilic group is an aminooxy group, a hydrazide, or thiosemicarbazide. In some embodiments, the electrophilic group is a carbonyl group, such as an aldehyde or ketone. As described herein, aminooxy groups, hydrazides, and thiosemicarbazides react with carbonyl groups (e.g., aldehydes and ketones) to form oxime, hydrazone, and thiosemicarbazone linkages, respectively. In some embodiments, the click chemistry partners are a conjugated diene and an optionally substituted alkene, In other embodiments, the click chemistry partners are an optionally substituted tetrazine and an optionally substituted trans-cyclooctene (TCO). In some embodiments, the click chemistry reactive pair includes tetrazine (Tz) and trans-cyclooctene (TCO). In other embodiments, the click chemistry partners are an alkyne and an azide. For example, a difluorinated cyclooctyne, a dibenzocyclooctyne, a biarylazacyclooctynone, or a cyclopropyl-fused bicyclononyne can be paired with an azide as a click chemistry pair. In other embodiments, the click chemistry partners are reactive dienes and suitable tetrazine dienophiles. For example, TCO, norbornene or biscyclononene can be paired with a suitable tetrazine dienophile as a click chemistry pair. In yet other embodiments, tetrazoles can act as latent sources of nitrile imines, which can pair with unactivated alkenes in the presence of ultraviolet light to create a click chemistry pair, termed a "photo-click" chemistry pair. Other suitable click chemistry handles are known to those of skill in the art (See e.g., Table 1; Spicer et al., "Selective chemical protein modification." *Nature Communications*. 2014; 5:4740). For two molecules to be conjugated via click chemistry, the click chemistry handles of the molecules have to be reactive with each other, for example, in that the reactive moiety of one of the click chemistry handles can react with the reactive moiety of the second click chemistry handle to form a covalent bond. Such reactive pairs of click chemistry handles are well known to those of skill in the art and include, but are not limited to, those described in Table 1.

In some embodiments, the agent linked to the sortase substrate is any radioactive molecule or compound useful for diagnostic and/or therapeutic applications, such as PET or SPECT, that can be conjugated to a sortase substrate peptide using nucleophile/electrophile pairs. For example, in some embodiments, a sortase substrate peptide and an agent to be conjugated each comprise click chemistry handles (e.g., as described herein) capable of specifically interacting with each other to form a covalent bond. In other embodiments, the sortase substrate peptide comprises an aminooxy group, a hydrazide, or thiosemicarbazide. For example, in some embodiments, a sortase substrate peptide is synthesized to an include a C-terminal amino acid comprising an aminooxy group, a hydrazide, or thiosemicarbazide (e.g., lysine- (K-)aminooxy; see, e.g., Examples). Such a sortase substrate peptide reacts with a radioactive agent comprising a carbonyl group. In some embodiments, the radioactive agent comprising a carbonyl group (e.g., aldehyde, ketone, etc.) is a carbohydrate comprising any radionuclide (isotope) useful in diagnostic and/or therapeutic applications, for example those described herein. In some embodiments, the radioactive agent is FDG or $^{14}C$—(U)-glucose. As described herein, FDG and $^{14}C$—(U)-glucose (and other reducing sugars) isomerize in solution to form an open-chain molecule having an aldehyde that can react with a nucleophilic group of a sortase substrate peptide (e.g., as described herein). In some embodiments, the sortase peptide substrate comprises a tetrazine handle and is reacted with an agent comprising a trans-cyclooctene handle. In other embodiments, the sortase peptide substrate comprises an azide handle and is reacted with an agent comprising a difluorinated cyclooctyne, a dibenzocyclooctyne, a biarylazacyclooctynone, or a cyclopropyl-fused bicyclononyne handle. In certain embodiments, a sortase substrate comprises a tetrazine dienophile handle and is reacted with an agent comprising a TCO, a norbornene or a biscyclononene handle. In yet other embodiments, a sortase substrate comprises a nitrile imine handle and is reacted with an agent comprising an unactivated alkenes in the presence of ultraviolet light. In certain embodiments, a sortase substrate comprises a cysteine handle and is reacted with an agent comprising a maleimide. For example the cysteine from a peptide (e.g., GGGC (SEQ ID NO: 124)) may be reacted with a maleimide that is associated with a chelating agent (e.g., NOTA).

In some embodiments, the sortase substrate peptide comprises a chelator. As one example, a sortase substrate peptide (e.g., GGGC (SEQ ID NO: 124)) may be reacted with maleimide-NOTA to generate the sortase substrate peptide fused to a chelator (e.g., GGG-NOTA). The sortase substrate peptide, comprising a chelator, can be tethered to a protein of interest, having a sortase recognition motif (e.g., LPXTG (SEQ ID NO: 1)) using a sortase-mediated transpeptidation reaction. The protein of interest fused to the chelator can then be treated with a radiolabel that binds the chelator (e.g., $^{64}Cu$) to generate a radiolabeled protein. For example, the sortase substrate peptide GGG-NOTA may be fused to a VHH protein having a LPXTG (SEQ ID NO: 1) sortase recognition motif to generate a VHH protein that is fused to the NOTA chelator (e.g., VHH-NOTA). The VHH-NOTA molecule can then be treated with $^{64}Cu$ to generate a $^{64}Cu$ labeled VHH protein. In other embodiments, the sortase substrate peptide, comprising a chelator, is first treated with a radiolabel (e.g., $^{64}Cu$) to generate a radiolabeled substrate peptide, which may then be tethered to a protein of interest, having a sortase recognition motif (e.g., LPXTG (SEQ ID NO: 1)) using a sortase-mediated transpeptidation reaction. It should be appreciated that the chelator may be any chelating molecule known in the art and the examples provided are not meant to be limiting. Accordingly, the metal bound by the chelator may be any suitable metal or radiolabeled metal known in the art capable of binding to the chelator.

In some embodiments, the sortase substrate peptide comprises an N-terminal sortase recognition motif, e.g., as described herein. In other embodiments, the sortase substrate peptide comprises a C-terminal sortase recognition motif, e.g., as described herein. In some embodiments, the sortase substrate peptide (e.g., having either an N-terminal or C-terminal sortase recognition motif) further comprises a nucleophilic group, e.g., as described herein. In some embodiments, the sortase substrate peptide comprises an oligoglycine or an oligoalanine sequence, for example 1-10 N-terminal glycine residues or 1-10 N-terminal alanine residues, respectively. In some embodiments, the sortase substrate peptide comprises the sequence GGG. In some embodiments, the sortase substrate peptide comprises the sequence $(G)_{n1}K$ (SEQ ID NO: 129), wherein n1 is an integer between 1 and 10, inclusive. In some embodiments, the sortase substrate peptide comprises the sequence GGGK (SEQ ID NO:81), wherein the lysine (K) is modified to include a nucleophilic group, e.g., as provided herein. In some embodiments, the lysine (K) is modified to include a click chemistry handle. In some embodiments, the lysine (K) is modified to include an aminooxy group, a hydrazide, or thiosemicarbazide. In some embodiments, the sortase substrate peptide comprises the sequence GGGK (SEQ ID NO:81), wherein the lysine (K) is modified to include an aminooxy group. In some embodiments, the sortase substrate peptide comprises an N-terminal sortase recognition motif, wherein any amino acid or other constituent of the substrate comprises a nucleophilic group as described herein. For example, in some embodiments, the sortase substrate peptide comprises the sequence $(G)_{n1}X$ (SEQ ID NO: 134), wherein n1 is an integer between 1 and 10, inclusive, and X is any amino acid, click chemistry handle, molecule, or compound having a nucleophilic group, e.g., as described herein. Methods for generating sortase substrate peptides comprising modified amino acids (e.g., modified to include nucleophilic groups) are known, and include peptide coupling reactions (e.g., synthesis). See, e.g., Nilsson et al., "Chemical Synthesis of Proteins." *Annu. Rev. Biophys. Biomol. Struct.* 2005; 34: 91-118; the entire contents of which are hereby incorporated by reference.

In some embodiments, the methods for modifying a sortase substrate peptide further involve the use of one or more catalysts. For example, because of the need to quickly and efficiently generate radioactive sortase substrate peptides, in some embodiments the use of a catalyst results in a fast and/or more efficient coupling reaction between the sortase substrate peptide and (radioactive) agent. Typically, the methods involve contacting the sortase substrate peptide and/or agent with a catalyst. In some embodiments, the catalyst is any catalyst capable of decreasing the reaction time and/or increasing the efficiency of the coupling reactions (e.g., the nucleophilic/electrophilic pairings) between sortase substrate peptides and (radioactive) agents described herein. The catalyst will be chosen based on the functional groups and chemistry being used to couple the sortase substrate peptide to the agent. For example, with use of certain click chemistry reactions such as azide-alkyne (e.g., Huisgen) cycloaddition (see Table 2), one of skill would choose a copper based catalyst. In some embodiments, the one or more catalysts is (are) chosen from the non-limiting list that includes m-phenylenediamine (mPDA), o-phenylenediamine, p-phenylenediamine, o-aminophenol, m-aminophenol, p-aminophenol, o-aminobenzoic acid, 5-methoxyanthranilic acid, 3,5-diaminobenzoic acid or aniline. In some embodiments, the catalyst is m-phenylenediamine (mPDA).

As described herein, it can be advantageous to modify a sortase substrate peptide in as short a time frame as possible, especially when conjugating (linking) a radioactive agent to the substrate that has a relatively short half-life. Thus, in some embodiments, the methods provided herein allow for the sortase substrate peptide to be modified (e.g., linked to a radioactive agent) in less 5 minutes, less than 10 minutes, less than 15 minutes, less than 20 minutes, less than 25 minutes, less than 30 minutes, less than 45 minutes, less than 60 minutes, less than 90 minutes, or less than 120 minutes. In some embodiments, the sortase substrate peptide is modified in about 1-30 minutes, about 2-25 minutes, about 3-20 minutes, about 4-15 minutes, or in about 5-10 minutes. In some embodiments, the methods provided herein allow for at least 90%, at least 95%, or at least 98% of the sortase substrate peptide to be covalently linked to an agent.

Methods of Using Sortagged, Radiolabeled Proteins

In another aspect, provided are methods of obtaining a radiologic image of a specific tissue or organ of a subject, comprising: (i) administering the radioactive protein as described herein, or the pharmaceutical composition thereof, to the subject; (ii) obtaining the radiologic image of the tissue or organ by capturing the radiation emitted. In certain embodiments, the gamma radiation is emitted. The provided imaging methods can facilitate diagnosing, monitoring, or treating a subject in need thereof. In certain embodiments, the radioactive protein or composition thereof is prepared and administered shortly before the imaging collection step.

The subject is typically a mammalian subject, e.g., a human. In some embodiments, the subject is a non-human animal that serves as a model for a disease or disorder that affects humans. The animal model may be used, e.g., in preclinical studies, to assess efficacy and/or determine a suitable dose.

In some aspects, the instant disclosure relates to the increasing awareness of the interplay between host stromal cells, tumor cells, and migratory cells, such as macrophages and lymphocytes, and raises a number of possibilities for non-invasive diagnosis of diseases and disorders, including cancers and other proliferative diseases as well as inflammatory disorders (Forssell et al., *Clin. Cancer Res.* 2007, 13, 1472-1479; Allavena et al., *Crit. Rev. Oncol. Hematol.* 2008, 66, 1-9). For example, activated macrophages are often present at the tumor margin. Depending on their functional properties (M1 or M2-type), macrophages help establish a microenvironment either detrimental or favorable to tumor growth. Therefore, the ability to non-invasively image their presence, as described in Example 2, using anti-Class II MHC antibody fragments, represents a significant improvement over prior art methods for the diagnosis, monitoring, and treatment of disease. Current methods rely on sampling peripheral blood to enumerate and characterize cells in the circulation, or more invasive strategies such as histological analysis of biopsies or at necropsy. However, as noted by other investigators: "Invasive measurements are prone to sampling errors and are poorly reflective of the dynamic changes in the location, number, and movement of lymphoid cells. These limitations indicate the need for non-invasive whole-body imaging methodologies that allow longitudinal, quantitative, and functional analyses of the immune system in vivo" (Nair-Gill et al., *Immunol. Rev.* 2008, 221, 214-228). Sites of an ongoing inflammatory or immune response provide clues as to the existence and location of tumor foci, which a biopsy can then confirm.

Prior art methods for protein (e.g., antibody) labeling have revolved mostly around chemical modification with metal chelators to enable installation of radioisotopes such as 64Cu, $^{68}$Ga, or $^{89}$Zr (Tanaka et al., *Org. Biomol. Chem.* 2008, 6, 815; Fani et al., *Contrast Media Mol. Imaging* 2008, 3, 53-63; Vosjan et al., *Nat. Protoc.* 2010, 5, 739-743). However, the creation of fluorine-carbon bonds in a manner that allows facile $^{18}$F labeling without causing collateral damage to proteins has remained a synthetic challenge (Furuya et al., *Curr. Opin. Drug Discov. Devel.* 2008, 11, 803-819; Truong et al., *J. Am. Chem. Soc.* 2013, 135, 9342-9345). $^{18}$F PET, relative to other available PET isotopes such $^{68}$Ga, $^{64}$Cu, $^{89}$Zr, and $^{124}$I, has four major advantages: lower energy positron emission, shorter half-life, reduced cost, and wider availability. While $^{18}$F PET imaging is used for diagnostic purposes and to monitor therapeutic efficacy, these approaches have relied mostly on agents that report on metabolic activity, such as $^{18}$F-fluorodeoxyglucose (FDG) or labeled precursors in the biosynthesis of nucleic acids, to score reductions in tumor size (Bohnen et al., *J. Nucl. Med.* 2012, 53, 59-71; Groheux et al., *Eur. J. Nucl. Med. Mol. Imaging* 2011, 38, 426-435; Youssef et al., *J. Nucl. Med.* 2012, 53, 241-248; Waldherr et al., *J. Nucl. Med. Off Publ. Soc. Nucl. Med.* 2005, 46, 114-120).

While the methods provided herein are amenable for labeling any protein (e.g., any type of antibody or antibody fragment), the use of single domain VHHs offers a number of advantages: they are smaller in size (~15 kDa) than Fab (~50 kDa), ScFv (~25 kDa), and "diabody" (a pair of scFvs connected to a pair of $C_H3$ domains; ~60 kDa) antibody derivatives, and VHHs lack an Fc portion. Technology to humanize these camelid VHHs has been developed (see e.g., Vincke et al., *J. Biol. Chem.* 2009, 284, 3273-3284; which is incorporated herein by reference), and several VHHs have been used already in a number of phase I and phase II clinical trials for therapeutic applications (see, e.g., De Meyer et al., *Trends Biotechnol.* 2014, 32, 263-270; which is incorporated herein by reference). Accordingly, in some embodiments, methods for using radiolabeled VHHs (e.g., those labeled according to the methods provided herein) are provided.

In some embodiments, the methods comprise (a) administering any of the compositions comprising a radiolabeled protein described herein (e.g., those comprising pharmaceutically acceptable carriers) to a subject; and (b) detecting the radiolabel in the subject. The step of detecting may be carried out by any procedure known in the art that may allow the imaging of the radiolabeled protein that is administered. For example, in some embodiments, detecting (e.g., imaging) may be carried out by PET and/or single-photon emission computed tomography (SPECT) imaging. In other embodiments, the imaging may be carried out by both PET and SPECT or by combined imaging methods such as PET/CT (PET with concurrent computed tomography imaging) or PET/MRI (PET with concurrent magnetic resonance imaging). The imaging procedure may result in one or more images of the region of observation of the subject, and in embodiments in which imaging results in more than one image, these multiple images may be combined, overlaid, added, subtracted, color coded or otherwise fused and mathematically manipulated by any method known in the art. The image produced may be a digital or analog image that may be displayed as a "hard" image on, for example, printer paper, photographic paper or film, or as an image on a screen, such as for example, a video or LCD screen.

The images produced using the imaging procedure embodied in the present invention may be analyzed by any method known in the art. For example, in one embodiment, the image may be reviewed by a physician or another medical professional who visually observes the derived images and grades the disease state based on the observable presence of radiolabeled protein in the images produced. In another embodiment, the images may be analyzed by a processor or processor system. For example, in one embodiment, image data derived from a PET or SPECT scan can be inputted into a processor that identifies individual pixels or groups of pixels whose brightness is greater than a predetermined threshold or an average background, and identified pixels may be characterized as indicating the presence of a radiopharmaceutical. In another embodiment, the image data may be derived from images scanned and inputted into a processor. In such embodiments, a similar process that identifies bright spots on the image may be used to locate the radiopharmaceuticals in the image. In certain embodiments, the analysis of the image may further include determining the intensity, concentration, strength or combination thereof of the output brightness, which may be correlated to the amount of radiolabeled protein in the image, an area or region of the image, or a particular spot on the image. Without wishing to be bound by theory, an area or spot on an image having a greater intensity than other areas or spots may hold a higher concentration of radiolabeled protein targeted to, for example, a tumor, and thus may have a higher concentration of the radioisotope attached to the region where the radiolabeled protein localizes. Images may also be analyzed by the spatial location of regions of interest to which the administered radiolabeled proteins are targeted. In other embodiments, analysis of the pharmacokinetics of the administered radiolabeled proteins may provide information on the appropriate timing of injection of the radiolabeled protein.

By identifying areas, regions, or spots on an image that correlate to the presence of a radiolabeled protein, the presence or absence of a diseased state may be determined. For example, in embodiments in which the protein binds a tumor cell, a tumor-associated cell (e.g., neovasculature cell), or a tumor antigen, identifying regions or spots where such protein concentrates indicates the presence of a tumor. In some embodiments, images that correlate to the presence of a radiolabeled protein are used to assess the state of an inflammatory response, e.g., in a disease or disorder involving inflammation. Accordingly, the methods provided herein are amenable for diagnosing, prognosing, or otherwise monitoring an inflammatory response. Exemplary inflammatory diseases/disorders include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, cancer, chronic prostatitis, conjunctivitis, Chagas disease, chronic obstructive pulmonary disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scleredoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis.

Compositions

According to other aspects, sortase-mediated radiolabeled proteins, radiolabeled sortase substrate peptides, and compositions thereof are provided. In some embodiments, compositions for labeling proteins and/or sortase substrate peptides are provided. In some embodiments, provided herein is a pharmaceutical composition comprising the radioactive protein as described herein, or a pharmaceutically acceptable salt, solvate, hydrate, tautomer, stereoisomer, isotopically labeled derivative, or prodrug thereof, as described herein, and a pharmaceutically acceptable carrier.

For example, in some embodiments, the radiolabeled proteins generated according to any of the inventive methods described herein, are provided in an effective amount in the pharmaceutical composition. In certain embodiments, the effective amount is a diagnostically effective amount. In certain embodiments, the effective amount is sufficient for a medical professional to obtain one or more images of an organ or tissue in a subject.

In some embodiments, the protein is linked (conjugated) to a radioactive agent, e.g., by means of the inventive methods provided herein involving sortagging technology. In some embodiments, the agent is a carbohydrate, e.g., a sugar. In some embodiments, the agent is FDG or $^{14}$C—(U)-glucose. In some embodiments, the agent comprises one or more radionuclide(s) suitable for use in diagnostic and/or therapeutic applications (e.g., PET). In some embodiments, the one or more radionuclides is (are) carbon-11, carbon-14, nitrogen-13, oxygen-15, fluorine-18, rubidium-82, copper-61, copper-62, copper-64, yttrium-86, gallium-68, zirconium-89, or iodine-124. In some embodiments, the agent is labeled with a radionuclide that is fluorine-18.

In some embodiments, the protein is any protein having or engineered to have a sortase recognition motif. In some embodiments, the protein is any diagnostic or therapeutic protein including, but not limited to, those described herein (e.g., an antibody, an affibody, a single-domain antibody, a Fab fragment, or a therapeutic peptide). In some embodiments, the protein comprises a VHH domain (e.g., VHH4, VHH7). In some embodiments, the protein is one that binds to a tumor cell, a tumor-associated cell (e.g., neovasculature cells) or a tumor antigen. In some embodiments, the protein is one that binds a marker of inflammation. In some embodiments, the protein is any antibody described herein, including those disclosed in Table 4 of Salsano and Treglia, "PET imaging using radiolabeled antibodies: future direction in tumor diagnosis and correlate applications." *Research and Reports in Nuclear Medicine.* 2013: 3; 9-17, and/or those described herein and disclosed in Wright and Lapi, "Designing the magic bullet? The advancement of immuno-PET into clinical use." *J. Nucl. Med.* 2013 August; 54(8):1171-4.

In some embodiments, the composition comprises an amount of radioactivity suitable for use in diagnostic and/or therapeutic applications, for example PET. In some embodiments, the composition comprises at least 10, at least 20, at lease 30, at least 40, at least 50, at least 75, at least 100, at least 150, at least 200, at least 250, at least 300, at least 350, at least 400, at least 450, at least 500, at least 550, at least 600, at least 700, at least 800, at least 900, or at least 1000 MBq of radioactivity.

In some embodiments, provided compositions further comprise a pharmaceutically acceptable carrier. Thus, in some embodiments, the invention provides pharmaceutical compositions comprising any of the labeled proteins described herein, for example, a protein that has been conjugated to a radiolabeled agent via sortagging technology.

A pharmaceutical composition may comprise a variety of pharmaceutically acceptable carriers. Pharmaceutically acceptable carriers are well known in the art and include, for example, aqueous solutions such as water, 5% dextrose, or physiologically buffered saline or other solvents or vehicles such as glycols, glycerol, oils such as olive oil, or injectable organic esters that are suitable for administration to a human or non-human subject. See, e.g., Remington: *The Science and Practice of Pharmacy,* 21$^{st}$ edition; Lippincott Williams & Wilkins, 2005. In some embodiments, a pharmaceutically acceptable carrier or composition is sterile. A pharmaceutical composition can comprise, in addition to the active agent (e.g., radiolabeled protein), physiologically acceptable compounds that act, for example, as bulking agents, fillers, solubilizers, stabilizers, osmotic agents, uptake enhancers, etc. Physiologically acceptable compounds include, for example, carbohydrates, such as glucose, sucrose, lactose; dextrans; polyols such as mannitol; antioxidants, such as ascorbic acid or glutathione; preservatives; chelating agents; buffers; or other stabilizers or excipients. The choice of a pharmaceutically acceptable carrier(s) and/or physiologically acceptable compound(s) can depend for example, on the nature of the active agent, e.g., solubility, compatibility (meaning that the substances can be present together in the composition without interacting in a manner that would substantially reduce the pharmaceutical efficacy of the pharmaceutical composition under ordinary use situations) and/or route of administration of the composition. The pharmaceutical composition could be in the form of a liquid, gel, lotion, tablet, capsule, ointment, cream, transdermal patch, etc. A pharmaceutical composition can be administered to a subject by various routes including, for example, parenteral administration. Exemplary routes of administration include intravenous administration; respiratory administration (e.g., by inhalation), intramuscular administration, nasal administration, intraperitoneal administration, oral administration, subcutaneous administration and topical administration. For oral administration, the agent(s) can be formulated with pharmaceutically acceptable carriers as tablets, pills, dragees, capsules, liquids, gels, syrups, slurries, suspensions, etc. In some embodiments an active agent may be administered directly to a target tissue. Direct administration could be accomplished, e.g., by injection or by implanting a sustained release implant within the tissue. Of course a sustained release implant could be implanted at any suitable site. In some embodiments, a sustained release implant may be particularly suitable for prophylactic treatment of subjects at risk of developing a recurrent cancer. In some embodiments, a sustained release implant delivers therapeutic levels of the active agent for at least 30 days, e.g., at least 60 days, e.g., up to 3 months, 6 months, or more. One skilled in the art would select an effective dose and administration regimen taking into consideration factors such as the patient's weight and general health, the particular condition being treated, etc. Exemplary doses may be selected using in vitro studies, tested in animal models, and/or in human clinical trials as standard in the art.

A pharmaceutical composition comprising a radioactive protein according to aspects of this invention may be delivered in an effective amount, by which is meant an amount sufficient to achieve a biological response of interest, e.g., reducing one or more symptoms or manifestations of a disease or condition. In some embodiments, an effective amount is the amount required to visualize, detect, or identify a given tissue using diagnostic procedures such as PET. The exact amount required will vary from subject to subject, depending on factors such as the species, age, weight, sex, and general condition of the subject, the severity of the disease or disorder, the particular labeled protein and its activity, its mode of administration, concurrent therapies, and the like. In some embodiments, a compound, e.g., a protein, is formulated in unit dosage unit form for ease of administration and uniformity of dosage, which term as used herein refers to a physically discrete unit of agent appropriate for the patient to be treated. It will be understood, however, that the total daily dosage will be decided by the attending physician within the scope of sound medical judgment.

According to some embodiments, sortase substrate peptides linked to a radiolabeled agent, and compositions comprising such, are provided. In some embodiments, sortase substrate peptides linked to a reactive moiety, such as a click chemistry handle (e.g., tetrazine), are provided. In some embodiments, the sortase substrate peptide is any sortase substrate peptide generated according to the inventive methods provided herein. In some embodiments, the sortase substrate peptide and agent are linked by an oxime, a hydrazone, a thiosemicarbazone, a heterocyclylene linkage, an amide linkage, an ester linkage, an ether linkage, a disulfide linkage or through use of click chemistry e.g., as described herein. In some embodiments, the agent is a carbohydrate, e.g., a sugar. In some embodiments, the agent is FDG or $^{14}$C—(U)-glucose. In some embodiments, the agent comprises one or more radionuclide(s) suitable for use in diagnostic and/or therapeutic applications (e.g., PET). In some embodiments, the one or more radionuclides is (are) carbon-11, carbon-14, nitrogen-13, oxygen-15, fluorine-18, rubidium-82, copper-61, copper-62, copper-64, yttrium-86, gallium-68, zirconium-89, or iodine-124. In some embodiments, the agent is labeled with a radionuclide that is fluorine-18.

In some embodiments, the sortase substrate peptide comprises either an N-terminal or C-terminal sortase recognition motif, e.g., any of those described herein. In some embodiments, the sortase substrate peptide comprises an oligoglycine or an oligoalanine sequence, for example 1-10 N-terminal glycine residues or 1-10 N-terminal alanine residues, respectively. In some embodiments, the sortase substrate peptide comprises the sequence GGG. In some embodiments, the sortase substrate peptide comprises the sequence $(G)_{n1}K$ (SEQ ID NO: 129), wherein n1 is an integer between 1 and 10, inclusive. In some embodiments, the sortase substrate peptide comprises the sequence GGGK (SEQ ID NO:81). In some embodiments, the sortase substrate peptide and agent are joined by an oxime linkage. In some embodiments, the sortase peptide substrate is linked to an agent that is or comprises FDG or $^{14}$C—(U)-glucose.

According to some embodiments, compositions for use in the inventive methods described herein are provided. For example, in some embodiments, compositions for use in radiolabeling a protein using sortagging technology are provided. Typically, the compositions comprise a radiolabeled sortase substrate peptide (e.g., as described herein), a sortase (e.g., as described herein), and a protein to be labeled (e.g., as described herein) comprising a sortase recognition motif. In some embodiments, the protein comprises a C-terminal sortase recognition motif (e.g., as described herein), and the sortase substrate peptide comprises an N-terminal sortase recognition motif (e.g., as described herein). In some embodiments, the protein comprises an N-terminal sortase recognition motif, and the sortase substrate peptide comprises a C-terminal sortase recognition motif. In some embodiments, the sortase substrate is linked (conjugated) to any radioactive agent described herein (e.g., FDG, $^{14}$C—(U)-glucose, $^{18}$F, etc.). In some embodiments, the sortase is any sortase described herein (e.g., sortase A from *Staphylococcus aureus* (SrtA$_{aureus}$), sortase A from *Streptococcus pyogenes* (SrtA$_{pyogenes}$), sortase B from *S. aureus* (SrtB$_{aureus}$), sortase B from *Bacillus anthracis* (SrtB$_{anthracis}$), or sortase B from *Listeria monocytogenes* (SrtB$_{monocytogenes}$). In some embodiments, the protein is any protein comprising (or engineered to comprise) a sortase recognition motif (e.g., an antibody, an affibody, a single-domain antibody, a Fab fragment, or a therapeutic peptide).

In some embodiments, compositions for use in modifying sortase substrate peptides are provided. In some embodiments, the composition comprises sortase substrate peptide (e.g., comprising a nucleophilic group as described herein) and a radioactive agent (e.g., comprising an electrophilic group as described herein). In some embodiments, the composition further comprises a catalyst (e.g., m-phenylenediamine (mPDA), o-phenylenediamine, p-phenylenediamine, o-aminophenol, m-aminophenol, p-aminophenol, o-aminobenzoic acid, or aniline).

In certain embodiments, the pharmaceutical compositions provided as described herein are of liquid dosage forms for oral or parenteral administration. In certain embodiments, the pharmaceutical compositions are pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Kits

Some aspects of this invention provide kits useful for labeling proteins with radioactive agents using sortagging technology, and/or for generating radiolabeled sortase substrate peptides.

In some embodiments, the kit comprises a sortase substrate peptide comprising a nucleophilic group (e.g., those described herein), a modifying agent that comprises an electrophilic group (e.g., those described herein), and a catalyst. In some embodiments, the nucleophilic group is an aminooxy group, a hydrazide, a thiosemicarbazide, or a click chemistry handle. In some embodiments, the electrophilic group is an aldehyde, a ketone, or a click chemistry handle. In some embodiments, the electrophilic/nucleophilic pairings are tetrazine (Tz) and trans-cyclooctene (TCO). In some embodiments, the sortase substrate peptide comprises the sequence GGGK (SEQ ID NO: 81), wherein the K is modified to include a nucleophilic group (e.g., an aminooxy group, a hydrazide, a thiosemicarbazide, or a click chemistry handle). In some embodiments, the modifying agent is any radioactive agent described herein (e.g., FDG, $^{14}$C—(U)-glucose, $^{18}$F—NaF, etc.). In some embodiments, the catalyst is m-phenylenediamine (mPDA), o-phenylenediamine, p-phenylenediamine, o-aminophenol, m-aminophenol, p-aminophenol, o-aminobenzoic acid, 5-methoxyanthranilic acid, 3,5-diaminobenzoic acid or aniline.

In some embodiments, a provided kit comprises a sortase substrate peptide that comprises or is linked to a radioactive agent (e.g., any of those described herein). In some embodiments, the kit comprises a sortase substrate peptide linked to an agent via an oxime linkage, and a sortase.

In some embodiments, the kit comprises one or more sortase(s) provided herein. In some embodiments, the sortase is sortase A from *Staphylococcus aureus* (SrtA$_{aureus}$), sortase A from *Streptococcus pyogenes* (SrtA$_{pyogenes}$), sortase B from *S. aureus* (SrtB$_{aureus}$), sortase B from *Bacillus anthracis* (SrtB$_{anthracis}$), or sortase B from *Listeria monocytogenes* (SrtB$_{monocytogenes}$).

In some embodiments, the kit comprises a radiolabeled protein generated according to an inventive method provided herein.

In some embodiments, the kit further comprises a buffer or reagent useful for carrying out a sortase-mediated transpeptidation reaction, for example, a buffer or reagent described in the Examples section.

The following working examples are intended to describe exemplary reductions to practice of the methods, reagents, and compositions provided herein and do not limited the scope of the invention.

EXAMPLES

Figure 1B:
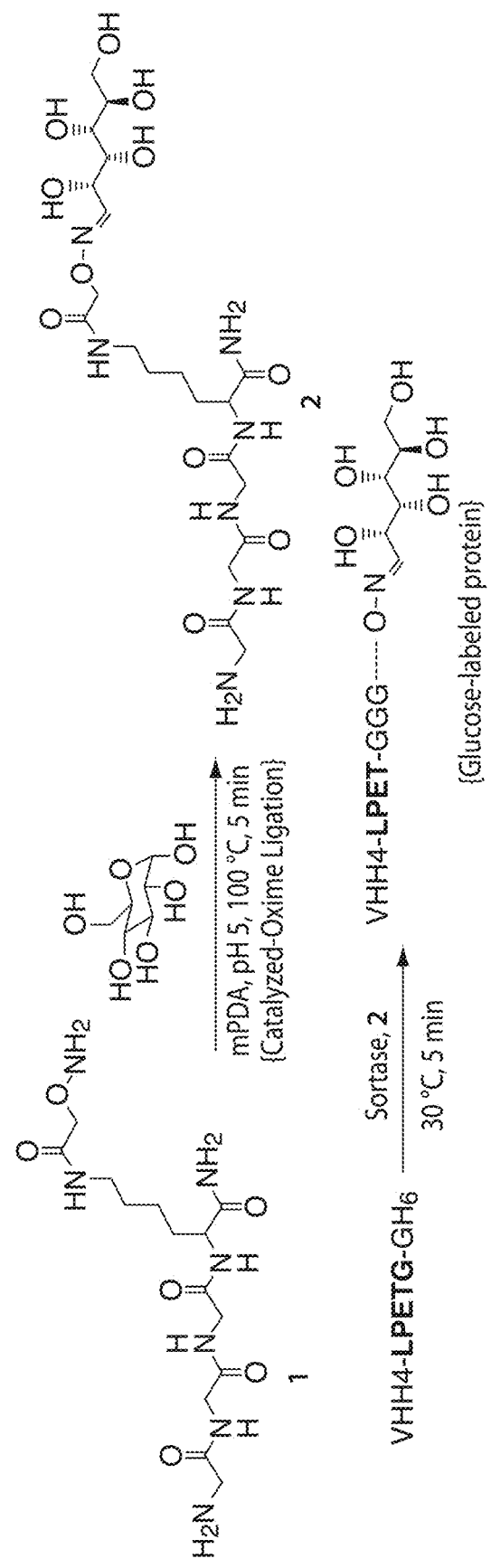
Figure 1C:
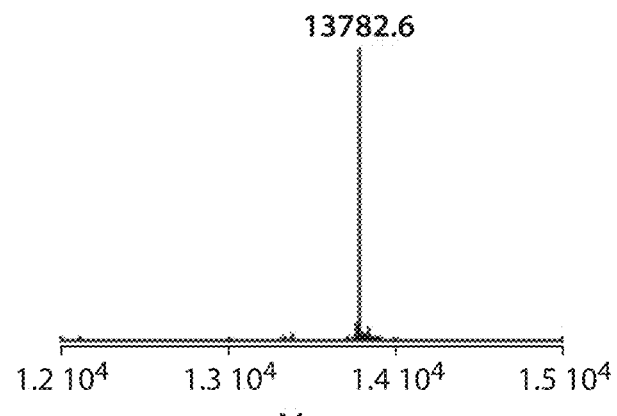
Figure 1D:
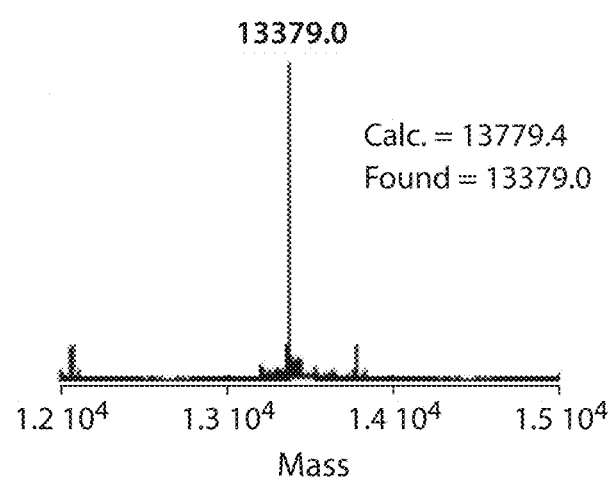

Example 1. Site-Specific Labeling of Proteins Using Glucose, 2-Deoxy-2-Fluoroglucose (FDG), and U-$^{14}$C-Glucose In a first step, a short synthetic peptide (Gly)$_3$-R (1, FIG. 1B) was generated, where R contains an aminooxy functionality that enables an oxime ligation reaction with a $^{18}$F-FDG; this compound occurs both in a hemiacetal cyclical form and as a linear aldehyde. The dynamic equilibrium between these two forms allowed the installation of $^{18}$F-glucose on the (Gly)$_3$-R peptide. The reaction was optimized using non-isotopically labeled glucose, and reaction products were characterized by LC-MS (FIGS. 1B, 1C, & 1D). In this approach, the aminooxy-functionalized peptide was incubated with glucose (or other aldehydes) in the presence of a catalyst at pH 5 with constant agitation at 100° C. for 5 to 10 min. The actual timing was determined by the concentrations of the catalyst, aldehyde and aminooxy compounds used in each specific reaction. The reaction was cooled on ice for 30 s and quickly added to a pre-prepared solution containing the protein of interest and sortase at 30° C. After 3 min of incubation, Ni-NTA beads were added and the reaction mixture was agitated for another 3 min at 30° C. The protein being labeled contained a polyhistidine tag C-terminal of the Gly in the LPXTG (SEQ ID NO:1) motif, which was lost from the desired product upon successful transacylation. The sortase itself also contained a His$_6$ tag (SEQ ID NO: 133), so that sortase and any remaining unreacted proteins could be removed by adsorption to Ni-NTA resin, while the labeled protein remained free in solution. Ni-NTA beads were removed by centrifugation; the supernatant was recovered and loaded on a size-exclusion desalting spin column, pre-washed with phosphate buffer. Centrifugation at 1000×g for 30 s provided the final purified labeled-protein of interest. In view of the short (110 min) half-life of $^{18}$F, it was important to keep the labeling strategy as short as possible to obtain maximum radiochemical yields without compromising purity and ease of preparation. Using this methodology, >95% labeling was achieved when incubating 1 mM of the Gly$_3$-aminooxy probe with 40 mM of glucose at 100° C. for 5 min. m-phenylenediamine (mPDA) was used as a catalyst, which is one of the most efficient of a series of catalysts that can catalyze the oxime ligation. Due to the fact that the pKa of mPDA is 4.9, the pH of the reaction was set between 5-5.3 to maximize the reaction rate.

Figure 2A:
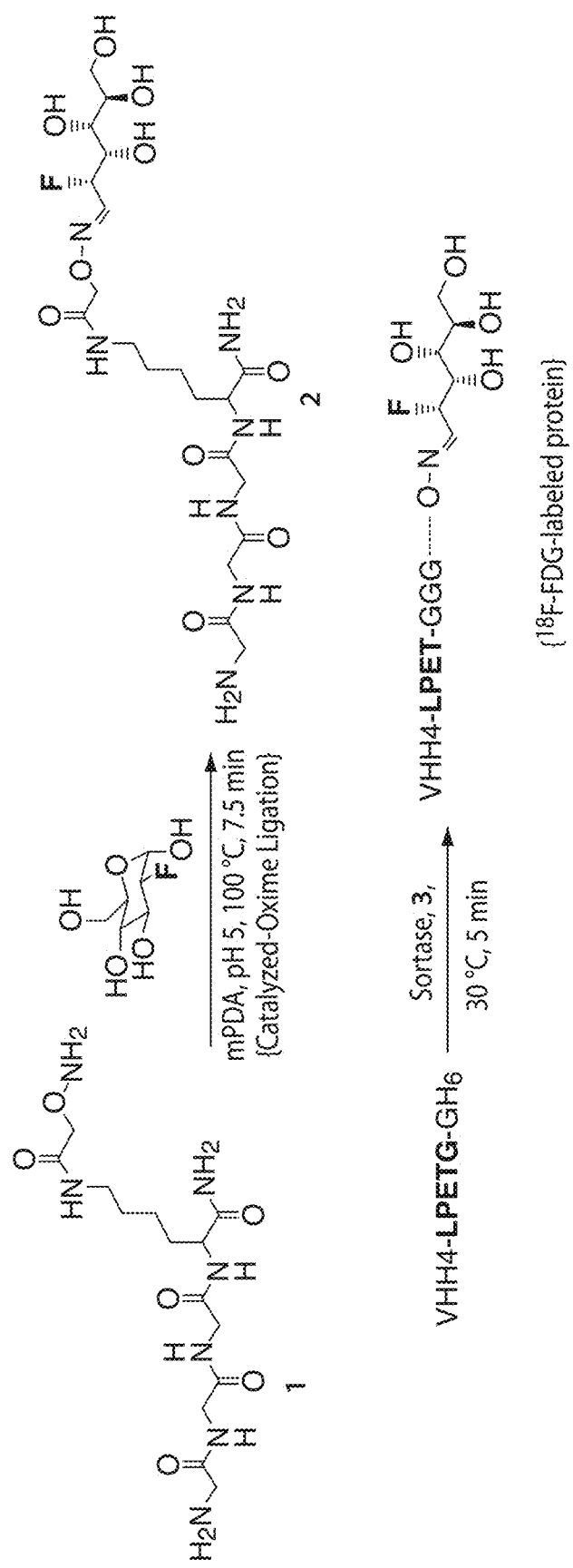
FIGS. 2A-2C show an exemplary site-specific labeling of VHH4 protein with fludeoxyglucose (FDG) using sortagging technology. First the sortase substrate peptide 1 is labeled via oxime ligation with FDG using mPDA as the catalyst. Next, the product (2) is added to the sortagging solution. The enzyme and non-sortagged protein is separated from the sortagged protein by incubating the solution with Ni-NTA beads. The product is analyzed with LC-MS analysis.
Figure 2B:
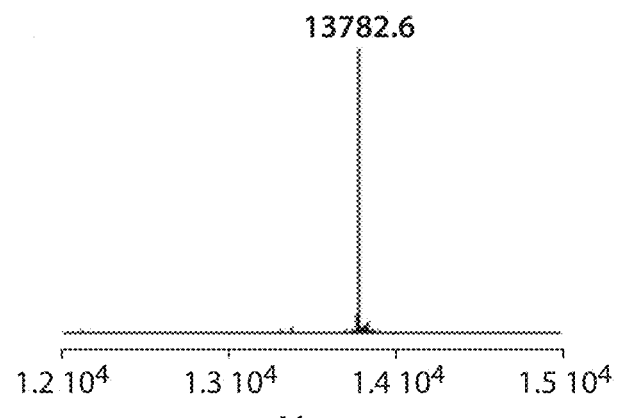
Figure 2C:
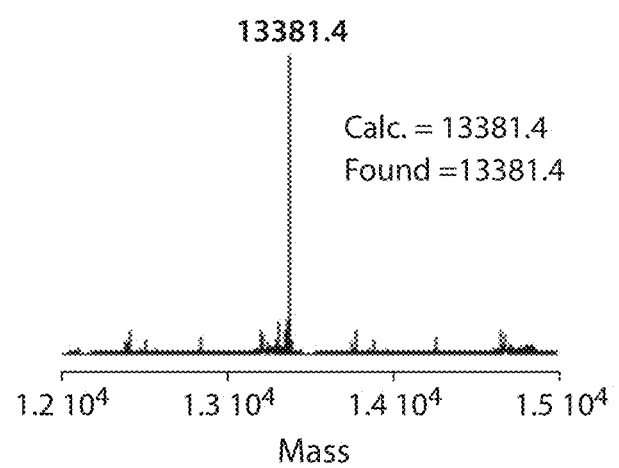
Figure 3A:
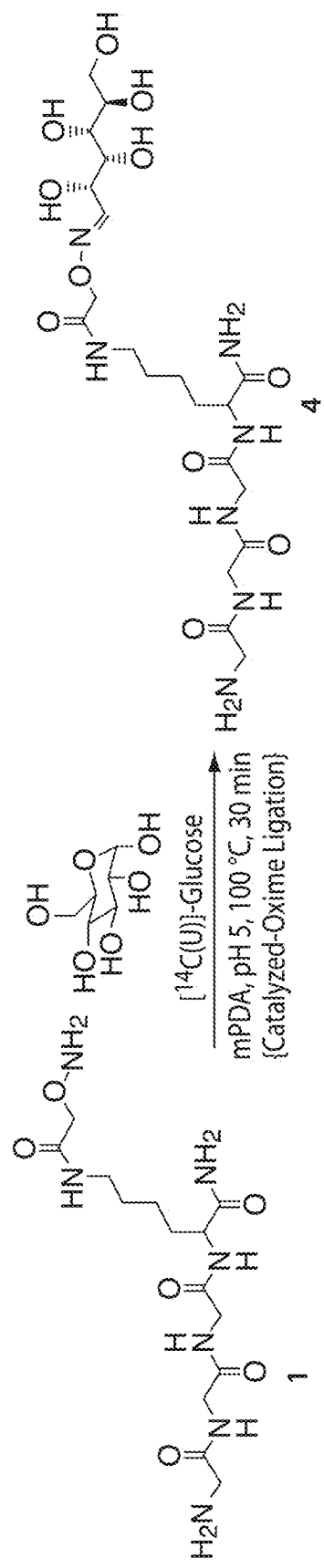
FIGS. 3A-3C show the site-specific labeling of VHH4 with $^{14}$C—(U)-glucose using sortagging.
Figure 3B:
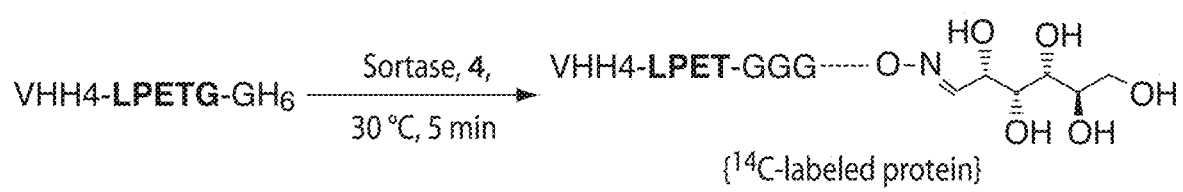
Figure 3C:
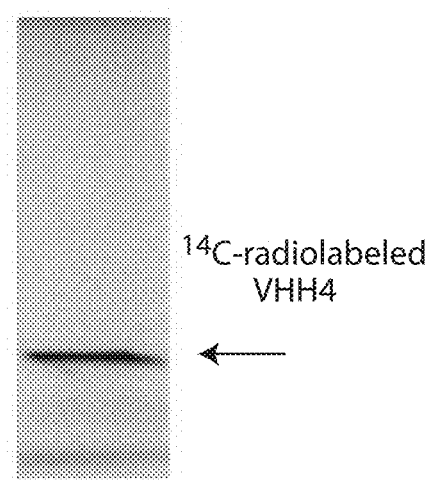
Figure 4A:
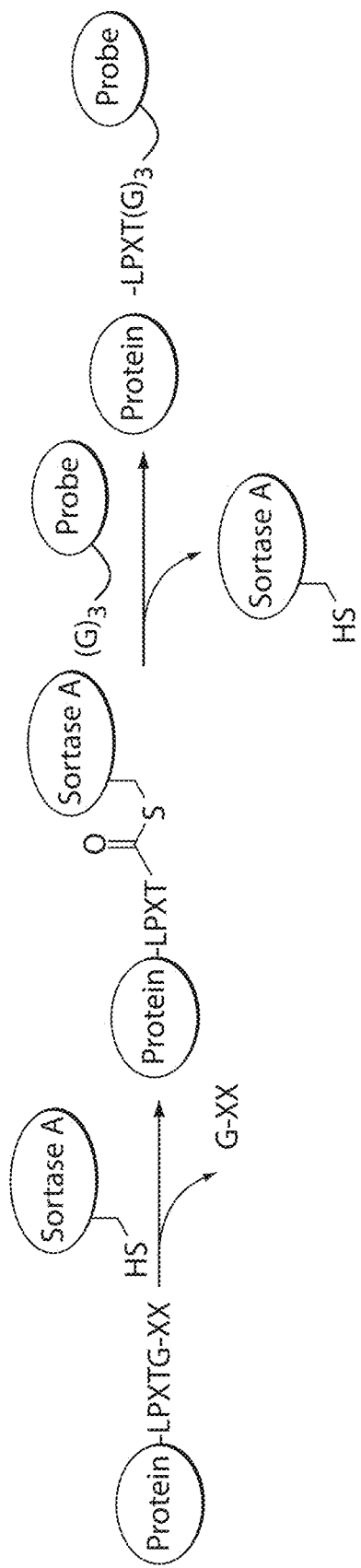
Figure 4B:
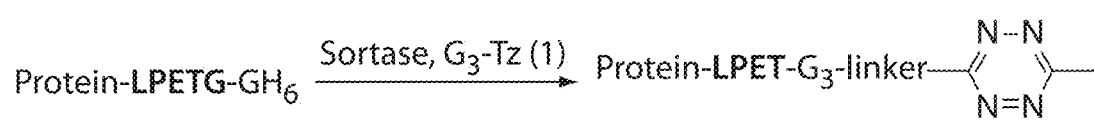
Figure 4C:
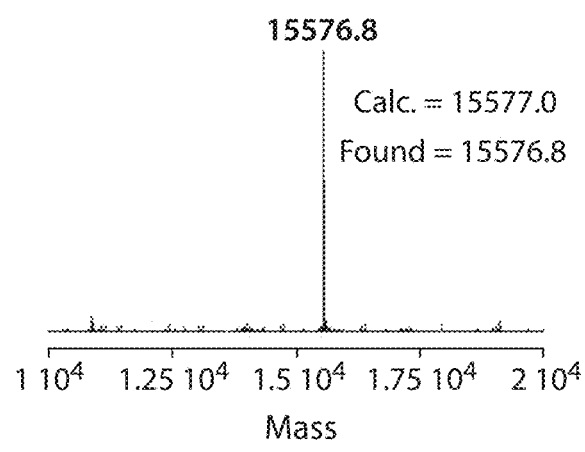
Figure 4F:
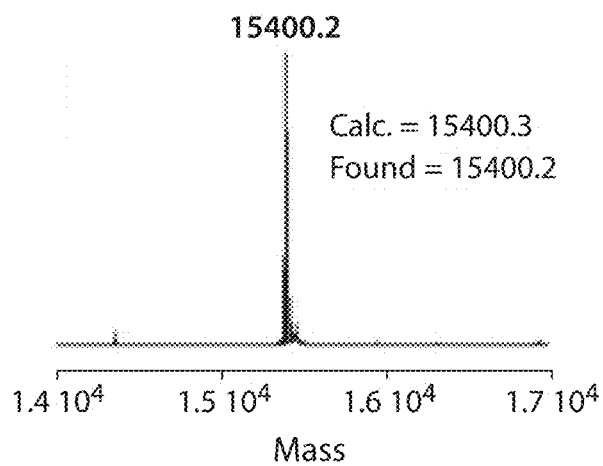
Figure 4G:
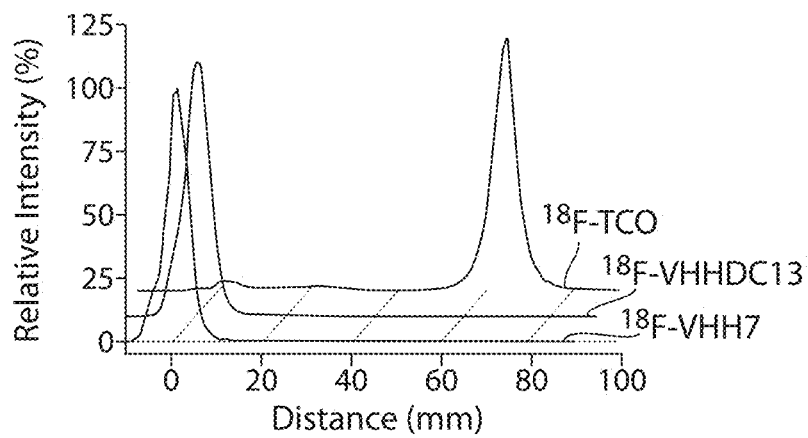
Figure 4H:
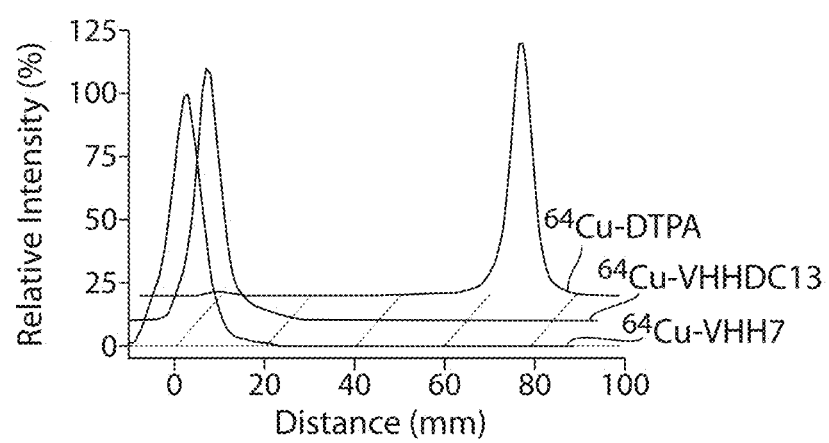

After establishing the above method using glucose, the aminooxy probe was modified with 2-deoxy-2-fluoroglucose (FDG). Similarly, >90% yield of FDG-labeled proteins was achieved in as little as 15 min following the methodology summarized above (FIG. 2). Product formation was confirmed via analysis by LC-MS (FIG. 2B, 2C). The feasibility of the method was further confirmed by radiolabeling a protein—a single domain antibody fragment derived from an anti-Class II MHC antibody (VHH4; unpublished)—using U-$^{14}$C-glucose. The desired product was obtained as assessed by SDS-PAGE and autoradiography, confirming the installation of $^{14}$C-glucose onto the protein of interest (FIG. 3).

Example 2. Non-Invasive Imaging of Class II MHC Positive Cells in a Tumor Model Using Site-Specifically $^{18}$F-Labeled and $^{64}$Cu-Labeled Single Domain Antibodies Non-invasive imaging of an immune response against a tumor remains a highly desirable and challenging goal. To this end, a labeling strategy was developed to generate a site-specifically $^{18}$F-labeled single domain antibody specific for murine Class II MHC products, $^{18}$F-VHH7. The $^{18}$F-VHH7 product was used to perform positron emission tomography (PET) imaging in mice, using wild type, MHC II$^{-/-}$ and NOD-SCID mice xenografted with human melanoma as targets. Not only was $^{18}$F-VHH7 rapidly cleared from the circulation, (t½<20 min), it also stained secondary lymphoid organs with remarkable specificity. Moreover, Class II MHC positive cells surrounding a melanoma xenografted into nude mice were clearly imaged with $^{18}$F-VHH7, which enables the possibility of early detection of inflammatory cells as an indicator of disease.

Materials and Methods

Synthesis of (Gly)$_3$-Tetrazine.

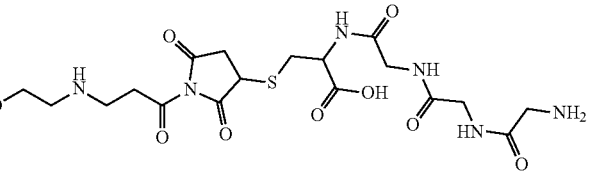

The tetrapeptide GGGC (SEQ ID NO: 124) was synthesized by standard solid phase peptide synthesis. Maleimide-tetrazine (from ClickChemistryTools) was dissolved in 0.1 M phosphate buffer (PB) pH 7. The tetrapeptide GGGC (SEQ ID NO: 124) was added and left to stir at room temperature for 3 h until TLC (1:1 Hex:EtOAc v/v) indicated near-complete conversion to the product. The solution was filtered and purified by reverse phase-HPLC with a semi-preparative column (Phenomenex, C$_{18}$ column, Gemini, 5 μm, 10×250 mm) at a flow rate of 5.0 mL/min; solvent A: 0.1% TFA in H$_2$O, solvent B: 0.1% TFA in CH$_3$CN. (G)$_3$-Tetrazine eluted at 30-35% solvent B. Fractions containing pure product were collected and lyophilized. LC-MS calculated for C$_{37}$H$_{54}$N$_{11}$O$_{13}$S [M+H]$^+$ 892.362, found 892.370.

Synthesis of (Gly)$_3$-NOTA.

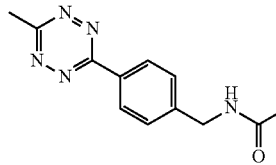

Maleimide-NOTA (from Macromolecules) was dissolved in 0.1 M PB pH 7. The tetrapeptide GGGC (SEQ ID NO: 124) was added at room temperature for 3 h until TLC (1:1 Hex:EtOAc v/v) indicated almost complete conversion to the product. The solution was purified by RP-HPLC on a semi-preparative column (Phenomenex, C$_{18}$ column, Gemini, 5 μm, 10×250 mm) at a flow rate of 5.0 mL/min; solvent A: 0.1% TFA in H$_2$O, solvent B: 0.1% TFA in CH$_3$CN. The desired product eluted from 15-20% solvent B. Fractions containing pure product were collected and lyophilized. LC-MS calculated for C$_{27}$H$_{45}$N$_{10}$O$_{11}$S [M+H]$^+$ 717.298, found 717.305.

Enzymatic Incorporation of Substrates into Proteins Using Sortase.

The penta-mutant sortase A, with an improved k$_{cat}$, was used (Chen, I., et al., "A general strategy for the evolution of bond-forming enzymes using yeast display.", Proc. Natl. Acad. Sci. U.S.A 2011; 108, 11399-11404; the entire contents of which are hereby incorporated by reference). Reaction mixtures (1 mL) contained Tris·HCl (50 mM, pH 7.5), CaCl$_2$) (10 mM), NaCl (150 mM), triglycine-containing probe (500 μM), LPETG-containing (SEQ ID NO: 2) probe (100 μM), and sortase (5 μM) (Theile, C. S., et al., "Site-specific N-terminal labeling of proteins using sortase-mediated reactions.", Nat. Protoc. 2013; 8, 1800-1807; Witte, M. D., et al. "Preparation of unnatural N-to-N and C-to-C protein fusions.", Proc. Natl. Acad. Sci. 2012; 109, 11993-11998; the entire contents of which are hereby incorporated by reference). After incubation at 4° C. with agitation for 2 h, reaction products were analyzed by LC-MS, with yields generally >90%. When the yield was below 90%, the reaction was allowed to proceed for an additional two hours, with addition of sortase to 10 μM and triglycine-containing probe to 750 μM. Ni-NTA beads were added to the reaction mixture with agitation for 5 min at 25° C. followed by centrifugation to remove sortase and any remaining unreacted His-tagged substrate. The final product—either the tetrazine-labeled protein or NOTA-labeled protein, was purified by size exclusion chromatography in PBS or Tris·HCl (50 mM, pH 7.5).

Synthesis of $^{18}$F-TCO.

2-[$^{18}$F]-(E)-5-(2-Fluoroethoxy)cyclooct-1-ene ($^{18}$F-TCO) was prepared as described (Keliher, E. J. et al. ChemMedChem 2011, 6, 424-427; incorporated herein by reference). [$^{18}$F]-Fluoride (no carrier added, (n.c.a.)) in H$_2$$^{18}$O, purchased from PETNET, was transferred to a microwave reaction vessel (10 mL) and diluted with Kryptofix 2.2.2 (33 mM in 300 μL MeCN) and K$_2$CO$_3$ (33 mM in 300 μL H$_2$O) solutions. The [$^{18}$F]—F/K222/K$_2$CO$_3$ solution, 87.3±22.6 mCi (3230.1±836.2 MBq), was dried by azeotropic distillation of water with MeCN (added at 2, 6 and 8 min) by microwave heating (98° C., 150 W, 15 min) under a stream of argon. After drying, (E)-2-(cyclooct-4-enyloxy)ethyl 4-methylbenzenesulfonate (4 mg, 30 mmol) in DMSO was added, the vessel was sealed and the reaction heated by

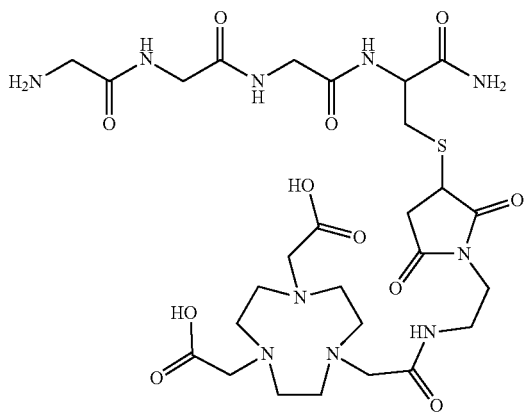 [SMILES: NCC(=O)NCC(=O)NCC(=O)NC(CSC1CC(=O)N(CCNC(=O)CN2CCN(CC(=O)O)CCN(CC(=O)O)CC2)C1=O)C(N)=O]

microwave (75 W) to 90° C. for 10 min. After cooling to 50° C., the mixture was diluted with MeCN (150 μL) and H$_2$O (750 μL) and subjected to preparative HPLC purification (1:1 MeCN/H$_2$O, 0.1% formic acid at 5.5 mL/min using a Macherey-Nagel Nucleodur C18 Pyramid 10×250 mm Vario-Prep column). $^{18}$F-TCO was collected (t$_R$=13.5 min) in 5-6 mL of solvent, diluted with H$_2$O (40 mL) and isolated by manual C18 solid phase extraction. Elution from the C18 cartridge with DMSO (4×200 μL) gave 22.1±4.0 mCi (817.6±149.5 MBq), a 35.6±4.9% decay-corrected radiochemical yield.

Synthesis and Characterization of $^{18}$F-VHHs.

In a typical reaction, a 1.5-mL centrifuge tube was loaded with VHH7-Tz in 1×PBS (40 μL, 150 μM), 1×PBS (300 μL), and $^{18}$F-TCO in DMSO (4.0 mCi (148.0 MBq), 100 μL). The tube was sealed and shaken at room temperature for 20 min. The mixture was analyzed by radio-TCO (ITLC, 100% MeCN, R$_f$ $^{18}$F-TCO=0.9, R$_f$ $^{18}$F-VHH7=0.0) showing 90% conversion to $^{18}$F-VHH7. The reaction mixture was loaded onto a PD-10 size-exclusion cartridge (GE Healthcare) and elution with 1×PBS provided 2.3 mCi (85.1 MBq) of $^{18}$F-VHH7 in 75.8% decay-corrected radiochemical yield. Starting with 5.3 mCi (196.1 MBq) $^{18}$F-TCO, $^{18}$F-VHHDC13 was prepared following the same procedure as described for $^{18}$F-VHH7 to give 2.8 mCi (103.6 MBq) after size-exclusion chromatography, a 69.7% decay-corrected radiochemical yield.

Synthesis and Characterization of $^{64}$Cu-VHHs.

In a typical reaction, a 1.5-mL centrifuge tube was loaded with VHH7-NOTA (400 μL, 20 μM in 200 mM NH$_4$OAc buffer (pH 6.5)) and $^{64}$CuCl$_2$ (5.7 mCi, 210.8 MBq) in 200 mM NH$_4$OAc buffer (75 uL, pH 6.5). The tube was sealed and shaken at 37° C. for 20 min. The mixture was analyzed by radio-TCO (ITLC, 50 mM EDTA pH 7, R$_f$ $^{64}$Cu/EDTA=1.0, R$_f$ $^{64}$Cu-VHH7=0.0) showing 98% conversion to $^{64}$Cu-VHH7. At this time the mixture was loaded onto a PD-10 size-exclusion cartridge and elution with 1×PBS provided 5.2 mCi (192.4 MBq) of $^{64}$Cu-VHH7 in 94.2% decay-corrected radiochemical yield. Starting with 3.5 mCi (129.5 MBq) $^{64}$CuCl$_2$, $^{64}$Cu-VHHDC13 was prepared following the same procedure as described for $^{64}$Cu-VHH7 to give 3.1 mCi (114.7 MBq) after size-exclusion chromatography, a 92.3% decay-corrected radiochemical yield. Prior to injection both $^{64}$Cu-VHH7 and $^{64}$Cu-VHHDC13 were analyzed by radio-TLC (ITLC, 50 mM EDTA pH 7, R$_f$ $^{64}$Cu/EDTA=1.0, R$_f$ $^{64}$Cu-VHH7 and $^{64}$Cu-VHHDC13=0.0) and were found to have 99.6 and 99.8% radiochemical purity, respectively.

PET-CT Imaging.

All procedures and animal protocols were approved by the Massachusetts General Hospital subcommittee on research animal care. For all imaging experiments, mice were anesthetized using 1.5% isoflurane in O$_2$ at a flow rate of ~1 L/min. Mice were imaged with PET-computed tomography (CT) using an Inveon small animal scanner (Siemens, Munich, Germany). Each PET acquisition took approximately 30 minutes. A high-resolution Fourier rebinning algorithm was used to rebin sinograms, followed by a filtered back-projection algorithm to reconstruct three-dimensional images without attenuation correction. Isotropic image voxel size was 0.796×0.861×0.861 mm, for a total of 128×128×159 voxels. Peak sensitivity of the Inveon accounts for 11.1% of positron emission, with a mean resolution of 1.65 mm. More than 100 counts were acquired per pixel, and the mean signal-to-noise ratio was greater than 20. CT images were reconstructed from 360 cone-beam x-ray projections with a power of 80 keV and 500 μA. The isotropic resolution of the CT images was 60 μm. Reconstruction of data sets, PET-CT fusion, and image analysis were done using IRW software (Siemens). Two- and three-dimensional visualizations were produced using the DICOM viewer OsiriX (The OsiriX Foundation, Geneva, Switzerland).

Blood Half-Life Measurement of $^{18}$F-VHHs.

Figure 6A:
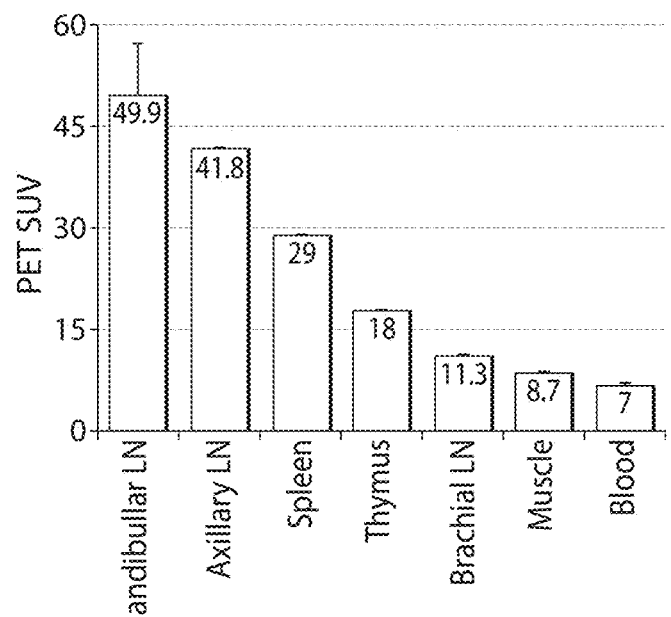
FIGS. 6A-6D show the pharmacokinetic profile of $^{18}$F-VHH7.
Figure 6B:
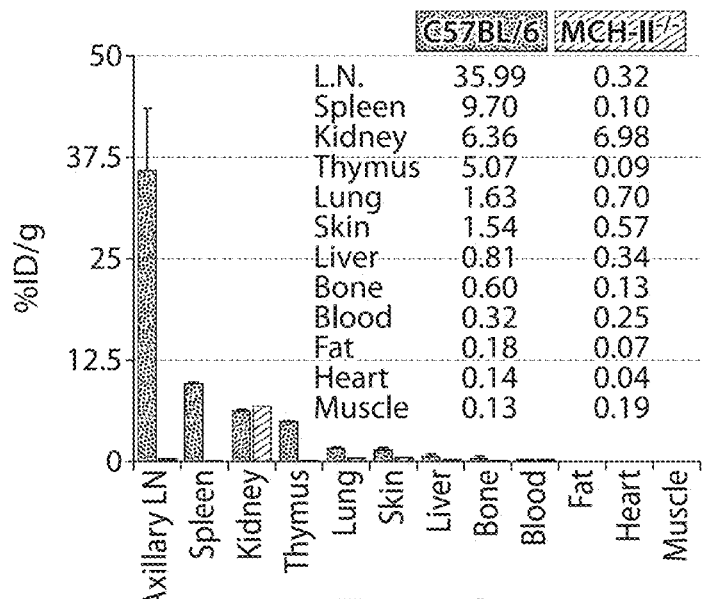
Figure 6C:
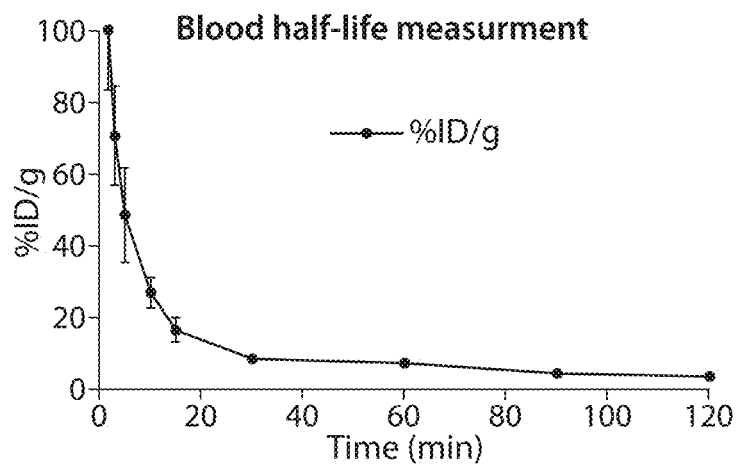
Figure 6D:
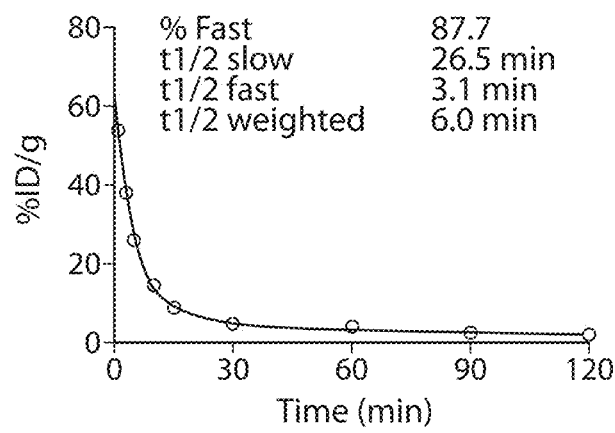

Mice were administered 30±3 uCi of $^{18}$F-VHH7 by intravenous tail-vein injection. Blood samples were obtained by retro-orbital puncture using tared, heparinized capillary tubes. Blood samples and capillaries were weighed and radioactivity was measured using a Perkin-Elmer Wallac Wizard 3" 1480 Automatic Gamma Counter. Non-linear regression analysis was performed using GraphPad Prism 4.0c. Values are expressed as percentages of the injected dose per gram of tissue and were fit to a bi-exponential decay model. Data is shown in FIG. 6C.

Biodistribution Analysis of 18F- or 64Cu-VHHs.

Mice were administered 296±19 uCi of labeled VHHs by intravenous tail-vein injection. At 2 h post-injection, mice were euthanized, perfused with 1×PBS (20 mL), and dissected. Blood, urine and tissues were excised and their wet weight was determined. Tissue radioactivity was measured with a Perkin-Elmer Wallac Wizard 3" 1480 Automatic Gamma Counter. Statistical analysis was performed using GraphPad Prism 4.0c. Values are expressed as percentages of the injected dose (excretion subtracted) per gram of tissue.

Results and Discussion

A challenge for immuno-PET using $^{18}$F as the tracer is its short half-life ($t_{1/2}$=110 minutes), requiring it to be used almost immediately after production. The approach exemplified here is reproducible and site-specific, without compromising the VHH's binding site, and is applicable to any other suitably modified biological entity such as cytokines. All of these steps—up to and including purification of the desired product—are compatible with the short half-life of $^{18}$F (~110 min.).

A facile two-step process was developed for labeling proteins equipped with a sortase recognition motif. The $^{18}$F-radionuclide was conjugated to the VHHs via the tetrazine (Tz)/trans-cyclooctene (TCO) reverse-electron demand Diels-Alder cycloaddition reaction. The TCO-Tetrazine reaction is the fastest known bioorthogonal reaction to date, with an estimated second order rate constant of 2000±400 M$^{-1}$s$^{-1}$ (Blackman, M. L. et al. Am. Chem. Soc. 2008, 130, 13518-13519; which is incorporated by reference). The requisite sortase nucleophile, GGG-tetrazine, which participates efficiently in sortase reactions, was synthesized in nearly quantitative yields. Thus, using $^{18}$F-TCO, prepared via a previously published method, (Keliher, E. J. et al. ChemMedChem 2011, 6, 424-427; incorporated herein by reference) >5 mCi of $^{18}$F-labeled VHH7 was readily produced in two steps.

A tosyl-trans-cyclooctene (TCO) was reacted with $^{18}$F—NaF for ~10 min to produce $^{18}$F-TCO. The product was purified via HPLC. Next, $^{18}$F-TCO was added to the Tz-modified protein, and the reaction was allowed to proceed for ~20 min at pH 7. The $^{18}$F-labeled protein product was then quickly purified via a PD-10 column pre-equilibrated with PBS, providing a radiolabeled protein solution ready for injection. The labeling experiments with $^{18}$F-TCO yielded $^{18}$F-VHH7 in 61±9% decay-corrected radiochemical yield (FIG. 4).

Antibody labeling strategies for PET often revolve around modification with metal chelators to enable installation of radioisotopes such as $^{64}$Cu, $^{68}$Ga, or $^{89}$Zr (Tanaka, K. et al.

"PET (positron emission tomography) imaging of biomolecules using metal-DOTA complexes: a new collaborative challenge by chemists, biologists, and physicians for future diagnostics and exploration of in vivo dynamics.", *Org. Biomol. Chem.* 2008; 6, 815-828.; Fani, M., et al. "68Ga-PET: a powerful generator-based alternative to cyclotron-based PET radiopharmaceuticals.", *Contrast Media Mol. Imaging* 2008; 3, 53-63.; Vosjan, M. J. W. D. et al. "Conjugation and radiolabeling of monoclonal antibodies with zirconium-89 for PET imaging using the bifunctional chelate p-isothiocyanatobenzyl-desferrioxamine.", *Nat. Protoc.* 2010; 5, 739-743.; the entire contents of each are hereby incorporated by reference). The longer half-life of $^{64}$Cu (12.7 h) relative to $^{18}$F (110 min) in principle allows a more extended imaging period to establish tissue penetration and dwell time of VHHs on their targets. A NOTA-(Gly)$_3$ sortase nucleophile was developed to enable site-specific labeling of VHHs via this high affinity copper chelating agent ($K_{eq}$ for $Cu^{2+}$: ~ $10^{21}$) (Delgado, R. et al. "Stabilities of divalent and trivalent metal ion complexes of macrocyclic triazatriacetic acids.", *Inorg. Chem.* 1999; 32, 3320-3326.; the entire contents of which are hereby incorporated by reference). The [$Cu^{2+}$—NOTA] complex is kinetically inert, with minimum metal exchange when exposed to other metals present in body (Zhang, Y. et al. "Positron Emission Tomography Imaging of CD105 Expression with a 64Cu-Labeled Monoclonal Antibody: NOTA Is Superior to DOTA.", *PLoS ONE.* 2011; 6, e28005.; the entire contents of which are hereby incorporated by reference). Site-specifically labeled [($^{64}$Cu)-NOTA]-VHHs were produced in high radiochemical yield (~90% decay corrected) (FIGS. 4E, 4F and 4H) and used $^{64}$Cu-VHH7 to image a C57BL/6 mouse at 4 h, 8 h, and 24 h post injection. VHH7 stayed on its target (secondary lymphoid organs) even after 24 hours (FIG. 8) but produced images with an inferior signal to noise ratio when compared with $^{18}$F-VHH7.

Figure 5A:
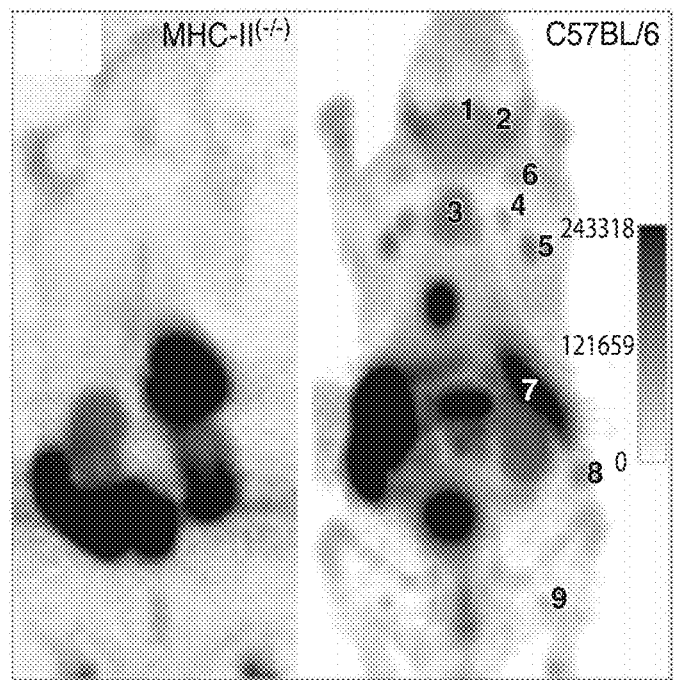
FIGS. 5A-5B show that $^{18}$F-VHH7 (anti mouse Class II MHC) detects secondary lymphoid organs.
Figure 5B:
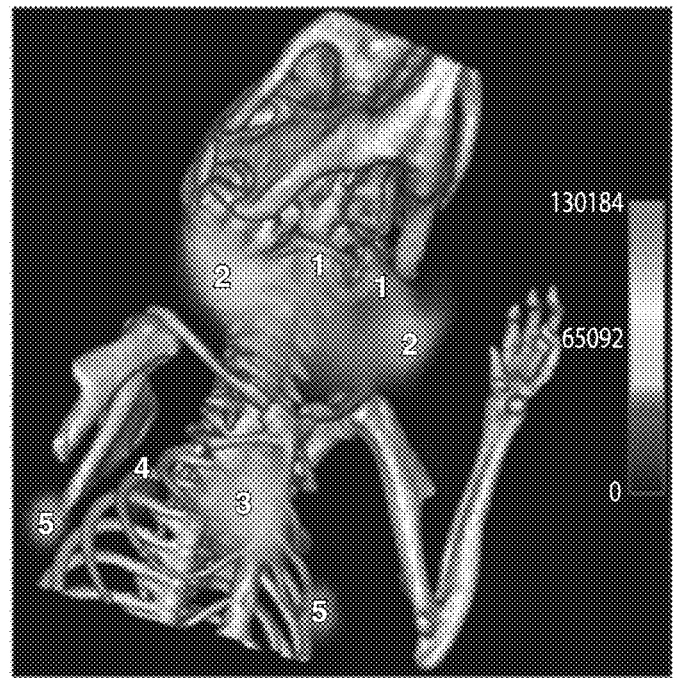

Fluorophores were installed in a sortase-catalyzed reaction, and these fluorescently labeled VHHs were used as staining agents for cytofluorimetry, establishing that VHH7 recognizes murine I-A products encoded by the H-2$^b$ and H-2$^d$ haplotypes present in the common laboratory strains of mice. Administration of $^{18}$F-VHH7 in vivo showed excellent visualization of normal lymph nodes, spleen and thymus with a high degree of specificity and high signal to noise ratios observed in MHC-II$^+$ mice (C57BL/6). Very little if any specific labeling is observed in MHC-II deficient mice (B6.129S2-H$_2$<dlAb1-Ea>/J); (FIG. 5).

$^{18}$F-VHH7 was also used for biodistribution analysis and blood half-life measurements in a C57BL/6 mouse model (FIG. 6). Results show a $t_{1/2}$ of <20 min and excellent specificity of VHH7 for normal lymph nodes, spleen and thymus in MHC-II$^+$ mice (C57BL/6). Very little specific labeling is observed in MHC-II deficient mice.

The application of anti-class II MHC single domain antibodies was also explored to determine whether it is feasible to image the behavior of lymphocytes in a xenograft tumor model. Both the distribution of macrophages at steady state and the evolution of their distribution and location over time in the course of such a response have never before been imaged non-invasively. The ability to monitor the presence or absence of macrophages endowed with markers such as Class II MHC during the course of clinical treatment is particularly important. These approaches are transposable to a clinical setting, because VHHs of this type, after suitable modification (humanization), have been used in Phase I and Phase II clinical trials for therapeutic indications (De Meyer, T. et al. *Trends Biotechnol.* 2014, 32, 263-270; which is incorporated by reference). The ability to assess the presence and distribution of the immunological checkpoint molecules presents an enormous enrichment of the diagnostic toolbox with which to monitor—if not predict—the clinical behavior of the appropriate patient populations.

In many tumor models, the margins of the tumor contain macrophages, which if activated should express Class II MHC products. Thus, PET imaging experiments were designed to investigate whether, in addition to the usual lymphoid structures as visualized by radiolabeled VHH7, it was also possible to detect the presence of macrophages around and possibly within a xenografted tumor. The Mel-Juso human melanoma cell line is positive for human Class II MHC products, and has been extensively characterized with respect to trafficking and surface display of Class II MHC molecules (Tulp, A. et al. *Nature* 1994, 369, 120-126.; Bakke, O.; et al. *Cell* 1990, 63, 707-716; which are incorporated by reference). As such, it is representative of a subset of human melanomas. Accordingly, Mel-Juso xenografts were created in NOD-SCID mice by subcutaneous inoculation. The SCID mice hosts contain some of the normal complement of murine Class II MHC$^+$ antigen presenting cells such as macrophages, but no B or T cells, and should thus still be visible upon PET imaging with radiolabeled VHH7. Result showed that by using $^{18}$F-VHH7, inflammation around the tumor is clearly visible (FIG. 7A-D). This important observation shows the possibility of early state detection of diseases such as multiple sclerosis (MS), diabetes, and cancers using this methodology.

Figure 7A:
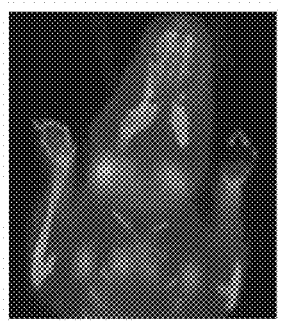
FIGS. 7A-7J depict imaging the presence of tumor-associated Class II MHC$^+$ cells using $^{18}$F-VHH7 (anti mouse Class II MHC). A NOD-SCID mouse was inoculated subcutaneously with human MelJuSo melanoma cells and imaged 25 days post injection. Tumor cells lack mouse class II MHC molecules.
Figure 7B:
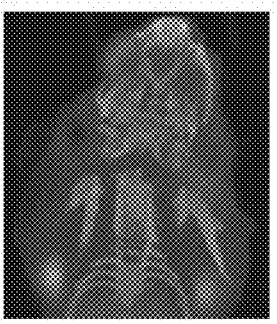
Figure 7C:
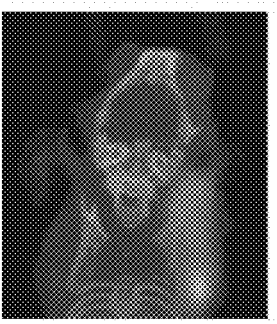
Figure 7D:
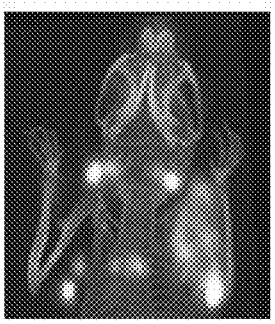
Figure 7E:
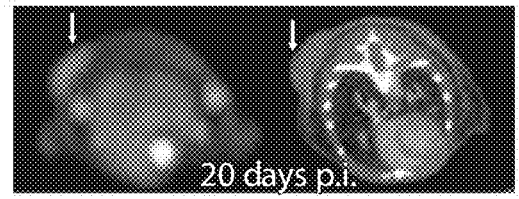
Figure 7F:
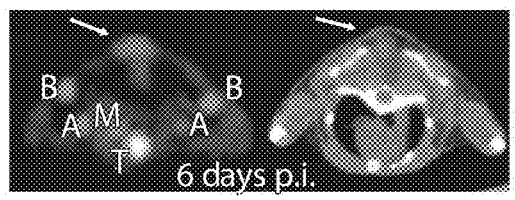
Figure 7G:
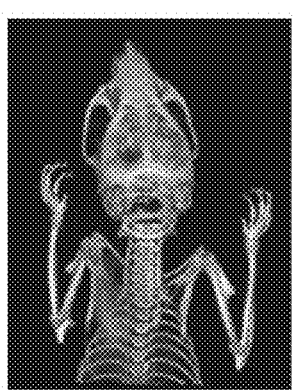
Figure 7H:
Figure 7I:
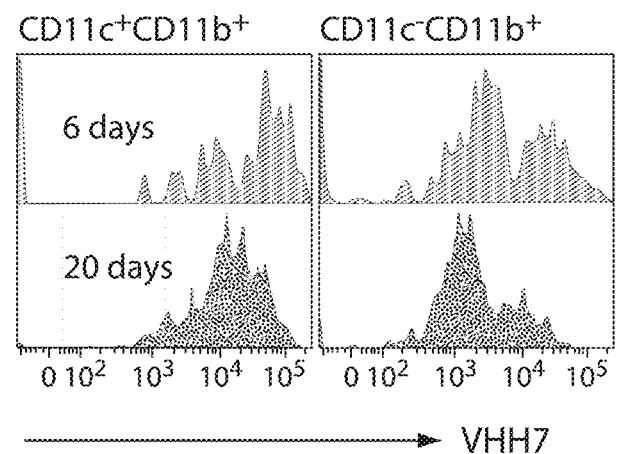
Figure 7J:
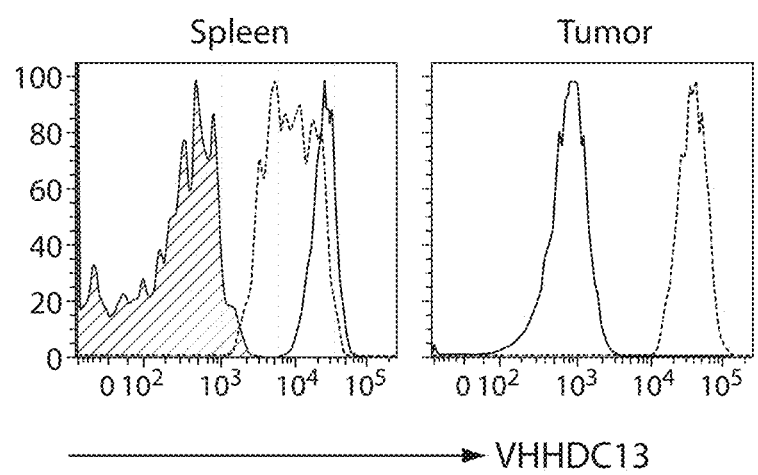
Figure 8A:
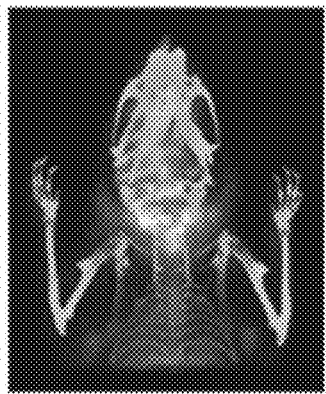
FIGS. 8A-8F show that $^{64}$Cu-VHH7 (anti mouse Class II MHC) and 64Cu-VHHDC13 (myeloid cell-specific) detect secondary lymphoid organs and inflammation.
Figure 8B:
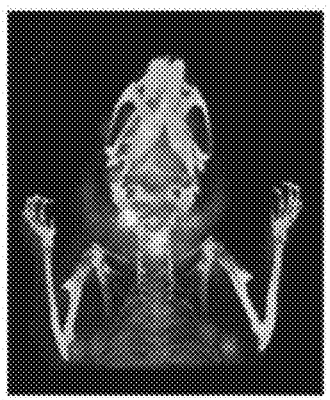
Figure 8C:
Figure 8D:
Figure 8E:
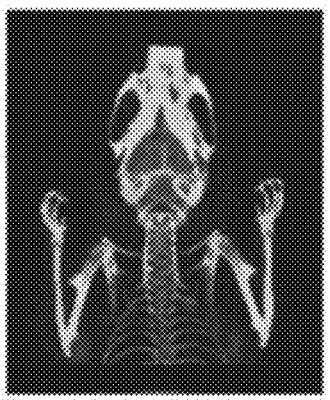
Figure 8F:
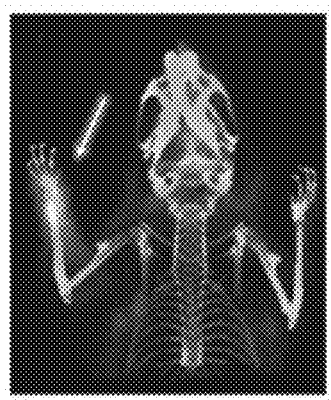

To determine if it is possible to image small tumors at earlier stages of growth NOD/SCID mice xenografted with $5 \times 10^6$ Mel-Juso human melanoma cells (FIG. 7 E-J) were imaged at 6 days (FIG. 7F), 20 days (FIG. 7E) and 27 days post-injection. Inflammation was detected at the site of the malignant growth as the earliest time point after injection, a time when the incipient tumors are not detectable by palpation, only by cytofluorimetry or histology (FIG. 7I). Cytofluorimetry on cell suspensions prepared from the excised tumors again confirmed the presence of tumor-infiltrating Class II MHC$^+$ cells. It may thus be worthwhile to explore early stage detection of diseases such as MS, diabetes, different infections or cancers, all characterized by an inflammatory signature (Keliher, E. J., et al. "High-Yielding, Two-Step $^{18}$F Labeling Strategy for $^{18}$F-PARP1 Inhibitors.", *ChemMedChem*, 2011; 6, 424-427; which are incorporated by reference).

Figure 9A:
FIGS. 9A-9B show 18F-VHH7 (anti mouse Class II MHC) and 18F-VHH DC13 (anti CD11b) detect secondary lymphoid organs and inflammation.
Figure 9B:
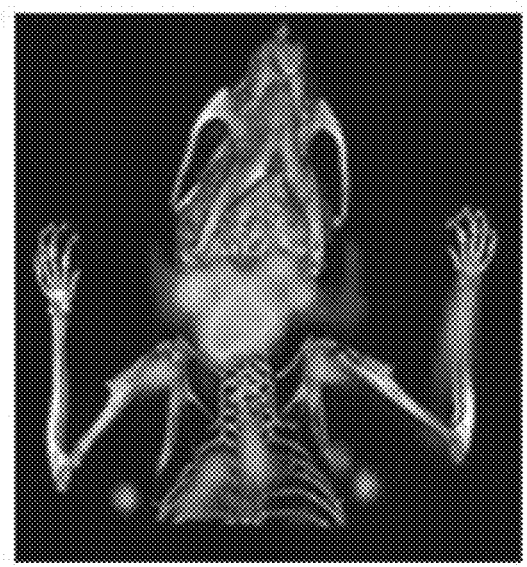

Inflammation in response to administration of complete Freund's adjuvant (CFA) was also examined using $^{18}$F-labeled VHH7 and VHH DC13. Subcutaneous administration of CFA into one of the front paws resulted in inflammation, imaged 24 h post-injection using $^{18}$F-labeled VHH7 and VHH DC13, a single domain antibody that recognizes the neutrophil, macrophage and dendritic cell marker CD11b, as determined by mass spectrometry of immunoprecipitates prepared with immobilized VHH DC13. VHHs revealed inflammation with remarkable selectivity, with VHH DC13 showing a stronger signal in the inflamed region relative to VHH7 (FIG. 9 A&B). Selective accumulation of $^{18}$F VHHDC13 when compared with the build-up of $^{18}$F VHH7 is consistent with the massive influx of CD11b$^+$ neutrophils generally observed at the site of injection 24 h after administration of CFA. It is thus possible to monitor inflammation and immune responses non-invasively by exploiting specific sentinels such as Class II MHC$^+$ or CD11b$^+$ cells. A VHH was generated that recognizes human HLA-DR molecules in a monomorphic pattern of reactivity.

The ability to monitor the presence or absence of activated macrophages as an indicator of inflammation will therefore be transposable to a clinical setting as a diagnostic tool.

In conclusion, exemplified here is the first enzyme mediated site-specific $^{18}$F-labeling and $^{64}$Cu-labeling of proteins using sortase. The method is highly efficient and compatible with the short half-life of $^{18}$F. Using this method, $^{18}$F-VHH7, the camelid-derived single domain antibody against murine MHC class II molecules, was produced and successfully used to visualize and map the secondary lymphatic organs including lymph nodes, thymus and spleen. Results showed that not only is VHH7 rapidly cleared from the circulation (t½<20 min), but also stained the secondary lymphoid organs with excellent specificity. This method thus represents a significant new tool for non-invasive imaging of the lymphatic system. Next, the application of the method to image inflammation was explored. Accordingly, xenograft mice models bearing human melanoma tumors were created and imaged with $^{18}$F-VHH7. Importantly, due to the infiltration of macrophages, it was possible to clearly see the inflammation around the tumor. Thus, this method is amenable for early detection of many diseases such as MS, diabetes and different types of cancers. Further, the methodology exemplified here can be used with other proteins and VHHs for PET imaging. For example, the anti-mouse CD3 VHH can be used to visualize CD4$^+$ and CD8$^+$ T cells as well as CD4$^+$CD8$^+$ thymocytes. These experiments can be performed in RAG2−/− mice as the negative control (complete absence of T cells) and in C57B/6 mice as the positive control. A comparison of the VHH7 and CD3 VHH should prove informative on the ability to distinguish between the Class II MHC-positive localization (antigen presenting cells, B cells) and T cell localization. Additionally, the anti-CD11b VHH can be used to distinguish between B cells and macrophages.

Figure 10A:
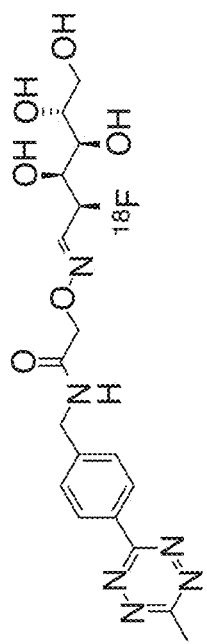
FIGS. 10A-10C show a schematic representation of the strategy for site-specific labeling of proteins with $^{18}$F using a pre-prepared sortagged protein and $^{18}$F-FDG oxime-tetrazine.
Figure 10A:
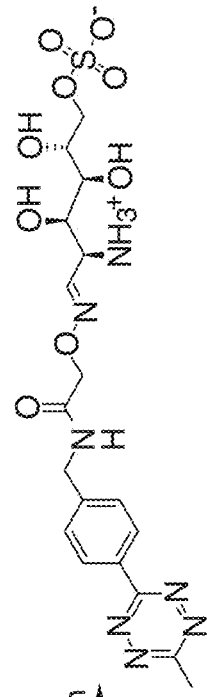
Figure 10B:
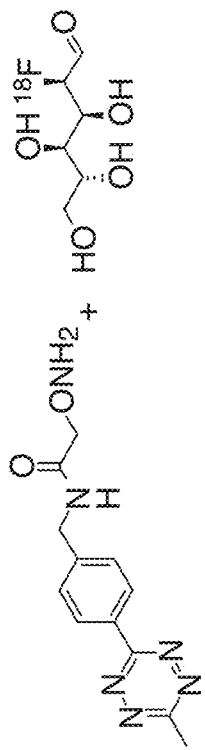
Figure 10B:
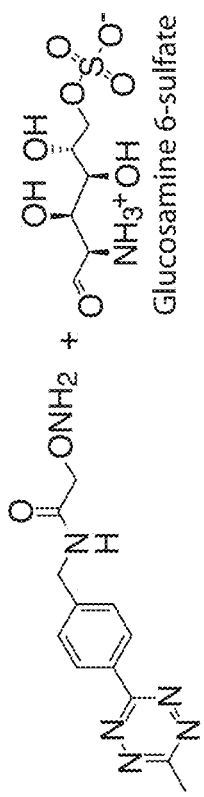

Example 3. $^{18}$F-Labeling of Proteins Using 18F-FDG Generated from a Catalyzed Oxime Ligation An $^{18}$F-FDG was added to a solution of Tetrazine-aminooxy and a catalyst to generate the $^{18}$F labeled click chemistry handle ($^{18}$F-FDG oxime-tetrazine) by oxime ligation (FIG. 10A). A series of catalysts, including m-phenylenediamine, p-phenylenediamine and p-anisidine were tested to optimize this reaction. The data showed that p-phenylenediamine (pPDA) was the most efficient catalyst for the reaction. The optimized condition for this reaction is as follows: [Tz-Aoxy]=350 mM, [pPDA]=400 mM, T=75° C. HPLC showed >95% conversion to the product in approximately 5 minutes.

Figure 10C:
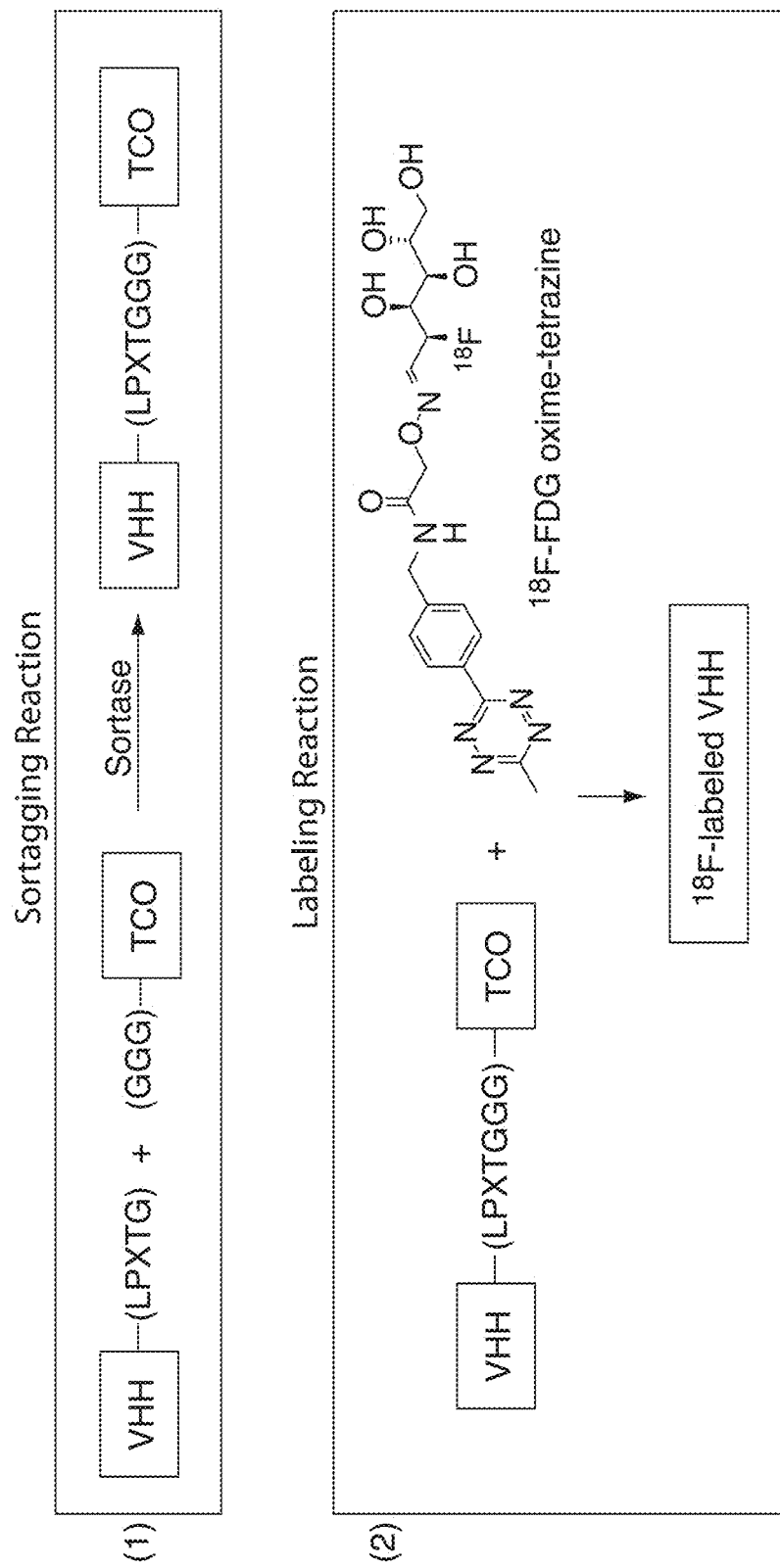

Following the oxime ligation reaction, the product is purified via HPLC to provide a 18F-labeled Tetrazine. The fraction from HPLC is mixed with 4×volume of 1% NaHCO$_3$ and is loaded into a solid phase extraction (SPE) column. The 18F-tetrazine will stick to the column and hence is concentrated. The 18F-tetrazine is eluted with pure acetonitrile or ethanol (or a similar organic solvent) from the SPE column to a final volume of ~1 mL. This can be further dried or be used as it is depending to the scale of the nanobody conjugation in the next step. The organic solvent can be up to ~25% of the volume for the final conjugation reaction and not higher. The $^{18}$F-FDG oxime-tetrazine product can then be used to label a pre-prepared sortagged VHH-TCO to form the final $^{18}$F-labeled VHH as shown in FIG. 10C.

All publications, patents and sequence database entries mentioned herein, including those items listed above, are hereby incorporated by reference in their entirety as if each individual publication or patent was specifically and individually indicated to be incorporated by reference. In case of conflict, the present application, including any definitions herein, will control.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

In some embodiments, click chemistry handles used can react to form covalent bonds in the absence of a metal catalyst. Such click chemistry handles are well known to those of skill in the art and include the click chemistry handles described in Becer,

What is claimed is:

1. A radioactive protein of Formula (II):

—$L^1$—$L^2$—$^{18}F$      (II)

wherein

Protein represents a protein;

$L^1$ is a peptide linker comprising -LPXTGGGK-, -LPXTGGG-, -NPXTGGGK-, -NPXTGGG-, -LPXTAAA-, -NPXTAAA-, -LPXTGGGGG-, or -LPGAG-, wherein each instance of X is independently any amino acid; and $L^2$ is a linker comprising optionally substituted heterocyclylene.

2. A pharmaceutical composition comprising the radioactive protein of claim 1 and a pharmaceutically acceptable carrier.

3. The radioactive protein of claim 1, wherein Protein is an antibody, a nuclear factor, a neuropeptide, a receptor protein, an enzyme, a structural protein, or a fragment thereof.

4. The radioactive protein of claim 1, wherein $L^1$ is -LPXTGGG-.

5. The radioactive protein of claim 1, wherein $L^2$ is of Formula (ii):

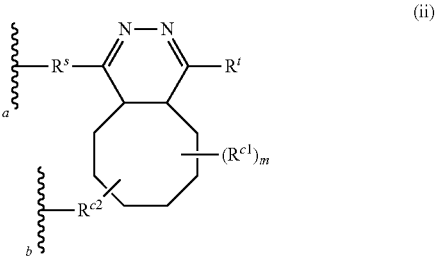

wherein
R$^t$ is hydrogen, optionally substituted aliphatic, optionally substituted heteroaliphatic, optionally substituted aryl, optionally substituted heteroaryl, or optionally substituted heterocyclyl;
R$^s$ is a bond, optionally substituted aliphatic, optionally substituted heteroaliphatic, optionally substituted arylene, optionally substituted heteroarylene, or optionally substituted heterocyclylene;
each instance of R$^{c1}$ is hydrogen, optionally substituted aliphatic, optionally substituted heteroaliphatic, optionally substituted aryl, optionally substituted heteroaryl, or optionally substituted heterocyclyl; or two R$^{c1}$ are joined to form an optionally substituted carbocyclic or optionally substituted heterocyclic ring;
R$^{c2}$ is a bond, optionally substituted aliphatic, optionally substituted heteroaliphatic, optionally substituted arylene, optionally substituted heteroarylene, or optionally substituted heterocyclylene;
m is 0, 1, 2, 3, 4, 5, 6, 7, or 8, as valency permits;
a is a point of attachment to L$^1$; and
b is a point of attachment to $^{18}$F.

6. The radioactive protein of claim 5, wherein L$^2$ is of Formula (ii-a):

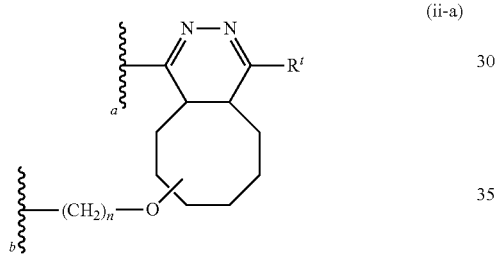

(ii-a)

wherein n is an integer between 1 and 8, inclusive.

7. The radioactive protein of claim 6, wherein R$^t$ is optionally substituted methyl, optionally substituted pyridine, or optionally substituted phenyl.

8. The radioactive protein of claim 1, wherein L$^2$ is of Formula (iii):

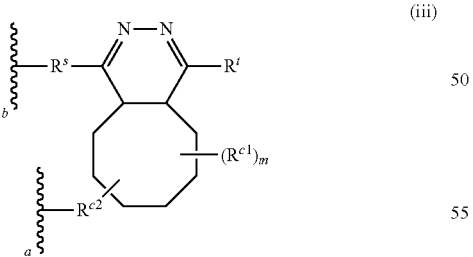

(iii)

wherein
R$^t$ is hydrogen, optionally substituted aliphatic, optionally substituted heteroaliphatic, optionally substituted aryl, optionally substituted heteroaryl, or optionally substituted heterocyclyl;
R$^s$ is a bond, optionally substituted aliphatic, optionally substituted heteroaliphatic, optionally substituted arylene, optionally substituted heteroarylene, or optionally substituted heterocyclylene;
each instance of R$^{c1}$ is hydrogen, optionally substituted aliphatic, optionally substituted heteroaliphatic, optionally substituted aryl, optionally substituted heteroaryl, or optionally substituted heterocyclyl;
R$^{c2}$ is a bond, optionally substituted aliphatic, optionally substituted heteroaliphatic, optionally substituted arylene, optionally substituted heteroarylene, or optionally substituted heterocyclylene;
m is 0, 1, 2, 3, 4, 5, 6, 7, or 8, as valency permits;
a is a point of attachment to L$^1$; and
b is a point of attachment to $^{18}$F.

9. The radioactive protein of claim 8, wherein L$^2$ is of Formula (iii-a):

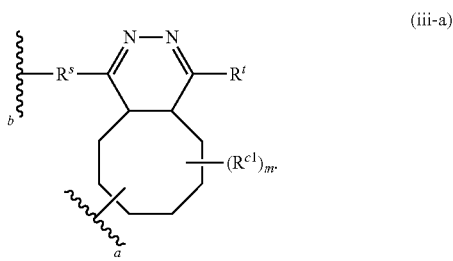

(iii-a)

10. The radioactive protein of claim 9, wherein -L$^2$-$^{18}$F is of Formula (iii-b):

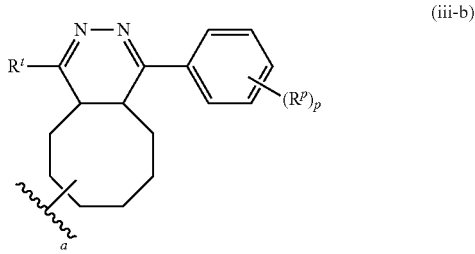

(iii-b)

wherein
each instance of R$^p$ is independently hydrogen, optionally substituted aliphatic, optionally substituted heteroaliphatic, optionally substituted aryl, optionally substituted heteroaryl, optionally substituted heterocyclyl, hydroxyl, or optionally substituted amino; provided at least one RP comprises $^{18}$F; and
p is 1, 2, 3, 4, or 5.

11. The radioactive protein of claim 10, wherein -L$^2$-$^{18}$F is of Formula (iii-b1):

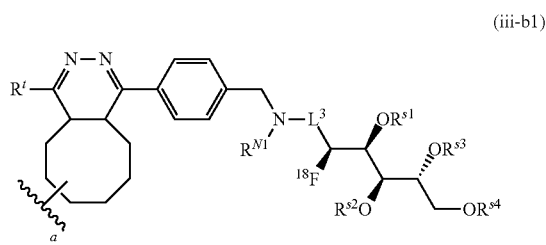

(iii-b1)

wherein
L$^3$ is a bond, optionally substituted aliphatic, optionally substituted heteroaliphatic, optionally substituted arylene, optionally substituted heteroarylene, or optionally substituted heterocyclylene;

$R^{N1}$ is independently hydrogen, optionally substituted aliphatic, optionally substituted heteroaliphatic, optionally substituted aryl, optionally substituted heteroaryl, or a nitrogen protecting group; and each of $R^{s1}$, $R^{s2}$, $R^{s3}$, and $R^{s4}$ is independently hydrogen, optionally substituted aliphatic, optionally substituted heteroaliphatic, optionally substituted aryl, optionally substituted heteroaryl, or an oxygen protecting group.

12. The radioactive protein of claim 10, wherein -$L^2$-$^{18}$F is of the formula:

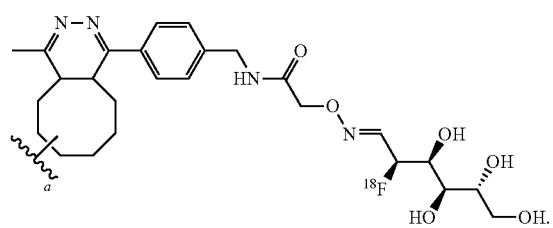

13. The radioactive protein of claim 10, wherein -$L^2$-$^{18}$F is of Formula (iii-b2):

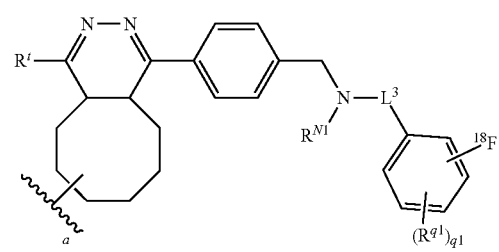

(iii-b2)

wherein $L^3$ is a bond, optionally substituted aliphatic, optionally substituted heteroaliphatic, optionally substituted arylene, optionally substituted heteroarylene, or optionally substituted heterocyclylene;

$R^{N1}$ is independently hydrogen, optionally substituted aliphatic, optionally substituted heteroaliphatic, optionally substituted aryl, optionally substituted heteroaryl, optionally substituted heterocyclyl, or a nitrogen protecting group;

each instance of $R^{q1}$ is independently hydrogen, optionally substituted aliphatic, optionally substituted heteroaliphatic, optionally substituted aryl, optionally substituted heteroaryl, optionally substituted heterocyclyl, hydroxyl, or optionally substituted amino; and q1 is 0, 1, 2, 3, or 4.

14. The radioactive protein of claim 10, wherein -$L^2$-$^{18}$F is of the formula:

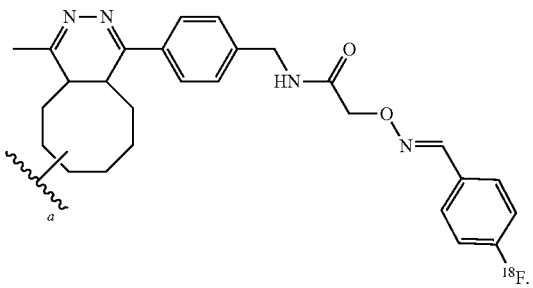

15. The radioactive protein of claim 10, wherein -$L^2$-$^{18}$F is of Formula (iii-b3):

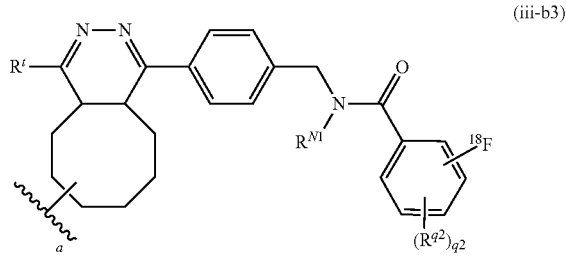

(iii-b3)

wherein $R^{N1}$ is independently hydrogen, optionally substituted aliphatic, optionally substituted heteroaliphatic, optionally substituted aryl, optionally substituted heteroaryl, or a nitrogen protecting group; and each instance of $R^{q2}$ is independently hydrogen, optionally substituted aliphatic, optionally substituted heteroaliphatic, optionally substituted aryl, optionally substituted heteroaryl, optionally substituted heterocyclyl, hydroxyl, or optionally substituted amino; and q2 is 0, 1, 2, 3, or 4.

16. The radioactive protein of claim 15, wherein -$L^2$-$^{18}$F is of the formula:

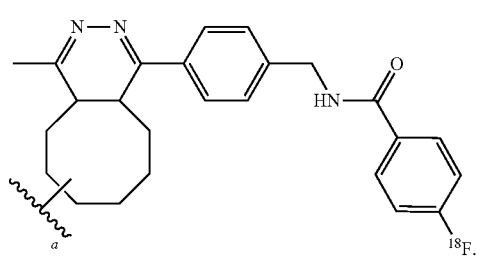

17. The radioactive protein of claim 1, wherein -L$^2$-$^{18}$F is of Formula (iii-c):

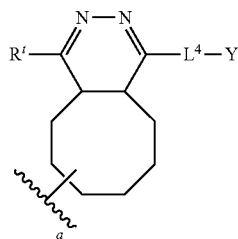

(iii-c)

wherein
R$^t$ is hydrogen, optionally substituted aliphatic, optionally substituted heteroaliphatic, optionally substituted aryl, optionally substituted heteroaryl, or optionally substituted heterocyclyl;

a is a point of attachment to L$^1$;

Y comprises CO, CH$_3$CN, CH$_3$CH$_2$CN, a monosubstituted amine, a disubstituted amine, a trisubstituted amine, pyridine, piperidine, a dialkylcyanamide, triphenylphosphine oxide, THF, DMF, NMF, 1,5-cyclooctadiene, norbornadiene, 1,2-ethylenediamine, tetramethylethylenediamine, 1,2-dimethoxyethane, diglyme, 2,5-dithiahexane, cycloheptatriene, benzene, toluene, xylene, mesitylene, naphthalene, tetraazacyclododecane, diethylenetriamine, trithiocylononane, 1,4,7-triazacyclononane-triacetic acid (NOTA), 1,4,7,10-tetraazacyclododecane-tetraacetic acid (DOTA), or triazacyclononane-phosphinate (TRAP), wherein Y chelates a pharmaceutically acceptable metal complex comprising $^{18}$F; and L$^4$ is a bond, optionally substituted aliphatic, optionally substituted heteroaliphatic, optionally substituted arylene, optionally substituted heteroarylene, or optionally substituted heterocyclylene.

18. The radioactive protein of claim 17, wherein -L$^2$-$^{18}$F is of Formula (iii-c1):

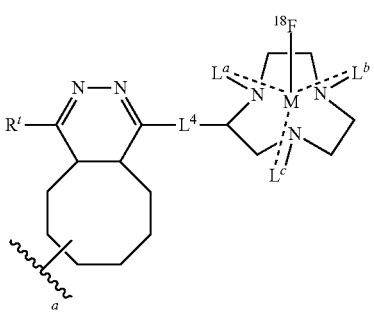

(iii-c1)

wherein
M is a pharmaceutically acceptable metal;
each of L$^a$, L$^b$, and L$^c$ is independently optionally substituted aliphatic, optionally substituted heteroaliphatic, optionally substituted arylene, optionally substituted heteroarylene, or optionally substituted heterocyclylene; and
--- is a coordination bond or is absent, as valency permits.

19. The radioactive protein of claim 18, wherein -L$^2$-$^{18}$F is of Formula (iii-c2):

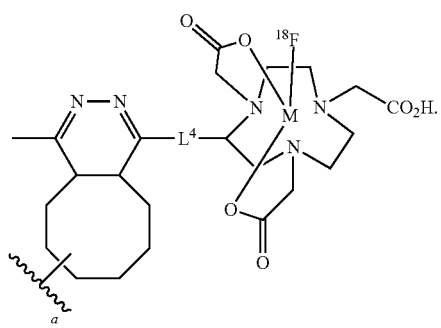

(iii-c2)

20. The radioactive protein of claim 1, wherein the radioactive protein is one of the following formulae:

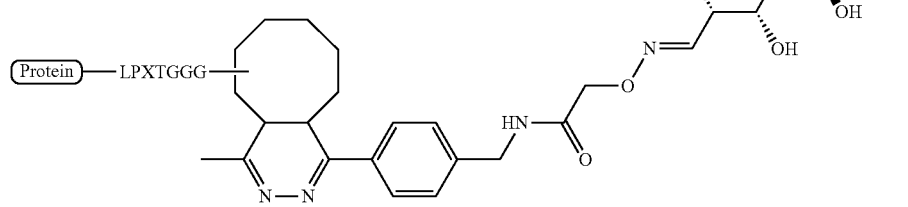

-continued
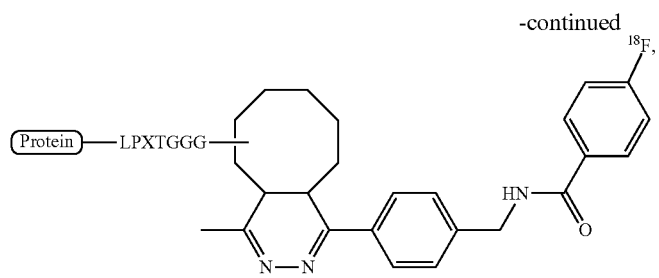
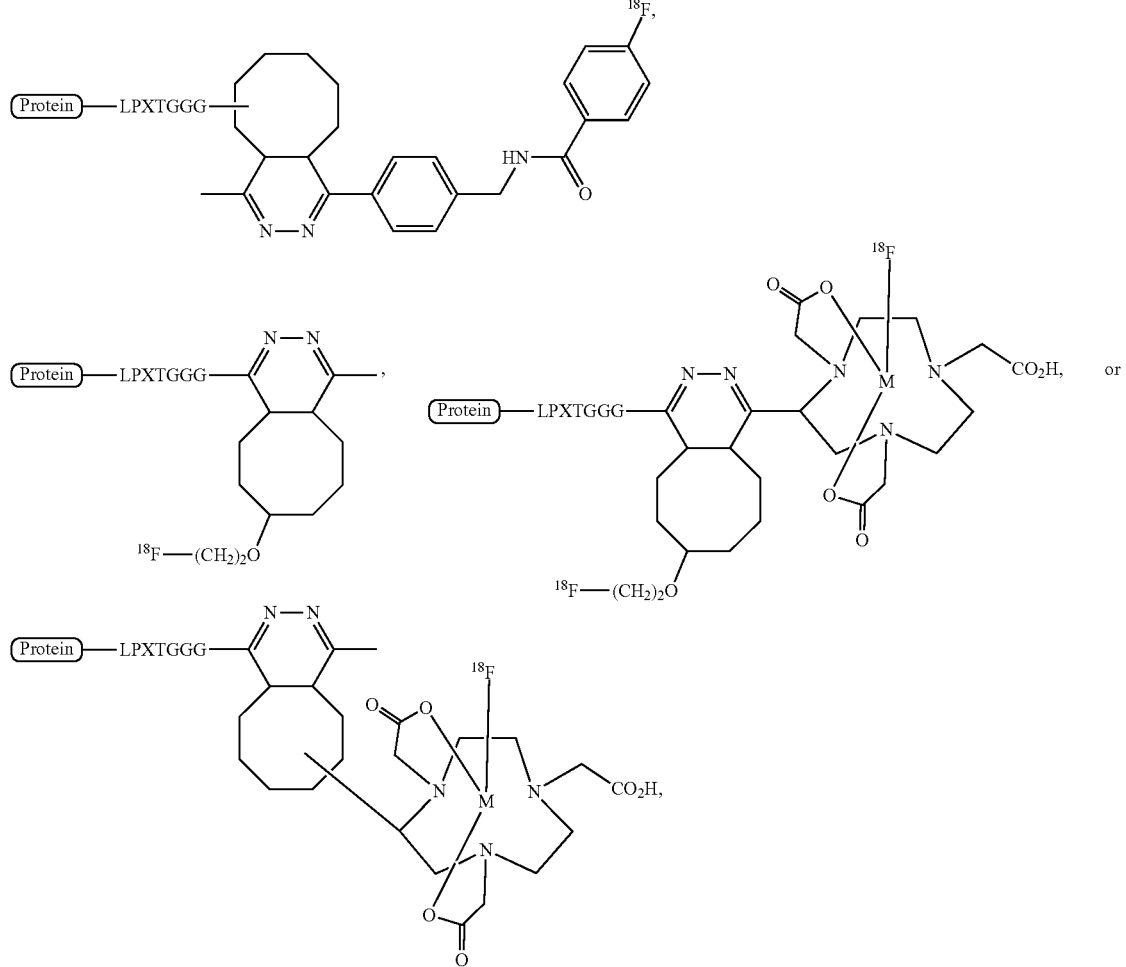
wherein M is a pharmaceutically acceptable metal.
21. The radioactive protein of claim 8, wherein the linker $L^2$ is of Formula (ii-b):
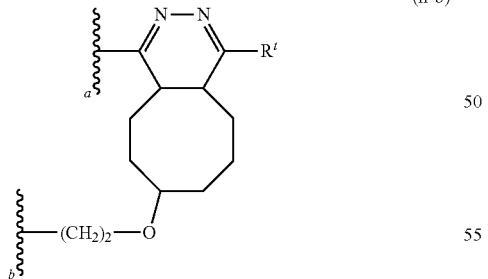
(ii-b)
wherein n is an integer between 1 and 8, inclusive.
* * * * *

```
                        SEQUENCE LISTING

<160> NUMBER OF SEQ ID NOS: 135

<210> SEQ ID NO 1
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 1

Leu Pro Xaa Thr Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 2

Leu Pro Glu Thr Gly
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 3

Leu Pro Glu Thr Ala
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 4

Asn Pro Gln Thr Asn
1               5

<210> SEQ ID NO 5
<211> LENGTH: 5
```

```
<212> TYPE: PRT
<213> ORGANISM: Artificial Sequence
<220> FEATURE:
<223> OTHER INFORMATION: Synthetic Polypeptide

<400> SEQUENCE: 5

Asn Pro Lys Thr Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 6

Leu Pro Lys Thr Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 7

Leu Pro Ala Thr Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 8

Leu Pro Asn Thr Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 9

Leu Pro Xaa Ala Gly
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 10

Leu Pro Asn Ala Gly
1               5
```

```
<210> SEQ ID NO 11
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 11

Leu Pro Xaa Thr Ala
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 12

Leu Pro Asn Thr Ala
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 13

Leu Gly Xaa Thr Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 14

Leu Gly Ala Thr Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 15

Ile Pro Xaa Thr Gly
1               5

<210> SEQ ID NO 16
```

```
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 16

Ile Pro Asn Thr Gly
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 17

Ile Pro Glu Thr Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 18

Asn Ser Lys Thr Ala
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 19

Asn Pro Gln Thr Gly
1               5

<210> SEQ ID NO 20
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 20

Asn Ala Lys Thr Asn
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 21

Asn Pro Gln Ser Ser
1               5

<210> SEQ ID NO 22
<211> LENGTH: 5
```

```
<212> TYPE: PRT
<213> ORGANISM: Artificial Sequence
<220> FEATURE:
<223> OTHER INFORMATION: Synthetic Polypeptide

<400> SEQUENCE: 22

Asn Ala Lys Thr Asn
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 23

Asn Pro Gln Ser Ser
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 24

Leu Pro Xaa Thr Ala
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 25

Leu Ala Xaa Thr Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 26

Leu Pro Xaa Thr Ala
1               5

<210> SEQ ID NO 27
<211> LENGTH: 5
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 27

Leu Ala Xaa Thr Gly
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 28

Leu Pro Asn Thr Ala
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 29

Gln Val Pro Thr Gly Val
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 30

Leu Pro Xaa Thr Ala
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 31

Leu Pro Ser Thr Ser
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 32

Leu Pro Lys Thr Gly
```

```
1               5
```

<210> SEQ ID NO 33
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 33

```
Leu Pro Ile Thr Gly
1               5
```

<210> SEQ ID NO 34
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 34

```
Leu Pro Asp Thr Ala
1               5
```

<210> SEQ ID NO 35
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 35

```
Ser Pro Lys Thr Gly
1               5
```

<210> SEQ ID NO 36
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 36

```
Leu Ala Glu Thr Gly
1               5
```

<210> SEQ ID NO 37
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 37

```
Leu Ala Ala Thr Gly
1               5
```

<210> SEQ ID NO 38
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 38

```
Leu Ala His Thr Gly
1               5
```

```
<210> SEQ ID NO 39
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 39

Leu Ala Ser Thr Gly
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 40

Leu Ala Glu Thr Gly
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 41

Leu Pro Leu Thr Gly
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 42

Leu Ser Arg Thr Gly
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 43

Val Pro Asp Thr Gly
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 44

Ile Pro Gln Thr Gly
1               5
```

<210> SEQ ID NO 45
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 45

Tyr Pro Arg Arg Gly
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 46

Leu Pro Met Thr Gly
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 47

Leu Pro Leu Thr Gly
1               5

<210> SEQ ID NO 48
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 48

Leu Ala Phe Thr Gly
1               5

<210> SEQ ID NO 49
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 49

Leu Pro Gln Thr Ser
1               5

<210> SEQ ID NO 50
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 50

Asn Pro Gln Ser
1

```
<210> SEQ ID NO 51
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 51

Leu Pro Ser Thr
1

<210> SEQ ID NO 52
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 52

Asn Ser Lys Thr
1

<210> SEQ ID NO 53
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 53

Asn Pro Gln Thr
1

<210> SEQ ID NO 54
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 54

Asn Ala Lys Thr
1

<210> SEQ ID NO 55
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 55

Leu Pro Ile Thr
1

<210> SEQ ID NO 56
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 56

Leu Ala Glu Thr
1

<210> SEQ ID NO 57
```

```
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 57

Asn Pro Gln Ser
1

<210> SEQ ID NO 58
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 58

Leu Pro Lys Thr
1

<210> SEQ ID NO 59
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 59

Leu Pro Ile Thr
1

<210> SEQ ID NO 60
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 60

Leu Pro Asp Thr
1

<210> SEQ ID NO 61
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 61

Ser Pro Lys Thr
1

<210> SEQ ID NO 62
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 62

Leu Ala Glu Thr
1

<210> SEQ ID NO 63
<211> LENGTH: 4
```

```
<212> TYPE: PRT
<213> ORGANISM: Artificial Sequence
<220> FEATURE:
<223> OTHER INFORMATION: Synthetic Polypeptide

<400> SEQUENCE: 63

Leu Ala Ala Thr
1

<210> SEQ ID NO 64
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 64

Leu Ala Glu Thr
1

<210> SEQ ID NO 65
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 65

Leu Ala Ser Thr
1

<210> SEQ ID NO 66
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 66

Leu Ala Glu Thr
1

<210> SEQ ID NO 67
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 67

Leu Pro Leu Thr
1

<210> SEQ ID NO 68
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 68

Leu Ser Arg Thr
1

<210> SEQ ID NO 69
<211> LENGTH: 4
<212> TYPE: PRT
```

```
<213> ORGANISM: Artificial Sequence
<220> FEATURE:
<223> OTHER INFORMATION: Synthetic Polypeptide

<400> SEQUENCE: 69

Leu Pro Glu Thr
1

<210> SEQ ID NO 70
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 70

Val Pro Asp Thr
1

<210> SEQ ID NO 71
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 71

Ile Pro Gln Thr
1

<210> SEQ ID NO 72
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 72

Tyr Pro Arg Arg
1

<210> SEQ ID NO 73
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 73

Leu Pro Met Thr
1

<210> SEQ ID NO 74
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 74

Leu Pro Leu Thr
1

<210> SEQ ID NO 75
<211> LENGTH: 4
<212> TYPE: PRT
<213> ORGANISM: Artificial Sequence
```

```
<220> FEATURE:
<223> OTHER INFORMATION: Synthetic Polypeptide

<400> SEQUENCE: 75

Leu Ala Phe Thr
1

<210> SEQ ID NO 76
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 76

Leu Pro Gln Thr
1

<210> SEQ ID NO 77
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 77

Asn Ser Lys Thr
1

<210> SEQ ID NO 78
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 78

Asn Pro Gln Thr
1

<210> SEQ ID NO 79
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 79

Asn Ala Lys Thr
1

<210> SEQ ID NO 80
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 80

Asn Pro Gln Ser
1

<210> SEQ ID NO 81
<211> LENGTH: 4
<212> TYPE: PRT
<213> ORGANISM: Artificial Sequence
<220> FEATURE:
```

<223> OTHER INFORMATION: Synthetic Polypeptide

<400> SEQUENCE: 81

Gly Gly Gly Lys
1

<210> SEQ ID NO 82
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 82

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 83
<211> LENGTH: 483
<212> TYPE: DNA
<213> ORGANISM: Artificial Sequence
<220> FEATURE:
<223> OTHER INFORMATION: Synthetic Polynucleotide

<400> SEQUENCE: 83
atgaaatacc tattgcctac ggcagccgct ggattgttat tactcgcggc ccagccggcc      60
atggcccagg tgcagctgca ggagtcaggg ggaggattgg tgcaaactgg gggctctctg     120
agactctcct gtgcagcctc tggagttgac ttcaattggt atagtatggg gtggttccgc     180
caggctccag ggaaggagcg tgaatacgtt gcaagtatag accaaggtgg tgaattagat     240
tatgccatct ccgtgaaggg acgatttact atctccagag acaacgccaa gaacatggtg     300
tatctccaaa tgaacagcct gaaacctgag gacacggccg tttattactg tgcagcagat     360
ttcagcgggc gcggcgcgag taatccagat aagtataaat actggggcca ggggacccag     420
gtcaccgtct cctcaggagg actgccggaa ccggcggcc accaccatca ccatcactaa     480
tag                                                                   483

<210> SEQ ID NO 84
<211> LENGTH: 159
<212> TYPE: PRT
<213> ORGANISM: Artificial Sequence
<220> FEATURE:
<223> OTHER INFORMATION: Synthetic Polypeptide

<400> SEQUENCE: 84

Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Glu Ser Gly Gly Gly
            20                  25                  30

Leu Val Gln Thr Gly Gly Ser Leu Arg Leu Ser Cys Ala Ala Ser Gly
        35                  40                  45

Val Asp Phe Asn Trp Tyr Ser Met Gly Trp Phe Arg Gln Ala Pro Gly
    50                  55                  60

Lys Glu Arg Glu Tyr Val Ala Ser Ile Asp Gln Gly Gly Glu Leu Asp
65                  70                  75                  80

Tyr Ala Ile Ser Val Lys Gly Arg Phe Thr Ile Ser Arg Asp Asn Ala
                85                  90                  95

```
Lys Asn Met Val Tyr Leu Gln Met Asn Ser Leu Lys Pro Glu Asp Thr
            100                 105                 110

Ala Val Tyr Tyr Cys Ala Ala Asp Phe Ser Gly Arg Gly Ala Ser Asn
        115                 120                 125

Pro Asp Lys Tyr Lys Tyr Trp Gly Gln Gly Thr Gln Val Thr Val Ser
    130                 135                 140

Ser Gly Gly Leu Pro Glu Thr Gly Gly His His His His His
145                 150                 155
```

<210> SEQ ID NO 85
<211> LENGTH: 501
<212> TYPE: DNA
<213> ORGANISM: Artificial Sequence
<220> FEATURE:
<223> OTHER INFORMATION: Synthetic Polynucleotide

<400> SEQUENCE: 85

```
atgaaatacc tattgcctac ggcagccgct ggattgttat tactcgcggc ccagccggcc      60
atggcccagg tgcagctgca ggagtcaggg ggaggattgg tgcaggctgg ggactctctg     120
agactctcct gcgcagcctc tggacgcacc ttcagtcgcg gtgtaatggg ctggttccgc     180
cgggctccag gaaggagcg tgagtttgta gcaatcttta gcgggagtag ctggagtggt      240
cgtagtacat actattcaga ctccgtaaag ggccgattca ccatctccag agacaacgcc     300
aagaacacgg tgtatctgca aatgaacggc ctgaaactg aggacacggc cgtttattac      360
tgtgcagcgg gatatccgga ggcgtatagc gcctatggtc gggagagtac atatgactac     420
tggggccagg gaccagtt caccgtctcc tcaggaggac tgccggaaac cggcggccac      480
caccatcacc atcactaata g                                              501
```

<210> SEQ ID NO 86
<211> LENGTH: 165
<212> TYPE: PRT
<213> ORGANISM: Artificial Sequence
<220> FEATURE:
<223> OTHER INFORMATION: Synthetic Polypeptide

<400> SEQUENCE: 86

```
Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Glu Ser Gly Gly Gly
            20                  25                  30

Leu Val Gln Ala Gly Asp Ser Leu Arg Leu Ser Cys Ala Ala Ser Gly
        35                  40                  45

Arg Thr Phe Ser Arg Gly Val Met Gly Trp Phe Arg Arg Ala Pro Gly
    50                  55                  60

Lys Glu Arg Glu Phe Val Ala Ile Phe Ser Gly Ser Ser Trp Ser Gly
65                  70                  75                  80

Arg Ser Thr Tyr Tyr Ser Asp Ser Val Lys Gly Arg Phe Thr Ile Ser
                85                  90                  95

Arg Asp Asn Ala Lys Asn Thr Val Tyr Leu Gln Met Asn Gly Leu Lys
            100                 105                 110

Pro Glu Asp Thr Ala Val Tyr Tyr Cys Ala Ala Gly Tyr Pro Glu Ala
        115                 120                 125

Tyr Ser Ala Tyr Gly Arg Glu Ser Thr Tyr Asp Tyr Trp Gly Gln Gly
    130                 135                 140

Thr Gln Val Thr Val Ser Ser Gly Gly Leu Pro Glu Thr Gly Gly His
145                 150                 155                 160
```

His His His His His
            165

<210> SEQ ID NO 87
<211> LENGTH: 206
<212> TYPE: PRT
<213> ORGANISM: S. aureus

<400> SEQUENCE: 87

Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
            20                  25                  30

Leu His Asp Lys Asp Lys Asp Glu Lys Ile Glu Gln Tyr Asp Lys Asn
        35                  40                  45

Val Lys Glu Gln Ala Ser Lys Asp Asn Lys Gln Gln Ala Lys Pro Gln
    50                  55                  60

Ile Pro Lys Asp Lys Ser Lys Val Ala Gly Tyr Ile Glu Ile Pro Asp
65                  70                  75                  80

Ala Asp Ile Lys Glu Pro Val Tyr Pro Gly Pro Ala Thr Pro Glu Gln
                85                  90                  95

Leu Asn Arg Gly Val Ser Phe Ala Glu Glu Asn Glu Ser Leu Asp Asp
            100                 105                 110

Gln Asn Ile Ser Ile Ala Gly His Thr Phe Ile Asp Arg Pro Asn Tyr
        115                 120                 125

Gln Phe Thr Asn Leu Lys Ala Ala Lys Lys Gly Ser Met Val Tyr Phe
    130                 135                 140

Lys Val Gly Asn Glu Thr Arg Lys Tyr Lys Met Thr Ser Ile Arg Asp
145                 150                 155                 160

Val Lys Pro Thr Asp Val Glu Val Leu Asp Glu Gln Lys Gly Lys Asp
                165                 170                 175

Lys Gln Leu Thr Leu Ile Thr Cys Asp Asp Tyr Asn Glu Lys Thr Gly
            180                 185                 190

Val Trp Glu Lys Arg Lys Ile Phe Val Ala Thr Glu Val Lys
        195                 200                 205

<210> SEQ ID NO 88
<211> LENGTH: 206
<212> TYPE: PRT
<213> ORGANISM: S. aureus

<400> SEQUENCE: 88

Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
            20                  25                  30

Leu His Asp Lys Asp Lys Asp Glu Lys Ile Glu Gln Tyr Asp Lys Asn
        35                  40                  45

Val Lys Glu Gln Ala Ser Lys Asp Lys Gln Gln Ala Lys Pro Gln
    50                  55                  60

Ile Pro Lys Asp Lys Ser Lys Val Ala Gly Tyr Ile Glu Ile Pro Asp
65                  70                  75                  80

Ala Asp Ile Lys Glu Pro Val Tyr Pro Gly Pro Ala Thr Pro Glu Gln
                85                  90                  95

Leu Asn Arg Gly Val Ser Phe Ala Glu Glu Asn Glu Ser Leu Asp Asp
            100                 105                 110

Gln Asn Ile Ser Ile Ala Gly His Thr Phe Ile Asp Arg Pro Asn Tyr
            115                 120                 125

Gln Phe Thr Asn Leu Lys Ala Ala Lys Lys Gly Ser Met Val Tyr Phe
        130                 135                 140

Lys Val Gly Asn Glu Thr Arg Lys Tyr Lys Met Thr Ser Ile Arg Asp
145                 150                 155                 160

Val Lys Pro Thr Asp Val Gly Val Leu Asp Glu Gln Lys Gly Lys Asp
                165                 170                 175

Lys Gln Leu Thr Leu Ile Thr Cys Asp Asp Tyr Asn Glu Lys Thr Gly
            180                 185                 190

Val Trp Glu Lys Arg Lys Ile Phe Val Ala Thr Glu Val Lys
        195                 200                 205

<210> SEQ ID NO 89
<211> LENGTH: 148
<212> TYPE: PRT
<213> ORGANISM: Artificial Sequence
<220> FEATURE:
<223> OTHER INFORMATION: Synthetic Polypeptide

<400> SEQUENCE: 89

Met Gln Ala Lys Pro Gln Ile Pro Lys Asp Lys Ser Lys Val Ala Gly
1               5                   10                  15

Tyr Ile Glu Ile Pro Asp Ala Asp Ile Lys Glu Pro Val Tyr Pro Gly
            20                  25                  30

Pro Ala Thr Arg Glu Gln Leu Asn Arg Gly Val Ser Phe Ala Glu Glu
        35                  40                  45

Asn Glu Ser Leu Asp Asp Gln Asn Ile Ser Ile Ala Gly His Thr Phe
    50                  55                  60

Ile Asp Arg Pro Asn Tyr Gln Phe Thr Asn Leu Lys Ala Ala Lys Lys
65                  70                  75                  80

Gly Ser Met Val Tyr Phe Lys Val Gly Asn Glu Thr Arg Lys Tyr Lys
                85                  90                  95

Met Thr Ser Ile Arg Asn Val Lys Pro Thr Ala Val Glu Val Leu Asp
            100                 105                 110

Glu Gln Lys Gly Lys Asp Lys Gln Leu Thr Leu Ile Thr Cys Asp Asp
        115                 120                 125

Tyr Asn Glu Glu Thr Gly Val Trp Glu Thr Arg Lys Ile Phe Val Ala
    130                 135                 140

Thr Glu Val Lys
145

<210> SEQ ID NO 90
<211> LENGTH: 453
<212> TYPE: DNA
<213> ORGANISM: Artificial Sequence
<220> FEATURE:
<223> OTHER INFORMATION: Synthetic Polynucleotide

<400> SEQUENCE: 90
atgaaatacc tattgcctac ggcagccgct ggattgttat tactcgcggc ccagccggcc      60
atggcccagg tgcagctgca ggagtcaggg ggaggattgg tgcaggctgg ggggtctctg     120
agactctcct gtgcagcctc tggaagcacc ctcagtagct atggcatggg ctggtaccgc     180
caggctccag ggaagcaacg tgaagtggtc gcaactatta gtgctactgg tagcataagc     240
tatgcagact ccgtgaaggg ccgattcacc atctccagag acagtgccaa gaacacgatg     300

```
tatctgcaac tgaacagcct gacacctgag gacacggccg tctattactg taacacaatt    360
tataggtcta ctctctactg gggccagggg acccaggtca ccgtctcctc aggaggactg    420
ccggaaaccg gcggccacca ccatcaccat cac                                 453
```

<210> SEQ ID NO 91
<211> LENGTH: 151
<212> TYPE: PRT
<213> ORGANISM: Artificial Sequence
<220> FEATURE:
<223> OTHER INFORMATION: Synthetic Polypeptide

<400> SEQUENCE: 91

```
Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Glu Ser Gly Gly Gly
            20                  25                  30

Leu Val Gln Ala Gly Gly Ser Leu Arg Leu Ser Cys Ala Ala Ser Gly
        35                  40                  45

Ser Thr Leu Ser Ser Tyr Gly Met Gly Trp Tyr Arg Gln Ala Pro Gly
    50                  55                  60

Lys Gln Arg Glu Val Val Ala Thr Ile Ser Ala Thr Gly Ser Ile Ser
65                  70                  75                  80

Tyr Ala Asp Ser Val Lys Gly Arg Phe Thr Ile Ser Arg Asp Ser Ala
                85                  90                  95

Lys Asn Thr Met Tyr Leu Gln Leu Asn Ser Leu Thr Pro Glu Asp Thr
            100                 105                 110

Ala Val Tyr Tyr Cys Asn Thr Ile Tyr Arg Ser Thr Leu Tyr Trp Gly
        115                 120                 125

Gln Gly Thr Gln Val Thr Val Ser Ser Gly Gly Leu Pro Glu Thr Gly
    130                 135                 140

Gly His His His His His
145                 150
```

<210> SEQ ID NO 92
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 92

```
Leu Pro Glu Thr Gly Gly His His His His His His
1               5                   10
```

<210> SEQ ID NO 93
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 93

```
Leu Pro Glu Thr
1
```

<210> SEQ ID NO 94

<400> SEQUENCE: 94

000

```
<210> SEQ ID NO 95
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 95

Thr Leu Xaa Thr Cys
1               5

<210> SEQ ID NO 96
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Xaa is Gln or Lys
<220> FEATURE:
<221> NAME/KEY: MISC_FEATURE
<222> LOCATION: (5)..(5)
<223> OTHER INFORMATION: Xaa is Ala or Ser

<400> SEQUENCE: 96

Leu Pro Xaa Thr Xaa Thr
1               5

<210> SEQ ID NO 97
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa is Ala or Ser

<400> SEQUENCE: 97

Leu Pro Xaa Thr Xaa
1               5

<210> SEQ ID NO 98
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: X is Asp, Glu, Ala, Asn, Gln, Lys, or Arg

<400> SEQUENCE: 98

Leu Pro Xaa Thr
1

<210> SEQ ID NO 99
<211> LENGTH: 5
```

```
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Xaa is Lys, Glu, Asn, Gln, or Ala

<400> SEQUENCE: 99

Leu Pro Xaa Thr Gly
1               5

<210> SEQ ID NO 100
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Xaa is Asp, Glu, Ala, Asn, Gln, Lys, or Arg

<400> SEQUENCE: 100

Leu Pro Xaa Thr Gly
1               5

<210> SEQ ID NO 101
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Xaa is Lys, Glu, Asn, Gln, or Ala

<400> SEQUENCE: 101

Leu Pro Xaa Thr
1

<210> SEQ ID NO 102
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Xaa is Lys, Ser, Glu, Leu, Ala, or Asn

<400> SEQUENCE: 102

Leu Pro Xaa Thr Gly
1               5

<210> SEQ ID NO 103
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Xaa is Lys, Ser, Glu, Leu, Ala, or Asn

<400> SEQUENCE: 103
```

Leu Pro Xaa Thr
1

<210> SEQ ID NO 104
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 104

Leu Pro Xaa Thr Gly Gly Gly Lys
1               5

<210> SEQ ID NO 105
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 105

Leu Pro Xaa Thr Gly Gly Gly
1               5

<210> SEQ ID NO 106
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 106

Asn Pro Xaa Thr Gly Gly Gly Lys
1               5

<210> SEQ ID NO 107
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 107

Asn Pro Xaa Thr Gly Gly Gly
1               5

<210> SEQ ID NO 108
<211> LENGTH: 7
<212> TYPE: PRT
<213> ORGANISM: Artificial Sequence
<220> FEATURE:
<223> OTHER INFORMATION: Synthetic Polypeptide
<220> FEATURE:

```
<221> NAME/KEY: misc_feature
<222> LOCATION: (3)..(3)
<223> OTHER INFORMATION: Xaa can be any naturally occurring amino acid

<400> SEQUENCE: 108

Leu Pro Xaa Thr Ala Ala Ala
1               5

<210> SEQ ID NO 109
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 109

Asn Pro Xaa Thr Ala Ala Ala
1               5

<210> SEQ ID NO 110
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 110

Leu Pro Xaa Thr Gly Gly Gly Gly Gly
1               5

<210> SEQ ID NO 111
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 111

Leu Pro Gly Ala Gly
1               5

<210> SEQ ID NO 112
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 112

Leu Pro Xaa Thr Gly Gly Asn His
1               5

<210> SEQ ID NO 113
<211> LENGTH: 13
<212> TYPE: PRT
<213> ORGANISM: Artificial Sequence
<220> FEATURE:
```

<223> OTHER INFORMATION: Synthetic Polypeptide

<400> SEQUENCE: 113

Leu Cys Thr Pro Ser Arg Gly Ser Leu Phe Thr Gly Arg
1               5                   10

<210> SEQ ID NO 114
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 114

Asp Ser Leu Glu Phe Ile Ala Ser Lys Leu Ala
1               5                   10

<210> SEQ ID NO 115
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 115

Val Leu Asp Ser Leu Glu Phe Ile Ala Ser Lys Leu Ala
1               5                   10

<210> SEQ ID NO 116
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 116

Gly Ser Gln Asp Val Leu Asp Ser Leu Glu Phe Ile Ala Ser Lys Leu
1               5                   10                  15

Ala

<210> SEQ ID NO 117
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 117

Gly Gly Gly Ser Leu Leu Gln Gly
1               5

<210> SEQ ID NO 118
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 118

Pro Asn Pro Gln Leu Pro Phe
1               5

<210> SEQ ID NO 119
<211> LENGTH: 7
<212> TYPE: PRT
<213> ORGANISM: Artificial Sequence

```
<220> FEATURE:
<223> OTHER INFORMATION: Synthetic Polypeptide

<400> SEQUENCE: 119

Pro Lys Pro Gln Gln Phe Met
1               5

<210> SEQ ID NO 120
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 120

Gly Gln Gln Gln Leu Gly
1               5

<210> SEQ ID NO 121
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 121

Met Arg His Lys Gly Ser
1               5

<210> SEQ ID NO 122
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 122

Gly Leu Asn Asp Ile Phe Glu Ala Gln Lys Ile Glu Trp His Glu
1               5                   10                  15

<210> SEQ ID NO 123
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 123

Gly Phe Glu Ile Asp Lys Val Trp Tyr Asp Leu Asp Ala
1               5                   10

<210> SEQ ID NO 124
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 124

Gly Gly Gly Cys
1

<210> SEQ ID NO 125
<211> LENGTH: 7
<212> TYPE: PRT
<213> ORGANISM: Artificial Sequence
<220> FEATURE:
```

```
<223> OTHER INFORMATION: Synthetic Polypeptide

<400> SEQUENCE: 125

Leu Pro Glu Thr Gly Gly Gly
1               5

<210> SEQ ID NO 126
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 126

Leu Pro Xaa Thr Gly Xaa Xaa
1               5

<210> SEQ ID NO 127
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 127

Leu Pro Glu Thr Gly Gly
1               5

<210> SEQ ID NO 128
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Xaa is Glu, Ala, Ser, or His

<400> SEQUENCE: 128

Asn Ala Xaa Thr Gly
1               5

<210> SEQ ID NO 129
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(10)
<223> OTHER INFORMATION: may be absent

<400> SEQUENCE: 129

Gly Gly Gly Gly Gly Gly Gly Gly Gly Gly Lys
1               5                   10

<210> SEQ ID NO 130
<211> LENGTH: 4
<212> TYPE: PRT
```

```
<213> ORGANISM: Artificial Sequence
<220> FEATURE:
<223> OTHER INFORMATION: Synthetic Polypeptide

<400> SEQUENCE: 130

Gly Gly Asn His
1

<210> SEQ ID NO 131
<211> LENGTH: 100
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(100)
<223> OTHER INFORMATION: may be absent

<400> SEQUENCE: 131

Gly Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly Gly
        35                  40                  45

Gly Gly Gly Gly Gly Gly Gly Gly Gly Gly Gly Gly Gly Gly Gly Gly
    50                  55                  60

Gly Gly Gly Gly Gly Gly Gly Gly Gly Gly Gly Gly Gly Gly Gly Gly
65                  70                  75                  80

Gly Gly Gly Gly Gly Gly Gly Gly Gly Gly Gly Gly Gly Gly Gly Gly
                85                  90                  95

Gly Gly Gly Gly
            100

<210> SEQ ID NO 132
<211> LENGTH: 100
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(100)
<223> OTHER INFORMATION: may be absent

<400> SEQUENCE: 132

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
            20                  25                  30

Ala Ala Ala Ala Ala Ala Ala Ala Ala Ala Ala Ala Ala Ala Ala Ala
        35                  40                  45

Ala Ala Ala Ala Ala Ala Ala Ala Ala Ala Ala Ala Ala Ala Ala Ala
    50                  55                  60

Ala Ala Ala Ala Ala Ala Ala Ala Ala Ala Ala Ala Ala Ala Ala Ala
65                  70                  75                  80

Ala Ala Ala Ala Ala Ala Ala Ala Ala Ala Ala Ala Ala Ala Ala Ala
                85                  90                  95

Ala Ala Ala Ala
            100
```

```
<210> SEQ ID NO 133
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 133

His His His His His His
1               5

<210> SEQ ID NO 134
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (2)..(10)
<223> OTHER INFORMATION: may be absent
<220> FEATURE:
<221> NAME/KEY: VARIANT
<222> LOCATION: (11)..(11)
<223> OTHER INFORMATION: Xaa may be any amino acid

<400> SEQUENCE: 134

Gly Gly Gly Gly Gly Gly Gly Gly Gly Gly Xaa
1               5                   10

<210> SEQ ID NO 135
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Xaa can be any naturally occurring amino acid

<400> SEQUENCE: 135

Leu Pro Xaa Thr Gly Gly
1               5
```